US007795001B2

(12) United States Patent
Midoh et al.

(10) Patent No.: US 7,795,001 B2
(45) Date of Patent: Sep. 14, 2010

(54) MIDECAMYCIN BIOSYNTHESIS GENES

(75) Inventors: Naoki Midoh, Odawara (JP); Shigeru Hoshiko, Yokohama (JP); Takeshi Murakami, Odawara (JP)

(73) Assignee: Meiji Seika Kaisha, Ltd., Tokyo-To (JP)

( * ) Notice: Subject to any disclaimer, the term of this patent is extended or adjusted under 35 U.S.C. 154(b) by 463 days.

(21) Appl. No.: 11/330,363

(22) Filed: Jan. 12, 2006

(65) Prior Publication Data

US 2006/0121577 A1 Jun. 8, 2006

Related U.S. Application Data

(62) Division of application No. 10/229,148, filed on Aug. 28, 2002, now Pat. No. 7,070,980.

(30) Foreign Application Priority Data

Jul. 19, 2002 (JP) ............................. 2002-210516

(51) Int. Cl.
*C12N 1/21* (2006.01)
*C12N 15/00* (2006.01)
*C07H 21/04* (2006.01)

(52) U.S. Cl. .............................. 435/252.3; 435/252.33; 435/252.31; 435/252.35; 435/320.1; 536/23.2; 536/23.7; 536/23.1

(58) Field of Classification Search .................... None
See application file for complete search history.

(56) References Cited

U.S. PATENT DOCUMENTS 5,876,991 A 3/1999 Dehoff et al.

OTHER PUBLICATIONS

Aparicio et al. Organization of the biosynthetic gene cluster for rapamycin in *Streptomyces hygroscopicus*: analysis of the enzymatic domains in the modular polyketide synthase. Gene, vol. 169, pp. 9-16, 1996.*
GenBank Accession No. U78289.1, GI: 2317859, Aug. 1997.*
Brown, T. "Unit 2.10 Hybridization Analysis of DNA Blots" in Current Protocols in Molecular Biology John Wiley & Sons, Inc. 1993, pp. 2.10.1-2.10-16.*
Pakula. Genetic Analysis of protein stability and function, Annu Rev Genet., vol. 23, pp. 289-310, 1989.
N. Bate, et al., The Mycinose-Biosynthetic Genes of *Streptomyces fradie*, Product of Tylosin, Journal of Industrial Microbiology & Biotechnology, vol. 23, (1999), pp. 118-122.
N. Bate, et al., "Multiple Regulatory Genes in the Tylosin Biosynthetic Cluster of *Streptomyces fradiae*", Chemistry & Biology, vol. 6, No. 9, (1999), pp. 617-624.
N. Bate, et al., "The Mycarose-Biosynthetic Genes of *Streptomyces fradiae*, Producer of Tylosin", Microbiology, vol. 146, (2000), pp. 139-146.
V.A. Birmingham, et al., "Cloning and Expression of a Tylosin Resistance Gene From a Tylosin-Producing Strain of *Streptomyces fradiae*", Mol. Gen. Genet, vol. 240, (1986), pp. 532-539.
E. Cundliffe, et al., "The Tylosin-Biosynthetic Genes of *Streptomyces fradiae*", Antonie Van Leeuwenhoek, vol. 79, (2001), pp. 229-234.

S.E. Fishman, et al., "Cloning Genes for the Biosynthesis of a Macrolide Antibiotic", Proc. Natl. Acad. Sci. USA, vol. 84, (Dec. 1987), pp. 8248-8252.
R. Fouces, et al., "The Tylosin Biosynthetic Cluster From *Streptomyces fradiae*: Genetic Organization of the Left Region", Microbiology, vol. 145, (1999), pp. 855-868.
A.R. Gandecha, et al., "Molecular Analysis of TRLRD, an MLS Resistance Determinant From the Tylosin Producer, *Streptomyces fradiae*", Gene, vol. 180, (1996), pp. 173-176.
A. R. Gandecha, et al., "Analysis of Four Tylosin Biosynthetic Genes From the TYLLM Region of the *Streptomyces fradiae* Genome", Gene, vol. 184, (1997), pp. 197-203.
O. Hara, et al., "Cloning of Midecamycin(MLS)-Resistance Genes From *Streptomyces mycarofaciens*, *Streptomyces lividans* and *Streptomyces coelicolor* A3(2)", The Journal of Antibiotics, vol. 43, No. 8, (1990), pp. 977-991.
O. Hara, et al., "A Macrolide 3—Acyltransferase Gene From the Midecamycin-Producing Species *Streptomyces mycarofaciens*", Journal of Bacteriology, vol. 174, No. 15, (1992), pp. 5141-5144.
L.A. Merson-Davies, et al., "Analysis of Five Tylosin Biosynthetic Genes From the TYLLBA Region of the *Streptomyces fradiae* Genome", Molecular Microbiology, vol. 13, No. 2, (1994), pp. 349-355.
P.R. Rosteck, et al., "Homology Between Proteins Controlling *Streptomyces fradiae* Tylosin Resistance and ATP-Binding Transport", Gene, vol. 102, (1991), pp. 27-32.
V.T.W. Wilson, et al., "Characterization and Targeted Disruption of a Glycosyltransferase Gene in the Tylosin Producer, *Streptomyces fradiae*", Gene, vol. 214, (1998), pp. 95-100.
K. Wu, et al., "The FK520 Gene Cluster of *Streptomyces hygroscopicus* Var. *Ascomyceticus* (ATCC 14891) Contains Genes for Biosynthesis of Unusual Polyketide Extender Units", Gene, vol. 251, (2000), pp. 81-90.
L. Jun, et al., "Phylogeny of Extra-Slowly-Growing Rhizobia Isolated From the Nodules of Soybean", Acta Microbiologica Sinica, vol. 36, (1996), pp. 416-422.
Scott, et al., The Pendred Syndrome gene encodes a chloride-iodide transport protein, Nat Genet., 21(4): 440-3, Apr. 1999.
Everett, et al., The Pendred Syndrome is caused by mutations in putative sulphate transporter gene (PDS). Nat. Genet. 17(4): 411-22, Dec. 1997.
Fetrow., Functional Analysis of the *Escherichia coli* genome using the sequence-to-structure-to-function paradigm: identification of proteins exhibiting the glutaredoxin/thioredoxin disulfide oxidoreductase activity, J. Mol Biol., 282(4): 703-11, Oct. 1998.
Kakavas, et al., Identification and Characterization of the niddamycin polyketide synthase genes from *Streptomyces caelestis*, Journal of Bacteriology, 179(23): 7515-7522, Dec. 1997.
Yiguang et al., Cloning of Midecamycin Biosynthetic Gense from *Streptomyces mycarofaciens*, 1748.5(4): 191-201, 1989.

* cited by examiner

*Primary Examiner*—Jennifer Dunston
(74) *Attorney, Agent, or Firm*—Oblon, Spivak, McClelland, Maier & Neustadt, L.L.P.

(57) ABSTRACT

The present invention provides an isolated polypeptide comprising a nucleotide sequence encoding a protein which is involved in midecamycin biosynthesis, wherein the protein contains an amino acid sequence selected from SEQ ID NOs: 2 to 10, 13, 14, 16, 19, 20, 22 to 26, and 28 to 38 or a modified amino acid sequence of the amino acid sequence having one or more amino acid modifications without affecting activity of the protein.

8 Claims, 8 Drawing Sheets

| Midecamycin | $R_1$ | $R_2$ | $R_3$ | X |
|---|---|---|---|---|
| $A_1$ | $-COCH_2CH_3$ | $-CHO$ | $-COCH_2CH_3$ | $-OH$ |
| $A_2$ | $-COCH_2CH_3$ | $-CHO$ | $-COCH_2CH_2CH_3$ | $-OH$ |
| $A_3$ | $-COCH_2CH_3$ | $-CHO$ | $-COCH_2CH_3$ | $=O$ |
| B | $-COCH_3$ | $-CHO$ | $-COCH_2CH_3$ | $-OH$ |
| DH | $-COCH_2CH_3$ | $-CH_2OH$ | $-COCH_2CH_3$ | $-OH$ |
| E | $-COCH_2CH_2CH_3$ | $-CHO$ | $-COCH_2CH_3$ | $-OH$ |
| $CH_3$ | $-COCH_2CH_3$ | $-CH_3$ | $-COCH_2CH_2CH_3$ or $-COCH(CH_3)_2$ | $-OH$ |

```
                        SEQUENCE LISTING

<160> NUMBER OF SEQ ID NOS: 48

<210> SEQ ID NO 1
<211> LENGTH: 84428
<212> TYPE: DNA
<213> ORGANISM: Streptomyces mycarofaciens
<220> FEATURE:
<221> NAME/KEY: CDS
<222> LOCATION: Complement((1)..(675))
<223> OTHER INFORMATION: ORF42 (fragment)
<220> FEATURE:
<221> NAME/KEY: CDS
<222> LOCATION: Complement((1168)..(2202))
<223> OTHER INFORMATION: ORF41
<220> FEATURE:
<221> NAME/KEY: CDS
<222> LOCATION: Complement((2220)..(3215))
<223> OTHER INFORMATION: ORF40
<220> FEATURE:
<221> NAME/KEY: CDS
<222> LOCATION: Complement((3237)..(4691))
<223> OTHER INFORMATION: ORF39
<220> FEATURE:
<221> NAME/KEY: CDS
<222> LOCATION: Complement((4695)..(5948))
<223> OTHER INFORMATION: ORF38
<220> FEATURE:
<221> NAME/KEY: CDS
<222> LOCATION: Complement((6048)..(6629))
<223> OTHER INFORMATION: ORF37
<220> FEATURE:
<221> NAME/KEY: CDS
<222> LOCATION: Complement((6653)..(7945))
<223> OTHER INFORMATION: ORF36
<220> FEATURE:
<221> NAME/KEY: CDS
<222> LOCATION: (8149)..(9015)
<223> OTHER INFORMATION: ORF35
<220> FEATURE:
<221> NAME/KEY: CDS
<222> LOCATION: (9012)..(9335)
<223> OTHER INFORMATION: ORF34
<220> FEATURE:
<221> NAME/KEY: CDS
<222> LOCATION: (9328)..(10458)
<223> OTHER INFORMATION: ORF33
<220> FEATURE:
<221> NAME/KEY: CDS
<222> LOCATION: (10521)..(11603)
<223> OTHER INFORMATION: ORF32
<220> FEATURE:
<221> NAME/KEY: CDS
<222> LOCATION: (11729)..(12961)
<223> OTHER INFORMATION: ORF31
<220> FEATURE:
<221> NAME/KEY: CDS
<222> LOCATION: Complement((13016)..(14044))
<223> OTHER INFORMATION: ORF30
<220> FEATURE:
<221> NAME/KEY: CDS
<222> LOCATION: Complement((14074)..(15096))
<223> OTHER INFORMATION: ORF29
```

```
<220> FEATURE:
<221> NAME/KEY: CDS
<222> LOCATION: (15643)..(17466)
<223> OTHER INFORMATION: ORF28
<220> FEATURE:
<221> NAME/KEY: CDS
<222> LOCATION: Complement((17522)..(18895))
<223> OTHER INFORMATION: ORF27
<220> FEATURE:
<221> NAME/KEY: CDS
<222> LOCATION: (19063)..(20229)
<223> OTHER INFORMATION: ORF26
<220> FEATURE:
<221> NAME/KEY: CDS
<222> LOCATION: Complement((20307)..(21743))
<223> OTHER INFORMATION: ORF25
<220> FEATURE:
<221> NAME/KEY: CDS
<222> LOCATION: Complement((21733)..(22527))
<223> OTHER INFORMATION: ORF24
<220> FEATURE:
<221> NAME/KEY: CDS
<222> LOCATION: Complement((22534)..(23571))
<223> OTHER INFORMATION: ORF23
<220> FEATURE:
<221> NAME/KEY: CDS
<222> LOCATION: Complement((23555)..(24463))
<223> OTHER INFORMATION: ORF22
<220> FEATURE:
<221> NAME/KEY: CDS
<222> LOCATION: Complement((24460)..(25650))
<223> OTHER INFORMATION: ORF21
<220> FEATURE:
<221> NAME/KEY: CDS
<222> LOCATION: Complement((25647)..(26105))
<223> OTHER INFORMATION: ORF20
<220> FEATURE:
<221> NAME/KEY: CDS
<222> LOCATION: Complement((26180)..(27391))
<223> OTHER INFORMATION: ORF19
<220> FEATURE:
<221> NAME/KEY: CDS
<222> LOCATION: (27937)..(28983)
<223> OTHER INFORMATION: ORF18
<220> FEATURE:
<221> NAME/KEY: CDS
<222> LOCATION: (29244)..(42779)
<223> OTHER INFORMATION: ORF1
<220> FEATURE:
<221> NAME/KEY: CDS
<222> LOCATION: (42823)..(48657)
<223> OTHER INFORMATION: ORF2
<220> FEATURE:
<221> NAME/KEY: CDS
<222> LOCATION: (48712)..(59802)
<223> OTHER INFORMATION: ORF3
<220> FEATURE:
<221> NAME/KEY: CDS
<222> LOCATION: (59850)..(64556)
<223> OTHER INFORMATION: ORF4
<220> FEATURE:
<221> NAME/KEY: CDS
<222> LOCATION: (64687)..(70365)
<223> OTHER INFORMATION: ORF5
<220> FEATURE:
<221> NAME/KEY: CDS
<222> LOCATION: (70365)..(71078)
<223> OTHER INFORMATION: ORF6
<220> FEATURE:
<221> NAME/KEY: CDS
<222> LOCATION: (71113)..(72360)
<223> OTHER INFORMATION: ORF7
<220> FEATURE:
<221> NAME/KEY: CDS
<222> LOCATION: (72400)..(73665)
<223> OTHER INFORMATION: ORF8
<220> FEATURE:
<221> NAME/KEY: CDS
<222> LOCATION: (73694)..(75043)
```

```
<223> OTHER INFORMATION: ORF9
<220> FEATURE:
<221> NAME/KEY: CDS
<222> LOCATION: Complement((75899)..(76570))
<223> OTHER INFORMATION: ORF10
<220> FEATURE:
<221> NAME/KEY: CDS
<222> LOCATION: Complement((76602)..(77765))
<223> OTHER INFORMATION: ORF11
<220> FEATURE:
<221> NAME/KEY: CDS
<222> LOCATION: (78039)..(79313)
<223> OTHER INFORMATION: ORF12
<220> FEATURE:
<221> NAME/KEY: CDS
<222> LOCATION: Complement((79391)..(81052))
<223> OTHER INFORMATION: ORF13
<220> FEATURE:
<221> NAME/KEY: CDS
<222> LOCATION: (81541)..(82356)
<223> OTHER INFORMATION: ORF14
<220> FEATURE:
<221> NAME/KEY: CDS
<222> LOCATION: (82760)..(83362)
<223> OTHER INFORMATION: ORF15
<220> FEATURE:
<221> NAME/KEY: CDS
<222> LOCATION: Complement((83495)..(84142))
<223> OTHER INFORMATION: ORF16
<220> FEATURE:
<221> NAME/KEY: CDS
<222> LOCATION: (84329)..(84428)
<223> OTHER INFORMATION: ORF17 (fragment)

<400> SEQUENCE: 1
gatcttcgtc tcgccgggtc cgcgggtcgc catgccgccc ccgccccgc cgcccatctg      60 ccgggacaac gactggcccc agccgcgcag ccgcggaagc atgtactgca tctgggccag     120
cgccacctga gccttgcctt cccgggactt ggcgtgctgc gcgaagatgt ccaggatcag     180
cgccgtacgg tccacgacct tgacgccac gacgtcctcc aggtggacca gctggctggg      240
gctgagttcc ccgtcgcaga ccacggtgtc ggcgccggtc tccgccacga tctcccgcag     300
ctcggcggcc ttgcccgatc cgatgtaggc cgccgggtcg ggcttctgcc gccgctggac     360
gactccgtcg cacaccatgg cgccggccgt ctccgcgagt gcggccaact cggcgaggga     420
gctctcggcc tcgtcggcag tgcccgacgt ccagacaccg acgagcacga cgtgctccag     480
gcggagcttc cggtactcca cctcggtgac gtcggagagt tcggtggaca gcccggcgac     540
ccggcgcagc gcggcccggt cgtcacggtc gtactgctcg ccgtccagaa cgtcgctgtc     600
cgccggcgtc aggcgttcgt ccatcagggc gtgggcacgc tgctgctggg cggtggggcc     660
ttcggtatga gtcatgtgga tcctttcgca ggagggagcc gtgggcgggg cgtcggcagg     720
gtcctggggc gaccggagg aacgagcaca gccggaggcg cgggaagccg ccgaagagac      780
ggacacggcg caaggggag ggccaaaggc aacggacggc gccaaggccg gagggcatct      840
cgtcgacaaa ggacgggggc gtgcgaacga cacggccgtc gagccctgac cgacgacttc     900
atcccgccgg acagctcaac agaaggccgc tacgagcgtc gcgctcagcg ccgcgtcaca     960
aaggtcgatg ccgaatctca cacgctgtcc acgatagagg aatctccggc cgatcacacc    1020
cgactatcac gggacatggc gcgtcctgcg gtactcgcca cccgcccgcc gccgcacggc    1080 tgccggtcg ccttgagcgg ggcacgtagg tgggcctgc cggtcgtgac ggtcccgtgc       1140
cgggcgaccg cggtcaccgg acagccttca atacggcccg gtgaaccccg acatgacgtt    1200
gcgcattctc ggtacggagc gctgaccgct gtgcagcgtt tcgaggcaag cgtgcgccac    1260
agcttctgca ttcggattga acgcctcctc caacggccat gacacggggg cggggcagtc    1320
```

```
gggcggggtt actctgcgga ccggtgcccg gagtgagtcg tagacgttct cggccactac    1380
ggcggcgact tccgcggcga atccgtaacg ggcccagctg gtgtcggcca cgacaaggcg    1440
tcccgtcttc gccactgatg tgcagatgag ggcgtcgtcc aagggacgga tacttcgtac    1500
gtcgatcacc tcgacgccga tgtcctgttc ccgcagggcg tcggccgcgc gttccgcctc    1560
gtggaccatg agggatgcgg caacaacggt gatgtcaccc cctgtgcgcg cgattcttcc    1620
ggctccgaac gggaccgcaa caggttgctc gggtacttct ccttcgattc cgtacaggcc    1680
gcggttctcc agcaggacga ccggcgtttc ggcctgcagg gcgctgacga ggaggccctt    1740
cgcgtcggcg ggcgaggcgg gggtggcgac gtagagcccg gggaagtgtc cgaacagtga    1800
ctgaaggctc tgtgagtggg tggcgccctg tccccagccg cggccgacca ggccgcgcat    1860
gacgatcggc gcactgccct ggttgccgta catgtagcgc cacttggcgg ccaggttgaa    1920
gatggcatcc atggccagga acatgaagtc gtcccgggtg tggacgacta tgggccgtat    1980
gcccatcgaa gcggcgccga cggctatgcc cgcgaaggcg ttctcccgt tggggatgtc     2040
catcacgcga gagggaccga attttttggaa ggcgtctgtg gtggtcccgt atatgccctt   2100
gtggtcgtcg acgccttgcc ctgcgagaat gatgtcgggg tcggctgcca tgcactgcac   2160
cgtggcttca cttatcgcct ggcaatacgt gatcttcggc atgtcgctgt cttctccact   2220
cagctctcgt atgtgcccgt gagcaggtcc gccacggcgg ggaacggact cgacctggcc   2280
gcagccacgg cttcgtgcaa ctcggcgcgg aattcggtct cccagcccgc gagttctgcc   2340
gtgatgtccg aatccgcaac gctgagggtt tccgtcgcac ggcggatcgg gcagcgtgcg   2400
acccaggatt cgacctcggc cttcgaacgg ccgctgatgt cgtagtccca gtggggaccg   2460
acgtgctcgc gccagcgata ggtgtcgagt tccaggaaat acggcccctt cccctggcgg   2520
cactgccgta cggctttccg cgctgcctcg aagacggcaa acacatcgtt tccatcgact   2580
cgttgcgtgg acatcccgta gccctgcgcg cgcccgctga tgctggttcc cacgggctga   2640
cgagcgtcaa tcggggagga gagggagtac tggttgttct cgcacacgaa gacgacgggg   2700
agacggtgca gcgcggcgaa gttcagcgac tcgtgaaaga ccccctcttc ggaggcgccg   2760
tcgccgaaga aagtggccgc gacccgaggt tcaccgcgca gggcgaagga ccaggccgcc   2820
ccgacggcga ccgagatcat ttctccgagg atggcagacg aggcaccgaa tccggcggcc   2880
ttgtcggtga ggtgcacgga tcctccgcgg cctgctgcgc agccgctctg cttgccgtac   2940
agttccgcga ccatggcggt gagatcacct cccttggcga ggtactgagc gtggcacctg   3000
tgcccgccgt agaccacgtc cttacggagc atggccgcac acacaccgac tgccgttgcc   3060
tcctggccga tggagaagtg gacgggcgtc cgcatttcct gttcgtcgcg gtagagatcg   3120
ccgagttcct cctccacaca ccgaatgcgc accatgtcgc gcagcagccg ccgttgtgtc   3180
atttttcctc cgagcagcga gaagagatgc agcatcacca aggcacgggg gcaggcctat   3240
cgaagaaagc cgcgctggtc cgcccacccg tcggcggtat cgacttcgag ctggttcagc   3300
cgtgcggtga cgacctggtc gaacccgtcc atgaagtact cgtcgccctc ggccggagga   3360
atctgcccac cgctggtcac aaagcgctcc accacctggg tcagcgttgt tccgggggag   3420
accttgccga tgctgtagcg gtccgctccg ggcagtcccg gaaaccggc ctcgcggtag    3480
aggtagacgt cgcccagcag atcgacctgg actgccacct gcggatgcgc ggtcggccgc   3540
atggtttccg gccgaatgcg cacgagttcg gcgtcggctc cggccgagag gctgttcagc   3600
gcgtacccgt agtcgacgtg cagggtgggt gtcctggccg cgaccttctc ccgaaagccg   3660
```

-continued

```
gtcagcgctt cctggaggtc cgcgcgctcg gcaccggaca ggaggccgtc gggccggccg    3720
ctgtagtcct cacggagggt gacgaagtcc agtggtcggt ccggcgccgc tgcgttcaac    3780
tcggcgatga agtcgacgag gtcgagcagg cgccggcccc gacccggcag gacgatgtag    3840
ttcaggccga gtttcaccgg ttcggcgcgt gcggaacgca gccgctggaa gcgctccagg    3900
ttggccttca cccgtccgaa agcggctttc tttcctgtgg ttgccgcgta ttccgcatcg    3960
ttcaacccgt acagcgaggt ccgcaccgcg tgcaggcgcc acaggccgcc ctgcctttcc    4020
agcgtccggt cggtaagcgc gaaggcgttg gtgtacaagg tgaggcggaa tccgcggccg    4080
gcggccctcc gaacgaggga gcccagcccg ggattggtga gcggctccag accgcccgac    4140
acgtacatgg cgtcggggtt gtccgttggc atgtcgtcga tgagcgcggc gaacatcttg    4200
ttgccgtcgt ccaggcggga gtgatcgtag cgggcgccgg tgacccgtac gcagaagtgg    4260
caacggaaca tgcaggtcgg ccccggatac agcccgaccg aatacgggaa caccggcttg    4320
tggtgcaaag cggcgtcgaa aacgcccttg cgttccagcg ggagcagggt gttcgtccag    4380
tacttgccgg aggggccgtt ctcaacggcc gagcgcaact gcgggacaac gccgaaaacg    4440
tccagcagac ggcggaaggc agatcggtcg actcctagtt gatgacgggc cttttccagc    4500
ggagtgaagg ggccggcgcc gtagatccgg gccagccgta ccaaatggcc ggcggcctcg    4560
cgcgcatccg cgtccgtcat atggccggca gtgaccagtt cgtgccggag agcctcggaa    4620
gcggccgccg gatcactgcc gggaagggtg cagaccgcta cggtgttcgc caccgcttct    4680
tgcctcacca tgagtcatcc caccctcttc cattcggaaa tgtcttgcat gagaagggcc    4740
gtcggctggt cactggagtg cgcctgacgc cagcgggcgg tcagctcggc cccgcgggtg    4800
gcggccagcc ggacgatgtc gcataccggg cggatatcct catgggagac cgtggacccg    4860
gtcggcaggg cgatgacccg cgccgagagg cgctcggtgt gcgggaggtg cgcgttccga    4920
cgggaccggt acggctccag ttggtggcag gccggcgaga agtagggctg gccaccacg     4980 ttttcggcgc gaagcaggcg gagcagcaga tcgcgatgga gcccggtgac ctcctcgtcg    5040
atctgcacga ccagatactg gtagttgttc cgttcgttct catcgaatgc gaagacggcc    5100
acacccggta ctccggagag ttccgtgcgg tagtgctcat agttgctttt gttgtgccgt    5160
acgacttcct caaacacgtc gagggacgtc agcccatgg ccgccgaggc ttcgctcatc     5220
ttcgcattgg tcccccggc ggaactgact tcttccaggc cgagtccgaa gttgtgaaga     5280
gagcggacac gatgggccag ctcgtcgtca tcggtgacga ccgcaccgcc ctcgaaggaa    5340
ttgacgacct tcgtcgcgtg aaagctgaat acctcggcgt cgccgaaccg gccgacaggt    5400
cttcctgccg aggtgctgcc gaatgcgtgc gccgcgtcga agaacagccg gatgccggct    5460
tccgcggcca gctcctccag gccgtcgaca tcacacggcc tacccacag atgcaccccg     5520 aaaatcgcgg aggtgcgcgg ggtgatggcg gcccgcaccc gctcgggatc cacacatccg    5580
gtgagtggat cgacgtcgca aagaccggc tccagtccga gccaccgcac tgcgtgcgcg     5640
gtcgccgcga acgtcagcgc cggcatgatc acttcaccgg tcaactcggc ggcgtgtacc    5700
agtagttgga gcgcgacggt cgcattgcag gtcgccacgc agttgcggac cccggccaga    5760
tcggcgaccc gcttctcgaa ctcctgggtc aggggtccgc cgttggtgag ccactggttg    5820
tccagcgccc aggtcagccg gtcgaacagc cgggaacggt cgatgggatt cgggcggccc    5880
accagaagcg gctgaaggaa gttggcgcgc ccccgaaca gcgcgagatc gccgagttcg      5940
cgtttcattt ccaccgtcca gaagagattc tcgcgctacc accggatcgt gcggtgcccg    6000
ttcgcgtcga aggtgtgcgt gtcactggtc aacgtcccct ggaagcgcta gcgaggacga    6060
```

```
acctcctcgt acgtgggcag cacgcccccg gccaccgccg cggcgagcgt gggggccgcc    6120
gcgtcgcgtg tggatcgcac cggcggtgcc gtcaggtccc agggcaggcc gagttcaggg    6180
tcgagggcgt cgacgtcgat gatggtgccg tgcacgtact cacgggtgca caggtagttc    6240
atgcaggtgt cgtcgctcag cgcgagatag gccaggccga tcccgtcggg caggtacacg    6300
gcggtgctgg accgcgggtc ctgtccgagc acgtcgtacc tgccgaaggt gggtgatccc    6360
acccgtaggt cgacgaccat ggtctgcacc gcgcccgga cacaggtgac gatctttccc     6420
tgaccgggcg gcacggtggt gctgtggata ccgcgcagca cattccgccc ggagacggtg    6480
tagttgacct gccggatctc tatcgcatgc ccggtggccg cccgcagcga ctcataccgc    6540
agcgcctcat agaacagacc tcgatggtcc ggaatgggtt cgggttcgat gcggtacgcg    6600
tcgcgtaccg ccatttcgtg tatgcgcatg gtgtccccgc cggttctgcc gctcagggca    6660
gcagtccctc gacggccgtg gcggctgcca cggcgccgcc ggcggcacgg atctgggcgc    6720
gcatgcccgc cacctgttcc ttgatgccct cgtcggccag cacccgccgt gccgtctcgc    6780
gcaggctctc ggtcgtcacc tcggacgtca ggagctgtgc gcccagcccg agttcggcga    6840
tccggcgcgc ggtggcgcgg ggctcgggca tcaccggcac cgccacgacc gggacgccgt    6900
gcgagaacgt gtccatggcc gtgctcatcc cgccatggtt caccaccagg tcggcgtgcg    6960
gcagcaggtc gccgtgcggc acaaagtcgt gcacctcgac gttgtcgggc agcgggccca    7020
actcgtccgg cctcaccccg ccgccgagca ccagcacgat gtgccacggc tcgtcgcgaa    7080
acgcctcgat acaggtgcgg aagaactccg gccgttcgtt gtagagggtg cccaggctca    7140
ccatgaccag cggccggtcg ccctccggcg gctgccaggt gccgtggaag gccacccggg    7200
gggagcacgg gccgacgaag tggtgccggt cgtcgaagga gtcgccggca tactggaagg    7260
accggggtat gtagagcagg gcggggccgc cgtggatcac cttggtgaac gcggcgagat    7320
cgttctcggc ccctgctcc ttgagcaacc gaccatccg ggcagcagaa tcgtgcagcg      7380
cggggtcgtc cggcggctcg gccgcgtcga ccggcggatg cagcgaccag tgctcgttgg    7440
cggcgtaggt gggggtgctg cggatgacgg ggatgcccca ccggtcagcg agcagccggc    7500
cggtccacag cgaggacggg tcgttcacga tcacatcggg gcggtccgcg gcgaagtgcg    7560
gctccagcag cgggagcgtg gacgtggtca tgtccagcag ccactccagc acacggatga    7620
actcgccctc gtcggtgtat tcctcggagt cctgccgcgg caccatctgc gcaaggaacc    7680
gttccttgtc catggggtag gtgacgactc cggcgccgac ccgtcgggcc cggtccgcga    7740
tctcctcagg cagcgcatag gtcacgcggt ggccgcgtgc caccagttcc tcggcgaccc    7800
ccagcgtggg attcagatgc ccggcgaccg ggaggatgaa gaacgcgata tgggccatgg    7860
tgaaatcctt cgtgaggtcg gggcaagtgc cgtcgtgacg tggggcgaac ggcgagaaac    7920 tccgaaggt tcgagacgcc cgcacattag gagtggccgg aggaatgagg caagtccgag     7980
atgacaaagt gcttgacgtg cactagatga caaagtcccc ggcaattcat ggattgtgtt    8040
catttcttga gagagaatgt cgaattgttg ccgtgaatgg cgcctcattg aggccggccg    8100
aaggcatccc agagttccgt cgttgtcccc gggaaacatg gaggttcggt gtccgacaac    8160
aacgcggagg gcccgctcgt cgtgatggga gccggcgtca tgggcacagc cattgctgcg    8220
ctcgccgtcg gccacggata ccgggtcacc ctgatcgacc gttccccga ggcccgcgcg     8280 gccgcccccg acaaggtcga actccaggtg cgcacggccc ggatgatgag cgcgctgccc    8340
tccggccggc ccatgggcga actggccacg gctgacacga cggacgccgc ggcggatgcg    8400
```

-continued

```
tgcgccgtga tcgaggcggt caccgaggac cccggggaga aggccgcggt gctggccggc    8460
ctcgcggccg cggtgagccc cggaacgctg ctgatcagca cacgtcgggg ctgcccatc    8520 gacgaactgg ccggcgccgt gccgcgcccg gaggacctcg tcggtgtgca cttcatgaat    8580
ccggcctacc tcatcgccac ggtggaggtg gtcctcgggc cgcgcagtgg ggacgcggcg    8640
gcggccgcgg cgcagaagct gctggcgggg ctggggcgcg agggcatcat cgtcggcgac    8700
ggcccgggct ttgtgaccag ccgcctcctg caccgaatga tcaacgacgc gatcgagttg    8760
gtccacgagg ggcgtgccgc cccggagacc gtggaccggc tcatgcgcga ctgcatcggc    8820
caccgcaccg ggccgttggc caccgcggac ctcatcggcc tggacaacct cgccgactcg    8880
ctcctggtga tgcacgcgcg gacgggctcc gaggcattcc gccccagcga attgctgctt    8940
gagaaggtcc gccggggaga gctcggccgc aagagcggcc ggggattcta cgactacgag    9000
gagagcacgc gatgatcgag acctccgacc cgacggggga cgcagccgtg gtgccggccg    9060
accatgacgt cgccgccgaa ctgctggagt tcctgacggc caaaaccagg acgaactggg    9120
aggcggacca ggacatcttc gccgtcggcg gcatgtcgtc gttgttcgcc atgcagctcg    9180
tcgtccacct ggagaagact tacgccatca ccatcagcgg cgccgacctg atgctcgaca    9240
acttccgcac ggtcgatgcg atggtccgcc tggtacgcag gctgggcccg agcgccgtcg    9300
gcaccggcgg cacgggtgac gacaacagtg agtgaggcga cggccaccag ggcggccgag    9360
ccgggcgccg aggaacgact cttcaccgat ctggtcggcg actcggccgc cgagtgggag    9420
cgcaccggcg agataccgcc ggagctgctg cgtgacctcg gtgccaaggg cctgctctgc    9480
gcgcaggttc ccctggccca tggcgggctc ggtttcacca gccggcgcaa cggcgaactg    9540
accgcgcatg tgggctcgtt gagcagctcc ctgcggagcg tgctgacctc gcagggcatg    9600
gccgcctgga cgctgcgccg gctggccggc gcggggcagc aggccacggt cgtcccccgg    9660
ctgacccgtg gggagctggc cgccgtgccc ttcagcgagg cggaggccgg cagcgatctg    9720
tccgctctgc acacgcgcat caccccggga cggcgatcaga tcgtcgtcga tggggccaag    9780
gtgtggtcga ccaacgcagc ctacgcggac ctgctgatcg tcttcgcccg cacagaggac    9840
ggcgcgggcg ccgtcgtggt gccggcaacg gctcccgggg tacgcatcga gcggatcacc    9900
gatccgtacg gctgccgcgc ggccggccac gccaacatcc ggctggacgg cgtacggctg    9960
ccggccgacg ctctgctcga cggtgtggac cgcacaccgt ccctgctcgt gaccaccgca    10020
ctcagctacg gcggatgtc cgtggcctgg ggctgtgtgg gcattctgcg cgcctgtctg    10080
gccgcggccg tccggcatgc cggcggcagg gagcagttcg gctcccggct ctccgatcac    10140
cagctcgtgg cccggcacct cgccgaactg ctgatcgccg agcagaccgc cagccgggcg    10200
tgcgagcacg ccagcgacct gtgggacgag gcagccccg acgtggtgac cgccacggtc    10260
atggccaagc acgtagcggc cacgggcgcg gcgcgcggtt cggcgcgggc gcttcaggtg    10320
ctggcctcgc aggctcccg cgaagggcat gtggtggctc gggcccaccg cgacgccaag    10380
ctcatggaaa tcatcgaggg cagcagcgag atctgcgagc tcatcctggc gcagcatgcc    10440
ctggcgaccg cgggatgacg ccggccccgc ggggtcgcgg ccccgggaag gaaggaacga    10500
cagtggaccc ggagaacgca atggcggacg gcgttgccac gaccacggtc aagtgcctgg    10560
tctgggacct ggacaacacc ctgtggcagg gcacgctgct ggaagacggt gaggtgcggc    10620
tcaggccggg cctgcgcgag acgatcgccg agctggactc gcgcggcatc ctcaactccg    10680
tggccagcaa gaacgaccac gaccacgcgt gggcgcagtt ggagcgcctc ggtctcgccg    10740
agtacttcgt gctccccgg atcggatggc ggccgaagtc ggagtcggtc cgcgggatcg    10800
```

-continued

```
ccgacgagct caacttcgcg ccgagcacca tggccttcat cgacgaccag ccgttcgagc   10860
gcgccgaggt ccgccatgtg ctgcccgagg tccgcaccta caccgcggag caggccgtcg   10920
acctcgtcac ccggccggag ttcagcccgg ccacgatcac ggtcgactcg cgccgccgcc   10980
gctcgatgta ccaggcgtcg ttccagcgcg acgcagaacg cgccgaattc gccgggcccg   11040
acgcggactt cctgcgctcg ctggacatcc ggatgcgggt cgcccgcgcc accccggag   11100 aactctcccg ggtggaggaa ctcaccctgc gcaccagcca gatgaacgcg accggggtgc   11160
actactccga ggccgatctg ctcgccctga tcgacgaccc ggatcacgag gtgctggtca   11220
ccacggtcac cgaccgcttc ggcccgtacg gcgcggtcgg cgtcatcctg ctccagcggt   11280
cctccggcat ctggcggatc aagctgctcg ccacgtcctg ccgggtggtg tccctcggcg   11340
cgggctccgc gctgctgcgc tggctgaccg accaggccca ccgggccggg gtgcatctgg   11400
ccgccgactt ccgggccacc gagcgcaatc ggatgatgga ggtcgcctac cgcttcgccg   11460
ggttctccga cgagccctgt gcctgccaga ccgcgctgga ccggacggag ggcgtcagcc   11520
ggctgcatct ggtgccgtcc gttcagcccg cctccgacac cctccgcctt gaggcccccg   11580
aactggcccc ggtccggggc tgaccccgtc cgaggccggc cccggtctcg gacggcgaag   11640
tgccccggtc tgcgaggccg aagcgtccgg ccgcgaaccg ccccgatcgg ccgtcgtcgt   11700
tcacctctgt acctcccgag aggactacat gatcaccact gcgtgccgca tctgtgacaa   11760
ccgtgagctg cttcccgtgc tggacctggg ggaccaggcg ctcaccgggg tgttcccggc   11820
gagccgtgac gaggccgtcc cctcggtgcc gctcgaactc gtgaaatgct ccccggccgg   11880
gtgcggtctg gtgcagctcc gtcacacccc ggaccccgcg ctgatgtacg gggacggcta   11940
cggctaccgc tccggcatcc ggccgttcat ggtcaaccac ctccagagca aggtcgcggc   12000
catccgcgaa ctggtcggcc tcggccccca ggacctggtc ctcgacatcg gcagcaacga   12060
ctccacgctg ctgcgcggct accccgcgga cggcccgcgc agggtcggga tcgatccgac   12120
cggccagaag ttccgcgagc tgtacccggc ggacgtggag ctggtcgtcg actacttctc   12180
gcgcgaggcg ttcacgaacc gcttcggttc cagcgcgcg aaggtggtca cctccatcgc   12240
gatgttctac gacctgccgg acccgatgcg cttcatgcgg gacgtccacg atgtcctcac   12300
cgatgacggc atctgggtca tggagcagag ctacctgccc gccatgctgg aagccgacgc   12360
ctatgacgtc gtctgtcacg agcacctgga gtactacgcg ctccggcaga tcgagtggat   12420
ggccgagcgg gtcgggctga ccgtgatcaa ggctgaactc accgatgtct acggcggcag   12480
cctctgtgtg accctcgcca agagcgcgag ccggtacccg aaggacgagg cgggcctggc   12540
ccgcatccgc gcccgtgaga ccgaggccga actcgacacg atggcccgt tcgaggcgtt   12600 cgcgcgccgt gtccaggacc agcgcgacgc cctgatcgac ttcctcgacc gctcccgcga   12660
ggcggggctg ctcaccgtgg gatacggcgc ctccaccaag gcaacgtga tcctccagta   12720 ctgcggtctc accgagcggg acctgccctg catcggcgag gtcagcgagg agaaagcggg   12780
ccgcttcacc cccggatcgg cgatcccgat cgtgtccgag gaggaggcca agctcctcaa   12840
gcccgaccaa ctgctggtgc tgccgtggat ctatcgcgac ggcttccttg agcgggagcg   12900
ggcctaccgg gaggcggcg gcaaactcgt cttcccgctg ccgagctga gcgtcgtgtg   12960 acaaggcgcg ccggccggcc cgatgccggc cggcgccccg ccggtcccgg tggctcagg   13020 cttccggggc ccggccgccg gcgggggaga agagggcgtc gagttcggtg agttcggcgt   13080
caccgaggac caggccgagg gcgcgaaccg ccgagtcaag ctgctccgtg gtccgcggac   13140
```

```
cgatcaccgc gccactgatc cccggccggg acaacaccca ggccaggccg acgtcggccg    13200
ggtgctcgcc gatgcggtcg cagaaccgct cgtacgcctc gatggtgggc cgcagctccg    13260
gcagcagcgt ctgcgcccgg ccctgcgccg acttcaccgc cgtaccggcc gccagcttgc    13320
gcagtgcccc gctcagcaga ccgccgtgca gcggcgacca ggcgaagacc cccagaccgt    13380
aggcgcgggc agccggcagc acttcccgtt cgacgtgccg gtcggccagg ttgtagaggc    13440
actgctcgga caccaggccg agggagcgcc gggccgccgc gttctcctgg gcggccgcga    13500
tgttccagcc cgcgaagttc gacgacccga cgtatcggac cttgccgtcg gccaccagcc    13560
ggtccatcgc ctgccagatt tcctcccagg aagcggcctc gtccatgcgg tgcatctgat    13620
agaggtcgat gtgctccacg ttcaggcggc gcagtgactg ctcgcaggcg gagatgatgt    13680
gccgcgccga caggccgtgg tcgttgatcc ggtcgctcat ctcctcgccg accttggtcg    13740
cgagcaccac gtcgtcacgt cgaccgcggc gctggcccag ccaccgcccg acgagctcct    13800
cggtgtgccc cttgtagagg cgccagccgt agatgtccgc ggtgtcgatg cagttgatgc    13860
cccggtcgag cgcctggtcc ataagccgca cggcgtcggc gtcctcgacg cgcccgctga    13920
agttcacggt gcccagccag agccggctca ccagcgtcgc gctgcggccg agccgggtgt    13980
gcgtgtgccc ttgcggggc tggtaccggt gtgtgtgccc tgcttgtgtg cggtcctcgc    14040
tcatccgcgt tccacccttc ggactcgacc cgttcaagaa ctcaccgccg ggtgcgcagc    14100
cggcggtgcg gggtgcacgg cggcgatcgc cgcgaccatg tcccgcagcc cctcggggaa    14160
ccgcacccgg ggagcccagc cggtcacagc ccggaaggcg gcggagtcgg actccgggct    14220
gtggaaatca cccgcttcgg cgtaagcggg gggtggcacg gcgacgaccg gagccggagt    14280
cccgccggtg tgctcggcca cgagaccagc cagggcggtg aacacgtcac cgagccgctc    14340
caggcggccg gttgcgacga tccagggctc gccctgtagc tccgccgcat gctccagggc    14400
agccgtgaag gcgcccgcag cgtcccggac gtggaggaag tcgcgcccga ccgatccgtc    14460
atgccacatg gtcagggctt cgccgtcgag ggcgcggcgg gtcatcgacg cgagcacgcc    14520
gcgcccggcg ccgccggaga gcgggctgtg ccgtacagg gtcgacagcc gcagcacgac    14580
gccgcggacg acgccctcgg ccgtggcctc gcgcaggatc ccctcggcgg cgatcttctg    14640
cgatgcgtag ccgcccaggg gggcggcgtt gcccgtgggg gacccggcct ggagcgtgct    14700
ggcgaaggcc acggccggcc gggcgccgct ccggccgcgc agcgcatcga caaggtcgcg    14760
catcatgccg acgttcaccc gctccgcgtg ctcgtcggcg gcgcgccagg actgctgtcc    14820
gccgatcccc gccgcgagat gaacgacggc gtccgcgccc tcggcggcgg ccgcgacggc    14880
gtccggccgg gcgaggtccg tccggcgcac ctcgatgtcc gccaccggtt cggccggcac    14940
acggctggga ccgcgcgcca ccaggcgcaa gcgcagcggc agtgcggcga gttcggccac    15000
cacggcggac ccgaggaatc ccgacgcgcc gagcaccgtg accaatggcc cgcgcggatg    15060
gtgcgaccgc ttgaacaact cggtagtgag cctcacacat tctcccctct gtgtgccgct    15120
cagcgtgccg agccctccag ggcgcgtcta cggaaacctg accttgtctg cggggtccg    15180
tccgggccgc ttgagcatcg tggcaggtgg tggtgtggca acacttccag ggcgtggatg    15240
gtggtccggc caccatccac gcgcttttgc tcaccggctc tccggtcggt aaagcagtcg    15300
ccgatccatc gactccgtcg gaatcggcg aaaaggatga acattatgg cgggtaggta    15360
ttgaggaagt gtgcgcggag gggttgtggt ggccctcaca gggctccgaa gatctgtgga    15420
cgggtgtagc gggaatgtaa tagcgttcca ttgatttggt aaaggcacgg agatggggga    15480
gcctgcggca tgagcgacct ggattctggt ggagaactgg ctgaaaaaga ccaggagggt    15540
```

```
gacgcaatca ccttccttga attcgttgcc cggtcggctc cgcgcggtga atacgaccgg   15600
ctcatggcgc gggcggaaag cgaaggcgca agcgaggaac ggatgcgccg tttggagcgc   15660
ttcaaccggc tcgccctcac cgcacagtcg atgatcgagt accgccgcga ccgcgaggcg   15720
gagctcgcgg cgctggtcga ggctgcccac gaattcgtcc gtgcccggca ctacaaggac   15780
ctgctcgact cggtcgcccg cagggcacgg ctgctgctca agctggatgt cgcctacgtc   15840
agcctgcaca aggagggcga gcccgacacg gagctgcaga gcgccgacgg caacgcggtc   15900
tcggtcgccg tcgcctccg gctgcccgtc agcggcgggc tgggcggtat ggtgcgcgcc   15960
tgccgcgccc ccttctggac gcccgactac ctcgcggaca ccagcatcaa ccacgtcgag   16020
agcatcgaca atgtcgtccg ctcggagggg ctgcgcgcgg tcctgggcgt gccgttgtgc   16080
gtcagggacg agtccatggg ggtgggggtg ctctacgtcg ccgaccgcca ggtccggcat   16140
ctcgcgccca acgaaatcac cctgctgtgc tcgctcgccg atctggccgc cgccgccatc   16200
gagcgcatcg tgctggtcga agagctccgg aacgacatcg gcggctgcag cgcggacgtc   16260
ggtgaggccc gcgcggcccct cacggtcgcc cgaaggtccg ccgacctcca gtcgcgcctg   16320
atcgccctga tcctggagcg gtgcgaggtc gacgctctac tggccgtcgc cgcagaggcg   16380
ttgggcggcg gtaccggcat ctgcaacccg ctgggccgac cgctcgccga gtacgggaaa   16440 ctgcgccca taccccccgc ggacctgcgc gcagcctgcg acagggctgc cgagactggc   16500
caccccaccc ccgccgacca gggggtatgg gtggcccgc tgtgccccgg ggagtgcaac   16560
tccggcttcc tcttaacgga gtgtcggtccc gcggcggacc actccgtcgt accgctgctc   16620
ctcgttgtcg cccgtgcgct ggcacttcat ctgcgcatcc agcacaacaa ctccgccaag   16680
accccgggcc accaggaatt cttcgacgac ctggtcgggg cgccgcgctc gccggccctc   16740
ctcagggagc gcgccctcct gttctccctc agtttccgcc gcccgcacgt cgtcctggtg   16800
gcgagcgcac cgcacggcgc cgcggcgcgg ttggagacct ccgccgcaga ctacgcgcag   16860
gaactcggcg ggttgtgcag cgtaccggat ggcgcggtcg tgctgctgct gcccggcgag   16920
gcccccgagg ccgtggcgca gaccgccgcc caggaactca ccacccgggt ggggcgctcg   16980
atcaccgtgg gggccgccgg ccccgcctcg accgtcgacg gcatcggcga cgcctatcgc   17040
gaggccgcgc agtgcctgga gacactcgcg gcgctcggcg ctgacggcgg caccgcctgc   17100
gcttctgacc tcggcttcct cggcatgctc ctggccgagg aaaacgatgt ccccggttac   17160
atcacgtcga ccatcgggcc cgtggtcgac tacgacaccc accgcttcac ggatctcatc   17220
gccacgctga gggcgtatct ggagtcgggc aggagcccca cccgcgccgc ggagacactg   17280
cgggtgcacc ccaacaccgt ctcgcgccga ctggaacgca tcggtcagtt gttgggggag   17340
gactggcagt gcccacagcg ggtgctggac atccaactgg ccctgcggct gcaccaggtg   17400
cgctcggtcc tctccccacg ccttgcctcc gcctccgggg ccgcactttg tccactgccc   17460
gagtgaccgt cggccgaccg gccggcgcgt ggcctgccgg tggccgcgcc atcgttcgtg   17520 gtcaccggc gatgggcacc tggtagtcgc accactgccc atcctgcgac agccgcagtg   17580
cgtgggcgat cgaagccagc gtcacatgcc ggtgccagcc ctggaacgag cgtccctcga   17640
agtcccggat gccgacatcg acactgaccg cggcgaagtc ggagtccacc cgttcggtca   17700
gcctcgccag ccgcagcagc gcactgtgcc ccgacgaggg gaggtcggtc agccacaggt   17760
ctgcggggcg ccggcggttg gctcgccaca cccccatcag cagcagcgtt cgccgcggga   17820
gcgcgccggg caggaccacg gcgagcggcg tgacgaagtt gaccgtgcca tggcactcca   17880
```

```
cggggcggcc cagccgcttg agttgctcca tgaggtgctg tgcgggcgag gtctgcgggc    17940
gctggcccag ctggacccgg ccggcagccg ggtccagcgg aaggtcgccg cccacccgca    18000
gcatgaaggg taggccggcc gtggtgagcg cgcgcaccag cggtggcacc gcggcggtcc    18060
gcgcgtccat caccaccggg cgtgccaccg tccggttcgc ctgtgcgatc ttcgtcacca    18120
gccgcgccac gtccctctcc tcacccggcg cttcgagccg tccgtcggcc tcgccgcccg    18180
gatcgccgtc cagcgtcaga tgccagctca ccggtgcagc cctcgtgtcg gaggccatcc    18240
acagtccgaa gctgcgctga cagctcatca cccggccgag gtcgggaacg aaccgccgtt    18300
gtaccccac ggagcgcacc cccgtcttgg agaccaccat cggccggatc acccaggcgt    18360
ccgggcgcag cccgtcgtcc acgtagcggg ccagggtcgc gcgcaccggg cgccagtccc    18420
aggtcgagct ggccacgaag tggtgcaggc tctgtgctga ggcccccgcc ccgccgaagt    18480
tggcgatgtt acgggcggtc ttgcgcccag tggcggtgag caagccgcgt aagtactggc    18540
caccccttct gcgctggtcg gcgcggcgca gcgaaccgag cagttcttcg cacgcttcgt    18600
acaccagtga ttcgacaccg tcgtgcgcgg cggaaccggg caaggagtgg ggggaatgcg    18660
gtttcgggcc aagggggga acgagcatcg cggtcctcgc agggcgttcg aattccggca    18720
actgcatgtg gcacagcctt ccggaatact cggggccctc ccagatgcgc tcggcacaca    18780
ctttcgcggc cgcctcggcc cccgcggtga gcaacggacg ggcggccggc agcgcacccg    18840
tacctgatgg ccaactcacc tgtacggacc gctggttggt gtcgggacac ctcatcgaat    18900
ggcgctacgg aacgacgccg ctacgtccgg tgattgcgaa atccattctt cctgacgttt    18960
tccggacgct gacaccactg tgtcagctgc cacttgccgg ctcagcggcc atgccctaga    19020
aatcccctct catccacgcc catttacctg cgaggtactg ctatgcccct gccgaaacac    19080
ctgccgtcgc tcggcggcat gcgggccatc gccgcactgg tggtgttctg ctctcatatc    19140
gcttcccagc cgttttttccg caacgccaag ataaactcca ccgcacaggt cccgctggac    19200
gtcctgggc cgctggcggt ctcgttcttc ttcatgctca gcggattcgt cctcacctgg    19260
gcgggcatgc ccgacccgtc caagcctgcc ttctggcgcc gccgttgggt tcgggtctac    19320
tcgctgcacc tgccggtcct gctgctcacg ctggcgatcg tgctgtggct gaaggaaccc    19380
aatatgggcg gtcggtgtg ggacggcttc ctcagcaacc tgctgctcgt ccagtcgtgg    19440
tgccccgact accaccagta cggcagcatg aacccggtgg cgtggtccct ctcctgcgag    19500
atgctgttct acgccgcctt cccgttcctg ttcgccttct tctccaagat gcgtgccgag    19560
cggctgtggt cctgggtcct gggcatctcc gtcgtcgccg cggccgtgcc cgccctcgcc    19620
ctgctgctcc cctcggcccc cacgctgccc tgggacccga acatgccgga gctccaatac    19680
tggttcatct acatgcttcc gccggtgcgg ctgctggaat tcgcgctcgg cgtcctgatg    19740
gcgcagatcg tcaggcgcgg ccgctggatc ggcccgaccc cggggggtgtg cgcgctgctg    19800
ttcgccggcg cgttcgcgct gtccttcgcc ctgccgtcct atctggctcg cgtagcgccg    19860
acggtcccgc tgatcgcgct gctgctcggc tccctggcag ctggcgacat acgcggtacc    19920
cggtcgtggc tgggcacccg gacgatggtg ctgctgggtg aactcacctt cgccttctac    19980
gtcatccact acctcgtcat ccagtacggg caccgcttcc tcggcggtga gctgagctac    20040
taccgacagt gggacacccc ggccgcgatc ggcctcaccg ttctcgccct cgggctcagc    20100
gtgggcctcg ccgcgctcct ccacttcttc gtggagaagc cggtcgtccg ggccctcggc    20160
cgctccggca aggcgtcccg cgcgtccaag gccccgcagc ccgagccgcc ggcgcccctg    20220
ctgtcctgag cgggtccggc ggcacaacag tgtgcggggt ggcgcccgca gggtgttcgc    20280
```

```
tgcccggtac cccgttcttc tgcgcctcag taggaggcgt gtgcgcaggc gatcagtgtg   20340
cgcagctcca cattgaggta gttgccgtgc gcgagcagtt cggtgagctg cccgagggtc   20400
gcccagcgga agccgggcgg gcagtccacc ggcagctcag ggccggcctc gacgaccgtg   20460
taccggttgc gcgcgtggta gaagcgccca ccctcctccg agagcaccgc gtcgtaccgt   20520
acgcggcccg gagcagcgga ctgcacgtac tccagatacg gcggcgggtt gcccttgccg   20580
cgcggccacg ccgacctgag ctgcacggtg gggccgaact cggcgaagtt cagcgtgccc   20640
acgtccgacc gggccgccac cagggcgtgc aacgccccgt tgatccgccg gacgaccagg   20700
gccatcagcc cctgggagca cgggcgcagc agcggctggg tccaggacgc cacctcgcgc   20760
tgctccgcgg tgacctcgac cgccatgatc tcgaagccct cgccgctgcg gtgccggatg   20820
gtggccccgg tccgttgcca gccgtcctcg tacacctggt tgagcgggac gctctgctgg   20880
cgcagcacac gcagcgcctg gacgtcggtg agacagccgg tgatcgcgtt gagctcgtgc   20940
agcggctcgg tctcccgta gaaggagcgc ctcagcgccg ccgggaagcc ttcgtcgtcg   21000
tcgccgggtg cgccgtgcgc agtcggcagg caggccagca cgctgcgggt gtccatattg   21060
acgaggtcgt cccggagcag caggcgacgg atctggccga gcgtcagcca gcggaacgag   21120
cagtgctccg ccacgcccga gtcgatctcg acgaccatgt tgcggttgcg tttgtgcagg   21180
aaccagtcgg cttgctccga ctgaatggca tcgaccagca cccggcgccc cggtcgctgg   21240
atgaagcggt ccaggaacgg cgtcgagcgg ccgcgatgca cctcgtcgaa gttgctgcgg   21300
gtggcctgca ccgtagggga gagctggagc ccgttgacgt tgccgggttc cggcttcgcc   21360
tgcatcagaa agtgcaacac cccgtcgaac tcgcgcgcca ggatgcccag cagccccact   21420
tcgggctgca cgatgatcgg ctggatgcgg tcgacggggt cgaggtcgga gctggtacgc   21480
agaccttcga cggagaagaa gcgacccgtc tcgtggcgca gattgccggt gccgtcttcg   21540
aaggaccacc gctgcaggtc gtggaaggga atcggctccg tgcggaagtg gtgggcccgc   21600
tggtactcga ccagccagcc ggtcacctcc gccatggggg tcacccggct gtcgagcacg   21660
tcggccgacc ggcgcacccg ctcggccgtc tgcaggcggg cggcgtagtc ggcctcggcg   21720
acggaccccg gttcaggccg catggctccc cctggcgccc gcgggagca gcggtgcgag   21780
ggtgtccatg agggcccgc acacctctgc gacctgctgg tagaggaaga agtgccgcc   21840
ggggaaggtc cgcacctggg cgccggcctc cgcgacggcc tgccatgccg ctgcctcggt   21900
cgccgtgacg ttggggtcgt cggcgccggt gaacacggtg agcgcggagg ccagcggcgc   21960
ccccgggcgg tgggtgtagg tccccacggc ccggtagtcg ttgcggatcg cgggcagcac   22020
caactgcagc agctcggggt cgttgagcag actctcgtcg gtgccttcga gcagcggag   22080
ctcagccagc agccggtcgt cgtcatagag gtgcacggtc atcggacggt tcacgatggg   22140
ggcccggcgg ccggagacca ccaatccggc cggcgccgcc cccgctgct ggagcacgcg   22200
ggcgacctcg taggccacgg tggcgccat gctgtgcccg aagagcacca ggggccggtc   22260
ggagtgcgtc gccagcacct cggccagggg ctcgaccagg cctcgatgg tcccgatcag   22320
cggctcgccg cggcggtcct ggcggccggg gtactggacg ccagcacct cgacctggtc   22380
gggcagcgtc tggacgaacg gcaggaagga cgtggccgag ccgccggcgt gcgggaagca   22440
gaccagccgc accgcaggtg cggcgcgcgg ccggtaccgg cgcagccaca ggtcgctcag   22500
gaggcgcgga tctgtcgatg cggacacgaa ggttcatcgt cctttcttga ggggcttcca   22560
ccacgcgcgg ttctcgcgat accagcgcac ggtctccgcc agtccctcgt cgataccgat   22620
```

```
ccgcggcgca tagcccagct cattggcgat cttggcgtag tcgacggagt agcggcggtc    22680
gtggcccttg cggtccggta cctcccgcac cgccgaccag tcggcttcgc acagcttcag    22740
caggcgttcg gtgagctcgg tgttggtcag ttcggtgccg ccgccgatgt tgtagacctc    22800
gccggggcgg ccgccccggg ccaccagggc gatgccccgg cagtggtcgt ccacgtgcag    22860
ccagtcgcgc cggttgccgc cgtcgccgta gagcgggacg gccgcccct caagcagatt    22920 gctgacgaac agcggaatga tcttctccgg gtactggtac gggccgtagt tgttggagca    22980
gcgggtgacg cacaccggca gcccgtgtgt ccggtggaag ccagcgcca gctggtcgga    23040 ggccgccttg gaggcggcgt aggggagtt ggggctcagc gggtggtcct cagaccacga    23100
cccttccgga atcgagccgt acacctcgtc cgtggagaca tgcacgaacc ggcccgggcg    23160
cacggccagc gcctcccgga ggaggacgtg ggtgcccagc acattggtgc gcacgaaggc    23220
gtccgcgtcg tcgatcgacc ggtccacatg cgactcggcc gcgaagtgca ccaccagatc    23280
ggcgcccgcc atggcaaggg cgacggtgct gcggtcgcag atgtcccccc ggacgaccct    23340
cagccgtgga cagtcgccca ccggcgccag attggccagg ttgcccgcgt aggtaagcgc    23400
gtccagcacc accacctcgg gcttgccgaa ctccggcagc gagccgttca gcagggcgtt    23460
cacaaagcgt gagccgatga agccggcccc tccggtgacc aggatccgca gcggtcgccg    23520
gctgatgccc cgggtgttgg tccacggttc cgtctcaggc agcgccggca tgggaagcca    23580
cctccatcag gtaggagccg tagcccgagt tgcccagctc gcagccgagc agatacagct    23640
cgtcggcgtt gatgaacccc atccgcaggg cgatctcctc gacgcaggcg atccgcaccc    23700
cctggcgctg ctccagcagt tggacgtact ggctggcctg gagcagcgag tcgtgggtac    23760
ccatgtccag ccaggcgaag ccgtgaccca gctcgatcaa ccgggcgcgt cgctgctcca    23820
gatagacctt gttgacgtcg gtgatctcca actcaccgcg tgcggacggc ctgatgttct    23880
tggcgatgtc gacgacgtcg ttgtcgtaga ggtacagccc ggtgacggcc aggttggagc    23940
ggggacgaac gggcttctcc tccagggaga gcagcagccc gtcccggtcg atctccccga    24000
cgccgtagcg ccctggatcg ctcaccggat agccgaacag cacacagccg tcaaggtggc    24060
ggatgctgcc ctggagcacg gaggagaacc cggggccgtg gaagatgttg tcgcccagga    24120
tcagcgccac cggggagttg ccgatgtggt ccgagccgat ggtgagggcc tgggcgatgc    24180
cctgggcctc gggctgctcc gcgtacgtga tgtcgaggcc gagccgggac ccgtcgccca    24240
gcagccgctg gaagagctcg atgtgctggg acgacgagat gaccaggatc tcgcggatgc    24300
cgcccagcat cagcacggac agcgggtagt agatcatcgg cttgttgtag accgggagca    24360
gctgcttgga cagcgtcccg gtcagggggc gcaggcgggt gccaccgcca ccggcgagga    24420
tgattccctt cattccggga caccccgata tggtctcggt catcgtatct ccgtcgatag    24480
aggaagacgg tggccgcccg gcgtcgcgcg ctccgtgtcg tccggcgccg gatacgccgg    24540
cagtcctacg gccgccgcgc ggaccgccgc tacgacggtc tggaacgcgt cgtccccgag    24600
gtggggcccg aggggaaggc tgaggctctc cgccgcacgg cgttcgctga gcgggtgggt    24660
gccgccggga gcgccggccg gatcgtcggc gtaggcgggg gtccggtggg gcggtacggg    24720
gtagtggatc agggtctcca ccccggcccg ttcgattcgg cggcgcagtt cgtcgcgttc    24780
cgcgcagcgg atcacataaa ggtgccacac cggatcggcc caggggcgg cggcggggac    24840 ggcaatctgc gggagggcac ccaagacctg gctgtagcgc tcggccgtgc gcactcggag    24900
ggcgttccag gccggcagcc gtggcagctt ggcgcgcagc acggcggcct ggaactcgtc    24960
gagccgcgag ttggtggcct gtacctcgtg ccggtacttc tcacgggagc cgcagttgcg    25020
```

```
cagcagccgg atccggtcgg ccagggcggc gtcgccggtg accaccgccc cgccgtctcc   25080
catggcgccg aggttcttgc cggggtagaa gctgaacgcg accacatggc ccgagccgat   25140
ccggcggccc cggtagcggg cgccgtgcgc ctgcgcggcg tcctccacca cggccaggcc   25200
gtgccgttcg gcgatcgcca gaagcgggtc cagatcggcc ggatgcccgt acagatgcac   25260
cggcatcacg gccctggtcc ggggagtgat cgccgcctcc acctgcgccg ggtccatgga   25320
cagcccgtcc ggcgtcgggt cgacacccac cggccgggcc ccggcggcgg acaccgccag   25380
ccaggtgccg atgaaggtgt gcgcgggcac caccacctcg tcaccggggc cgatgccgag   25440
cgcgcgcagc gccagctcca gggcgtcgca gccgctgccg accgccacgc agtggtcgtt   25500
gtcgcagtac gcggcgaatt ccgcctcgaa ccccgccagt ccgcacccca gcagatagcg   25560
tccggaggcg gacacccgcc gaagggcccc gtcgatgtcg gcccgcagct cccgataggc   25620
cgcacccgcg tcgaggaagg gcacgttcac ttgatgctcc atgcgtcgcg caggaatgtg   25680
tcgtagtcgc ggtagtagtc ggactcctcg tagtgccgcg aggcgaggac gagggcgacg   25740
gagtccggtg cgaagtcctt gagcactcgc cacaccatgg gcccgatgta gagcccggcc   25800
cccggttcgt cgagccggta cgtggtgctc tggaagccgt cgtccaggct gatcgagaat   25860
ccgccgtgca cggcgatgac gagctgctcc agagtgcggt gcccgtgcag ccccggggc   25920 ggtgacgact ccggctgccc gtgcatgtag tagacgcgct tgatgsggaa gcccacggtg   25980
atgccggact cgaccacgga gaggctgccg cgcgggtcga tgtgctgttc cagcctgatc   26040
agccgacacg gtttgatcct gccgactcgc acggcgtggg aggactcggc tgcgttctcg   26100
gccatggcgg cgctcctctc gggatgggcg cggctctgcg gctgatgcgg accgcggaac   26160
ccgtgggacg gcggcccggt cagcgccact cgacgtggac gggcaggtac ttcgcggtga   26220
gctgatcggc ctcgtagtag cgggtgttgc cgtggtcgat gcggaattcc ctgacctgat   26280
ccagcatcag ttccagtacc accttgcctt cctgacgtgc caggaaggcg cccaggcagt   26340
ggtgaatacc gatgccgaac gccatgtggc gggagctgct tgagcgtcgg atgtcgaagg   26400
tgtcgggctc cgggaagtgt tcggggtcgc ggttggccga ctggctccag gcgatgacca   26460
tctggccctt cttcatttcc gggccgagga tgtcggtgtc ctccttgagg aagcggaaga   26520
tgttgttgaa ggggctgcgg tagcgcagtg tctcctccac cgcaccggtc accagctcgc   26580
ggtcggcgcg caggtccgcc agcgcctgcg ggttctcctc cagtaccagg aagaggttgc   26640
tgagcagcgt gcttgacgag acgtggccgg cggtgagcag cagggccacg atgttgacga   26700
tctccacgtc ggtgagcttg cggccgtcct gctcggcctg gaccaggccg ctgatcaggt   26760
cgtcgaccgg ggcctcgcgc ttggcgtgga tctggtgcag gagatagtcg gtcatctcct   26820
tgagggcggg ggcgatcgtc tcgctgaagt tgtccgggag gttcgggtac tccaggccct   26880
cgttggtgag cagggtgtcg acccacccgc ggaacacatc gcggtcaccg gacggtatgc   26940
ccagcagctc ggcgatgacg atgacgggca gggcgtagga gaggtcgccg acgacgtcga   27000
tggtctcctg gccgcgcacc gcatcgagga gctcctgagt gacggcccgg atgcggggtt   27060
ccagacgggc catccgccgc ggggtgaacg cctggctgac cagcttgcgc atcgggccgt   27120
gggcgggcgg gtcgagggcg ccgatggtcc ccggcccgat gaccatctcc agctcggggcg   27180 gggtcggcat gacctcgttg aagtcggagg agaagaactg cggattgttg agaccgtca   27240 ggtagtcgtc gtaacggaag acctgccagg catgccgact ctcgtcccag aagacccgggt   27300 gatgggtccg gttgaaggcg aaccagtcca ggagttcctg ggcgttcgcc tccttgctga   27360
```

```
gttcgagtgg cactgtcgga gcctcggaca tcggccattc tccttgggaa gtggtacggc   27420
ggaccgagca cgcgacgcgg gcacttcggt ctctcgacgc cggtgagcct atgaatcgct   27480
caagatcgcc agcaagggag acctgacaca atgacctccc cgtccgcccc cgcggacggg   27540
aaaccgccgg ggctgccgca gcggcgccgg caacctgaca cattcaccgc tcgccggttg   27600
tcctcgccgt cccggtgctg aacacttcac tgttcacgtg cgagagggat gcacggagaa   27660 ataccagaa ttccgcgccg gagaacacga tgaaccggca gcggaaaccg gacccgctgg    27720
acatctccct tttcccttgt cgacgccgag gcatgggtcg gcggtgcacc ggccggagtc   27780
cgcgggtgat cggcgcgctg aagtagccgt cacgggccca cggggtgcgc ggccccattc   27840
ccgccggcgc tctcctccgc cagcgcgcac caggatgccc gcgcggggcc gaccggcctg   27900
cggtccgggc agaaccacag gaaggcggta caacccgtga agatccttgt catcggaggc   27960
tcgcagttcg tgggccgggc cttcgtcgcc gaggccctgg gccgcggcca tgaagtcacc   28020
accttcaaca gaggtgtcag cgctgccgac ctgccgggcg tcaaggcgat ccgcgggac    28080 cgacaggtgc ccgccgacct ggagcggctg gtcgaccagg gcggccgctg ggacgcggtc   28140
gtggacacct gcgcggctatgt gccgcaggtc gtcggcgccg ccgcccgcgc actctccggc   28200
catgccgaca cctacctcta cgtctccagc ctggcggccg tccgcgactg gggcacggcg   28260
ccctcgatca cgacgattc ccccacccac gactgttccc cggaggccgg gccggacgac    28320
ggcgactacg gcttcctcaa ggccggctgc gaacgcgccg tcgtccgcga tttcgccggc   28380
gacgccctcg tcttccgggc cggagtgatc gtcggcccgc acgacaacgt cggccagctg   28440
gattcctggc tgtggcggct gcgcacggcc gagggcgagc gtcggcgggt gctcgcgccc   28500
ggcgccccgg acgtcggcat gcgcatcatc gacgcgcggg acatcgccct cttcggcctg   28560
cgctgcctgg aggagcggcg caccggcccc ttcgtggtcg tggcgcccga gcggcacgcc   28620
acctatggcg agttgctggc cgcgtgcgcc gccgccaccg gctcgcgggc ggaactggtc   28680
tgggccgacg acgccttcct cctggagcgt gaggtggagc cctggagcga tctcgcgatg   28740 tgggtccccct ggccggacgc cctgcgcatg tggacgaccg ccgccgaccg ggccgaggcc   28800
gcgggcctga tctccgcccc gatcaccgag acagtgcgcg acgcctgggc ggtcctgagc   28860
gaccggacgc cgccccagct tcccctcgtc aactcctggg gcctccgggc cggcctcccg   28920
cccgagcggg agcgggagtt gctggccgcg tgggacgcgc accggcgggc cacgcgcgcg   28980
taatcgacgg ccgcacgcac acggcggcac cgtcggcacg gcagacctga cacaattcgg   29040 cttcctttc ccgggggata actgccggag gatttggctc cgtcgatgtc tgccgccctc    29100
cttcggcagc tgcccgggaa aaccgcgaac ttgacacaat gcttctcgat gctggccgtt   29160
cccttcgtgc agccattcag acgcagtacg atcctaaaga tcagaagagg caggaattct   29220
gtggcctggc gagagcttga ggaatgctgg tgtctggaga tctcgtgact tcccgaattg   29280
acgaccgatc cgatgcaatt gccgttgtcg gaatgtcctg tcgatttccc ggcgccccgg   29340
gagtcgaaga attctggaaa ctgctgaccg acggaacgga agccgtcagt cgcgcggccg   29400
atggccgtcg gcgcggcatg atcgaggcgg tcggcgactt cgacgccacg ttcttcggca   29460
tgtcaccgcg cgaggccgcc gagaccgatc cgcagcagcg cctgctgctc gaactcggct   29520
gggaggccct ggaggacgcc ggaatcgtcc cgggtcgct gcgcggcgag gcggtcggca    29580
tcttcgtcgg tgccatgcac aacgactacg ccaccctgct gcaccgggcc ggcgcaccgg   29640
ccggcgccca caccgccacc ggcctccagc ccgccatgct cgccaaccgg ctctcctacg   29700
tcctgggaac gcgcggccgc agcctggcgg ttgacaccgc gcagtcgtcg tcgctggtcg   29760
```

```
ccgtggccct cgcggtcgag agcctgcgcg ccggaacctc ccgcatcgcc atcgcaggcg    29820
gcgtcaacct gatcctcgcc gacgagggct cggccaccat ggagcggctc ggcgcgctct    29880
cccccgacgg gcgttgctac accttcgacg cccgcgccaa cggctatgtg cgtggcgagg    29940
gcggtgccgc cgtcgtactg aagcccctcg ccgacgcctt ggccgacggc gacccggtgt    30000
actgcgtggt gcgcagcgcc gccactggca acgacggcgg cggccccggg ctgacctccc    30060
ccgaccacga aggccaggaa gccgtgctcc gggcggcctg cgcccaggcc ggagtcgacc    30120
ccgcaaaggt gcgcttcgtc gaactgcacg gcaccggcac ccccgtgggc gacccggtcg    30180
aggcacgggc cctgggtgcg gtccacggct ccgggcggcc ggcggacgca cccctgctgg    30240
tgggctccgt gaagaccaac atcggccacc tggaaggcgc agccggcatc gcggggctgg    30300
tcaaggccgc actctgcctg cggaatcgca ccctgcccgg ctcgctcaac ttcgtcaccc    30360
cccaccccgc catccctctg gaccggctcc ggctgaaggt gcagacgacc ccgaccacgc    30420
tgcaccccga tccggacggc tccccctgc tggcgggtgt cagctccttc ggtatcggcg    30480
gcaccaactg ccatgtcgtc ctggagcacc tgcccgagcc ggcccccacc acaagggaag    30540
ccctacccgc cccgcacctg gtcccgcccc tgctgttgtc ggcccgttcc cacccggcac    30600
tgctggccca ggcggcgcgg ctccgtgacc acctgagccg caccgctgcc gacccgcagg    30660
acgtcgctta ctccctggcc accacacgct ccctcttcga gcaccgcgcc gcgctgccct    30720
gcggcaaccg cgaggagttg gtcgccgccc tcgacgcact cgcccacggc aggatcacgg    30780
cgggcgtgcg agtcgactcg gctgtgtcgg gtggacggc tgtgttgttt acgggtcagg    30840
gtgcgcagtg ggttggtatg gggcgtgagt tgtatggggtt ggatggggtg tttgctgcgg    30900
cgttggatga ggttttgggt gtggtggggg aggtgggtgg ttggtctttg cgtgaggtga    30960
tgtttggtga gggtggtggt gttggggtgg ggttgttgga tggtacggag tttgcgcagc    31020
ctgctttgtt tgcgttggag gtggcgttgt ttcgggctgt ggaggctcgg ggggtgcggg    31080
cttcggtggt gttggggcat tcggtggggg aggttgctgc tgcgtgtgtg gcggggggtgt    31140
tttcgcttgc ggatgcggcg cggttggtgg tggcgcgtgg tcggttgatg ggtgcgttgc    31200
ctgtgggtgg ggggatgttg tcggttcgtg cgtctgaggc cgaacttgtt gatgttgtgg    31260
ctgggttggg tggtcgggtg tcggtggctg cggtcaatgg tccggcgtcg gtggtgttgt    31320
ctggtgagtg tggtgcgttg gatgttgttg cggcgcggtt gggtgggcgt ggggtggagt    31380
gcaagcggtt ggtggtgtcg catgcgtttc attcggcgtt gatggatccg atgttggagg    31440
agtttcgtgg ggttgctgag agtgtggagt atcggcggcc gtgtgtgccg gtggtgtcga    31500
atgtgacggg tggggtggtt gggtttgatg agttgggttg tgccgagtat tgggtgcggc    31560
atgcgcggga gcggtgcgt ttcgctgagg ggattcgggc tgctcgtgct cttggtgtgg    31620
atacgttcct ggaggtgggt ccgcatgcgg ttttgacggc gatggctggt cagtgtcttg    31680
atgctgagga ggctgacttg gcgtttgtgc cggtcctgcg gcgtgatcgg ccggcattgc    31740
agaccttcac caccgcactc gccactctgc acaccgtga tgccgaactc gacgccgtgc    31800
cgctccattc aggcagcgat gcccggcgga tcgacctgcc cacctacccc ttccaacgcc    31860
gtactcactg gtcgccggcg ctgagccacg acacgcggc cggcgtcgtg cgggcctcga    31920
ccgctaccga gatccggggg aacgacgaga tcccggagag tgccgaggca ctccttcggg    31980
acccggccga cgggtcgctc gcggcatccc cggagccggc gacacccgac cagctcgtcc    32040
ggctggtccg cgagaccact gctgccgtcc tgggccacga cgaccccgac gagatcgtcc    32100
```

```
tcgaccgcac cttcacctct cagggcctgg aatcggtgac cgcggtcgaa ctccgcgacc   32160
tactgaaccg ggccacgggg ctgaccctcg cggccacgct cgtctacgac ctgcccaccc   32220
cgcgcgccgt cgccgattac ctgtcggccg cgatgctcgc gaccgacgat gcgaactcca   32280
gcgcgcacca aaccaccgcg gcggcgacca cccggagcgg tgcgcggaac gacgacccga   32340
tcgccatcgt cggcgtcggc tcccacttcc ccggcggcgt ggactcgcgc gccggcctgt   32400
gggatctgct ggcctccggc accgacgcga tctcgtcctt ccccaccgac cgtggttggg   32460
atctcaacga gctgtacgac cccgagcccg gcatcccgg caagacctat gtgcgtcagg   32520
gcggcttcct gcatcaggcg gccgagttcg acgcggagtt cttcggcatc tcgccgcgcg   32580
aggcgaccgc catggacccc cagcagcggc tgctgctgga gacctcctgg gaggcgctgg   32640
aggacgccgg agtgtgcccc gagtcgctgc gcggcaccaa caccggcgtg ttcatcggcg   32700
cagtcgcacc ggagtacggc ccgaggctcc acgagggagc ggacgggtac gaggggtatc   32760
tgctcaccgg caccacggcg agcgtggcct ccggccggat cgcctacacc ttcggcacgc   32820
gcgggccggc gctcacggtg gataccgcgt gttcgtcgtc gttggtggcg ttgcacctgg   32880
cggtgcagtc gttgcggcgg ggtgagtgtg atatggcgtt ggccggcgga ccacggtga   32940 tgtccggccc cggcatgttc gtggagttct cccggcagcg tgggttggcg tcggatgggc   33000
ggtgcaaggc gttctccgcc gatgccgacg gcacggcctg gtccgagggc gtcgccgttc   33060
tggcgctgga gcgtctctcc gacgcccgcc gcgccggtca ccgggtgctg cgctggtcc   33120 ggggcagcgc ggtcaaccag gacggcgcca gcaacggtct caccgcgccc agcggtcccg   33180
cgcaggagag tgtcatccgt gaggcgttgg cggatgccgg gttggggccg ggtgatgtgg   33240
atgtggtgga ggcgcatggt acgggtacgg cgttgggtga tccgatcgag gctggtgcgt   33300
tgctggccac gtatggatgt gagcgggtgg gtgatccgtt gtggttgggg tcgctgaagt   33360
ccaacatcgg gcacactcag gccgccgcgg gtgtcgccgg tgtcatcaag atggtggagg   33420
ccctgcgcca tggcacgctg ccgcggacgc tccacgccga ccgccccagc acacacgtcg   33480
actggtcttc ggggggcgtg gagttgctga ccgaggcgcg cccgtggccg gagcgggagg   33540
gccggccgcg gcgggccgcg gtgtcggcct tcggtgtcag cggtaccaac gctcacctgg   33600
tcattgaaga gccccccgtg gagttgcctg ctggtgctgg tgctggtgct ggtgctggtg   33660
ctggggtgtc ttcggttgtg gcgtggccgt tgtcggctcg ttcgggtgag gcgttgcggg   33720
cgcaggcggt gcggttgcgt gagcatgtgg agcgtgttgg ggctgatccg gttgatgttg   33780 cctttcgtt ggcggtgacg cgtgcgtcgt tcggtgagcg tgcggtggtc gttggtggtg   33840
accgtgcgga gttgctggcg gggcttgatg cgcttgctgg ggggcgtcgg gggccggggg   33900
ttgtccgggg ctcggctgtg tcgggtggga cggctgtgtt gtttacgggt cagggtgcgc   33960
agtgggttgg tatggggcgt gagttgtatg ggttggatgg ggtgtttgct gcggcgttgg   34020
atgaggtgtt gggtgtggtg ggggaggtgg gtggttggtc tttgcgtgag gtgatgtttg   34080
gtgagggtgg tggtgttggg gtggggttgt tggatggtac ggagtttgcg cagcctgctt   34140
tgtttgcgtt ggaggtggcg ttgtttcggg ctgtggaggc tcgggggtg cgggcttcgg   34200 tggtgttggg gcattcggtg gggggaggttg ctgctgcgtg tgtggcgggg gtgttttcgc   34260
ttgcggatgc ggcgcggttg gtggtggcgc gtggtcggtt gatgggtggg ttgcctgtgg   34320 gtgggggat gttgtcggtt cgtgcgtctg aggccgaact tgctgatgtt gtggctgggt   34380
tgggtggtcg ggtgtcggtg gctgcggtca atgtccggc gtcggtggtg ttgtctggtg   34440
agtgtggtgc gttggatgtt gttgcggcgc ggttgggtgg gcgtggggtg gagtgcaagc   34500
```

```
ggttggtggt gtcgcatgcg tttcattcgg cgttgatgga gccgatgttg gaggagtttc   34560
gtggggttgc tgagagtgtg gagtatcggc ggccgtgtgt gccggtggtg tcgaatgtga   34620
cgggtggggt ggttgggttt gatgagttgg gttgtgccga gtattgggtg cggcatgcgc   34680
gggaggcggt gcgtttcgct gagggatac gggctgctcg tgctcttggt gtggatacgt    34740
tcctggaggt tggtccgcat gcggttttga cggcgatggc tggtcagtgt cttgatggag   34800
aggaggctga cttggcgttt gtgccggtcc tgcggcgtga tcggccggca tcgcagacct   34860
tcaccaccgc actcgccacg ctttgtgttc ggggcactga ggtcgattgg gccacgccgc   34920
accggaagag tggtgcacaa cgcattgacc tgcccacgta ccccttccag cgcgcccgat   34980
actggcttga ccccgcccct gcaatggcgc tcactaccgt ggccgccagt tcggccgagg   35040
ccgcggcgac ggccactgag gggacagccc tggaaacggc cgggctccgc taccgcatcg   35100
cctggcaggc cgccgccacg gaccgcggca cctctcgctc ggcggggcac gtggtgctac   35160
tcacctcgga cgacgacgcg accgaatccg gacttgccgc cgcgattacc cgcgaactcg   35220
ccgtgcgcgg cgccgaggta cgcaccgcga tcctgccagt cggcaccgac cgcgagacgg   35280
ccgcagacct gctacgaacc tccggtgacg cgccgcacg cagcacgcac gtcctgtggc    35340
tcgccccggc cgagcccgac acggccgacg ccgtcgcgct gatccaggcc ctgggcgagg   35400
cagggcacga cgcccactg tggatcgcca cgcgtgacgc ggtggccgtc cagccggcg     35460
agaagctgtc cgtcgccgga gcgcagctct gggggctcgg gcaggtcgcc gccctcgaac   35520
tgttccagcg ctggggcggc ctggtggacc tgcccgagaa cccgtcgccc gctgcggtcc   35580
gcgcgttcgt cggggcgctg ttcgcggagg gtgacgacaa ccagatcgcg gtgcggccct   35640
ccggcgtgta cgtccgccgc gtggcccccg ccccgcccc cgctcccgcc ctcatcgggc    35700
aggctgcgca ggacgaccgg tccggcccgt ccgatggact cgatgggaac aatggaaccg   35760
cgccggtgaa ctggcacccc tccggcaccg tactgatcac cggtggcacc ggggccctcg   35820
gcgcacaggt ggcccgcagg ctcgcccgag cgggcgcgcc gcatctgctc ctggtcagcc   35880
gccgtggacc ggacgcccct ggtacgggcg aactggtcgg ggaactgaca gcgcacggca   35940
ccgaagtgac cgtcacggcc tgtgacgccg ccaccgcga tgcgctcgcc gagctgctcg    36000
cgagcattcc cgaggatcgc ccctcaccg ccgtactgca cgcggcaggt gtgctcgacg    36060
acggcgtgct cgacgcgctc accccgatc ggctcgacgc cgtactgcgc gccaaggtaa    36120
ccgtggcccg ccacctggac gagctcaccg caggcatacc gctggatgcc tttgtgctct   36180
tctcctccat cgtcggggtg tgggcaacg gcggccaggg cggctatgcg gcggccaacg    36240
ccgcgctcga tgccctggcg caccggcgcc gggcccgggg acagcgtgcc acgtcgattg   36300
cctgggggcc gtgggccggc gccggaatgg cggccggcgc aggctcgaag gccttccagc   36360
gggatggcat ccaggctctg gatcccgagc gtgcactcaa tgtgctggac gacgtggttc   36420
gcgccgacga gacgtctgtg gccgccgagc cctctttgat cgtcgccgat gtggactgga   36480
gcacgttcgt cggggcgctcc gtcgcccgac gcacctgggc gcttttcgac ggtgttccgg   36540
ccgcctgctc cgcgcgttcc gccaggccg cacagggccg ttcgcgcac gccccgggag    36600
agcggccgca ccacgcggc attggtggga gcggagacgg agcggacgag gaccgccct     36660
ggctctctgc cggcccctcc tcgccggaac ggcggcgggc actgctcgac ttggtgcgct   36720
ccgaggccgc cgagatcctg cgtcacggtt cggctgccgc ggtcgacccg gagaccgcgt   36780
tccgggccgc cgggttcgac tccctcaccg tgctcgaact gcgtaatcgt ctgaccgccg   36840
```

```
ccatcgggct gaacctgccg agcaccctgc tgttcgacta tccgaacccg aacgccctgg   36900
ccgaccatct gcacgacgaa ttgttcggtg ctgacagcga agcaccgctc gccgcgaaca   36960
cgcccacccg ggcctcggcc gacgaccgcg agccgattgc ggtcgttggt atggcctgtc   37020
gttatccggg tggggtggcg cgccggagg aactgtggga cctggtggcc ggaggcgggc    37080
atgcgatctc cccgttgcct gccaaccgag gttgggacct tgaggggctc tacgacccgg   37140
agccgggcgt gccgggtaag agctatgtgc gtgaggggg ttttctgcac ggggcggccg    37200
agttcgatgc ggagttcttc ggtgtttcgc cgcgtgaggc ggcggcgatg gatccgcagc   37260
agcggttgtt gttggagacg tcgtgggagg cgttggagcg ggccgggatc gtgccggctg   37320
cgctgcgcgg cacccgcacc ggagtcttca ccggcatctc ccagcaggac tacgccgccc   37380
agttgggga cgcggccgag acctacggcg gccatgtgct caccggaaac ctcggaagtg    37440
tggtctccgg ccgggttgct tactccttgg gtttggaggg gccggcgctc acggtggata   37500
ccgcgtgttc gtcgtcgttg gtggcgttgc atctggcggt gcagtcgttg cggcggggtg   37560
agtgcgatat ggcgttggcc ggtggtgtga cggtgatggc gacgccgacg gtgtttgtgg   37620
agttttcccg gcagcgtggg ttggcgtcgg atgggcggtg caaggcgttt gcggagggtg   37680
ctgatggtac tgcttggggt gagggtgttg gtgtgctgtt ggtggagcgg ctgtccgatg   37740
cccgtcgcct tggtcactcg gtgttggcgg tggtgcgggg gagtgcggtt aatcaggacg   37800
gtgccagtaa tggtttgacg gcgcccagtg gtccggctca gcagagggtg atccgtgagg   37860
cgttggcgga tgccgggttg gggtcgggtg atgtggatgt ggtggaggcg catggtacgg   37920
gtacggcgtt gggtgatccg atcgaggctg gtgcgttgct ggccacgtat gggcgtgagc   37980
gggtgggtga tccgttgtgg ttggggtcgc tgaagtccaa catcgggcac actcaggccg   38040
ccgcgggtgt gggtggtgtc atcaagatgg tggaggcgct gcgtcatggc acgttgcctc   38100
gcactctcca cgtcgatgct ccctcttcga aggtcgagtg gggttcgggt gcggtggagc   38160
tgttgaccga ggctcgagcc tggccccggc gggcggatcg caagcgccgt gcggccgtct   38220
ccgccttcgg cgtcagcggc accaacgctc atgtcgtcat cgaggaaccg cccgccgagg   38280
tgtcggccga gtcgctggtc gagttgcctg ctggtgctgg tgctggtgct ggtgctggtg   38340
ctggtgctgg tgctggtgct ggggtgtctt cggttgtggc gtggtcgttg tcggctcgtt   38400
cgggtgaggc gttgcgggcg caggcggtgc ggttgcgtga gcatgtggag cgtgttgggg   38460
ctgatccggt tgatgttgcc ttttcgttgg cggtgacgcg tgcgtcgttc ggtgagcgtg   38520
cggtggtcgt tggtggtgac cgtgcggagt tgttggcggg gctgggggct gttgctgctg   38580
gggatgcgct gtcggcgtg gtgcgtggtt cggcggtgcg ggggcgaaag gttgcggctt    38640
tgtttacggg tcagggtgcg cagtgggttg gtatggggcg tgagttgtat gggttggatg   38700
gggtgtttgc tgcggcgttg gatgaggttt tgggtgtggt ggggaggtg ggtggttggt    38760
cttttgcgtga ggtgatgttt ggtgagggtg gtggtgttgg ggtggggttg ttggatggta   38820
cggagtttgc gcagcctgct ttgtttgcgt tggaggtggc gttgtttcgg gctgtggagg   38880
ctcgggggt gcgggcttcg gtggtgttgg ggcattcggt gggggaggtt gctgctgcgt    38940
gtgtggcggg ggtgttttcg cttgcggatg cggcgcggtt ggtggtggcg cgtggtcggt   39000
tgatgggtgg gttgcctgtg gtgggggga tgttgtcggt tcgtgcgtct gaggccgaac    39060
ttgctgatgt tgtgctgggg ttgggtggtc gggtgtcggt ggctgcggtc aatggtccgg   39120
cgtcggtggt gttgtctggt gagtgtgtg cgttggatgt tgttgcggcg cggttgggtg    39180
ggcgtggggt ggagtgcaag cggttggtgg tgtcgcatgc gtttcattcg gcgttgatgg   39240
```

```
agccgatgtt ggaggagttt cgtggggttg ctgagagtgt ggagtatcgg cggccgtgtg   39300
tgccggtggt gtcgaatgtg acgggtgggg tggttgggtt tgatgagttg ggttgtgccg   39360
agtattgggt gcggcatgcg cgggaggcgg tgcgtttcgc tgaggggata cgggctgctc   39420
gtgctcttgg tgtggatacg ttcctggagg tgggtccgca tgcggttttg acggcgatgg   39480
ctggtcagtg tcttgatgga gaggaggctg acttggcgtt tgtgccggtc ctgcggcgtg   39540
atcggccggc attgcagacc ttcaccaccg cactcgccac tctgcacacc cgtgatgccg   39600
aactcgacgc cgtggcgctc cattcaggca gcgatgcccg gcggatcgac ctgcccacct   39660
accccttcca acgccgtagc tactgggcga ccggttcggt gcctggtgcc accggcacct   39720
cggccgcggc ccgcttcggg ctcgtatgga aggaccaccc gttcctcagc ggcgcgacgc   39780
cgatagccgg ctccgattcg ctgctcctca ccggcagggt ggcgccttcc gcatacccgt   39840
ggctggccga tcacgccatt tccggcacgg tgctgctccc tgggacgcg atcgccgacc    39900
tgctgctgcg ggccgccgac gaggtgggcg cgggcggtgt cgaggaattc atgctccacg   39960
cgcccctgct cctccccgaa cagggcggac ttcagctcca ggtgctggtc gaggcggccg   40020
atgaacgagg ctgtcgcacc gtctcgctcg ccgcacgtcc cgagaatccg gggcgcgatg   40080
gcgaggcgcc ggagtggacc aggcacgcgg agggtgtgct cgcgcccgaa ggcccgatcg   40140
caccggagac cgcatgggcc gttgggatct ggccgccgcc cggggctgag ccggtcgacg   40200
tcgaggagct gtacgagggg ttcgccgcgc acggctacgg ctacggcccg gccttcaccg   40260
gactgtccgg ggtgtggcgc cgtggtgagg agctcttcgc cgaggtgcag ctgcccgacg   40320
gggtggcgaa cggggataat ttcggcattc atccggccct cttcgacgcg gctctccatc   40380
catggcgtgc cggcgggctg gtgcccgaca cgggcggcac gacgctggtg ccgttctcct   40440
ggcagggcat tggtctccac gccaccggag ccgagacact gcgggtccgg ctggcgacgg   40500
cgggtgacgg tgccgacgcc gccttctcgg tgcaggccgc cgaccggcc ggccggcccg    40560
tcctcaccct ggacgcgcta ctgcttcgcc cggtggccct gggtacggac aacgcgtcgg   40620
cgtcggggct gctgtaccac gtcgactggc agccggtgcc gcggcaggca gttgcccccg   40680
gctcccgtgg ctggacggtt ctcgggcccg ccgcgagcga aacggcgacg gtggaggtgg   40740
cacaggagga gagcgcgacc ctacgagccc tgcccggcgc gcagcccgct gtccacgccg   40800
acctcaccgc tctgcgcgcc gccctggccg ccggaaccgc cgttcccggg ctggtagtgg   40860
tgccgcccac cggcacccac ctcgtcgagc cgggcgcggg tacgggcggg ggcgcggaga   40920
cgggtgccgc aggctggggc gacgaccccg tgcgcgccgc cctcgggcgc ggcctggccc   40980
tggtacggga gtgaccgag gacgaacgcc tggtgggcgc ccagcttgcc gtcctcaccc    41040
gggggcggt cgaggcccgg cccggcgacg tgccggatct ggcgggtgca gccttgtggg    41100
ggctgctccg ctccgcgcag tcggagtacc ccgaccgctt caccctcgtc gacctggatg   41160
actccccga gtcctgggct gccctgcccc aggctctggc gtcgggagag ccgcaactcg    41220
ccttgcgcgc cgggaccgta ctcgctccgg ctctcgtgcc gatcgccgac cctgcgacgg   41280
ccgcgacctc ggccgtggcc tcgatggcga gtggcgcgtc gacagcgacc gatgttcccg   41340
ctgcggacgc cgcattcgac cccgacggga ccgtactgat caccggcgcc accggcgccc   41400
tggggcggcg ggtggtcccg cacctggcac gtcagcacgg cgtgcggcat atgctcctgg   41460
tcagcaggcg cggcccggac gccccgaagg ccgcctcct ggagcgggag ctcgccgacc    41520
tgcaggtcac cgcgaccttc gcgatgtgcg acctcgccga ccccgcggac atccggaagg   41580
```

```
tcatctccgc ggtgccgccg gcgcacccgc tgaccggtgt cgtgcacacc gccggcatgc   41640
tggacgacgg agccctcgcc ggcctgacgc cggcgcggct cgataccgtc ctccggccga   41700
aagccgacgc cgtacggaac ctgcacgagg ccactctcga ccagccgttg cgcgcgttcg   41760
tcctgttctc tgcagcggcc gggctcctgg gccgcccggg gcagggctcc tacgcggcgg   41820
ccaacgcggt cctcgacgcg tttgcgcggg accgtcgtgc ggccgggctg cctgctgtgt   41880
ccctggcctg gggactgtgg gacgaacggg caggcatggc cggcggcctg gacgacgtgg   41940
cactccgtcg gctgcgccgc gagggcatcg cggccatgcc gcccgagcaa gccctcgacc   42000
tgctcgacct ggccctgacc acgcaccggg acgggcccgc ggtcctcgtc ccgctcctac   42060
tcgacggggc cgccctgcgc cgaacggcca aggagcacgg cgcgaccgcg gtgccaccgt   42120
tgttgcgcgc cctgctcccc gcggccctgc gccgcgggag cagcggcacc ggtaccgcgg   42180
caacggccgc caaccggcgg ggcaagggcg cggagcctgt cgccggacgc gtcgcgcgga   42240
tcgtggcgct cctggcagat gagaggtccg cggccctgct ggacctggtc accgagcagg   42300
tcgccgaggt actcggtcac gcgtcggccg ccgaagtcga ccccgaacgt cccttccggg   42360
acatcggctt cgactccctg gcggcggtgg agctgcgcaa ccgcctcggc cgcctggtcg   42420
acctgcggct gccgaccaca ctcgccttcg accgccccac gccgaaggac gtggccgagt   42480
ggctcgacgg ggagttgccc cgccccgccg gttcgtcagc cgattcctcc gcgctggagg   42540
ggatcgacga actcgcccgg gccgtcgccc tgctgggccc ggacgacgcc cggcgagccg   42600
aggtacggca gcggctcact gggctgctgg ccgagctcga caccccgggg cacggcactg   42660
ccggcccccg agaccgcacc gccccgccg atgccgagag caccccggcg actgtggcgg   42720
gccggcttga cgaggcgact gacgacgaga tcttcgcctt cctggacgag cagctgtgac   42780
cgcaccgtgg accaccgca tgccgaggag ttggtggcag caatgaccgc cgagaacgac   42840
aagatccgca gctatctgaa gcgtgccacc gccgaactgc acaagaccaa gtcccgcctg   42900
gccgaggtcg agtcggcgag ccgggagccg attgcggtcg ttggtatggc ttgtcgttat   42960
ccgggtgggg tggcggcgcc ggaggatttg tgggatctgg tggtcgcggg tacggacgcg   43020
atctccccgt tccccgccga ccgtggctgg gacgtcgagg ggctgtatga cccggacccc   43080
gatgcggtgg gtcgcagcta tgtgcgtgag gggggttttc tgcacggggc ggccgagttc   43140
gatgcggagt tcttcggtgt ttcgccgcgt gaggcggcgg cgatggatcc gcagcagcgg   43200
ttgttgttgg agacgtcgtg ggaggcgttg gagcgggccg ggatcgtgcc ggctgcgctg   43260
cgcggcaccc gcaccggagt cttcaccggc gtgatgtatg acgactacgg atcgcagttc   43320
gattccgcac cgccggagta cgagggctac ctcgtgaatg gcagcgcggg cagcatcgca   43380
tccggccggg ttgcttactc cttgggtttg gaggggccgg cgctcacggt ggataccgcg   43440
tgttcgtcgt cgttggtggc gttgcatctg gcggtgcagt cgttgcggcg gggtgagtgc   43500
gatatggcgt tggccggtgg tgtgacggtg atggcgacgc cgacggtgtt tgtggagttt   43560
tcccggcagc gtgggttggc tcccgacggg cggtgcaagg cgtttgcgga gggtgctgat   43620
ggtactgctt ggggtgaggg tgttggtgtg ctgttggtgg agcggctgtc cgatgccgt   43680 cgccttggtc actcggtgtt ggcggtggtg cggggagtg cggttaatca ggacggtgcc   43740
agtaatggtt tgacgcgcgcc cagtggtccg gctcagcaga gggtgatccg tgaggcgttg   43800
gcggatgccg ggttggggtc gggtgatgtg gatgtggtgg aggcgcatgg tacgggtacg   43860
gcgttgggtg atccgatcga ggctggtgcg ttgctggcca cgtatgggcg tgagcgggtg   43920
ggtgatccgt tgtggttggg gtcgctgaag tccaacatcg ggcacactca ggccgccgcg   43980
```

```
ggtgtgggtg gtgtcatcaa gatggtggag gcgctgcgtc atggcacgtt gcctcgcact    44040
ctccacgtcg atgctccctc ttcgaaggtc gagtgggggtt ggggcgcggt ggagctgttg    44100
accgaggctc gagcctggcc ccggcgggcg gatcgcaagc gccgtgcggc cgtctccgcc    44160
ttcggcgtca gcggcaccaa cgctcatgtc gtcatcgagg aaccgcccgc cgaggtgtcg    44220
gccgagtcgc tggtcgagtt gcctgctggt gctggtgctg tgctggtgc tggtgctggt    44280
gctggggtgt cttcggttgt ggcgtggtcg ttgtcggctc gttcgggtga ggcgttgcgg    44340
gcgcaggcgt gcggttgcg tgagcatgtg gagcgtgttg gggctgatcc ggttgatgtt    44400
gccttttcgt tggcggtgac gcgtgcgtcg ttcggtgagc gtgcggtggt cgttggtggt    44460
gaccgtgcgg agttgttggc ggggctgggg gctgttgctg ctggggatgc gctgtcgggc    44520
gtggtgcgcg gttcggcggt gcggggcga aaggttgcgg ctttgtttac gggtcagggt    44580
gcgcagtggg ttggtatggg gcgtgagttg tatgggttgg atgggtgtt tgctgcggcg    44640
ttggatgagg ttttgggtgt ggtgggggag gtgggtggtt ggtctttgcg tgaggtgatg    44700
tttggtgagg gtggtggtgt tggggtgggg ttgttggatg gtacggagtt tgcgcagcct    44760
gctttgtttg cgttggaggt ggcgttgttt cgggctgtgg aggctcgggg ggtgcgggct    44820
tcggtggtgt tggggcattc ggtggggggag gttgctgctg cgtgtgtggc ggggggtgttt    44880
tcgcttgcgg atgcggcgcg gttggtggtg gcgcgtggtc ggttgatggg tgggttgcct    44940
gtgggtgggg ggatgttgtc ggttcgtgcg tctgaggccg aacttgctga tgttgtggct    45000
gggttgggtg gtcgggtgtc ggtggctgcg gtcaatggtc cggcgtcggt ggtgttgtct    45060
ggtgagtgtg gtgcgttgga tgttgttgcg gcgcggttgg gtgggcgtgg ggtggagtgc    45120
aagcggtttgg tggtgtcgca tgcgtttcat tcggcgttga tggagccgat gttggaggag    45180
tttcgtgggg ttgctgagag tgtggagtat cggcggccgt gtgtgccggt ggtgtcgaat    45240
gtgacgggtg gggtggttgg gtttgatgag ttgggttgtg ccgagtattg ggtgcggcat    45300
gcgcgggagg cggtgcgttt cgctgagggg atacgggctg ctcgtgctct tggtgtggat    45360
acgttcctgg aggtgggtcc gcatgcggtt ttgacggcga tggctggtca gtgtcttgat    45420
ggagaggagg ctgacttggc gtttgtgccg gtcctgcggc gtgatcggcc ggcatcgcag    45480
accttcacca ccgcactcgc cactctgcac acccggggcc taccggtacc gccgacgccc    45540
tcgatgcctg ccgcccggcg gatcgacctg cccacctacc ccttccaacg gaaccgctac    45600
tggctggcgg ccccgccgcg gcccacgacc ggcggggtgt cggcagccgg tcagcgtgcg    45660
gtggagcatc cgctgctcgc cgccgccgtg gaactcccgg gcgccggcac cgaggtgtgg    45720
accgccggga tctccgccgc ggacctcccc tggctcgccg accacctggt gtgggaccgc    45780
ggagtggtcc ccggggctgc cctgctggag ttggtgctcc aggtgggaag ccggatcgga    45840
ctgccccgcg ttgccgaact gacctttgag accgcgctgg cctgggccac ggacaccccg    45900
ctccagatcc gggtcgtcgt ggacgctcct gcctccgtcc ccgacggggc ccgtgaggtg    45960
agcctttact cccggcccga acccgtcgcc cgcaccccgc accccgctgg atccccgcac    46020
ctggcggcgg agcacggcga caacggctgg accggcacg cttccggcgt gctcgctccg    46080
gccgccgacc attcccacga ctccgaccca gccgcaccca gcaccttcgc cgaactcacc    46140
ggtgcctggc cgcccgccgg cgccgagcct ctcgacatcg ccgagcagta tctcgctcttc    46200
gcagcggtcg gagtgcgcta cgaaggcgcc ttcgtgggggc tgcgcgcggc gtggcgccgc    46260
ggcgacgaga tcttcgccga agtgcggtta cccgatgtgc acgccgccga cgccacccgc    46320
```

```
tacggggtgc atcccgccct gctcgacgcg gccctgcacc ccatcgcgct gctcgacccg    46380
ttgggcgacg gcggacacgg cctgctgccg ttctcctgga ccgacgttca gcactacggt    46440
tccggcggac acgcactccg ggtacgggtg gctgccgccg acggcggagc ggtgtcgatc    46500
tccgtggtgg accgcgaggg tgccctgtc ctcgccgccc gctccctggc gctgcgccgc     46560
atcgccgcgg accggctgcc cgccgccccc gccgctcccc tgtaccgcat ggactggttg    46620
ccgctacccg agcgagtgcc cgccgccacg gccgcgcgct gggccgtcgt cgggccggcg    46680
gccgaagtca ccgcggccgg gctgcgcgcc gtcggcgtcg atgcccgtgc ccacgtgtcc    46740
cccctcggcg agccgctgcc gccggaggcc ggtacggacg ccgaagtgtg cctcctcgac    46800
ctgaccgcgg tcgatggcac ggcgcccac ggcgggctcc tggacgaggt gcgcgcgacg      46860
gtgcgccggg cgctggaagc cgtacagacc ccgctcgccg gcactgatcc cctgacggac    46920
gcgcgtacgg gcactcctac cggcgggccg cggctcgtcg tcctcacccg gggagcggcc    46980
ggtccggagg gtgcgcggc cgatccggcg ggcgccgccg tctgggggct gatccggtc       47040
gcccagaccg agcagcccgg ccgcttcacc ctggtcgaca tcgacagggc gaagacgtcg    47100
ctgcggaccc tggccgggct gccggccgcg gacgccgctc agatcgcggt gcgcgacgga    47160
cgggccaccg tccccccgcct cgtacggggtg gtcgacaccg acagcaccgg tgccggggag   47220
ctggtcgaga tgctggaccc caacggcact gtgctgatca ccggaggtac cggagcactg    47280
gccgcagaga ccgcacggca cctggtggaa cgacacaagg caggtcggct tctgctcgtc    47340
agcaggcgcg gtgcggaggc gccgggtgcc gccgaactgg tggcggaact cgccgccttg    47400
ggcgccgagg tcaccgtccg ggcctgtgac gtcgctgacc gcgacgcgct gcgccgcctg    47460
ctcggtgagt tgcccgccga gcacccctg agctgtgtgg tgcacaccgc cggtgtgctc     47520
gatgacgggg tgctctccgc ccagacgacc gagcggatcg acgccgtgct gcgtcccaag    47580
gtcgacgccg ccgtccacct ggatcagctg acccgtgaac tcgggccggt gccattggtg    47640
ttgtactcct cggtctctgc ctctcttggc agcgccggcc aggccgggta cgccgcggcc     47700
aacgcgttcc tggacgcgtt ggccgcccgc cggcgcgccg acgggcaccc tgcgctgtcg    47760
ctcggctggg gctggtgggc cggtgcgggc atggccaccg gtctggaggg cgccgacgcc    47820
gcgcgcatcc ggcgctccgg catcgtcccg ctcgaccctg cggacgcgct ggagctgctc    47880
gaccgggcgc tggcccggcc cgagccgcg ctgctgccgg tacggctcga cctgcccgcc      47940
ctgcgcgctg cggcccgcgc caccgcgcca ccggaggtgc tgcgcgagct cgccggtgtc    48000
ccggccgatt ccggggccgc gctgggtgcc ggggacggg tcggcaacgg ccaacggccc      48060
gaccccgcca gccggccga ggcactggcg gccggctcg cgccgcgctc cgcagccgag        48120
cgcacggccc tcctgctcga cctggtgcgt ccgaggtcg cggcggtgct gggccacgga      48180
gaccccgccg cggtgggcgc cggcggtcc ttcaaggacg ccggattcga ctccctcacc      48240
gccgtcgacc tccgcaaccg gctgaacgcg cgcactgggc tgcgactgcc cgcgacgctc    48300
gtgttcgacc accccacacc gttgtccctc gccgagctgc tgcgcgccga cctggaggcg    48360
gccggcctgg tggggccac cggtccggcg acgggcgaac caaccggccc cgaggacctg     48420
tccagcgtgc tggaccggtt ggagtccagc ctcaccgcga ccgacaacgg cgacgcccgc    48480
tcggccgccg cgcggcggtt gtgcagtctg ctggccatgc tcaccgctgg ctcgggcgag    48540
catccggggc agggctccgg cgaaagcccc cggggttccg gcgatgcggt gctcgaccgc    48600
ctccaatcgg cctccgacga cgacttgttc gaccttttcg acagcgattt ccagtgagcc    48660
agacggcgtc gcgcgccggc cactcgaccg cttccacccc tgaccctga catgacgcag     48720
```

```
aggagaaccg tgtctgcaac gaacgaggag aagctgcggg agtaccttcg gcgcgcgatg  48780
gccgacctgc acagcacgcg cgatcggctg cgcgaggtcg agtcggcgag ccgggagccg  48840
attgcggtcg ttggtatggc ctgtcgttat ccgggtgggg tggcggcgcc ggaggatttg  48900
tgggatctgg tggtcgcggg tacggacgcg atctccccgt tccccgccga ccgtggctgg  48960
gacgtcgagg ggctgtatga cccggacccc gatgcgatgg gtcgcagcta tgtgcgtgag  49020
gggggttttc tgcacgaggc ggccgagttc gatgcggagt tcttcggtgt ttcgccgcgt  49080
gaggcggcgg cgatggatcc gcagcagcgg ttgttgttgg agacgtcgtg ggaggcgttg  49140
gagcgggccg ggatcgtgcc ggctgcgctg cgcggcaccc gcaccggagt cttcaccggc  49200
gtgatgtacc acgactacgg cagccatcag gtcggcaccg ccgccgaccc cagtggacag  49260
ctcggcctcg gcaccacggg cagcgttgca tccggccggg tcgcctacac cctgggctg   49320
cagggccccg ccgtgaccgt ggataccgcg tgttcgtcgt cgttggtggc gttgcatctg  49380
gcggtgcagt cgttgcggcg gggtgagtgc gatatggcgt tggccggtgg tgtgacggtg  49440
atggcgacgc cgacggtgtt tgtggagttt cccggcagc gtgggttggc gtcggatggg  49500
cggtgcaagg cgtttgcgga gggtgctgat ggtactgctt ggggtgaggg tgttggtgtg  49560
ctgttggtgg agcggctgtc cgatgcccgt cgccttggtc actcggtgtt ggcggtggtg  49620
cggggagtg cggttaatca ggacggtgcc agtaatggtt tgacggcgcc cagtggtccg  49680
gctcagcaga gggtgatccg tgaggcgttg gcggatgccg ggttggggtc gggtgatgtg  49740
gatgtggtgg aggcgcatgg tacgggtacg gcgttgggtg atccgatcga ggctggtgcg  49800
ttgctggcca cgtatgggcg tgagcgggtg ggtgatccgt tgtggttggg gtcgctgaag  49860
tccaacatcg ggcacactca ggccgccgcg ggtgtgggtg tgtcatcaa gatggtggag  49920
gcgctgcgcc atggcacgtt gcctcgcact ctccacgtcg atgcccccctc ctcgaaggtc  49980
gagtgggatt cgggtgcggt ggagctgttg accgaggccc gagcctggcc ccggcgggcg  50040
gatcgcaagc gccgtgcggc cgtctcggcc ttcggcgtca gcggcaccaa cgcgcacgtc  50100
gtcatcgagg aaccgcccgc cgaggtgtcg gccggcggta ctcccgtgac tccttccacc  50160
gtggtctggc cgctgtccgc cgagaccgcc cccgccctgc gcgcccaggc cgcacgcctg  50220
cgcgcgcacc ttgagcgtct cccccggcgcg gctcccgccg acatcggcca cgcgctggcc  50280
gccgaccgcg ccgcccctcac ccaccgtgcc gtgctgctcg gtgccaacag cgcccccatg  50340
gacgccctcg ccgcccctggc tgccggtgaa accatcccgg acaccgtcac cggtaccgcg  50400
gcggacatcc gccgcgttgc cttcgtcttc cccggccagg gcacccagtg ggccggcatg  50460
ggcgccgaac tgctggacga ggcccccggcc ttcgctgccg aagtggagcg ctgccagcgc  50520
gcgttcgccc cgtacgtgga ctggtcactc accgacgtcc tgcgcggcgc acccggggcg  50580
cccgccctcg accgcgtcga cgtcattcag ccggccgcct tcgcggtgat ggtggcgctc  50640
gcggcactgt ggcgctcgct cggcgtcgaa cccgccgccg tcatcggcca ctcccagggc  50700
gagatcgccg cggcctgtgt ggccggcgcg ctctccctgg acgacgccgc ccggatcgtg  50760
gccctgcgct cccagatcat cgcccgcgaa ctggcggggc gggcgggcat ggcctcggtg  50820
gccctgccct cggccgacgt cgaggcgcgg ctcgatgtcg ccggcggcat cgagatcgcc  50880
gccgtcaacg gcccccagtc gaccgtcgtc tgcggggagc cggccgccct ggaggcgctg  50940
ctgcgcaccc tggaggacga aggccaccgg gtccgccgga tcgatgtcga ctacgcctcc  51000
cactcccacc atgtcgagag catccgggag gaactcgcca ccgttctcgc cgcggtccgg  51060
```

-continued

| | | | | | |
|---|---|---|---|---|---|
| ccgcacggga | gcggtgtgcc | cttctactcc | accgtcgacg | cggccctcct | ggagacgacc | 51120 |
| gcgctcgatg | ccggctactg | gtaccgcaac | ctgcggctcc | cggtgcggtt | cgaaccgacc | 51180 |
| gttcgcgcca | tgctcgccga | cggcgtcgac | gcgttcgtgg | aatgctccgc | gcaccccgtc | 51240 |
| ctcaccttcg | gcatccgcca | gaccatggag | agcctagacg | tcgccgcacc | ggccgtcggc | 51300 |
| tcgctgcggc | gcgacgaggg | tgggctgcgg | cgcttcctca | cctccgtcgc | ggaggcccag | 51360 |
| gtctccggcg | tgccggtgga | cctggccagg | ctccaccccg | gggcgcgccg | ggtggagttg | 51420 |
| cccacctacg | ccttccagcg | cgaacgctac | tgggtcggct | ccgcccgtcc | cgagtgggcg | 51480 |
| gaggccgccg | aagccggtga | gagcatttcg | gagcccggcg | accggcttgg | ctaccacgtc | 51540 |
| gggtggaagg | ggctgcgcgc | cgtcaccggc | ggctggcgcc | ccggcctgcg | cctgctgata | 51600 |
| gtgcccgccg | gagaaacgca | cgccgccctc | gccgactccg | tggaacaggc | gatcgcttcc | 51660 |
| ttcggaggaa | cgatccggcg | catcgccgtg | gacccggccc | gtaccggccg | cgccgaactg | 51720 |
| cagggcctgc | tcgaaccggc | cgtcaacggc | gacaccaccg | tcaccggcat | ggtctcgctg | 51780 |
| ctcggactct | gcaccgacgg | ccacccccgat | caccggccg | tgcccaccgg | ggtcaccgcc | 51840 |
| accctcgcct | tggtccaggc | cctggccgaa | ctcggcggca | ccgcaccgct | gtggaccgtc | 51900 |
| acccagggcg | cggtggccac | cgcgccggac | gaggttccgt | gcaccgccgg | agcccaactg | 51960 |
| tggggcctgg | gccgggtcgc | ggcgctggaa | ctgcccgagt | tgtggggcgg | cctcgtcgac | 52020 |
| ctgcccgagc | ggcccgccgc | ccgggtcttc | gagcgccttg | ccggtgtcct | cgccgaagcc | 52080 |
| ggtgccgagg | accagatcgc | catcagggcg | gcgggcgtct | tcggccgccg | cgtcctgccg | 52140 |
| aacccggccg | actccgcccc | gccggtctgg | cgcgcccggg | ggacggtcct | gatcgccggc | 52200 |
| gacctcacga | cggtgcccgg | ccgggtcgtc | cgctccttcc | tggaggacgg | cgcagaccgc | 52260 |
| gtggtgctgg | ccgggccgga | cgccgacgcg | gaggccgcca | ccgccggcct | caccggagcc | 52320 |
| gtcgtccccg | tccgctgcga | cgtcaccgac | cgctccgccc | tggccggcct | actcaacgag | 52380 |
| cacgcgccca | ccgtcgtcgt | gcacgccccg | gcgctcgtgc | cgctggtccc | cctgaaggac | 52440 |
| acggagcccg | gcgacatcgc | cgtcgccgtc | gccgtcaaga | ccgcggccgc | cgaacacctg | 52500 |
| gtggacttgg | cgcccgccgc | cggcctcgac | gcgctggtgc | tgttctcctc | ggtgtccggc | 52560 |
| gtgtggggcg | gcgctgcgca | gggctgctac | gcggccgcca | ccgcgcacct | cgacgcgctc | 52620 |
| gccgagcgcg | cccgcgccgg | cggggtgccc | gccgtctctg | tggcctggag | cccgtgggcc | 52680 |
| ggcggcgcac | tcgccgacgg | tgccgacgcg | gagttcctca | accggcgcgg | cctcgccccc | 52740 |
| ctcgacccgg | acgcggcggt | gcggtccctg | cgccgcatgt | ggagcgcgg | ccgcacctgc | 52800 |
| ggagcggtcg | ccgatatcga | gtggaaccgc | ttcgccgcct | cctacacctc | ggtgcgcccg | 52860 |
| gccgtgctgt | tcgacgatgt | tcccgaggtg | tggcgactgc | gcgcggccga | acgcgccgcg | 52920 |
| ggcaccggcg | actcggtcac | ctccgaactc | gtccgcgaac | tgactgcgca | gtccggccac | 52980 |
| aagcggcacg | tcaccctgct | gcggctggtc | cgcacccacg | ccgccgccgt | cctcgggcag | 53040 |
| tcctccagcg | aggcggtgaa | cagcgcccgc | gccttccgcg | acctcggctt | cgactcgctg | 53100 |
| accgcgctca | aactgcgcaa | caggctcagc | gccgccaccg | gctcaacct | gccgcctcc | 53160 |
| ctggtcttcg | accactccaa | tccggccgcg | ctcgccggc | acctcggcga | cgaactgctc | 53220 |
| gaccgcggcg | acaccgccgc | ccagaccggc | cccgcggcca | cggcgcagac | ggacgagccc | 53280 |
| atcgccgtca | tcggcatggc | ctgccggctg | cccggcgggg | tccgttcgcc | cgaggacctg | 53340 |
| tgggacctgc | tcaccggaga | ggtcgacgcc | atcaccccct | tccccaccga | ccgggggtgg | 53400 |
| aacaacgacg | tcctctacga | ccccgacccc | gactcgcccg | gacaccacac | ctatgtgcgc | 53460 |

```
gggggcggat tcctgcacga cgcggccgag ttcgaccccg gtttcttcgg catcagccct    53520
cgcgaggccc tggccatgga cccgcagcag cggctgatcc tggagaccgc ctgggagtcc    53580
ttcgaacgag ccgggatcga cccggtggag ctgcgcggta gccgcaccgg cgtcttcgta    53640
ggcaccaacg ggcagcacta cgtgcccttg ctccaggagg gggacgagaa cttcgacggc    53700
tacgtagcca ccggcaactc cgcaagtgtg atgtccggcc ggctctccta cgtcttcggc    53760
ttggagggcc ccgccgtcac cgtcgacacc gcctgctcgg cctcccttgc cgcgctgcac    53820
ctggcggtgc agtcgctgcg gcggggtgag tgcgacatgg cgctggtcag cggcgccacg    53880
gtgatgtcca cccccgagat gctggtggag ttcgcccgcc agcgggcggt ttcgccggac    53940
ggccgctgca aggcgttcgc cgaggcgcg gatggcgtgg gcctcgccga gggcgccggc    54000
atgctgttgg tggagcggct gtccgatgcc cgtcgccttg gtcactcggt gttggcggtg    54060
gtgcggggga gtgcggttaa tcaggacggt gccagtaatg gtttgacggc gcccagtggt    54120
ccggctcagc agagggtgat ccgtgaggcg ttggcggatg ccgggttggg gtcgggtgat    54180
gtggatgtgg tggaggcgca tggtacgggt acggcgttgg gtgatccgat cgaggctggt    54240
gcgttgctgg ccacgtatgg gcgtgagcgg gtgggtgatc cgttgtggtt ggggtcgctg    54300
aagtccaaca tcgggcacac tcaggccgcc gccggtgtcg ccggtgtcat caagatggtg    54360
gaggccctgc gccacggcac gttgccccgc agccttcaca tcgacgctcc ctcctcgaag    54420
gtggaatggg gtgaggggc cgtggagttg ctcaccgagg cacggccctg gccccagcag    54480
gccgaccggc cgcgccgcgc cggcatctcc tcgttcggca tcagcggcac caacgttcac    54540
gtcatcgtcg aggagccgcc ggagcccacc gcgcccgagt cgctctggcc cgatgcggcc    54600
gccgacggcg acgtctggtc cgaggagtgg tggcgcgagg tgaccgtgcc gctgatgatg    54660
tcggcgcaca acgaggccgc gctgtgcgac caggcacgga ggctgcgcgc ggacctgctt    54720
gcccaccccg aactgcaccc ggccgacgtc ggctactccc tgatcaccac ccgcacccgc    54780
ttcgagcatc gggccgccgt ggtcggcgag aacttcacgg agctgatcgc ggcgctcgac    54840
gatctcatcg agggccgtcc gcatccgctc gtgatgcggg gcaccgccgg caccgccgac    54900
caggtcgtgt tcgtcttccc cggccagggc tcgcagtggg ccgagatggg cgacgggctg    54960
ttcgagcggt ccagcgtctt ccgggagacc gcacacgcct gcgacgccgc gctccggccc    55020
tacctcgact ggtccgtgct ggacgtgctg cgacgggagc ccgacgcacc ctcgctcgac    55080
cgggtcgacg tggtgcagcc cgtgctgttc accatgatgg tctcgctcgc cgcgacctgg    55140
cgctcgctgg gcgtcgaacc ggccgcggtc gtcgggcact cccagggcga gatcgccgcc    55200
gcccatgtcg ccggcgggct ttcgctggac gacgcggcgc gcatcgtcgc cctgcgcagc    55260
caggcgtggc tgcagcttgc gggcaagggc ggcatggtcg cggtgaccat gtccgagcgt    55320
gagctgcgac cccggctgga gttctgggc gaccggctcg ccgtcgccgc cgtcaacagc    55380
cccgagacct gcgccgtcgc gggcgacccg gacgccctgg ccgaactggt cgccgaactc    55440
gcctcccagg gcgtgcccgc ccgcccgatt cccggcgtcg acaccgcagg gcactcgccg    55500
caggtcgata cgctcgaaga ccagttacgg gaagtgctcg ccccggtcgc gccctcgtcc    55560
tccgacatcc cgttctactc gacggtcacc ggtgggctgc tcgacaccgc cgagctggac    55620
gccgactact ggtaccgcaa catgcgcgaa ccggtggagt tcgagaaggc caccgcgcg    55680
ctgatcgccg acggtcacga cgtgttcctg gagaccagcc cgcacccat gctcgccatc    55740
tccctccagg agacgatcag cgacgccggt gcctccgcgg cggtcctcgg cacgctgcgc    55800
```

```
cgtggccagg gcggcccgcg ctggctgggt gtcgccgtct gccgcgccta cacccacggc    55860
gtggagatcg acgccgaggc cctcttcggc cccgactcgc gtccggtggg cctgcccacc    55920
tacccgttcc agcgcgagcg ctactggtac agccccgtca gccgcggcga cgaccccgcc    55980
tccctcggcc tggacgcggc cgaccatccg ctgctcggcg gaggcgtgga actgcccggc    56040
tccggcgacc agatgtacac cgcccgtatc ggcaccgacg ccgtcccctg gttggtcgac    56100
cacgcgctga tggggacggt gctgctgccc ggtgccgtgt tcaccgacct cgcgctgtgg    56160
gccggccgcc agaccggcac cggccggatc gaggaactca ccctggccgc accctggtg    56220
ctgcccgagt ccggcggcgt ctggctgcgg ctgaacgtcg gcgccccgga caccgacgag    56280
gcccgccgct tcgcggtgca cgcccgcccc gagggcgccg ccgactggac cctgcacgcc    56340
gagggcctgc tcaccgcgga gcacgcgccc gacgcgccgg acgcctcggc ggtgaccccg    56400
tcgcacggcg ccgaacagct ggacaccggc gacttctacg agcggttcac cgaactcggt    56460
tacagctacg gccgttcttc cgtggactgg tcagcgccc accgtgccgg ctccgacctc    56520
cacgcggagg tcgcgctacc cgctcaggcc cagggcgacg cggcacggtt cgggcttcat    56580
ccggcgctgc tggacgcggc gctgcaaacc atgagcctgg gcggcttctt ccccgaggac    56640
ggccggatcc ggatgcccct cgcgctgcgt ggtgtccggc tgtaccgcac cggagcggac    56700
cggctgcggg tgcggatctc ccccgtcgcc gaggacgccg tccgcatcca gtgcgcggat    56760
accgaggggc ggatggtcgc cgagatcgac tcgttcctca tgcggccggt cgaccccgaa    56820
caactccggg gcgccgccc ggtcagcgcc gacgcgctct ccgcgtcgc ctggcgggag    56880
cggcccggca gcggcccggc caccggcacc gcttccgcga tccgctgggc ggtcgcggga    56940
ccggacgccc tgggcctggc cgaggccgcc gatgcacacc tgcccgatgc gctcggcccg    57000
gacggtccgc ggccggccac ggccggcgaa ccggccccgg acgccgtcgt gttcggcgta    57060
ccggccggga ccggcgatgt cgccgccgat gcacacgccg tcgcctgccg ggtgctggac    57120
ctcgtccagc gctggctcgc ggccccggcc gtcccggagg gtacccgcct ggtcgtggcc    57180
acccgtggcg cggtcgccgt gcgcgacgac gccgaggtga ccgacccggc cgcggccgcc    57240
gcatggggcc tgctgcgctc cgcgcaggcc gaggagcccg accggttcct gctgctggac    57300
ctggacgacg acccgcgtc cgcccgggcc gtgcccgccg ccctcgcctc cggcgaaccg    57360
cagaccgcgg tgcgcgccgg ccgggtgtac gtgcccccggc tggagcgggc cggtgccggt    57420
ggggacgggg cgttcgtccc gccggagcag ggcgcctggc ggctgggccg cggcgttgac    57480
cgtaccctcg acgccctggc gccggtgccc gccccggacg cgaacgcccc gctggaacac    57540
ggccaggtgc gggtcgcggt gcgcgccgcc ggcgtgaact ccgcgacgc cctgatcgcc    57600
ctgggcatgt acccgggcga ggccgagatg ggcaccgagg gcgccggcgt cgtcgtggag    57660
accggccccg gagtcaccgg ggtcgccgcc ggcgaccggg tgctgggcct gtggaacggt    57720
ggcttcggcc cggtgtgcgt ggccgaccac cggctgctcg cgccgatccc ggacggctgg    57780
tcgtacgccc gggccgcgtc ggtacccgcg gtgttcctca gcgcctacta cggactggtt    57840
gccctggcgg acctgcgccc gggagagaag gtgctggtgc acgccgccgc cggaggcgtc    57900
ggcatggccg cggtgcagat cgcccaccac ctcggcgccg aggtgctggc aaccgcgagc    57960
agcggcaagt gggacgtcct gcgcgccatg ggcatcccg acgaccatct cgcctcctcc    58020
cgcacctcg acttcgccac cgccttcgcc ggcgcggacg gtgcgcccgg tgccgatgtc    58080
gtcctcaact cgctcaccaa ggagttcgtg gacgcctccc tcggactgct ccctcccggc    58140
ggccggttcc tggagctggg gaaggccgat gtgcgcaccc ccgaacaggt cgctgccgac    58200
```

```
caccccggag tccgctaccg ggcgttcgac ctccacgagg ccggacccga tgaactcggc   58260
cggatgctac gggagttgat ggagctgttc gccagcggag cgctgcaccc gctgcccgtc   58320
gtcactcacg acgtacgccg ggccgcggac gccctgcgca ccatcagcca ggcccggcac   58380
accggaaagc tcgtcctgac catgccgccc gcctggcacc cgtacggcac ggtgctcatc   58440
accggcggca ccggcaccat cggcagccgc atcgcccgcc acctggtcac cgcccacggc   58500
gtgcgccatc tgctgatcgc cgcgcgcaac ggtccggacg gcgagggcgc cgcggagctg   58560
gtcgccgagc tcgccggcct gggcgccgag gccaccgtcg tcgcctgcga tgtcgccgac   58620
gcggacgcgg tccgccggtt gctcgccgac gtgccggccg agcgtccgct gacggccgtg   58680
gtgcacagcg ccggtgtcct cgatgacggc gtgctgccca cgctcacccc cgagcggatg   58740
tggcgcgtgc tgcggcccaa ggtggcggcc gccgtccacc tggacgaact cacccgtgac   58800
ctcgacctct cggcgttcgt cctcttctcc tccagtgccg gcctgctggg cagcccggcc   58860
cagggcaact acgcggcggc caacgccacg ctcgacgccc tcgccgcccg cggcggggcc   58920
ctgggcctcc cgtcggtgtc gatggcctgg ggcctgtggt ccgacacgag ccggatggcc   58980
gacgggctcg accaggagcg cctccagcgg cgcttcacac gcagcggctt cccgcccctg   59040
tccgcaggtc tgggcaccgc gctgttcgac gccgccctgc gggtggacga ggccgtgcag   59100
gtcccgttgc ggctcgaccc ggccgcgctg cgcgccaccg gaaccatcgc gcctctcctg   59160
tcggacctcg tcaccccccgc ctcggccgcc cgtccggtg cccgggcccc ggggcggccg   59220
cacaccccgc aggatgcgcg gcacaccggc gagtccctcg ccgaacagct ggcccggctc   59280
tcccccgagg agcgccacga ccagctgctc aacctggtgc gcgagcacgt ggccgcggtg   59340
ctgggccacg gctccgccgc ggaggtccac tccgaccggc cgttccgcga tgtgggattc   59400
gactccctca cggccgtgga gttgcgcaac cggatgggcg cggccaccgg ggtccggctc   59460
cccgccaccc tggtgttcga ccaccccacc ccggccgcga tggccacgca cctcgccggc   59520
ctactggtgc ccgagcagca ggccaccacc gtgccgctgc tggccgacct cgaccggatc   59580
gagaaggcgc tggccgccct cacccccgaa ggtctcgcgg cggtcgcgcc cgcacccgcc   59640
gcccgcgccg aggtcgccct gcgcctggac gccctggccg gtcgctggcg cgccctccat   59700
gacggcacca ccgatgccgc cgacgacatc gccgacgcgc tgagcgccgc cgacgacgac   59760
gagatcttcg cgttcatcga cgagcggtac ggcgagtcgt gaccactggc ccggcacccc   59820
gtcgccgtc ctcgaaggga agtaccacca tggcgaacga agacaagctg cgcacctacc   59880
tcaagcgcgt gacggccgag ctgcaccggg ccaccgagca gctgcgcacc ctcgacgagc   59940
gggcccatga gccgatcgcg atcgtcgggg cggcctgccg gctgcccggc ggtgtccgcg   60000
gcccggagga tctgtgggat ctgctgctcg cggagaccga cgcggtcggc caggccccgg   60060
ccgaccgtgg ctgggacgtg gcggcgatgt actcacccga cccggaccag gcgggcacca   60120
cgtactgccg cgagggcggc ttcgtccgcg gcatcgacca gttcgacccc ggcccgttcg   60180
ggatctcccc caacgaggcg ctcaccatgg acccccagca gcggctgctg ctggagacct   60240
cctgggaagc gctggagcgg gccggcatcg cccccgcagtc cctggccggc agccgcaccg   60300
gcgtgttcgc cggggcgtgg gagagcggct accagaaggg cgtgcaaggg gtcgatgccg   60360
acctggaggc ccagctcctg gccggcatcg tcagcttcac cgcggggccgg tcgcctatg   60420
ccctgggcct ggagggcccg gcgttgacga tcgacaccgc gtgttcgtcg tcgctggtgg   60480
cgttgcacct ggcggtgcag tcgctgcgcc ggggcgaatg tgatctcgcg ctggccggcg   60540
```

```
gcgccacggt catcgccgac cccgccctct tcgtccagtt ctcccggcag cgcgggctcg   60600
cccccgacgg ccgctgcaag gcgttcgccg aggccgccga tggcttcggc cccgccgagg   60660
gcgccggcat gctgttggtg gagcggctgt ccgacgctcg ccgccttggt cactcggtgt   60720
tggcggtggt gcggggagt gcggttaatc aggacggtgc cagtaatggt ttgacggcgc    60780
ccagtggtcc ggctcagcag agggtgatcc gtgaggcgtt ggcggatgcc gggttggggc   60840
cgggtgatgt ggatgtggtg gaggcgcatg gtacgggtac ggcgttgggt gatccgatcg   60900
aggctggtgc gttgctggcc acgtatgggc gtgagcgggt gggtgatccg ttgtggttgg   60960
ggtcgctgaa gtccaacatc gggcacactc aggccgccgc gggtgtcgcc ggtgtcatca   61020
agatggtgga ggccctgcgc cacggcacgt tgccccgcag ccttcacatc gacgctccct   61080
cctcgaaggt ggaatgggt gaggggggccg tggagttgct caccgaggca cggccctggc   61140
cccagcaggc cgaccggccg cgccgcgccg gcatctcctc gttcggcgtc agcggcacca   61200
acgcgcacgt cgtcctggag caggctccga ccgccccgga cgtccttacc gagccccggg   61260
cgtcggccgc cctcccggtc accgtcctcc cactgtccgc cgccggcgcg agcccctcc    61320 gcgaacaggc acgccggctc gccgaacacc tggtcgccca cgcggagatc accccgccc    61380 acgccgccta ctccgccgcc acgggccgcg ccacgctcgc gaaccgtgcc gtggtcctcg   61440
ccgacgaccg ggaaccgctg atcgcccggc tgaccgcgct cgccgagggc aggagagacg   61500
ccgacgtcac cgtcggcgag gcgggcagtg gccggccccc cgtcttcgtc tttcccggcc   61560
agggttccca gtgggctggt atgggcgccg aactgctgga gatggccccg gtcttccggg   61620
ccaaggcgga agagtgcgcg cgggcgctcg cgccccacct cgactggtcg gtgctcgatg   61680
tgctgcgcgg cgcgccggac gccccgccga tcgaccgggc ggacgtggtc cagccggcac   61740
tcttcaccat gatgatctcc cttgccgcgt tgtgggaggc ccatggcgtc cggcccgccg   61800
ccgtcgtcgg tcactcccag ggcgaggtcg ccgccgctta cgtggccggc atcctctccc   61860
tcgatgacgc ggcccgggtg atcgccgaac gcagcaggct gtggggccgg ctggccggca   61920
acggcggcat gctcgccgtc atggcccggg ccgaccgggt ccgcgagctg gtggagccct   61980
gggcacagcg gatctccgtc gccgcggtca acggccccgc ctcggtcacg gtcgccggcg   62040
acactgcggc gctggaggag ttcagcgagc ggctgtccgc cgacagggtg ctgcgctggc   62100
cgctcgccgg cgtcgacttc gccggccact cgcctcaggt ggaacagttc cgcaccgagc   62160
ttctcgcgac gctcgccggt gtccggccga ccgccgcccg gctgccgttc ttctccaccg   62220
taaccgccgg agcccacgcc cccgaaggtc tggacgccgc gtactggtac cggaacatgc   62280
gcgaaccggt ggagttcgag tccgccctgc gggcgctgct cgccagggt caccgctcct    62340 tcatcgagat gggcccgcat cccctgcttg gtgccgcgat caacgaggtg gccgaagacg   62400
agggtgtgca tgccaccgcg ctgtccaccc tctaccgcga ctccggcggc ctggaccggt   62460
tccgcgcctc ggcgggcgcc gcgttcgccc acggagtccg cgtcgactgg gctccgttct   62520
tcgaaggcac gggcgcccgc cgcgtgtccc tgcccaccta cgccttccgc gcgaccggt    62580 tctggctgcc gaccgccacc agccggcgcg ccgccgacgc tgcggccatc gccaccgcca   62640
ccgcctccga cgcctggcgc tatcgcgtca cctggacagc cctggagacc gtcgactccg   62700
gcgcgccgtc cggacgctgg ctgttggtgg agaccaccga cgccgcgccg ggcgaggccg   62760
acgccgcggc atcggcgctg ggcacggccg gcgcggtggt ggagcgctgg acgctggacc   62820
cgaccgtggc cacgcggggcc ggtctgaccg aacggcttgc cggactcacg gcggaacccc   62880
agggcctggc cggagtgttg gttctacccg gccaggcagc cgacaccgca ccggccgacg   62940
```

```
cctccccgct cgacgagagc acggccgccg tcctgctcgt gacccaggcc gtgacggacg   63000
gcgcgccgaa ggcgcggatc tgggtggcca ctcgggggggc ggtcgcggtc gagtccgatg   63060
acgtgccatg tgtgagggc gctcgggtgt ggggacttgg gctggtggcg gccttggagg   63120
caccgatgca gtgggtggt ctggtcgatt tgcccgtcaa gcctggagag gttgactggc   63180
gacgtcttgc cgccgccctc tccaccagta gcggtgagga ccaggtagcc atacgtggca   63240
cgggcaccta cggtcgccga ctgctgccgg cagcaccagc agcggtgcgc ggctcgtggc   63300
gcccgcgggg atgtgtgttg gtcaccgggg ggaccggtgg cctgggcggc cacgtggcgc   63360
ggtggttggc acgtgaaggc gcagaacacg tggtactggc aggacgtcgc ggtgcggagg   63420
cgccaggggc tggggagctg gaacaagagc tgctgggctt ggggacgaag gtgactgtcg   63480
tggcgtgcga tatcagcgac cggacgtcag tgatgcagtt gctggatgcg ataaaggggc   63540
tgggaacccc gctgcgtggg gtgttccatg ccgcaggagt tgcacaagtg acgccgttgg   63600
ccgaggtgga gcttgacgag gccgctgacg tgctggcagg aaaggcagtg ggggccgagc   63660
tgctggacga gttcacagcc gatgccgagc tggacacctt tgtactcttc tcttccggtg   63720
cagcggtatg gggcagcggc ggccagtcgg tctatgcggc agccaacgca cacctgaacg   63780 cttttggctga acgacgccgt gcacaaggcc gccccgccac ctccgtcgcc tggggcctct   63840
ggggcggcag cggcatgggc gcgggcgacg gcgtcaccga cttctatgcc gagcgcggac   63900
tcgcgcccat gcggccggat ttggggatcg aggccctgca cggagcgctc aaccaggacg   63960
acacctgcgt cacggtcgcc gacatcgatt gggagcactt cgtcaccggg ttcaccgcct   64020
tccggcccag tcccctgatc tccgacatcc cccaggtccg cgaactgcgg gccgccgcgc   64080
ccacgctcga cgcctcggac gaactgcgcg gccgtattga tgctgccctc acccccccgcg   64140 agcgcaccaa ggtgctggtg gacctggtcc gcacggtggc ggcagagatc ctgggccacg   64200
acgggatcgg ccgcatcggc cacgacgtcg ccttcaagga cctcggcttc gactcgctgg   64260
ccgccgtgcg gctgcgcggc cggctggccg agtcgaccgg gctcaccctg ccgcgacgg   64320 tcatcttcga tcaccccacc gtggaccagc tcggcgccgc gctgttggcg gagctgaccg   64380
acggaagcaa ccagggcggt gccgtggtcc cggcctgtgc cggcgggaac gagacgccgg   64440
cgcacacacc ggaggccacg gcccacgacg tcgagatcga cgaactcgac gcggacgacc   64500
tcatccggct ggcaacggcc ggcaaggaca acggtgatga cgctctgtca ggttagggag   64560
cccgcgacac cgcgaccacg cggtggaccg tcctacctgt agcgccccctt accgagagctc   64620 ccgaaccggc agcgtcccgc agcaccgacg acccccccca agagcgagca gacgaggaag   64680
ccgaagatgt caccctccat ggacgaagtg ctcggtgcac tgcgcacctc ggtcaaggag   64740
accgagcggc tgcgtcgacg caaccgcgag ctcctggccg ccacgcgtga gcccatcgcg   64800
atcgtgggca tggcgtgccg cttccccggc ggcgtggtca gccccgacga cctgtgggag   64860
ctcaccgcgg acggcgtcga cgcggtcacc cgttttccca ccgaccgagg ctgggacgaa   64920
gccgccgtct actcgcccga ccctgacacg cccggtacca cctactgccg cgaaggcggc   64980
ttcctcaacg gtgtcggcga cttcgatgcc gccttcttcg gcgtctcgcc caacgaggca   65040
ctggtgatgg accccagca gcggctgttg ctggagacgt cgtgggaggc actggagcgc   65100
gccggtgtcg tccccgcggc gctgcgcggc agccgtaccg gcgtgttcgt cggggccgcg   65160
cacaccggct acatcgccga caccgcgcgg gcacccgaag gcaccgaggg ctatctgctg   65220
accggaaacg ccgacgcggt gctgtccggc cggatcgcct acaccctggg cctggagggc   65280
```

-continued

```
ccggcgctga cgatcgggac ggcttgctcg tcgtcgctgg tggcgttgca cctggcggtg   65340
cagtcgctgc gccggggcga gtgtgatctc gcgctggccg gcggcgtcgc ggtcatgccc   65400
gacccgacgg tgttcgtgga gttctcccgg cagcgtgggt tggccccga  cgggcggtgc   65460 aaggcgtttg cggagggtgc tgatggtact gcttggggtg agggtgttgg tgtgctgttg   65520
gtggagcggc tgtccgatgc ccgtcgcctt ggtcactcgg tgttggcggt ggtgcggggg   65580
agtgcggtta atcaggacgg tgccagtaat ggtttgacgg cgcccagtgg tccggctcag   65640
cagagggtga tccgtgaggc gttggcggat gccgggttgg ggtcgggtga tgtggatgtg   65700
gtggaggcgc atggtacggg tacgcgcttg ggtgatccga tcgaggctgg tgcgttgctg   65760
gccacgtatg ggcgtgagcg ggtgggtgat ccgttgtggt tggggtcgct gaagtccaac   65820
atcgggcaca ctcaggccgc cgcggtgtg  ggtggtgtca tcaagatggt ggaggcgctg   65880
cgccatggca cgttgcctcg cactctccac gtcgatgccc cctcctcgaa ggtcgagtgg   65940
gattcgggtg cggtggagct gttgaccgag gctcgagcct ggccccggcg ggcggatcgc   66000
aagcgccgtg cggccgtctc cgccttcggc gtcagcggca ccaacgctca tgtcgtcatc   66060
gaggaaccac ctgccgtggc cgcgaccggc ggcagcgacg acgccgacca cgccccactg   66120
gccgcgaccc ccctcccctg ggtggtctcc gcccgctccg aggacgcgct gtgcggccag   66180
gccgaccggc tcgccgccgc cgtcgcccgc cggtggcccg agaacgacac cgacgccgct   66240
ctcaccactg tcgccgacgt cggccactcc ctggccacca ccagggaggc tctggatcac   66300
cgagtcgtct tgctggtgaa cgacgcccga gccgccgggg aggacctcgc tgccctggcc   66360
gccggtcgga caccggacac cgtggtaacc ggcgtcgccc ggcgcggccg cggcctggcc   66420
ttcctctgct ctggccaggg cgcccagcgg ctcggcaccg ggcacgcact ccgtacgagg   66480
ttccccgtct tcgccggggc cctcgatgag atcacctcgg agttcgacgc ccacctcgaa   66540
cgccccctgc tctccgtgct gttcgccgac cccgcttcac ccgacgccgc actgctggac   66600
cgcaccgact acacccagcc cgcgctgttt gccgtcgaga ccgcgctctt ccggctcttc   66660
gagagctggg gtctggtgcc ggacgtcctt ctgggcact  cgatcggcgg cctggtggcg   66720
gcgcacgccg caggggtgtt ctcgacggcc gacgccgccc ggctggtggc ggcgcgcggc   66780
cggctgatgc gggccctgcc cgagggtggc gcgatggtcg cggtgcaggc caccgagcag   66840
gaggccgccg ggctgaagtc cgtcgccgac ggcggcgcgg tcatcgccgc gctcaacgga   66900
ccgcaggccc tggtgctctc cggcgacgag gcggccgtac tggccgcggc ccgtgaactg   66960
gccgcccggg gacgccgtac gaagcgcctc gcggtgagcc atgccttcca ctcgccctgt   67020
atggacgcca tgctcgccga cttccgcgcg gtcgccgaaa cggtcgccta ccaccctccc   67080
cggctgccgg tggtctccga tgtgaccggc gaactcgcca ccgccgcaga gctgatggac   67140
cccgactact ggacctgcca ggtgcgggag ccggtgcgct tcgccgacgc cgtgcgcacc   67200
gcgcgggccc gcgacgccgc gaccttcatc gaactcggcc cggacgccgt cctctccggc   67260
atggcggagg agtgcctggc aggcgaggcc gacacagcgt tcgcccccgc gctgcgccgc   67320
ggacgcccgg agggcgacac cgcgctgcgc gccgccgcca tcgcgttcgt ccgcggcgcc   67380
gacctcgact ggtccgcgct ctacagcggt accggcgcgc gccgtatcga ccttcctacc   67440
tacgccttcc agcaccgccg ctactggctc gccccctccg actcctcgtc cacggccgcc   67500
cccgctacct ccgccccctc cgcaggaacc gccgtagcgg ccaccgcgac cgtggacgac   67560
gacgccctgt ggaccgcggt gcgcgcgggc gacgccgcct cggcggcagt acggctgggc   67620
gccgaaggcg caggcatcga ggaccacctg cacgcggtcc tcccgcactt cgccgcctgg   67680
```

```
cacgaccggc accgcacggc agcggagacc gccggactgc gctatcgcgt tgcctggcat   67740
ccgctgtcct cagacgttgt caggttcagc ccctcggatc gctggctgat ggtcgagcat   67800
gggcaccgta cggactccgc ggacgccgcg gaccgggcgc tgcgcgcggc cggcgcgcag   67860
gtgctccgcg tggtgtggcc cctggaggaa gacacgggag agccgcagga ggaagcgcgg   67920
gaccggaacg ccctggcggc ccggttggcc gaactcgcgc ggagtccgga gggcttggcc   67980
ggcgtactcg tgctccccga tacgggcgga gggatgctcg ctgggcgccc ggggctggac   68040
gagggaacgg cgatggtgct gcaggtggtt caggcaatgg ctgacgccgc gccgacggcc   68100
cgggtgtggg tggccactcg gggggcggtg gcggtcgagt ccggtgacgt gccatgtgtg   68160
atgggtgcgc gggtgtgggg acttgggctg gtggcggctt tggaggcgcc ggtgcagtgg   68220
ggtggtctgg tcgatgtgcc tgctgagcct ggagggcgtg actggcggcg tcttgctgct   68280
gtcatttccg gtagctgcgg tgaggaccag gtagccgtac gtggttccgg catctacggc   68340
cgtcgtctgc tgccggtggc gcccgaagtg gcgcgcagct cgtggcgtcc ccgtggatgt   68400
gtgttggtca ccggggggac cggtggcctg ggcggccacg tggcgcggtg gttggcacgt   68460
gaaggcgcag aacacgtggt actggcagga cgtcgcggta cggaggcgcc aggggctggg   68520
gagctggaac gagagttggt ggggctgggg gcgaaggtga gttttgtggc gtgcgatgtg   68580
agtgatcggg cgtcggtggt ggagctgctg gatgggattg aggggttggg ggtgccgctg   68640
cgtggggtgt ttcacgccgc gggcgttgcg caggtgacgc cgctgggtga agtgggcgtt   68700
gctgaggctg ctgatgtgct ggcagggaag acgatggggg ccgagctgct ggatgagctc   68760
acagcgggtg ccgagctgga tgcctttgtg ctgttctcct ctggtgcggc ggtatggggc   68820
agcggtgggc agtccgtcta tgcggcgccc aatgcgcacc tggatgcgct ggccgcacgg   68880
cgccgtgcgc aaggccgccc cgccacctcc gtcgcctggg gcgtctggga cggcaccggc   68940
atgggcgagc tcgcccccga gggatatctc gaccgccacg gcctgacccc cctccgcccg   69000
gagacagcca tcgccgccct gcgccaggcc atcgacagcg gcgacgccac ggcgaccgtg   69060
gccgacatcg actgggaaca gttcgcccag ggcttcaccg ccttccggcc cagcccctg    69120 atctccgaca tccccgccgc tcgtacggcg ctcgccgtcc cgcgatccgc cgacggcacc   69180
gccaccgcac ccgacctcgt acgggcgcgg cccgaagacc ggccgcggct cgccctggaa   69240
ctggtgctcc gccacatcgc cgcggtcctc ggccacaccg acgagagccg ggttgacgcg   69300
cggacaccct tccgggacct cggcttcgac tcgctggcag cggtgcggct cgccgccaa    69360 ctggccgagg acaccgggct cgacctgccc ggcgccctcg tcttcgacca cgaggacccg   69420
gccgcgctgg cggaccacct ggccaccctg gccgacgccg gaccaccgg gcgcaaccag    69480 ggtgccgcac cggccgaaag cgggctgctc gccggcttcc gcaccgccgt cgaacagggc   69540
agatccgccg aggccgtgga actgatggcg tccctggcca cgttccgcac cgcgttcacc   69600
cgggaagact ccggcaccac gtgccccgcg ccagtgctcc tcgcggccgg accagccacc   69660
cgacccacgc tgtactgctg tgccggcacc gcggccacct cgggcccgg cgagtacgcc     69720 gccttcgccg acgggctgcg cgacagccgc acaacggtcg tcctcccgct gtccgggttc   69780
ggcagcccgc cggaaccgct gcccgcctcc ctcgacgccc ttctcgatgc acaggccgac   69840
gccctgctgg agcacgccgc gggcaagccg ttcgcgctcg ccgccactc cgccggcgcg   69900 aacatcgccc atgccctggc ccaccggttg gacgagcgcg gcaccggccc cacggccgtc   69960
gtgctgatgg acgtctaccg cccagaggat cccggcgcga tgggcgtctg gcgcgaagac   70020
```

```
ctgctgcgct gggccctcga ccgcagcacc gtcaccctgg aggaccaccg gctcaccgcc   70080
atggccggct accaccggct gctgctcgac accaggctca ccgcactacg cgccccggtc   70140
ctgctcgtcc gggcgtccga ccgctgcgc gagtggcccg ccgacgcggg ccgaggcgac    70200
tggcgctccc aggttccgtt cgcccggacc gtcgccgagg tgcccggcaa tcacttcacc   70260
atgctcaccg aacacgcgcg gcacaccgcg tccgtcgtgc acgactggct gggtgccgac   70320
ccgcggccag ccgagcccac cctgctcacc ggaggaaaac actgatgtac gccaacgaca   70380
tcgcggccct ctacgacctg gtccacgaag ggaagggcaa ggactaccgg caggaggccg   70440
aggagatcgc ccagttggtg cgagcccacc gcccggccac ccggtcgctg ctcgacgtcg   70500
cctgcggaac cggccagcac ctgcgccacc tcgacggcct cttcgaccac gtcgagggct   70560
tggagctctc ccaggacatg ctggccatcg ccatcggccg gaacccggat gtcaccctcc   70620
acgagggaga tatgcgctcc ttcgcgctgg gccgccggtt cgatgcggtg atctgcatgt   70680
tcagctccat cggccattta cggaccaccg acgaactcga cagcaccctg cggtgcttcg   70740
ccggccacct tgagcccggc ggcgccatcg tcatcgaacc tggtggttc cccgactcct    70800 tcacccccgg ctacgtcggc gccagcgtca ccgaggcggg cgagcgcacc atctgccggg   70860
tctcgcactc cgtgcgggag ggggacgcca cacgcattga ggtgcactac ctggtcgccg   70920
agccaggcgg cggcattcgc cacctcaccg aggaccacac catcaccctg ttcccacgcg   70980
ccgactatga gcgcgccttc gagcgtgccg gctgcgacgt gcgctaccag gagggcggct   71040
cctccggccg cggactgttc atcggcagcc gccgctgacg cggattccgc cccgagacga   71100
cgagaggaac ccatgccaat ccctgccacg gcgccggcgc ccgtgaacgc cggcacccgg   71160
gagctcggcc gccggcttca actgaccccgt gccgcgcagt ggtgcgcggg taatcagggc   71220
gacccgtacg cgctgatcct gcgcgccacc gccgaccccg cccgctcga acgggagatc    71280 cgcgcccgcg gaccatggtt ccgcagcgag ttgaccggcg cttgggtgac cgcggatccc   71340
gaggtggcgg cagccgcgct ggccgacccg cgcctttgca cgctcgaccg cgccggccgt   71400
cgtccggacg cggaactgct gccctcgca gaggctttcc cctgccatga gcgtgcagag    71460
ctcgcccggc tacgggcgct ggccgccccg gtgctgagtc gctgcgcccc ggccgaggcg   71520
ccctgcgagg cgcgtaccgc cgctcgtcgg ttgctccgcc gtctccttcc ctccgacggc   71580
gccgggttcg acctcgtcac cgaggtcgcc cggccgtacg ccgtcgggct ggtgctccgg   71640
cttctcggcg tgccggactg cgaccgcgac accatgggc gggcgctcgc cggctgcgct    71700
ccccaacttg acgcccggtt ggccccgcag accctggctg tcgctcggga gtccaccgac   71760
gccgtccaga ccttggccga ccatgtcccg gaactcgttg ctgagaagca gcgggccgtc   71820
gagagcgccg agccccggcc cgacgatgtt ctcgccctcc tcctgcgcga cggtgccgcc   71880
ccccgcgatg tcgagcggat cgcgctgctc ctcgccatcg gcaccccga gcccgcggcc    71940 accgccgtcg cgaacacggt gcaccggctg ctgaaccggc cggggagtg gggacgtgtc   72000 cgccggaccc cggccgccgc gcgggccgtc gaccggaccc tgcgcgaccg gcccccggcc   72060
cgactggaga gcagggtcgc cagcaccgac cttgagctcg gtggttgccg gatcgccgcc   72120
gacgaccacg tcgtggtgct ggccgccgcg gggcgggacg ctccggggcc cgagccgctc   72180 ggcggccgg acggaccgca cttggccctc gccctcccgc tcatccggct ggccgccacc    72240
accgctgtcc aggtcatggc cggacgcctg cccggactga gggtcgagga cgagcctctg   72300
acccggccgc gctccccggt cgtatgcgcc tgtgcccgct tccgggtcca cccgggatga   72360
ccctgccgcc cgtacacccc ggcccgaact ggagtcaccg tgcgcgtcct gctgacctcc   72420
```

```
ctagcccaca acacccacta ctacagcctg gtgcccttgg cgtgggccct acgcgcggcc   72480
gggcacgagg tgcgggtggc gagcccgccc tcgctcaccg atgtcatcac ctccaccggg   72540
ctgcccgccg tccccgtcgg cgacgaccag cccgccgccg aactgctcgc cgagatgggc   72600
ggcgacctcg tccctatca gcggggcttt gagttcgccg aggtggagcc cgcccaggag   72660
accacctggg agcatctgct cggccagcag agcatgatgt ccgccttgtg cttcgcgccg   72720
ttcagcggcg ccgccacgat ggacgacatc gtcgacttcg cccgcgactg cgtcccgac    72780 ctcgtcgtat gggaaccctg gacctacgcc gggccgatcg cggctcgtgc ctgcggcgcc   72840
gctcacgcgc gtatcctctg ggccccgac gccatcggac ggtcccggcg gcgcttcctc    72900
gaagcgctcg aacagagtgcc ggaggagctg cgcgaggacc ccatcgccga atggctcggc  72960
tggacgctgg accggtacgg gtgcgccttc gacgaacgcg acgtgctcgg ccactgggtg   73020
atcgacccgg ggccccgcag tacccgactg gacctgggac agaccaccggt ccccatgtgc  73080 tacgtgccct ataacgggcg cgccgtcatc gaaccctggc ttgccgagaa gcccgagcgc   73140
cctcgcgtct gcctcactct cgggatctcc gcccgcgaga cctacggccg cgacgcggtc   73200
tcctactccg agttgcttca ggcgctgggc cgcatggaga tcgaggtggt ggccacccctc  73260 gatgcctcgc agcagaagcg cctcggcagc cttcccgaca acgtcgtgcc ggtggacttc   73320
gtgccgctcg acgcgctgct gccgagctgt ccgcgcatca tccaccacgg cggcgcgggc   73380
acttggtcca ccgccctgct ccacggcgta ccgcagatcc tgctgcccgc gctgtgggac   73440
gcgccgctca aggcccagca gctccagcgc ctgtcggccg gactcaacct gcccgccgcg   73500
accctcacgg cgcgccgctt ggccgacgcg gtgcacacgg ccgtacacga tcccgcgatc   73560
cgggcgggcg cgcggcggct gcgcgaggag atgctcgccg accccacgcc cgccgcaatc   73620
gtccccacgc tggagcgcct caccgccctg caccgggcgg cctgacgcaa cgttcgaacg   73680
gagccgatcc accatgcccg acagtcatgc cctgagcgag ctgctcgccg cgatccgcgc   73740
gcccgaccac accccgcgagg acatcgccgc gctgcccctg cccgaatcct tccgggccgt  73800
gaccgtccac aaagaggaca ccgagatgtt ccgcggcatg accagcgcgg acaaggaccc   73860
gcgcaagtcg ctgtgcgtcg acgaggtgcc ggttcccgaa ctcgggcccg gcgaggccct   73920
gatagcggtg atgccagct cggtcaacta caacaccgtg tggtcgtccc tcttcgagcc   73980
gatgccgacc ttcggcttcc tggagcgcta cgggcgcacc tcgccgctgg ccgctcgtca   74040
cgacctgccg taccacatcc tcggctccga cctggccggc gtggtgctac gcaccggccc   74100
gggggtgaat gtttgggcgc ccggcgacga ggtcgtggcg cactgtctgt cggtggagct   74160
ggagagcccg gacggacacg acgacaccct gctcgacccg gcccagcgga tctgggcttt   74220
cgagaccaac ttcggcggcc tggccgagat agccctggtc aaggccaacc agctgatgcc   74280
caaggccgca cacctcacct gggaggaggc cgccgcaccg gtctggtga actccaccgc    74340 ctaccgtcag ctggtctccc gcaacggcgc cggcatgaag cagggcgaca acgtgttgat   74400
ctggggcgcc agcggcggtc tgggctcgta cgccacccag ctcgccctcg ccggtggggc   74460
caaccccgtc tgtgtggtct ccaaccagcg caaggccgag gtgtgccggg ccatgggcgc   74520 ggggggcgatc atcgaccgct cggccgagga ctaccgcttc tggagcgacg agcagaccca   74580
gaatccgcgg gagtggaagc ggttcggtgc ccgtatccgg gagttgaccg gtggtgagga   74640
cgtggacatc gtcttcgagc atcctggccg ggagacgttc ggggcgtctg tctacgtcgc   74700
ccgccggggc ggcaccatcg tcacctgcgc ctccacttcc ggctaccgtc acgagttcga   74760
```

```
caaccgctat ctgtggatgc acctcaagcg catcgtcggc acccacttcg ccaactaccg   74820
cgaggcatgg gaggcgaacc gcctcgtcac caaagggaag atccacccca ccctctcctg   74880
cacctacccg ctggccgaca ccgcgctcgc cgtccacgac gtgcaccgca acgtccacca   74940
gggcaaggtc ggcgtgctgt gtctggcccc gatggagggt ctgggcgtgc gcgacgagga   75000
gatgcgcgcg cagcacctcg acgcgatcaa ccgattccgc tgaccgctcc tttgtcccga   75060
ggcatatccg ccgctcgtcc cggaggacac gtcaaaggag gggcccacag tccgaaagcg   75120
gtttcatgca ggcgctcggc tggggtttcc cagccgagcg ttgtgcgtgg gctttggtcg   75180
cgatggccgc cggctgttgg agggccagga tgattgccgt gatgcgcgag ctgagcaggg   75240
gcctgttgtc ttcgctggtg tggtagcggg agacggagca cttcaccttc cgagtgctga   75300
tccgggggcg gcgaaccggc agtgcctcgg cggtgaggat gcgggcgaag tccgtgtcag   75360
gccagagggt gtcgtccagg acgccgcagg cgttctggag gtgctcgcgc gcggtctgca   75420
gggcgacggt gagctgatgc ggtccggttc caggccgccg ccgaagtgcc ggcctcgaag   75480
ggccggcact tcggcggtga ccgtacccg atccgtcgc acggccgctc tactcggctt     75540
gatcagcagc atgccgtggt ggttgcggtc gtcatggtgt ccaacttgtc cttggattcc   75600
ggcatttgat gttcatcggt tcctcgcagg ccacctgacc cacgtaagca cccttcgggg   75660
gccgggcaag aagcccgtat ccggccggtt gtccggaacg ccagcggaga cgccggcctt   75720
ctcctccgcg gagcccttgg gtttctcctc cgggcttcac accccgccga taccggcggc   75780
gcataccaga gtggggacgg gccctgagca ccggcccgga accatcctgt cgacagcaac   75840
tgtcgtccct cttcagcgag gcgtccgagt cgtcggccgc ggcaccgggt cgcggtactt   75900
actcccgtcg tcgggcgagg gtgatcccat cggcgacggt cagcagagcg atgtccacgc   75960
gctcgtcgtc gcgcagcagg tcgttgaggg tgcgcacggc cactgtgtcg gggtcgtcgg   76020
cggccgggtc ggccactcgg ccgaagaaca gggtgttgtc gatcgccacc agcccgccgg   76080
ggcggaccag tgccagcgcc tgctcgtagt agtgcaagta cccggccttg tcggcgtcga   76140
cgaagaccag gtcgaacgcg ccgtccccgt cgcgctcccg cagctcggcg agtgtccggg   76200
cggcgtcgcc gatgcgcagg tcgatcaggc cgtccacccc ggcgcgttgc cagaacgggg   76260
cgccaatccc gggccacttg tcgctgatgt cgcaggtgac gatccggccg ccggcaggca   76320
gtgcccgtgc catgcacagc gtgctgtaac cggtgaacgt cccgatctcc agcacccgcc   76380
gggcgccgac gagccggatc agcagaccga ggaactgcgc ctcctcgggc atgatctgca   76440
tggcacgccc cccggggagc tgcgcggtca tgtcgtgcag ctcccgcagc aggccgtctt   76500
cccgcagagc gacgcttcgg gcgtagtcca gcagcgcggg gctgagagtg gtctggtctg   76560
ccacgctcac agtcctttcc aggaaagctt gttcggtgac gtcaggcgcg ggtgagtttc   76620
ggagcctcgt cggttgcggg gtctggtgcg gtggcgaccg gcggcggcg ccgagcaga    76680
cgcatgcagg ggttctccac gacggtgtgc agcagcccac cggccacgat cgcgaccgcc   76740
agcatcgcca gggccagcgc tcccgcgctc gcggtgctcc actggcgcgc gtagcccagt   76800
tcgccgccca tcagccggtg cccgtagcgg atgaccatga agtgaaccag atagaaggcg   76860
aaggaccact cgcccagccg caccagtacc gccgagcgca aaccggtgcg caggccctgc   76920
acatcggcat tggccaaagc ggtgatcagc agggcggcgg gcacgatgga gcacgcggcg   76980
atggtgaaca tcgggggcac cacctgggtg acgccgtagg ccgcggcgag cagcagcgcg   77040
gaggacacca ctccggggcc ccgccacacg cccgtgcgca ggatcagcgc catcacgatg   77100
ccgaggacga actccagcat ccgcaccggc ggcagccagc aggcgaacca cagctcgttg   77160
```

```
agcggcatcc cggggccgt ctcggcgctc gccgggaact ggctcgtcac gaacggtaca   77220
caaatcacgg ccgcggcaat accggcggca caccaccaca gccgccgtac cggaatcttc   77280
cgcaccagcc gataccacag cgggaacgtc agatagaaag cgaattcaca ggagagcgac   77340
caactcgggg tgttgaaccc ggcgataatc gtgggttcgg gaagccagga ctgcaccagc   77400
agaagatcgg gaaccagacc gtcccatacg gaaccaccgg gcagagtcgg ctccgcgagg   77460
gagaaaatga tgacgcccgc tatgaggaaa gttacgaggt gcagcgggta gatcttggca   77520
aatcggcgcc gccagaaagt cgtgacgagg tccttgtcac gggccgacca cgccagaaca   77580
aaaccgctga gcaggaagaa gaccgagacc gcgatcgaac cgagcgtggt gatgtgtagc   77640
agcgcggttc cgacctgctg gtcagcgaag aattgctgct gggcaatgtg acaggcgaat   77700
accgctaagg ccgcgaacca gcgaaggccg gtgagcgacg gcaggcggac gacacgaggc   77760
ggcatcgatt gctcgctctc cttctggagg gggaaaagtg aggccgggtg aacgcagaga   77820
aacggtcagg gcagtctgcg gcgcgagcaa ttcggccgac aacgcggaga tgacacagtc   77880
aacggtcgac ggtacggaac gccgggcgtc cggtgaacct gacaaagtcg atcttgccgg   77940
tgatgggagc ggttcctagc attggccggc gcagtcccac gctgtcgcga cacccccaa    78000 cacgtgtgtc gcccgccccc acgattcgga aggcagtgat gagaacaccg actgatgacc   78060
gcgcccccgt acccgccgac gaggccgtcg atctgatgga cccgcgggtt ctcaacgatc   78120
cgttcggcac cttcgcccgg atcagggaac aggcgccgtt ggtgcgcggc cggtacccct   78180
ggggcgaccc cttctggatg gtgacgcgct acgtcgacgt caaggcggtg ctctccgatc   78240
cggacctggt gaacaacccc cggaacgtac cggggatgga cctgccccat ctcttcgccc   78300
agggcctcga cgaggccgac tttccccagc ggtacgcccg ctatctgctc gacagtgtcc   78360
tgttccagga tggccaggac catgcgcggc tgcggaaggt gtccgggcgg gccttcaccg   78420
cgcgccgcgt cgcccaacta cggcccacca tggcggcgat ggtcgaaggg ttgatccggg   78480
cactgccggg ccgcgcacgc aacggagcgg tcgatctcct ggagcacttc gcctatccga   78540
tatccatcgg caccatctgc gagatcgtcg gagttcccga ggccgagcgg gagcagtggc   78600
gggtctggag ctcggccttc tacaccatgg accgcgcgct cctggagccc gcggtgggcg   78660
gcatggccga ccgcctgcac accatgatcg aacagcgtcg cgccgagccg accggcgatc   78720
tgctcaccgg cctggtccag gccgagggcg acgacgggga gcggctcacc gaggtggaga   78780
tcgtcgccct cgtcctcgcc ttcatcaccg ccgggaacga ggccaccgcc cagctcatcg   78840
gcaacggtgt cgccgccctg ctcactcacc ccgaacagct cgcgctgctc cgctccgagc   78900
gcgagctgct tccgggcgcg gtccacgaga tcatgcgctg gtgcggcccg gtgcagatca   78960
cccaaccgcg cttcgccacc cgcgacctcc gggtcggcgg tatgccggtg cgcaagggcg   79020
agcaggtcat ggccgtcata ggcgctgccg gatacgatcc ggcagtcttc cccgcccccg   79080
agcggttcga catcacccgg acgccccagc tccgccgtga cacccatgtc ggcttcgggt   79140
tcggcccgca ctactgcctg ggcgcggccc tcgccctcca ggaggccgag gtggcgatcg   79200
acgcactgct gcaccacttc cccggcctcg cctggccgt ggcgccgtcc gacctggagc   79260
gccagctctt ccccggcgcc tggcggctga gcgccctgcc gctgcggctc tgacgccctc   79320
gccccggcgc gccacggggc ggtacccggc catgccgag caccgccccg tggtgcacgc   79380
cgcaccggat tcacgccgtg gcgaatgcgg tgatccggcc ctcgcgcagc gacagatgcg   79440
agccgctgaa ccgggaccgc atccggcggt cgtgggtgac gaccaccacg gcgccctggt   79500
```

```
agtccgccaa cgcctgctcc aactcctcca cgagcacggg ggagaggtgg ttggtgggct   79560
cgtccagcaa cagcaggtcc accgggtcgc tcaccagccg cgcgagctcg atccgccgcc   79620
gctgcccgta cgagaggtcg cccacccgct gttccagttc cgccgggctg aacaggccca   79680
gcgagagcaa ctcctcggtg tggtcgtcga gatggccggg gcggccgtgc gcgaatgcct   79740
ccgtcacggt cagcccggcc ggccagggca cctgctcctg ccgcagatgc cctacgcgcc   79800
cggacacgtg caccgtcccg ctgtccggtg ccagttcccc ggccagcacc cgcaacagtg   79860
tggtcttgcc cgccccgttg ggccggtga tcagcagccg ctcgccggga tgtacggata   79920
ccgacgccac ctccagccgg tccccgacgc gcacctcgga gagctcggcc accggggcct   79980
gcgccgttgc gtccgggccc gcggtggcga tgtgggccgt gaaggtcagc gggtcggccg   80040
gcggggcaac ggggttctcc gtcagtcggg ccatccgttc cttggcgttg cggatgcggc   80100
tcatggcgcc gtgcccgcgg cctcgcgacc ggaaggcacc gtggccgaag acggcgaacg   80160
gcaccttgcg cggaatgttg tccagtcgcg acacgttgga ggtgaccagc tcccggttgc   80220
ggtccagctc ggcgcgccac tcctcgtact cgcgcagccg ccgctcacgc tccgcggcct   80280
tcgcggtgag gtagccctcg tagccgttcc cgtagcgact caccttcccg gcgttcactt   80340
ccaggatggt ggtggtgagc cgctccagga agactcggtc gtgggtgacc gcgatcacgg   80400
tgccgcgatg tgcccgcaga tggttctcca gccagctcac cgcctggtcg tccaggtcgt   80460
tggtcggctc gtccagcgcc agcagttcgg gcgccgacgc cagcgtcgcg gccagggcca   80520
gccgcgagca ctcgccccg gagagggtgc ccagccggcg attgcggtcc aggctcggca   80580
ggccgagccc gtgcagtgcg atgtccaccc gggcgtcggc ctcgtagccg ccgcgagcct   80640
ggtactgctc gaccaggtcg gcgtaggttt ccagaagagc ggccagttcc cggtccgggc   80700
ctgcccgata gggccgttcg gccagctcgg cctcggcccg ccgcaccccc gcctcaatct   80760
cgcgcagctc gaccatggca aggtcgacgg cgtcttgaac ggtggcctcg ggggcaagtt   80820
ccagtgtctg cgccagatag ccggtgccgc cgggagcgac cacggtgacg gccccgttgt   80880
cggcctgctc ccgcccggcg atcagcttga gcagggtgga cttgccggag ccgttgtcgc   80940
cgatgatgcc gaccttctcg cccggcttga tggtgaaacc gacccggtcg agtaccacac   81000
ggtcgttgta gcgcttggtg atgtcatgca gggctagttg cgcggtaagc atgtgaggtc   81060
ctcctgaata acggccgagg atggatgggg atccgcgcac acgacagact gtccgggcgc   81120
gatggcccaa cagagaacgc cgatacggcc gatgacgtcg gaacggcgta tttcagaagt   81180
gcacggatgg atgcggcgga gcagagctcg acgcggcgac accctcaact attacagaga   81240
acccataaca tccactctat gcggcaaatg actgtcgtgg caagcgtgtc gaccatgaag   81300
agacggcgac gagtgccggg tcgcatcgca ccggagtgca atccaatgcc cggaacctcc   81360
cgggtcatcc ggaggattcg ccggaagtgc ctgttcaggc ggggggtcgcc atcaaatccc   81420 gaagggctcg ccggtcgtga tcgcgccttc aggtggctga attgcatcag ggttgtggac   81480 cttttgatgga ctttcggatc atggataggt aggttcggcg gggtgaagtc aagacctccg   81540
atgtcgccga tatctgcatc cgctcccgcc gtgtcgcgca gcaccgctcg gcgggaattg   81600
gggcaaaatt tcttccgatc ggcagccgct gcctgccgtt tttccgatca actcgatgct   81660
ttttgtgccg acttgcccgg ctccttagcc gacgttttaa ccgttgagat aggcgcggc   81720 tccggccggg tgaccaaggc actggcgtcg gctggacgct ccttactcgc ggtggagatc   81780
gatgcctatt gggcacgtcg gctgaccgcc gaatcacttc ccgatgtcac ggtggtgaac   81840
gaggactttc tgaacttgca gctgcccagg cagccaatcc gtctgattgg caatcttccc   81900
```

```
tttgtgtccg gaaccaagat actgaggcgc tgcctggagc tggggccgaa tcggatgtgc    81960
caggcggtat tcctgcttca gcgtgagtat gtgggcaagc ggaccggtgc ctggggcggc    82020
aatcttttca cgcccagtg ggagccgtgg tatacgttcg aagggggct ggctttctcc     82080 cgtaacgaat tcagccctgt accgcgcgcc gacacccaga cgctggtggt gatgccgcgc    82140
cgtcggccgt ccgtgccctg gcgtgagcgc accgactatc agcggttcac ccaacagatc    82200
ttcgacactg gtcagatgac gatcggtgag gccgcccgga aggtgctgcg ccgcggccat    82260
gcacagttcg tgcgcagtgc cggggtgcgg ccggccgatc gagtcaagga tctcacggtc    82320
cgggactggg ccgcactgtt ccgcgcgaac ccttagcggg ccgactgatg gcgcctcccg    82380
ggccctgccc ggggggcga accgtctgtg tacgaaaggc tgtatacagg caagttctct    82440
cagggagggt cctcacgatg cggggatcc atcagagggc cgcgcttcct tgagcttgcg    82500
cagcagctcc cgcttctgct cctgcggatt gacgccgcca ccgtgagctc cgcccgttct    82560
cccgccgcgc atcgccttgc gggagaggtt ggcgcgggtt ccgccgagac ccagcatgtt    82620
tcctgctctc ctggccatgg gtttctcctt tcgccgatga gacgagtcga tccgtctcgt    82680
tgtgctcacg agtctgggcg atgcgtctcg tcatgtcaag acgatacgta tcgcctcgcc    82740
atgctctacg ctgtgcgtca tgccctccaa ccgcgtcccc gaagccgtcc accgccctcg    82800
ccgcacccac agcgcgatcc tgggcgccac gctggaactc gttcaggagg tcggatatcc    82860
caagctgacc atcgaaggcg tcgccgcccg ggcggcgtc ggcaaacaga ccatctaccg    82920
tcggtggccc tccaaggcgg cgatactccg ggacgcggtc gtctgcctga ccgaggacat    82980
cgcgcggacc gcgaccgcga tccccgacac cggcgatctg gaggccgacc tcaaggccgt    83040
tctgcggtcc accgtcgacg tcatgagcca cccggagtac gacgtgcccg cccgggccct    83100
cgccgccgcc ggtatcgctg acccgaagct cggcgaggag ctggtgacgc gcctggtgga    83160
gcctcaatta cggctctgct tggagcgctt gggctccgcc cggagtccg gtcagattgc     83220 gccggacatc gatacgcgga tcgccgtgga gatgctggcg ggcccatcg cccatcgctg     83280 gctgctgaag agcgcgcctc tcacccacga gtacgccgag gccctcgtcg agctcacgct    83340
ccggggcctg gcgccgcgct gagggcgcgc cgccggccgg cctgacaccg gaaacggctc    83400
ggcaggcccg cccgcgacgt cgaagcgccc ccgtcgccca ctcacaccac aaacggaacc    83460
tcgcgttcgc caaccgtggt tccgtcacgc ttcatcacca gcgggctcgg actcgccgct    83520
cttgctcgtg gaagtccttc gattcctgtg aaacaccgcg agcaccgtgt gccggcgcgt    83580
cttccgcctt ctctgcaccc agtgaagtcc ggcgaaccct gtaggcggag gaggacctgg    83640
gtgccgtcga agaccaaggc cgatccgtac acggtgatcc gccccgacgc acgctccggt    83700
ccgtcgaatc gagctcttcg gcggaagcgc gatgtcggca tcgaaggtcg tcggatctgc    83760
catgcgcctt cgtcaaggag tggggccgat cctcggcagc accttccgtc tgctcatcca    83820
ccaggagcag acgatgggca tcgcccggga actggccggc tacccccctcc gcggcgccga    83880 cctgctgtgc cgtgcgattg agcaaccggt gcgtcgtgga ccacgacc gtgagtacca     83940 ccaagcggtg gtactcgagc cggacgtgga agatctccgc gaggccgcca gagcatggga    84000
gggcctgcac gggattccga cccagcctgt gagaaatcgt gagattcgag agcgcgcggg    84060
gcgtgagcga gatgtcgacg cgcccctgc aatgccgctt ctccgggccc gaaggcccg     84120 gccctgatcg tgagcaaggc accgcgtccg taccagccga tcatggtgag ctacgacgag    84180
ccgggtcgcc tggtcgtcca cgtcgtctcc acggtgagca tctgacctac atggatcccg    84240
```

-continued

```
tttcgggcgc gatcggcggg ccgtgctctg acggctcttc ctgacccgag tgtcaggacc    84300
gcgtcacggc gtcggttagc gtgtcggggt gagcgagaag accctgcagc accggatcga    84360
cggtcccgac ggcgcccccg tgctcgtcct gggggccgcc ctcgggacga cctggcacat    84420
gtgggatc                                                              84428
```

<210> SEQ ID NO 2
<211> LENGTH: 4511
<212> TYPE: PRT
<213> ORGANISM: Streptomyces mycarofaciens

<400> SEQUENCE: 2

```
Met Leu Val Ser Gly Asp Leu Val Thr Ser Arg Ile Asp Asp Arg Ser
  1               5                  10                  15

Asp Ala Ile Ala Val Val Gly Met Ser Cys Arg Phe Pro Gly Ala Pro
                 20                  25                  30

Gly Val Glu Glu Phe Trp Lys Leu Leu Thr Asp Gly Thr Glu Ala Val
             35                  40                  45

Ser Arg Ala Ala Asp Gly Arg Arg Gly Met Ile Glu Ala Val Gly
         50                  55                  60

Asp Phe Asp Ala Thr Phe Phe Gly Met Ser Pro Arg Glu Ala Ala Glu
 65                  70                  75                  80

Thr Asp Pro Gln Gln Arg Leu Leu Leu Glu Leu Gly Trp Glu Ala Leu
                 85                  90                  95

Glu Asp Ala Gly Ile Val Pro Gly Ser Leu Arg Gly Glu Ala Val Gly
            100                 105                 110

Ile Phe Val Gly Ala Met His Asn Asp Tyr Ala Thr Leu Leu His Arg
        115                 120                 125

Ala Gly Ala Pro Ala Gly Ala His Thr Ala Thr Gly Leu Gln Pro Ala
    130                 135                 140

Met Leu Ala Asn Arg Leu Ser Tyr Val Leu Gly Thr Arg Gly Pro Ser
145                 150                 155                 160

Leu Ala Val Asp Thr Ala Gln Ser Ser Ser Leu Val Ala Val Ala Leu
                165                 170                 175

Ala Val Glu Ser Leu Arg Ala Gly Thr Ser Arg Ile Ala Ile Ala Gly
            180                 185                 190

Gly Val Asn Leu Ile Leu Ala Asp Glu Gly Ser Ala Thr Met Glu Arg
        195                 200                 205

Leu Gly Ala Leu Ser Pro Asp Gly Arg Cys Tyr Thr Phe Asp Ala Arg
    210                 215                 220

Ala Asn Gly Tyr Val Arg Gly Glu Gly Gly Ala Ala Val Val Leu Lys
225                 230                 235                 240

Pro Leu Ala Asp Ala Leu Ala Asp Gly Asp Pro Val Tyr Cys Val Val
                245                 250                 255

Arg Ser Ala Ala Thr Gly Asn Asp Gly Gly Pro Gly Leu Thr Ser
            260                 265                 270

Pro Asp His Glu Gly Gln Glu Ala Val Leu Arg Ala Ala Cys Ala Gln
        275                 280                 285

Ala Gly Val Asp Pro Ala Lys Val Arg Phe Val Glu Leu His Gly Thr
    290                 295                 300

Gly Thr Pro Val Gly Asp Pro Val Glu Ala Arg Ala Leu Gly Ala Val
305                 310                 315                 320

His Gly Ser Gly Arg Pro Ala Asp Ala Pro Leu Leu Val Gly Ser Val
                325                 330                 335
```

-continued

```
Lys Thr Asn Ile Gly His Leu Glu Gly Ala Ala Gly Ile Ala Gly Leu
                340                 345                 350

Val Lys Ala Ala Leu Cys Leu Arg Asn Arg Thr Leu Pro Gly Ser Leu
            355                 360                 365

Asn Phe Val Thr Pro His Pro Ala Ile Pro Leu Asp Arg Leu Arg Leu
        370                 375                 380

Lys Val Gln Thr Thr Pro Thr Thr Leu His Pro Asp Pro Asp Gly Ser
385                 390                 395                 400

Pro Leu Leu Ala Gly Val Ser Ser Phe Gly Ile Gly Gly Thr Asn Cys
                405                 410                 415

His Val Val Leu Glu His Leu Pro Glu Pro Ala Pro Thr Thr Arg Glu
            420                 425                 430

Ala Leu Pro Ala Pro His Leu Val Pro Pro Leu Leu Ser Ala Arg
        435                 440                 445

Ser His Pro Ala Leu Leu Ala Gln Ala Ala Arg Leu Arg Asp His Leu
    450                 455                 460

Ser Arg Thr Ala Ala Asp Pro Gln Asp Val Ala Tyr Ser Leu Ala Thr
465                 470                 475                 480

Thr Arg Ser Leu Phe Glu His Arg Ala Ala Leu Pro Cys Gly Asn Arg
                485                 490                 495

Glu Glu Leu Val Ala Ala Leu Asp Ala Leu Ala His Gly Arg Ile Thr
            500                 505                 510

Ala Gly Val Arg Val Asp Ser Ala Val Ser Gly Gly Thr Ala Val Leu
        515                 520                 525

Phe Thr Gly Gln Gly Ala Gln Trp Val Gly Met Gly Arg Glu Leu Tyr
    530                 535                 540

Gly Leu Asp Gly Val Phe Ala Ala Leu Asp Glu Val Leu Gly Val
545                 550                 555                 560

Val Gly Glu Val Gly Gly Trp Ser Leu Arg Glu Val Met Phe Gly Glu
                565                 570                 575

Gly Gly Gly Val Gly Val Gly Leu Leu Asp Gly Thr Glu Phe Ala Gln
            580                 585                 590

Pro Ala Leu Phe Ala Leu Glu Val Ala Leu Phe Arg Ala Val Glu Ala
        595                 600                 605

Arg Gly Val Arg Ala Ser Val Val Leu Gly His Ser Val Gly Glu Val
    610                 615                 620

Ala Ala Ala Cys Val Ala Gly Val Phe Ser Leu Ala Asp Ala Ala Arg
625                 630                 635                 640

Leu Val Val Ala Arg Gly Arg Leu Met Gly Ala Leu Pro Val Gly Gly
                645                 650                 655

Gly Met Leu Ser Val Arg Ala Ser Glu Ala Glu Leu Val Asp Val Val
            660                 665                 670

Ala Gly Leu Gly Gly Arg Val Ser Val Ala Val Asn Gly Pro Ala
        675                 680                 685

Ser Val Val Leu Ser Gly Glu Cys Gly Ala Leu Asp Val Val Ala Ala
    690                 695                 700

Arg Leu Gly Gly Arg Gly Val Glu Cys Lys Arg Leu Val Val Ser His
705                 710                 715                 720

Ala Phe His Ser Ala Leu Met Asp Pro Met Leu Glu Glu Phe Arg Gly
                725                 730                 735

Val Ala Glu Ser Val Glu Tyr Arg Arg Pro Cys Val Pro Val Val Ser
            740                 745                 750

Asn Val Thr Gly Gly Val Val Gly Phe Asp Glu Leu Gly Cys Ala Glu
```

```
                755                 760                 765
Tyr Trp Val Arg His Ala Arg Glu Ala Val Arg Phe Ala Glu Gly Ile
770                 775                 780

Arg Ala Ala Arg Ala Leu Gly Val Asp Thr Phe Leu Glu Val Gly Pro
785                 790                 795                 800

His Ala Val Leu Thr Ala Met Ala Gly Gln Cys Leu Asp Ala Glu Glu
                805                 810                 815

Ala Asp Leu Ala Phe Val Pro Val Leu Arg Arg Asp Arg Pro Ala Leu
                820                 825                 830

Gln Thr Phe Thr Thr Ala Leu Ala Thr Leu His Thr Arg Asp Ala Glu
                835                 840                 845

Leu Asp Ala Val Ala Leu His Ser Gly Ser Asp Ala Arg Arg Ile Asp
850                 855                 860

Leu Pro Thr Tyr Pro Phe Gln Arg Arg Thr His Trp Ser Pro Ala Leu
865                 870                 875                 880

Ser His Gly His Ala Ala Gly Val Val Arg Ala Ser Thr Ala Thr Glu
                885                 890                 895

Ile Arg Gly Asn Asp Glu Ile Pro Glu Ser Ala Glu Ala Leu Leu Arg
                900                 905                 910

Asp Pro Ala Asp Gly Ser Leu Ala Ala Ser Pro Glu Pro Ala Thr Pro
                915                 920                 925

Asp Gln Leu Val Arg Leu Val Arg Glu Thr Thr Ala Ala Val Leu Gly
                930                 935                 940

His Asp Asp Pro Asp Glu Ile Val Leu Asp Arg Thr Phe Thr Ser Gln
945                 950                 955                 960

Gly Leu Glu Ser Val Thr Ala Val Glu Leu Arg Asp Leu Leu Asn Arg
                965                 970                 975

Ala Thr Gly Leu Thr Leu Ala Ala Thr Leu Val Tyr Asp Leu Pro Thr
                980                 985                 990

Pro Arg Ala Val Ala Asp Tyr Leu Ser Ala Ala Met Leu Ala Thr Asp
                995                 1000                1005

Asp Ala Asn Ser Ser Ala His Gln Thr Thr Ala Ala Ala Thr Thr Arg
1010                1015                1020

Ser Gly Ala Arg Asn Asp Asp Pro Ile Ala Ile Val Gly Val Gly Ser
1025                1030                1035                1040

His Phe Pro Gly Gly Val Asp Ser Arg Ala Gly Leu Trp Asp Leu Leu
                1045                1050                1055

Ala Ser Gly Thr Asp Ala Ile Ser Ser Phe Pro Thr Asp Arg Gly Trp
                1060                1065                1070

Asp Leu Asn Glu Leu Tyr Asp Pro Glu Pro Gly Ile Pro Gly Lys Thr
                1075                1080                1085

Tyr Val Arg Gln Gly Gly Phe Leu His Gln Ala Ala Glu Phe Asp Ala
                1090                1095                1100

Glu Phe Phe Gly Ile Ser Pro Arg Glu Ala Thr Ala Met Asp Pro Gln
1105                1110                1115                1120

Gln Arg Leu Leu Leu Glu Thr Ser Trp Glu Ala Leu Glu Asp Ala Gly
                1125                1130                1135

Val Cys Pro Glu Ser Leu Arg Gly Thr Asn Thr Gly Val Phe Ile Gly
                1140                1145                1150

Ala Val Ala Pro Glu Tyr Gly Pro Arg Leu His Glu Gly Ala Asp Gly
                1155                1160                1165

Tyr Glu Gly Tyr Leu Leu Thr Gly Thr Thr Ala Ser Val Ala Ser Gly
                1170                1175                1180
```

```
Arg Ile Ala Tyr Thr Phe Gly Thr Arg Gly Pro Ala Leu Thr Val Asp
1185                1190                1195                1200

Thr Ala Cys Ser Ser Ser Leu Val Ala Leu His Leu Ala Val Gln Ser
            1205                1210                1215

Leu Arg Arg Gly Glu Cys Asp Met Ala Leu Ala Gly Gly Ala Thr Val
        1220                1225                1230

Met Ser Gly Pro Gly Met Phe Val Glu Phe Ser Arg Gln Arg Gly Leu
        1235                1240                1245

Ala Ser Asp Gly Arg Cys Lys Ala Phe Ser Ala Asp Ala Asp Gly Thr
    1250                1255                1260

Ala Trp Ser Glu Gly Val Ala Val Leu Ala Leu Glu Arg Leu Ser Asp
1265                1270                1275                1280

Ala Arg Arg Ala Gly His Arg Val Leu Ala Leu Val Arg Gly Ser Ala
            1285                1290                1295

Val Asn Gln Asp Gly Ala Ser Asn Gly Leu Thr Ala Pro Ser Gly Pro
        1300                1305                1310

Ala Gln Glu Ser Val Ile Arg Glu Ala Leu Ala Asp Ala Gly Leu Gly
        1315                1320                1325

Pro Gly Asp Val Asp Val Val Glu Ala His Gly Thr Gly Thr Ala Leu
    1330                1335                1340

Gly Asp Pro Ile Glu Ala Gly Ala Leu Leu Ala Thr Tyr Gly Cys Glu
1345                1350                1355                1360

Arg Val Gly Asp Pro Leu Trp Leu Gly Ser Leu Lys Ser Asn Ile Gly
            1365                1370                1375

His Thr Gln Ala Ala Ala Gly Val Ala Gly Val Ile Lys Met Val Glu
        1380                1385                1390

Ala Leu Arg His Gly Thr Leu Pro Arg Thr Leu His Ala Asp Arg Pro
        1395                1400                1405

Ser Thr His Val Asp Trp Ser Ser Gly Gly Val Glu Leu Leu Thr Glu
    1410                1415                1420

Ala Arg Pro Trp Pro Glu Arg Glu Gly Arg Pro Arg Ala Ala Val
1425                1430                1435                1440

Ser Ala Phe Gly Val Ser Gly Thr Asn Ala His Leu Val Ile Glu Glu
            1445                1450                1455

Pro Pro Val Glu Leu Pro Ala Gly Ala Gly Ala Gly Ala Gly Ala Gly
        1460                1465                1470

Ala Gly Val Ser Ser Val Val Ala Trp Pro Leu Ser Ala Arg Ser Gly
        1475                1480                1485

Glu Ala Leu Arg Ala Gln Ala Val Arg Leu Arg Glu His Val Glu Arg
    1490                1495                1500

Val Gly Ala Asp Pro Val Asp Val Ala Phe Ser Leu Ala Val Thr Arg
1505                1510                1515                1520

Ala Ser Phe Gly Glu Arg Ala Val Val Gly Gly Asp Arg Ala Glu
            1525                1530                1535

Leu Leu Ala Gly Leu Asp Ala Leu Ala Gly Gly Arg Arg Gly Pro Gly
        1540                1545                1550

Val Val Arg Gly Ser Ala Val Ser Gly Gly Thr Ala Val Leu Phe Thr
    1555                1560                1565

Gly Gln Gly Ala Gln Trp Val Gly Met Gly Arg Glu Leu Tyr Gly Leu
    1570                1575                1580

Asp Gly Val Phe Ala Ala Ala Leu Asp Glu Val Leu Gly Val Val Gly
1585                1590                1595                1600
```

-continued

```
Glu Val Gly Gly Trp Ser Leu Arg Glu Val Met Phe Gly Glu Gly Gly
            1605                1610                1615

Gly Val Gly Val Gly Leu Leu Asp Gly Thr Glu Phe Ala Gln Pro Ala
        1620                1625                1630

Leu Phe Ala Leu Glu Val Ala Leu Phe Arg Ala Val Glu Ala Arg Gly
        1635                1640                1645

Val Arg Ala Ser Val Val Leu Gly His Ser Val Gly Glu Val Ala Ala
    1650                1655                1660

Ala Cys Val Ala Gly Val Phe Ser Leu Ala Asp Ala Ala Arg Leu Val
1665                1670                1675                1680

Val Ala Arg Gly Arg Leu Met Gly Gly Leu Pro Val Gly Gly Gly Met
            1685                1690                1695

Leu Ser Val Arg Ala Ser Glu Ala Glu Leu Ala Asp Val Val Ala Gly
        1700                1705                1710

Leu Gly Gly Arg Val Ser Val Ala Ala Val Asn Gly Pro Ala Ser Val
        1715                1720                1725

Val Leu Ser Gly Glu Cys Gly Ala Leu Asp Val Val Ala Ala Arg Leu
    1730                1735                1740

Gly Gly Arg Gly Val Glu Cys Lys Arg Leu Val Val Ser His Ala Phe
1745                1750                1755                1760

His Ser Ala Leu Met Glu Pro Met Leu Glu Glu Phe Arg Gly Val Ala
            1765                1770                1775

Glu Ser Val Glu Tyr Arg Arg Pro Cys Val Pro Val Val Ser Asn Val
        1780                1785                1790

Thr Gly Gly Val Val Gly Phe Asp Glu Leu Gly Cys Ala Glu Tyr Trp
        1795                1800                1805

Val Arg His Ala Arg Glu Ala Val Arg Phe Ala Glu Gly Ile Arg Ala
    1810                1815                1820

Ala Arg Ala Leu Gly Val Asp Thr Phe Leu Glu Val Gly Pro His Ala
1825                1830                1835                1840

Val Leu Thr Ala Met Ala Gly Gln Cys Leu Asp Gly Glu Glu Ala Asp
            1845                1850                1855

Leu Ala Phe Val Pro Val Leu Arg Arg Asp Arg Pro Ala Ser Gln Thr
        1860                1865                1870

Phe Thr Thr Ala Leu Ala Thr Leu Cys Val Arg Gly Thr Glu Val Asp
        1875                1880                1885

Trp Ala Thr Pro His Arg Lys Ser Gly Ala Gln Arg Ile Asp Leu Pro
    1890                1895                1900

Thr Tyr Pro Phe Gln Arg Ala Arg Tyr Trp Leu Asp Pro Ala Pro Ala
1905                1910                1915                1920

Met Ala Leu Thr Thr Val Ala Ala Ser Ser Ala Glu Ala Ala Ala Thr
            1925                1930                1935

Ala Thr Glu Gly Thr Ala Leu Glu Thr Ala Gly Leu Arg Tyr Arg Ile
        1940                1945                1950

Ala Trp Gln Ala Ala Ala Thr Asp Arg Gly Thr Ser Arg Ser Ala Gly
        1955                1960                1965

His Val Val Leu Leu Thr Ser Asp Asp Asp Ala Thr Glu Ser Gly Leu
    1970                1975                1980

Ala Ala Ala Ile Thr Arg Glu Leu Ala Val Arg Gly Ala Glu Val Arg
1985                1990                1995                2000

Thr Ala Ile Leu Pro Val Gly Thr Asp Arg Glu Thr Ala Ala Asp Leu
            2005                2010                2015

Leu Arg Thr Ser Gly Asp Gly Ala Ala Arg Ser Thr His Val Leu Trp
```

-continued

```
            2020                2025                2030
Leu Ala Pro Ala Glu Pro Asp Thr Ala Asp Ala Val Ala Leu Ile Gln
        2035                2040                2045

Ala Leu Gly Glu Ala Gly His Asp Ala Pro Leu Trp Ile Ala Thr Arg
    2050                2055                2060

Asp Ala Val Ala Val Gln Pro Gly Glu Lys Leu Ser Val Ala Gly Ala
2065                2070                2075                2080

Gln Leu Trp Gly Leu Gly Gln Val Ala Ala Leu Glu Leu Phe Gln Arg
            2085                2090                2095

Trp Gly Gly Leu Val Asp Leu Pro Glu Asn Pro Ser Pro Ala Ala Val
        2100                2105                2110

Arg Ala Phe Val Gly Ala Leu Phe Ala Glu Gly Asp Asp Asn Gln Ile
    2115                2120                2125

Ala Val Arg Pro Ser Gly Val Tyr Val Arg Arg Val Ala Pro Ala Pro
2130                2135                2140

Ala Pro Ala Pro Ala Leu Ile Gly Gln Ala Ala Gln Asp Asp Arg Ser
2145                2150                2155                2160

Gly Pro Ser Asp Gly Leu Asp Gly Asn Asn Gly Thr Ala Pro Val Asn
        2165                2170                2175

Trp His Pro Ser Gly Thr Val Leu Ile Thr Gly Gly Thr Gly Ala Leu
            2180                2185                2190

Gly Ala Gln Val Ala Arg Arg Leu Ala Arg Ala Gly Ala Pro His Leu
        2195                2200                2205

Leu Leu Val Ser Arg Arg Gly Pro Asp Gly Pro Gly Thr Gly Glu Leu
    2210                2215                2220

Val Gly Glu Leu Thr Ala His Gly Thr Glu Val Thr Val Thr Ala Cys
2225                2230                2235                2240

Asp Ala Ala Asp Arg Asp Ala Leu Ala Glu Leu Leu Ala Ser Ile Pro
            2245                2250                2255

Glu Asp Arg Pro Leu Thr Ala Val Leu His Ala Ala Gly Val Leu Asp
        2260                2265                2270

Asp Gly Val Leu Asp Ala Leu Thr Pro Asp Arg Leu Asp Ala Val Leu
    2275                2280                2285

Arg Ala Lys Val Thr Val Ala Arg His Leu Asp Glu Leu Thr Ala Gly
    2290                2295                2300

Ile Pro Leu Asp Ala Phe Val Leu Phe Ser Ser Ile Val Gly Val Trp
2305                2310                2315                2320

Gly Asn Gly Gly Gln Gly Gly Tyr Ala Ala Ala Asn Ala Ala Leu Asp
            2325                2330                2335

Ala Leu Ala His Arg Arg Arg Ala Arg Gly Gln Arg Ala Thr Ser Ile
        2340                2345                2350

Ala Trp Gly Pro Trp Ala Gly Ala Gly Met Ala Ala Gly Ala Gly Ser
        2355                2360                2365

Lys Ala Phe Gln Arg Asp Gly Ile Gln Ala Leu Asp Pro Glu Arg Ala
    2370                2375                2380

Leu Asn Val Leu Asp Asp Val Val Arg Ala Asp Glu Thr Ser Val Ala
2385                2390                2395                2400

Ala Glu Pro Ser Leu Ile Val Ala Asp Val Asp Trp Ser Thr Phe Val
            2405                2410                2415

Gly Arg Ser Val Ala Arg Arg Thr Trp Ala Leu Phe Asp Gly Val Pro
        2420                2425                2430

Ala Ala Cys Ser Ala Arg Ser Ala Gln Ala Ala Gln Gly Arg Ser Ala
        2435                2440                2445
```

```
His Ala Pro Gly Glu Arg Pro His His Gly Gly Ile Gly Gly Ser Gly
    2450                2455                2460

Asp Gly Ala Asp Glu Asp Arg Pro Trp Leu Ser Ala Gly Pro Ser Ser
2465                2470                2475                2480

Pro Glu Arg Arg Arg Ala Leu Leu Asp Leu Val Arg Ser Glu Ala Ala
            2485                2490                2495

Glu Ile Leu Arg His Gly Ser Ala Ala Ala Val Asp Pro Glu Thr Ala
        2500                2505                2510

Phe Arg Ala Ala Gly Phe Asp Ser Leu Thr Val Leu Glu Leu Arg Asn
    2515                2520                2525

Arg Leu Thr Ala Ala Ile Gly Leu Asn Leu Pro Ser Thr Leu Leu Phe
    2530                2535                2540

Asp Tyr Pro Asn Pro Asn Ala Leu Ala Asp His Leu His Asp Glu Leu
2545                2550                2555                2560

Phe Gly Ala Asp Ser Glu Ala Pro Leu Ala Ala Asn Thr Pro Thr Arg
            2565                2570                2575

Ala Ser Ala Asp Asp Arg Glu Pro Ile Ala Val Val Gly Met Ala Cys
        2580                2585                2590

Arg Tyr Pro Gly Gly Val Ala Ala Pro Glu Glu Leu Trp Asp Leu Val
    2595                2600                2605

Ala Gly Gly Gly His Ala Ile Ser Pro Leu Pro Ala Asn Arg Gly Trp
    2610                2615                2620

Asp Leu Glu Gly Leu Tyr Asp Pro Glu Pro Gly Val Pro Gly Lys Ser
2625                2630                2635                2640

Tyr Val Arg Glu Gly Gly Phe Leu His Gly Ala Ala Glu Phe Asp Ala
            2645                2650                2655

Glu Phe Phe Gly Val Ser Pro Arg Glu Ala Ala Ala Met Asp Pro Gln
        2660                2665                2670

Gln Arg Leu Leu Leu Glu Thr Ser Trp Glu Ala Leu Glu Arg Ala Gly
    2675                2680                2685

Ile Val Pro Ala Ala Leu Arg Gly Thr Arg Thr Gly Val Phe Thr Gly
    2690                2695                2700

Ile Ser Gln Gln Asp Tyr Ala Ala Gln Leu Gly Asp Ala Ala Glu Thr
2705                2710                2715                2720

Tyr Gly Gly His Val Leu Thr Gly Asn Leu Gly Ser Val Val Ser Gly
            2725                2730                2735

Arg Val Ala Tyr Ser Leu Gly Leu Glu Gly Pro Ala Leu Thr Val Asp
        2740                2745                2750

Thr Ala Cys Ser Ser Ser Leu Val Ala Leu His Leu Ala Val Gln Ser
    2755                2760                2765

Leu Arg Arg Gly Glu Cys Asp Met Ala Leu Ala Gly Gly Val Thr Val
    2770                2775                2780

Met Ala Thr Pro Thr Val Phe Val Glu Phe Ser Arg Gln Arg Gly Leu
2785                2790                2795                2800

Ala Ser Asp Gly Arg Cys Lys Ala Phe Ala Glu Gly Ala Asp Gly Thr
            2805                2810                2815

Ala Trp Gly Glu Gly Val Gly Val Leu Leu Val Glu Arg Leu Ser Asp
        2820                2825                2830

Ala Arg Arg Leu Gly His Ser Val Leu Ala Val Val Arg Gly Ser Ala
    2835                2840                2845

Val Asn Gln Asp Gly Ala Ser Asn Gly Leu Thr Ala Pro Ser Gly Pro
2850                2855                2860
```

```
                        -continued

Ala Gln Gln Arg Val Ile Arg Glu Ala Leu Ala Asp Ala Gly Leu Gly
2865                2870                2875                2880

Ser Gly Asp Val Asp Val Val Glu Ala His Gly Thr Gly Thr Ala Leu
            2885                2890                2895

Gly Asp Pro Ile Glu Ala Gly Ala Leu Leu Ala Thr Tyr Gly Arg Glu
        2900                2905                2910

Arg Val Gly Asp Pro Leu Trp Leu Gly Ser Leu Lys Ser Asn Ile Gly
    2915                2920                2925

His Thr Gln Ala Ala Ala Gly Val Gly Gly Val Ile Lys Met Val Glu
    2930                2935                2940

Ala Leu Arg His Gly Thr Leu Pro Arg Thr Leu His Val Asp Ala Pro
2945                2950                2955                2960

Ser Ser Lys Val Glu Trp Gly Ser Gly Ala Val Glu Leu Leu Thr Glu
            2965                2970                2975

Ala Arg Ala Trp Pro Arg Arg Ala Asp Arg Lys Arg Arg Ala Ala Val
        2980                2985                2990

Ser Ala Phe Gly Val Ser Gly Thr Asn Ala His Val Ile Glu Glu
    2995                3000                3005

Pro Pro Ala Glu Val Ser Ala Glu Ser Leu Val Glu Leu Pro Ala Gly
    3010                3015                3020

Ala Gly Ala Gly Ala Gly Ala Gly Ala Gly Ala Gly Ala Gly Ala Gly
3025                3030                3035                3040

Val Ser Ser Val Val Ala Trp Ser Leu Ser Ala Arg Ser Gly Glu Ala
            3045                3050                3055

Leu Arg Ala Gln Ala Val Arg Leu Arg Glu His Val Glu Arg Val Gly
        3060                3065                3070

Ala Asp Pro Val Asp Val Ala Phe Ser Leu Ala Val Thr Arg Ala Ser
    3075                3080                3085

Phe Gly Glu Arg Ala Val Val Val Gly Gly Asp Arg Ala Glu Leu Leu
    3090                3095                3100

Ala Gly Leu Gly Ala Val Ala Ala Gly Asp Ala Leu Ser Gly Val Val
3105                3110                3115                3120

Arg Gly Ser Ala Val Arg Gly Arg Lys Val Ala Ala Leu Phe Thr Gly
            3125                3130                3135

Gln Gly Ala Gln Trp Val Gly Met Gly Arg Glu Leu Tyr Gly Leu Asp
        3140                3145                3150

Gly Val Phe Ala Ala Ala Leu Asp Glu Val Leu Gly Val Gly Glu
    3155                3160                3165

Val Gly Gly Trp Ser Leu Arg Glu Val Met Phe Gly Glu Gly Gly Gly
    3170                3175                3180

Val Gly Val Gly Leu Leu Asp Gly Thr Glu Phe Ala Gln Pro Ala Leu
3185                3190                3195                3200

Phe Ala Leu Glu Val Ala Leu Phe Arg Ala Val Glu Ala Arg Gly Val
            3205                3210                3215

Arg Ala Ser Val Val Leu Gly His Ser Val Gly Glu Val Ala Ala Ala
        3220                3225                3230

Cys Val Ala Gly Val Phe Ser Leu Ala Asp Ala Ala Arg Leu Val Val
    3235                3240                3245

Ala Arg Gly Arg Leu Met Gly Gly Leu Pro Val Gly Gly Gly Met Leu
    3250                3255                3260

Ser Val Arg Ala Ser Glu Ala Glu Leu Ala Asp Val Val Ala Gly Leu
3265                3270                3275                3280

Gly Gly Arg Val Ser Val Ala Ala Val Asn Gly Pro Ala Ser Val Val
```

-continued

```
                3285                3290                3295
Leu Ser Gly Glu Cys Gly Ala Leu Asp Val Val Ala Ala Arg Leu Gly
    3300                3305                3310

Gly Arg Gly Val Glu Cys Lys Arg Leu Val Val Ser His Ala Phe His
    3315                3320                3325

Ser Ala Leu Met Glu Pro Met Leu Glu Glu Phe Arg Gly Val Ala Glu
    3330                3335                3340

Ser Val Glu Tyr Arg Arg Pro Cys Val Pro Val Val Ser Asn Val Thr
3345                3350                3355                3360

Gly Gly Val Val Gly Phe Asp Glu Leu Gly Cys Ala Glu Tyr Trp Val
    3365                3370                3375

Arg His Ala Arg Glu Ala Val Arg Phe Ala Glu Gly Ile Arg Ala Ala
    3380                3385                3390

Arg Ala Leu Gly Val Asp Thr Phe Leu Glu Val Gly Pro His Ala Val
    3395                3400                3405

Leu Thr Ala Met Ala Gly Gln Cys Leu Asp Gly Glu Glu Ala Asp Leu
    3410                3415                3420

Ala Phe Val Pro Val Leu Arg Arg Asp Arg Pro Ala Leu Gln Thr Phe
3425                3430                3435                3440

Thr Thr Ala Leu Ala Thr Leu His Thr Arg Asp Ala Glu Leu Asp Ala
    3445                3450                3455

Val Ala Leu His Ser Gly Ser Asp Ala Arg Arg Ile Asp Leu Pro Thr
    3460                3465                3470

Tyr Pro Phe Gln Arg Arg Ser Tyr Trp Ala Thr Gly Ser Val Pro Gly
    3475                3480                3485

Ala Thr Gly Thr Ser Ala Ala Ala Arg Phe Gly Leu Val Trp Lys Asp
    3490                3495                3500

His Pro Phe Leu Ser Gly Ala Thr Pro Ile Ala Gly Ser Asp Ser Leu
3505                3510                3515                3520

Leu Leu Thr Gly Arg Val Ala Pro Ser Ala Tyr Pro Trp Leu Ala Asp
    3525                3530                3535

His Ala Ile Ser Gly Thr Val Leu Leu Pro Gly Thr Ala Ile Ala Asp
    3540                3545                3550

Leu Leu Leu Arg Ala Ala Asp Glu Val Gly Ala Gly Gly Val Glu Glu
    3555                3560                3565

Phe Met Leu His Ala Pro Leu Leu Leu Pro Glu Gln Gly Gly Leu Gln
    3570                3575                3580

Leu Gln Val Leu Val Glu Ala Ala Asp Glu Arg Gly Cys Arg Thr Val
3585                3590                3595                3600

Ser Leu Ala Ala Arg Pro Glu Asn Pro Gly Arg Asp Gly Glu Ala Pro
    3605                3610                3615

Glu Trp Thr Arg His Ala Glu Gly Val Leu Ala Pro Glu Gly Pro Ile
    3620                3625                3630

Ala Pro Glu Thr Ala Trp Ala Val Gly Ile Trp Pro Pro Gly Ala
    3635                3640                3645

Glu Pro Val Asp Val Glu Glu Leu Tyr Glu Gly Phe Ala Ala Asp Gly
    3650                3655                3660

Tyr Gly Tyr Gly Pro Ala Phe Thr Gly Leu Ser Gly Val Trp Arg Arg
3665                3670                3675                3680

Gly Glu Glu Leu Phe Ala Glu Val Gln Leu Pro Asp Gly Val Ala Asn
    3685                3690                3695

Gly Asp Asn Phe Gly Ile His Pro Ala Leu Phe Asp Ala Ala Leu His
    3700                3705                3710
```

-continued

Pro Trp Arg Ala Gly Gly Leu Val Pro Asp Thr Gly Thr Thr Leu
         3715                3720                3725

Val Pro Phe Ser Trp Gln Gly Ile Gly Leu His Ala Thr Gly Ala Glu
         3730                3735                3740

Thr Leu Arg Val Arg Leu Ala Thr Ala Gly Asp Gly Ala Asp Ala Ala
3745                3750                3755                3760

Phe Ser Val Gln Ala Ala Asp Pro Ala Gly Arg Pro Val Leu Thr Leu
         3765                3770                3775

Asp Ala Leu Leu Leu Arg Pro Val Ala Leu Gly Thr Asp Asn Ala Ser
         3780                3785                3790

Ala Ser Gly Leu Leu Tyr His Val Asp Trp Gln Pro Val Pro Arg Gln
         3795                3800                3805

Ala Val Ala Pro Gly Ser Arg Gly Trp Thr Val Leu Gly Pro Ala Ala
         3810                3815                3820

Ser Glu Thr Ala Thr Val Glu Val Ala Gln Glu Glu Ser Ala Thr Leu
3825                3830                3835                3840

Arg Ala Leu Pro Gly Ala Gln Pro Ala Val His Ala Asp Leu Thr Ala
         3845                3850                3855

Leu Arg Ala Ala Leu Ala Ala Gly Thr Ala Val Pro Gly Leu Val Val
         3860                3865                3870

Val Pro Pro Thr Gly Thr His Leu Val Glu Pro Gly Ala Gly Thr Gly
         3875                3880                3885

Gly Gly Ala Glu Thr Gly Ala Ala Gly Trp Gly Asp Asp Pro Val Arg
         3890                3895                3900

Ala Ala Leu Gly Arg Gly Leu Ala Leu Val Arg Glu Trp Thr Glu Asp
3905                3910                3915                3920

Glu Arg Leu Val Gly Ala Gln Leu Ala Val Leu Thr Arg Gly Ala Val
         3925                3930                3935

Glu Ala Arg Pro Gly Asp Val Pro Asp Leu Ala Gly Ala Ala Leu Trp
         3940                3945                3950

Gly Leu Leu Arg Ser Ala Gln Ser Glu Tyr Pro Asp Arg Phe Thr Leu
         3955                3960                3965

Val Asp Leu Asp Asp Ser Pro Glu Ser Trp Ala Ala Leu Pro Gln Ala
         3970                3975                3980

Leu Ala Ser Gly Glu Pro Gln Leu Ala Leu Arg Ala Gly Thr Val Leu
3985                3990                3995                4000

Ala Pro Ala Leu Val Pro Ile Ala Asp Pro Ala Thr Ala Ala Thr Ser
         4005                4010                4015

Ala Val Ala Ser Met Ala Ser Gly Ala Ser Thr Ala Thr Asp Val Pro
         4020                4025                4030

Ala Ala Asp Ala Ala Phe Asp Pro Asp Gly Thr Val Leu Ile Thr Gly
         4035                4040                4045

Ala Thr Gly Ala Leu Gly Arg Arg Val Val Pro His Leu Ala Arg Gln
         4050                4055                4060

His Gly Val Arg His Met Leu Leu Val Ser Arg Arg Gly Pro Asp Ala
4065                4070                4075                4080

Pro Glu Ala Ala Leu Leu Glu Arg Glu Leu Ala Asp Leu Gln Val Thr
         4085                4090                4095

Ala Thr Phe Ala Met Cys Asp Leu Ala Asp Pro Ala Asp Ile Arg Lys
         4100                4105                4110

Val Ile Ser Ala Val Pro Pro Ala His Pro Leu Thr Gly Val Val His
         4115                4120                4125

```
Thr Ala Gly Met Leu Asp Asp Gly Ala Leu Ala Gly Leu Thr Pro Ala
    4130                4135                4140

Arg Leu Asp Thr Val Leu Arg Pro Lys Ala Asp Ala Val Arg Asn Leu
4145                4150                4155                4160

His Glu Ala Thr Leu Asp Gln Pro Leu Arg Ala Phe Val Leu Phe Ser
            4165                4170                4175

Ala Ala Ala Gly Leu Leu Gly Arg Pro Gly Gln Gly Ser Tyr Ala Ala
        4180                4185                4190

Ala Asn Ala Val Leu Asp Ala Phe Ala Arg Asp Arg Arg Ala Ala Gly
    4195                4200                4205

Leu Pro Ala Val Ser Leu Ala Trp Gly Leu Trp Asp Glu Arg Ala Gly
4210                4215                4220

Met Ala Gly Gly Leu Asp Asp Val Ala Leu Arg Arg Leu Arg Arg Glu
4225                4230                4235                4240

Gly Ile Ala Ala Met Pro Pro Glu Gln Ala Leu Asp Leu Leu Asp Leu
            4245                4250                4255

Ala Leu Thr Thr His Arg Asp Gly Pro Ala Val Leu Val Pro Leu Leu
        4260                4265                4270

Leu Asp Gly Ala Ala Leu Arg Arg Thr Ala Lys Glu His Gly Ala Thr
    4275                4280                4285

Ala Val Pro Pro Leu Leu Arg Gly Leu Leu Pro Ala Ala Leu Arg Arg
4290                4295                4300

Gly Ser Ser Gly Thr Gly Thr Ala Ala Thr Ala Ala Asn Arg Arg Gly
4305                4310                4315                4320

Lys Gly Ala Glu Pro Val Ala Gly Arg Val Ala Arg Ile Val Ala Leu
            4325                4330                4335

Leu Ala Asp Glu Arg Ser Ala Ala Leu Leu Asp Leu Val Thr Glu Gln
        4340                4345                4350

Val Ala Glu Val Leu Gly His Ala Ser Ala Ala Glu Val Asp Pro Glu
    4355                4360                4365

Arg Pro Phe Arg Asp Ile Gly Phe Asp Ser Leu Ala Ala Val Glu Leu
4370                4375                4380

Arg Asn Arg Leu Gly Arg Leu Val Asp Leu Arg Leu Pro Thr Thr Leu
4385                4390                4395                4400

Ala Phe Asp Arg Pro Thr Pro Lys Asp Val Ala Glu Trp Leu Asp Gly
            4405                4410                4415

Glu Leu Pro Arg Pro Ala Gly Ser Ser Ala Asp Ser Ser Ala Leu Glu
        4420                4425                4430

Gly Ile Asp Glu Leu Ala Arg Ala Val Ala Leu Leu Gly Pro Asp Asp
    4435                4440                4445

Ala Arg Arg Ala Glu Val Arg Gln Arg Leu Thr Gly Leu Leu Ala Glu
4450                4455                4460

Leu Asp Thr Pro Gly His Gly Thr Ala Gly Pro Arg Asp Arg Thr Ala
4465                4470                4475                4480

Pro Ala Asp Ala Glu Ser Thr Pro Ala Thr Val Ala Gly Arg Leu Asp
            4485                4490                4495

Glu Ala Thr Asp Asp Glu Ile Phe Ala Phe Leu Asp Glu Gln Leu
        4500                4505                4510

<210> SEQ ID NO 3
<211> LENGTH: 1944
<212> TYPE: PRT
<213> ORGANISM: Streptomyces mycarofaciens

<400> SEQUENCE: 3
```

-continued

```
Met Thr Ala Glu Asn Asp Lys Ile Arg Ser Tyr Leu Lys Arg Ala Thr
  1               5                  10                  15

Ala Glu Leu His Lys Thr Lys Ser Arg Leu Ala Glu Val Glu Ser Ala
             20                  25                  30

Ser Arg Glu Pro Ile Ala Val Gly Met Ala Cys Arg Tyr Pro Gly
         35                  40                  45

Gly Val Ala Ala Pro Glu Asp Leu Trp Asp Leu Val Ala Gly Thr
     50                  55                  60

Asp Ala Ile Ser Pro Phe Pro Ala Asp Arg Gly Trp Asp Val Glu Gly
 65                  70                  75                  80

Leu Tyr Asp Pro Asp Pro Asp Ala Val Gly Arg Ser Tyr Val Arg Glu
                 85                  90                  95

Gly Gly Phe Leu His Gly Ala Ala Glu Phe Asp Ala Glu Phe Phe Gly
             100                 105                 110

Val Ser Pro Arg Glu Ala Ala Met Asp Pro Gln Gln Arg Leu Leu
             115                 120                 125

Leu Glu Thr Ser Trp Glu Ala Leu Glu Arg Ala Gly Ile Val Pro Ala
 130                 135                 140

Ala Leu Arg Gly Thr Arg Thr Gly Val Phe Thr Gly Val Met Tyr Asp
145                 150                 155                 160

Asp Tyr Gly Ser Gln Phe Asp Ser Ala Pro Pro Glu Tyr Glu Gly Tyr
                 165                 170                 175

Leu Val Asn Gly Ser Ala Gly Ser Ile Ala Ser Gly Arg Val Ala Tyr
             180                 185                 190

Ser Leu Gly Leu Glu Gly Pro Ala Leu Thr Val Asp Thr Ala Cys Ser
             195                 200                 205

Ser Ser Leu Val Ala Leu His Leu Ala Val Gln Ser Leu Arg Arg Gly
 210                 215                 220

Glu Cys Asp Met Ala Leu Ala Gly Gly Val Thr Val Met Ala Thr Pro
225                 230                 235                 240

Thr Val Phe Val Glu Phe Ser Arg Gln Arg Gly Leu Ala Pro Asp Gly
                 245                 250                 255

Arg Cys Lys Ala Phe Ala Glu Gly Ala Asp Gly Thr Ala Trp Gly Glu
             260                 265                 270

Gly Val Gly Val Leu Leu Val Glu Arg Leu Ser Asp Ala Arg Arg Leu
             275                 280                 285

Gly His Ser Val Leu Ala Val Val Arg Gly Ser Ala Val Asn Gln Asp
 290                 295                 300

Gly Ala Ser Asn Gly Leu Thr Ala Pro Ser Gly Pro Ala Gln Gln Arg
305                 310                 315                 320

Val Ile Arg Glu Ala Leu Ala Asp Ala Gly Leu Gly Ser Gly Asp Val
                 325                 330                 335

Asp Val Val Glu Ala His Gly Thr Gly Thr Ala Leu Gly Asp Pro Ile
             340                 345                 350

Glu Ala Gly Ala Leu Leu Ala Thr Tyr Gly Arg Glu Arg Val Gly Asp
             355                 360                 365

Pro Leu Trp Leu Gly Ser Leu Lys Ser Asn Ile Gly His Thr Gln Ala
 370                 375                 380

Ala Ala Gly Val Gly Gly Val Ile Lys Met Val Glu Ala Leu Arg His
385                 390                 395                 400

Gly Thr Leu Pro Arg Thr Leu His Val Asp Ala Pro Ser Ser Lys Val
                 405                 410                 415
```

-continued

```
Glu Trp Gly Trp Gly Ala Val Glu Leu Leu Thr Glu Ala Arg Ala Trp
            420                 425                 430

Pro Arg Arg Ala Asp Arg Lys Arg Ala Ala Val Ser Ala Phe Gly
        435                 440                 445

Val Ser Gly Thr Asn Ala His Val Val Ile Glu Glu Pro Pro Ala Glu
    450                 455                 460

Val Ser Ala Glu Ser Leu Val Glu Leu Pro Ala Gly Ala Gly Ala Gly
465                 470                 475                 480

Ala Gly Ala Gly Ala Gly Ala Gly Val Ser Val Ala Trp Ser
                485                 490                 495

Leu Ser Ala Arg Ser Gly Glu Ala Leu Arg Ala Gln Ala Val Arg Leu
            500                 505                 510

Arg Glu His Val Glu Arg Val Gly Ala Asp Pro Val Asp Val Ala Phe
            515                 520                 525

Ser Leu Ala Val Thr Arg Ala Ser Phe Gly Glu Arg Ala Val Val Val
    530                 535                 540

Gly Gly Asp Arg Ala Glu Leu Leu Ala Gly Leu Gly Ala Val Ala Ala
545                 550                 555                 560

Gly Asp Ala Leu Ser Gly Val Val Arg Gly Ser Ala Val Arg Gly Arg
                565                 570                 575

Lys Val Ala Ala Leu Phe Thr Gly Gln Gly Ala Gln Trp Val Gly Met
            580                 585                 590

Gly Arg Glu Leu Tyr Gly Leu Asp Gly Val Phe Ala Ala Ala Leu Asp
        595                 600                 605

Glu Val Leu Gly Val Val Gly Glu Val Gly Gly Trp Ser Leu Arg Glu
    610                 615                 620

Val Met Phe Gly Glu Gly Gly Val Gly Val Gly Leu Leu Asp Gly
625                 630                 635                 640

Thr Glu Phe Ala Gln Pro Ala Leu Phe Ala Leu Glu Val Ala Leu Phe
                645                 650                 655

Arg Ala Val Glu Ala Arg Gly Val Arg Ala Ser Val Val Leu Gly His
            660                 665                 670

Ser Val Gly Glu Val Ala Ala Cys Val Ala Gly Val Phe Ser Leu
        675                 680                 685

Ala Asp Ala Ala Arg Leu Val Val Ala Arg Gly Arg Leu Met Gly Gly
    690                 695                 700

Leu Pro Val Gly Gly Met Leu Ser Val Arg Ala Ser Glu Ala Glu
705                 710                 715                 720

Leu Ala Asp Val Val Ala Gly Leu Gly Gly Arg Val Ser Val Ala Ala
                725                 730                 735

Val Asn Gly Pro Ala Ser Val Val Leu Ser Gly Glu Cys Gly Ala Leu
            740                 745                 750

Asp Val Val Ala Ala Arg Leu Gly Gly Arg Gly Val Glu Cys Lys Arg
        755                 760                 765

Leu Val Val Ser His Ala Phe His Ser Ala Leu Met Glu Pro Met Leu
    770                 775                 780

Glu Glu Phe Arg Gly Val Ala Glu Ser Val Glu Tyr Arg Arg Pro Cys
785                 790                 795                 800

Val Pro Val Val Ser Asn Val Thr Gly Gly Val Val Gly Phe Asp Glu
                805                 810                 815

Leu Gly Cys Ala Glu Tyr Trp Val Arg His Ala Arg Glu Ala Val Arg
            820                 825                 830

Phe Ala Glu Gly Ile Arg Ala Ala Arg Ala Leu Gly Val Asp Thr Phe
```

```
                835                 840                 845
Leu Glu Val Gly Pro His Ala Val Leu Thr Ala Met Ala Gly Gln Cys
    850                 855                 860

Leu Asp Gly Glu Glu Ala Asp Leu Ala Phe Val Pro Val Leu Arg Arg
865                 870                 875                 880

Asp Arg Pro Ala Ser Gln Thr Phe Thr Thr Ala Leu Ala Thr Leu His
                885                 890                 895

Thr Arg Gly Leu Pro Val Pro Pro Thr Pro Ser Met Pro Ala Ala Arg
            900                 905                 910

Arg Ile Asp Leu Pro Thr Tyr Pro Phe Gln Arg Asn Arg Tyr Trp Leu
            915                 920                 925

Ala Ala Pro Pro Arg Pro Thr Thr Gly Gly Val Ser Ala Ala Gly Gln
        930                 935                 940

Arg Ala Val Glu His Pro Leu Leu Ala Ala Val Glu Leu Pro Gly
945                 950                 955                 960

Ala Gly Thr Glu Val Trp Thr Gly Arg Ile Ser Ala Ala Asp Leu Pro
                965                 970                 975

Trp Leu Ala Asp His Leu Val Trp Asp Arg Gly Val Val Pro Gly Ala
            980                 985                 990

Ala Leu Leu Glu Leu Val Leu Gln Val Gly Ser Arg Ile Gly Leu Pro
        995                 1000                1005

Arg Val Ala Glu Leu Thr Phe Glu Thr Ala Leu Ala Trp Ala Thr Asp
    1010                1015                1020

Thr Pro Leu Gln Ile Arg Val Val Asp Ala Pro Ala Ser Val Pro
1025                1030                1035                1040

Asp Gly Ala Arg Glu Val Ser Leu Tyr Ser Arg Pro Glu Pro Val Ala
                1045                1050                1055

Arg Thr Pro His Pro Ala Gly Ser Pro His Leu Ala Ala Glu His Gly
            1060                1065                1070

Asp Asn Gly Trp Thr Arg His Ala Ser Gly Val Leu Ala Pro Ala Ala
        1075                1080                1085

Asp His Ser His Asp Ser Asp Pro Ala Ala Pro Ser Thr Phe Ala Glu
    1090                1095                1100

Leu Thr Gly Ala Trp Pro Pro Ala Gly Ala Glu Pro Leu Asp Ile Ala
1105                1110                1115                1120

Glu Gln Tyr Ser Leu Phe Ala Ala Val Gly Val Arg Tyr Glu Gly Ala
                1125                1130                1135

Phe Arg Gly Leu Arg Ala Ala Trp Arg Arg Gly Asp Glu Ile Phe Ala
            1140                1145                1150

Glu Val Arg Leu Pro Asp Val His Ala Ala Asp Ala Thr Arg Tyr Gly
        1155                1160                1165

Val His Pro Ala Leu Leu Asp Ala Ala Leu His Pro Ile Ala Leu Leu
    1170                1175                1180

Asp Pro Leu Gly Asp Gly Gly His Gly Leu Leu Pro Phe Ser Trp Thr
1185                1190                1195                1200

Asp Val Gln His Tyr Gly Ser Gly Gly His Ala Leu Arg Val Arg Val
                1205                1210                1215

Ala Ala Ala Asp Gly Gly Ala Val Ser Ile Ser Val Val Asp Arg Glu
            1220                1225                1230

Gly Ala Pro Val Leu Ala Ala Arg Ser Leu Ala Leu Arg Arg Ile Ala
        1235                1240                1245

Ala Asp Arg Leu Pro Ala Ala Pro Ala Ala Pro Leu Tyr Arg Met Asp
    1250                1255                1260
```

-continued

```
Trp Leu Pro Leu Pro Glu Arg Val Pro Ala Ala Thr Ala Ala Arg Trp
1265                1270                1275                1280

Ala Val Val Gly Pro Ala Ala Glu Val Thr Ala Ala Gly Leu Arg Ala
                1285                1290                1295

Val Gly Val Asp Ala Arg Ala His Val Ser Pro Leu Gly Glu Pro Leu
            1300                1305                1310

Pro Pro Glu Ala Gly Thr Asp Ala Glu Val Cys Leu Leu Asp Leu Thr
        1315                1320                1325

Ala Val Asp Gly Thr Ala Pro His Gly Gly Leu Leu Asp Glu Val Arg
    1330                1335                1340

Ala Thr Val Arg Arg Ala Leu Glu Ala Val Gln Thr Pro Leu Ala Gly
1345                1350                1355                1360

Thr Asp Pro Leu Thr Asp Ala Arg Thr Gly Thr Pro Thr Gly Gly Pro
                1365                1370                1375

Arg Leu Val Val Leu Thr Arg Gly Ala Ala Gly Pro Glu Gly Gly Ala
            1380                1385                1390

Ala Asp Pro Ala Gly Ala Ala Val Trp Gly Leu Ile Arg Val Ala Gln
        1395                1400                1405

Thr Glu Gln Pro Gly Arg Phe Thr Leu Val Asp Ile Asp Arg Ala Lys
    1410                1415                1420

Thr Ser Leu Arg Thr Leu Ala Gly Leu Pro Ala Ala Asp Ala Ala Gln
1425                1430                1435                1440

Ile Ala Val Arg Asp Gly Arg Ala Thr Val Pro Arg Leu Val Arg Val
                1445                1450                1455

Val Asp Thr Asp Ser Thr Gly Ala Gly Glu Leu Val Glu Met Leu Asp
            1460                1465                1470

Pro Asn Gly Thr Val Leu Ile Thr Gly Gly Thr Gly Ala Leu Ala Ala
        1475                1480                1485

Glu Thr Ala Arg His Leu Val Glu Arg His Lys Ala Gly Arg Leu Leu
    1490                1495                1500

Leu Val Ser Arg Arg Gly Ala Glu Ala Pro Gly Ala Ala Glu Leu Val
1505                1510                1515                1520

Ala Glu Leu Ala Ala Leu Gly Ala Glu Val Thr Val Arg Ala Cys Asp
                1525                1530                1535

Val Ala Asp Arg Asp Ala Leu Arg Arg Leu Leu Gly Glu Leu Pro Ala
            1540                1545                1550

Glu His Pro Leu Ser Cys Val Val His Thr Ala Gly Val Leu Asp Asp
        1555                1560                1565

Gly Val Leu Ser Ala Gln Thr Thr Glu Arg Ile Asp Ala Val Leu Arg
    1570                1575                1580

Pro Lys Val Asp Ala Ala Val His Leu Asp Gln Leu Thr Arg Glu Leu
1585                1590                1595                1600

Gly Pro Val Pro Leu Val Leu Tyr Ser Ser Val Ser Ala Ser Leu Gly
                1605                1610                1615

Ser Ala Gly Gln Ala Gly Tyr Ala Ala Ala Asn Ala Phe Leu Asp Ala
            1620                1625                1630

Leu Ala Ala Arg Arg Arg Ala Asp Gly His Pro Ala Leu Ser Leu Gly
        1635                1640                1645

Trp Gly Trp Trp Ala Gly Ala Gly Met Ala Thr Gly Leu Glu Gly Ala
    1650                1655                1660

Asp Ala Ala Arg Ile Arg Arg Ser Gly Ile Val Pro Leu Asp Pro Ala
1665                1670                1675                1680
```

```
Asp Ala Leu Glu Leu Leu Asp Arg Ala Leu Ala Arg Pro Glu Pro Ala
            1685                1690                1695

Leu Leu Pro Val Arg Leu Asp Leu Pro Ala Leu Arg Ala Ala Ala Arg
        1700                1705                1710

Ala Thr Ala Pro Pro Glu Val Leu Arg Glu Leu Ala Gly Val Pro Ala
            1715                1720                1725

Asp Ser Gly Ala Ala Leu Gly Ala Gly Gly Arg Val Gly Asn Gly Gln
        1730                1735                1740

Arg Pro Asp Pro Ala Ser Pro Ala Glu Ala Leu Ala Ala Arg Leu Ala
1745                1750                1755                1760

Pro Arg Ser Ala Ala Glu Arg Thr Ala Leu Leu Asp Leu Val Arg
        1765                1770                1775

Ala Glu Val Ala Ala Val Leu Gly His Gly Asp Pro Ala Ala Val Gly
            1780                1785                1790

Ala Gly Arg Ser Phe Lys Asp Ala Gly Phe Asp Ser Leu Thr Ala Val
        1795                1800                1805

Asp Leu Arg Asn Arg Leu Asn Ala Arg Thr Gly Leu Arg Leu Pro Ala
    1810                1815                1820

Thr Leu Val Phe Asp His Pro Thr Pro Leu Ser Leu Ala Glu Leu Leu
1825                1830                1835                1840

Arg Ala Asp Leu Glu Ala Ala Gly Leu Val Gly Ala Thr Gly Pro Ala
        1845                1850                1855

Thr Gly Glu Pro Thr Gly Pro Glu Asp Leu Ser Ser Val Leu Asp Arg
            1860                1865                1870

Leu Glu Ser Ser Leu Thr Ala Thr Asp Asn Gly Asp Ala Arg Ser Ala
        1875                1880                1885

Ala Ala Arg Arg Leu Cys Ser Leu Leu Ala Met Leu Thr Ala Gly Ser
    1890                1895                1900

Gly Glu His Pro Gly Gln Gly Ser Gly Glu Ser Pro Arg Gly Ser Gly
1905                1910                1915                1920

Asp Ala Val Leu Asp Arg Leu Gln Ser Ala Ser Asp Asp Leu Phe
            1925                1930                1935

Asp Leu Phe Asp Ser Asp Phe Gln
        1940

<210> SEQ ID NO 4
<211> LENGTH: 3696
<212> TYPE: PRT
<213> ORGANISM: Streptomyces mycarofaciens

<400> SEQUENCE: 4

Met Thr Gln Arg Arg Thr Val Ser Ala Thr Asn Glu Glu Lys Leu Arg
1               5                   10                  15

Glu Tyr Leu Arg Arg Ala Met Ala Asp Leu His Ser Thr Arg Asp Arg
            20                  25                  30

Leu Arg Glu Val Glu Ser Ala Ser Arg Glu Pro Ile Ala Val Val Gly
        35                  40                  45

Met Ala Cys Arg Tyr Pro Gly Gly Val Ala Ala Pro Glu Asp Leu Trp
    50                  55                  60

Asp Leu Val Val Ala Gly Thr Asp Ala Ile Ser Pro Phe Pro Ala Asp
65                  70                  75                  80

Arg Gly Trp Asp Val Glu Gly Leu Tyr Asp Pro Asp Pro Asp Ala Met
            85                  90                  95

Gly Arg Ser Tyr Val Arg Glu Gly Gly Phe Leu His Glu Ala Ala Glu
        100                 105                 110
```

```
Phe Asp Ala Glu Phe Phe Gly Val Ser Pro Arg Glu Ala Ala Met
    115                 120                 125
Asp Pro Gln Gln Arg Leu Leu Leu Glu Thr Ser Trp Glu Ala Leu Glu
130                 135                 140
Arg Ala Gly Ile Val Pro Ala Ala Leu Arg Gly Thr Arg Thr Gly Val
145                 150                 155                 160
Phe Thr Gly Val Met Tyr His Asp Tyr Gly Ser His Gln Val Gly Thr
                165                 170                 175
Ala Ala Asp Pro Ser Gly Gln Leu Gly Leu Gly Thr Thr Gly Ser Val
            180                 185                 190
Ala Ser Gly Arg Val Ala Tyr Thr Leu Gly Leu Gln Gly Pro Ala Val
        195                 200                 205
Thr Val Asp Thr Ala Cys Ser Ser Leu Val Ala Leu His Leu Ala
    210                 215                 220
Val Gln Ser Leu Arg Arg Gly Glu Cys Asp Met Ala Leu Ala Gly Gly
225                 230                 235                 240
Val Thr Val Met Ala Thr Pro Thr Val Phe Val Glu Phe Ser Arg Gln
                245                 250                 255
Arg Gly Leu Ala Ser Asp Gly Arg Cys Lys Ala Phe Ala Glu Gly Ala
            260                 265                 270
Asp Gly Thr Ala Trp Gly Glu Gly Val Gly Val Leu Leu Val Glu Arg
        275                 280                 285
Leu Ser Asp Ala Arg Arg Leu Gly His Ser Val Leu Ala Val Val Arg
    290                 295                 300
Gly Ser Ala Val Asn Gln Asp Gly Ala Ser Asn Gly Leu Thr Ala Pro
305                 310                 315                 320
Ser Gly Pro Ala Gln Gln Arg Val Ile Arg Glu Ala Leu Ala Asp Ala
                325                 330                 335
Gly Leu Gly Ser Gly Asp Val Asp Val Val Glu Ala His Gly Thr Gly
            340                 345                 350
Thr Ala Leu Gly Asp Pro Ile Glu Ala Gly Ala Leu Leu Ala Thr Tyr
        355                 360                 365
Gly Arg Glu Arg Val Gly Asp Pro Leu Trp Leu Gly Ser Leu Lys Ser
    370                 375                 380
Asn Ile Gly His Thr Gln Ala Ala Gly Val Gly Gly Val Ile Lys
385                 390                 395                 400
Met Val Glu Ala Leu Arg His Gly Thr Leu Pro Arg Thr Leu His Val
                405                 410                 415
Asp Ala Pro Ser Ser Lys Val Glu Trp Asp Ser Gly Ala Val Glu Leu
            420                 425                 430
Leu Thr Glu Ala Arg Ala Trp Pro Arg Arg Ala Asp Arg Lys Arg Arg
        435                 440                 445
Ala Ala Val Ser Ala Phe Gly Val Ser Gly Thr Asn Ala His Val Val
        450                 455                 460
Ile Glu Glu Pro Pro Ala Glu Val Ser Ala Gly Gly Thr Pro Val Thr
465                 470                 475                 480
Pro Ser Thr Val Val Trp Pro Leu Ser Ala Glu Thr Ala Pro Ala Leu
                485                 490                 495
Arg Ala Gln Ala Ala Arg Leu Arg Ala His Leu Glu Arg Leu Pro Gly
            500                 505                 510
Ala Ala Pro Ala Asp Ile Gly His Ala Leu Ala Ala Asp Arg Ala Ala
        515                 520                 525
```

```
Leu Thr His Arg Ala Val Leu Leu Gly Ala Asn Ser Ala Pro Met Asp
    530                 535                 540

Ala Leu Ala Ala Leu Ala Ala Gly Glu Thr Ile Pro Asp Thr Val Thr
545                 550                 555                 560

Gly Thr Ala Ala Asp Ile Arg Arg Val Ala Phe Val Phe Pro Gly Gln
                565                 570                 575

Gly Thr Gln Trp Ala Gly Met Gly Ala Glu Leu Leu Asp Glu Ala Pro
                580                 585                 590

Ala Phe Ala Ala Glu Val Glu Arg Cys Gln Arg Ala Phe Ala Pro Tyr
                595                 600                 605

Val Asp Trp Ser Leu Thr Asp Val Leu Arg Gly Ala Pro Gly Ala Pro
    610                 615                 620

Gly Leu Asp Arg Val Asp Val Ile Gln Pro Ala Ala Phe Ala Val Met
625                 630                 635                 640

Val Ala Leu Ala Ala Leu Trp Arg Ser Leu Gly Val Glu Pro Ala Ala
                645                 650                 655

Val Ile Gly His Ser Gln Gly Glu Ile Ala Ala Ala Cys Val Ala Gly
                660                 665                 670

Ala Leu Ser Leu Asp Asp Ala Ala Arg Ile Val Ala Leu Arg Ser Gln
                675                 680                 685

Ile Ile Ala Arg Glu Leu Ala Gly Arg Gly Met Ala Ser Val Ala
    690                 695                 700

Leu Pro Ser Ala Asp Val Glu Ala Arg Leu Asp Val Ala Gly Gly Ile
705                 710                 715                 720

Glu Ile Ala Ala Val Asn Gly Pro Gln Ser Thr Val Val Cys Gly Glu
                725                 730                 735

Pro Ala Ala Leu Glu Ala Leu Leu Arg Thr Leu Glu Asp Glu Gly His
                740                 745                 750

Arg Val Arg Arg Ile Asp Val Asp Tyr Ala Ser His Ser His His Val
    755                 760                 765

Glu Ser Ile Arg Glu Glu Leu Ala Thr Val Leu Ala Ala Val Arg Pro
    770                 775                 780

His Gly Ser Gly Val Pro Phe Tyr Ser Thr Val Asp Ala Ala Leu Leu
785                 790                 795                 800

Glu Thr Thr Ala Leu Asp Ala Gly Tyr Trp Tyr Arg Asn Leu Arg Leu
                805                 810                 815

Pro Val Arg Phe Glu Pro Thr Val Arg Ala Met Leu Ala Asp Gly Val
                820                 825                 830

Asp Ala Phe Val Glu Cys Ser Ala His Pro Val Leu Thr Phe Gly Ile
                835                 840                 845

Arg Gln Thr Met Glu Ser Leu Asp Val Ala Ala Pro Ala Val Gly Ser
    850                 855                 860

Leu Arg Arg Asp Glu Gly Gly Leu Arg Arg Phe Leu Thr Ser Val Ala
865                 870                 875                 880

Glu Ala Gln Val Ser Gly Val Pro Val Asp Leu Ala Arg Leu His Pro
                885                 890                 895

Gly Ala Arg Arg Val Glu Leu Pro Thr Tyr Ala Phe Gln Arg Glu Arg
                900                 905                 910

Tyr Trp Val Gly Ser Ala Arg Pro Glu Trp Ala Glu Ala Ala Glu Ala
    915                 920                 925

Gly Glu Ser Ile Ser Glu Pro Gly Asp Arg Leu Gly Tyr His Val Gly
    930                 935                 940

Trp Lys Gly Leu Arg Ala Val Thr Gly Gly Trp Arg Pro Gly Leu Arg
```

-continued

```
                945                 950                 955                 960
Leu Leu Ile Val Pro Ala Gly Glu Thr His Ala Ala Leu Ala Asp Ser
                965                 970                 975
Val Glu Gln Ala Ile Ala Ser Phe Gly Gly Thr Ile Arg Arg Ile Ala
            980                 985                 990
Val Asp Pro Ala Arg Thr Gly Arg Ala Glu Leu Gln Gly Leu Leu Glu
            995                1000                1005
Pro Ala Val Asn Gly Asp Thr Thr Val Thr Gly Met Val Ser Leu Leu
           1010                1015                1020
Gly Leu Cys Thr Asp Gly His Pro Asp His Pro Ala Val Pro Thr Gly
1025                1030                1035                1040
Val Thr Ala Thr Leu Ala Leu Val Gln Ala Leu Ala Glu Leu Gly Gly
               1045                1050                1055
Thr Ala Pro Leu Trp Thr Val Thr Gln Gly Ala Val Ala Thr Ala Pro
           1060                1065                1070
Asp Glu Val Pro Cys Thr Ala Gly Ala Gln Leu Trp Gly Leu Gly Arg
           1075                1080                1085
Val Ala Ala Leu Glu Leu Pro Glu Leu Trp Gly Gly Leu Val Asp Leu
           1090                1095                1100
Pro Glu Arg Pro Ala Ala Arg Val Phe Glu Arg Leu Ala Gly Val Leu
1105                1110                1115                1120
Ala Glu Ala Gly Ala Glu Asp Gln Ile Ala Ile Arg Ala Ala Gly Val
               1125                1130                1135
Phe Gly Arg Arg Val Leu Pro Asn Pro Ala Asp Ser Ala Pro Pro Val
           1140                1145                1150
Trp Arg Ala Arg Gly Thr Val Leu Ile Ala Gly Asp Leu Thr Thr Val
           1155                1160                1165
Pro Gly Arg Val Val Arg Ser Phe Leu Glu Asp Gly Ala Asp Arg Val
           1170                1175                1180
Val Leu Ala Gly Pro Asp Ala Asp Ala Glu Ala Ala Thr Ala Gly Leu
1185                1190                1195                1200
Thr Gly Ala Val Val Pro Val Arg Cys Asp Val Thr Asp Arg Ser Ala
               1205                1210                1215
Leu Ala Gly Leu Leu Asn Glu His Ala Pro Thr Val Val His Ala
           1220                1225                1230
Pro Ala Leu Val Pro Leu Val Pro Leu Lys Asp Thr Glu Pro Gly Asp
           1235                1240                1245
Ile Ala Val Ala Val Ala Val Lys Thr Ala Ala Ala Glu His Leu Val
           1250                1255                1260
Asp Leu Ala Pro Ala Ala Gly Leu Asp Ala Leu Val Leu Phe Ser Ser
1265                1270                1275                1280
Val Ser Gly Val Trp Gly Gly Ala Ala Gln Gly Cys Tyr Ala Ala Ala
               1285                1290                1295
Thr Ala His Leu Asp Ala Leu Ala Glu Arg Ala Arg Ala Gly Gly Val
           1300                1305                1310
Pro Ala Val Ser Val Ala Trp Ser Pro Trp Ala Gly Gly Ala Leu Ala
           1315                1320                1325
Asp Gly Ala Asp Ala Glu Phe Leu Asn Arg Arg Gly Leu Ala Pro Leu
           1330                1335                1340
Asp Pro Asp Ala Ala Val Arg Ser Leu Arg Arg Met Leu Glu Arg Gly
1345                1350                1355                1360
Arg Thr Cys Gly Ala Val Ala Asp Ile Glu Trp Asn Arg Phe Ala Ala
               1365                1370                1375
```

```
Ser Tyr Thr Ser Val Arg Pro Ala Val Leu Phe Asp Asp Val Pro Glu
        1380                1385                1390

Val Trp Arg Leu Arg Ala Ala Glu Arg Ala Ala Gly Thr Gly Asp Ser
        1395                1400                1405

Val Thr Ser Glu Leu Val Arg Glu Leu Thr Ala Gln Ser Gly His Lys
        1410                1415                1420

Arg His Val Thr Leu Leu Arg Leu Val Arg Thr His Ala Ala Ala Val
1425                1430                1435                1440

Leu Gly Gln Ser Ser Ser Glu Ala Val Asn Ser Ala Arg Ala Phe Arg
                1445                1450                1455

Asp Leu Gly Phe Asp Ser Leu Thr Ala Leu Glu Leu Arg Asn Arg Leu
        1460                1465                1470

Ser Ala Ala Thr Gly Leu Asn Leu Pro Ala Ser Leu Val Phe Asp His
        1475                1480                1485

Ser Asn Pro Ala Ala Leu Ala Arg His Leu Gly Asp Glu Leu Leu Asp
        1490                1495                1500

Arg Gly Asp Thr Ala Ala Gln Thr Gly Pro Ala Ala Thr Ala Gln Thr
1505                1510                1515                1520

Asp Glu Pro Ile Ala Val Ile Gly Met Ala Cys Arg Leu Pro Gly Gly
                1525                1530                1535

Val Arg Ser Pro Glu Asp Leu Trp Asp Leu Leu Thr Gly Glu Val Asp
                1540                1545                1550

Ala Ile Thr Pro Phe Pro Thr Asp Arg Gly Trp Asn Asn Asp Val Leu
                1555                1560                1565

Tyr Asp Pro Asp Pro Asp Ser Pro Gly His His Thr Tyr Val Arg Gly
        1570                1575                1580

Gly Gly Phe Leu His Asp Ala Ala Glu Phe Asp Pro Gly Phe Phe Gly
1585                1590                1595                1600

Ile Ser Pro Arg Glu Ala Leu Ala Met Asp Pro Gln Gln Arg Leu Ile
                1605                1610                1615

Leu Glu Thr Ala Trp Glu Ser Phe Glu Arg Ala Gly Ile Asp Pro Val
                1620                1625                1630

Glu Leu Arg Gly Ser Arg Thr Gly Val Phe Val Gly Thr Asn Gly Gln
        1635                1640                1645

His Tyr Val Pro Leu Leu Gln Glu Gly Asp Glu Asn Phe Asp Gly Tyr
        1650                1655                1660

Val Ala Thr Gly Asn Ser Ala Ser Val Met Ser Gly Arg Leu Ser Tyr
1665                1670                1675                1680

Val Phe Gly Leu Glu Gly Pro Ala Val Thr Val Asp Thr Ala Cys Ser
                1685                1690                1695

Ala Ser Leu Ala Ala Leu His Leu Ala Val Gln Ser Leu Arg Arg Gly
                1700                1705                1710

Glu Cys Asp Met Ala Leu Val Ser Gly Ala Thr Val Met Ser Thr Pro
                1715                1720                1725

Glu Met Leu Val Glu Phe Ala Arg Gln Arg Ala Val Ser Pro Asp Gly
        1730                1735                1740

Arg Cys Lys Ala Phe Ala Glu Ala Ala Asp Gly Val Gly Leu Ala Glu
1745                1750                1755                1760

Gly Ala Gly Met Leu Leu Val Glu Arg Leu Ser Asp Ala Arg Arg Leu
                1765                1770                1775

Gly His Ser Val Leu Ala Val Val Arg Gly Ser Ala Val Asn Gln Asp
        1780                1785                1790
```

```
Gly Ala Ser Asn Gly Leu Thr Ala Pro Ser Gly Pro Ala Gln Gln Arg
    1795                1800                1805

Val Ile Arg Glu Ala Leu Ala Asp Ala Gly Leu Gly Ser Gly Asp Val
        1810                1815                1820

Asp Val Val Glu Ala His Gly Thr Gly Thr Ala Leu Gly Asp Pro Ile
1825                1830                1835                1840

Glu Ala Gly Ala Leu Leu Ala Thr Tyr Gly Arg Glu Arg Val Gly Asp
            1845                1850                1855

Pro Leu Trp Leu Gly Ser Leu Lys Ser Asn Ile Gly His Thr Gln Ala
        1860                1865                1870

Ala Ala Gly Val Ala Gly Val Ile Lys Met Val Glu Ala Leu Arg His
    1875                1880                1885

Gly Thr Leu Pro Arg Ser Leu His Ile Asp Ala Pro Ser Ser Lys Val
    1890                1895                1900

Glu Trp Gly Glu Gly Ala Val Glu Leu Leu Thr Glu Ala Arg Pro Trp
1905                1910                1915                1920

Pro Gln Gln Ala Asp Arg Pro Arg Arg Ala Gly Ile Ser Ser Phe Gly
            1925                1930                1935

Ile Ser Gly Thr Asn Val His Val Ile Val Glu Glu Pro Pro Glu Pro
            1940                1945                1950

Thr Ala Pro Glu Ser Leu Trp Pro Asp Ala Ala Ala Asp Gly Asp Val
    1955                1960                1965

Trp Ser Glu Glu Trp Trp Arg Glu Val Thr Val Pro Leu Met Met Ser
    1970                1975                1980

Ala His Asn Glu Ala Ala Leu Cys Asp Gln Ala Arg Arg Leu Arg Ala
1985                1990                1995                2000

Asp Leu Leu Ala His Pro Glu Leu His Pro Ala Asp Val Gly Tyr Ser
            2005                2010                2015

Leu Ile Thr Thr Arg Thr Arg Phe Glu His Arg Ala Ala Val Val Gly
            2020                2025                2030

Glu Asn Phe Thr Glu Leu Ile Ala Ala Leu Asp Asp Leu Ile Glu Gly
            2035                2040                2045

Arg Pro His Pro Leu Val Met Arg Gly Thr Ala Gly Thr Ala Asp Gln
    2050                2055                2060

Val Val Phe Val Phe Pro Gly Gln Gly Ser Gln Trp Ala Glu Met Gly
2065                2070                2075                2080

Asp Gly Leu Phe Glu Arg Ser Ser Val Phe Arg Glu Thr Ala His Ala
            2085                2090                2095

Cys Asp Ala Ala Leu Arg Pro Tyr Leu Asp Trp Ser Val Leu Asp Val
            2100                2105                2110

Leu Arg Arg Glu Pro Asp Ala Pro Ser Leu Asp Arg Val Asp Val Val
    2115                2120                2125

Gln Pro Val Leu Phe Thr Met Met Val Ser Leu Ala Ala Thr Trp Arg
    2130                2135                2140

Ser Leu Gly Val Glu Pro Ala Ala Val Val Gly His Ser Gln Gly Glu
2145                2150                2155                2160

Ile Ala Ala Ala His Val Ala Gly Gly Leu Ser Leu Asp Asp Ala Ala
            2165                2170                2175

Arg Ile Val Ala Leu Arg Ser Gln Ala Trp Leu Gln Leu Ala Gly Lys
        2180                2185                2190

Gly Gly Met Val Ala Val Thr Met Ser Glu Arg Glu Leu Arg Pro Arg
    2195                2200                2205

Leu Glu Phe Trp Gly Asp Arg Leu Ala Val Ala Ala Val Asn Ser Pro
```

-continued

```
                2210                2215                2220
Glu Thr Cys Ala Val Ala Gly Asp Pro Asp Ala Leu Ala Glu Leu Val
2225                2230                2235                2240

Ala Glu Leu Ala Ser Gln Gly Val Pro Ala Arg Pro Ile Pro Gly Val
                2245                2250                2255

Asp Thr Ala Gly His Ser Pro Gln Val Asp Thr Leu Glu Asp Gln Leu
            2260                2265                2270

Arg Glu Val Leu Ala Pro Val Ala Pro Ser Ser Ser Asp Ile Pro Phe
        2275                2280                2285

Tyr Ser Thr Val Thr Gly Gly Leu Leu Asp Thr Ala Glu Leu Asp Ala
    2290                2295                2300

Asp Tyr Trp Tyr Arg Asn Met Arg Glu Pro Val Glu Phe Glu Lys Ala
2305                2310                2315                2320

Thr Arg Ala Leu Ile Ala Asp Gly His Asp Val Phe Leu Glu Thr Ser
                2325                2330                2335

Pro His Pro Met Leu Ala Ile Ser Leu Gln Glu Thr Ile Ser Asp Ala
            2340                2345                2350

Gly Ala Ser Ala Ala Val Leu Gly Thr Leu Arg Arg Gly Gln Gly Gly
        2355                2360                2365

Pro Arg Trp Leu Gly Val Ala Val Cys Arg Ala Tyr Thr His Gly Val
    2370                2375                2380

Glu Ile Asp Ala Glu Ala Leu Phe Gly Pro Asp Ser Arg Pro Val Gly
2385                2390                2395                2400

Leu Pro Thr Tyr Pro Phe Gln Arg Glu Arg Tyr Trp Tyr Ser Pro Val
                2405                2410                2415

Ser Arg Gly Asp Asp Pro Ala Ser Leu Gly Leu Asp Ala Ala Asp His
            2420                2425                2430

Pro Leu Leu Gly Gly Gly Val Glu Leu Pro Gly Ser Gly Asp Gln Met
        2435                2440                2445

Tyr Thr Ala Arg Ile Gly Thr Asp Ala Val Pro Trp Leu Val Asp His
    2450                2455                2460

Ala Leu Met Gly Thr Val Leu Leu Pro Gly Ala Val Phe Thr Asp Leu
2465                2470                2475                2480

Ala Leu Trp Ala Gly Arg Gln Thr Gly Thr Gly Arg Ile Glu Glu Leu
                2485                2490                2495

Thr Leu Ala Ala Pro Leu Val Leu Pro Glu Ser Gly Gly Val Trp Leu
            2500                2505                2510

Arg Leu Asn Val Gly Ala Pro Asp Thr Asp Glu Ala Arg Arg Phe Ala
        2515                2520                2525

Val His Ala Arg Pro Glu Gly Ala Ala Asp Trp Thr Leu His Ala Glu
    2530                2535                2540

Gly Leu Leu Thr Ala Glu His Ala Ala Asp Ala Pro Asp Ala Ser Ala
2545                2550                2555                2560

Val Thr Pro Ser His Gly Ala Glu Gln Leu Asp Thr Gly Asp Phe Tyr
                2565                2570                2575

Glu Arg Phe Thr Glu Leu Gly Tyr Ser Tyr Gly Pro Phe Phe Arg Gly
            2580                2585                2590

Leu Val Ser Ala His Arg Ala Gly Ser Asp Leu His Ala Glu Val Ala
        2595                2600                2605

Leu Pro Ala Gln Ala Gln Gly Asp Ala Ala Arg Phe Gly Leu His Pro
    2610                2615                2620

Ala Leu Leu Asp Ala Ala Leu Gln Thr Met Ser Leu Gly Gly Phe Phe
2625                2630                2635                2640
```

```
Pro Glu Asp Gly Arg Ile Arg Met Pro Phe Ala Leu Arg Gly Val Arg
            2645                2650                2655

Leu Tyr Arg Thr Gly Ala Asp Arg Leu Arg Val Arg Ile Ser Pro Val
        2660                2665                2670

Ala Glu Asp Ala Val Arg Ile Gln Cys Ala Asp Thr Glu Gly Arg Met
    2675                2680                2685

Val Ala Glu Ile Asp Ser Phe Leu Met Arg Pro Val Asp Pro Glu Gln
2690                2695                2700

Leu Arg Gly Gly Arg Pro Val Ser Ala Asp Ala Leu Phe Arg Val Ala
2705                2710                2715                2720

Trp Arg Glu Arg Pro Gly Ser Gly Pro Ala Thr Gly Thr Ala Ser Ala
            2725                2730                2735

Ile Arg Trp Ala Val Ala Gly Pro Asp Ala Leu Gly Leu Ala Glu Ala
            2740                2745                2750

Ala Asp Ala His Leu Pro Asp Ala Leu Gly Pro Asp Gly Pro Arg Pro
        2755                2760                2765

Ala Thr Ala Gly Glu Pro Ala Pro Asp Ala Val Val Phe Gly Val Pro
    2770                2775                2780

Ala Gly Thr Gly Asp Val Ala Ala Asp Ala His Ala Val Ala Cys Arg
2785                2790                2795                2800

Val Leu Asp Leu Val Gln Arg Trp Leu Ala Ala Pro Ala Val Pro Glu
            2805                2810                2815

Gly Thr Arg Leu Val Val Ala Thr Arg Gly Ala Val Ala Val Arg Asp
            2820                2825                2830

Asp Ala Glu Val Thr Asp Pro Ala Ala Ala Ala Ala Trp Gly Leu Leu
        2835                2840                2845

Arg Ser Ala Gln Ala Glu Glu Pro Asp Arg Phe Leu Leu Leu Asp Leu
    2850                2855                2860

Asp Asp Asp Pro Ala Ser Ala Arg Ala Val Pro Ala Ala Leu Ala Ser
2865                2870                2875                2880

Gly Glu Pro Gln Thr Ala Val Arg Ala Gly Arg Val Tyr Val Pro Arg
            2885                2890                2895

Leu Glu Arg Ala Gly Ala Gly Gly Asp Gly Ala Phe Val Pro Pro Glu
            2900                2905                2910

Gln Gly Ala Trp Arg Leu Gly Arg Gly Val Asp Arg Thr Leu Asp Gly
        2915                2920                2925

Leu Ala Pro Val Pro Ala Pro Asp Ala Asn Ala Pro Leu Glu His Gly
    2930                2935                2940

Gln Val Arg Val Ala Val Arg Ala Ala Gly Val Asn Phe Arg Asp Ala
2945                2950                2955                2960

Leu Ile Ala Leu Gly Met Tyr Pro Gly Glu Ala Glu Met Gly Thr Glu
            2965                2970                2975

Gly Ala Gly Val Val Val Glu Thr Gly Pro Gly Val Thr Gly Val Ala
            2980                2985                2990

Ala Gly Asp Arg Val Leu Gly Leu Trp Asn Gly Gly Phe Gly Pro Val
        2995                3000                3005

Cys Val Ala Asp His Arg Leu Leu Ala Pro Ile Pro Asp Gly Trp Ser
    3010                3015                3020

Tyr Ala Arg Ala Ala Ser Val Pro Ala Val Phe Leu Ser Ala Tyr Tyr
3025                3030                3035                3040

Gly Leu Val Ala Leu Ala Asp Leu Arg Pro Gly Glu Lys Val Leu Val
            3045                3050                3055
```

-continued

His Ala Ala Ala Gly Gly Val Gly Met Ala Ala Val Gln Ile Ala His
         3060                3065                3070

His Leu Gly Ala Glu Val Leu Ala Thr Ala Ser Ser Gly Lys Trp Asp
         3075                3080                3085

Val Leu Arg Ala Met Gly Ile Pro Asp His Leu Ala Ser Ser Arg
     3090                3095                3100

Thr Leu Asp Phe Ala Thr Ala Phe Ala Gly Ala Asp Gly Ala Pro Gly
3105                3110                3115                3120

Ala Asp Val Val Leu Asn Ser Leu Thr Lys Glu Phe Val Asp Ala Ser
             3125                3130                3135

Leu Gly Leu Leu Pro Pro Gly Gly Arg Phe Leu Glu Leu Gly Lys Ala
         3140                3145                3150

Asp Val Arg Thr Pro Glu Gln Val Ala Ala Asp His Pro Gly Val Arg
     3155                3160                3165

Tyr Arg Ala Phe Asp Leu His Glu Ala Gly Pro Asp Glu Leu Gly Arg
     3170                3175                3180

Met Leu Arg Glu Leu Met Glu Leu Phe Ala Ser Gly Ala Leu His Pro
3185                3190                3195                3200

Leu Pro Val Val Thr His Asp Val Arg Arg Ala Ala Asp Ala Leu Arg
         3205                3210                3215

Thr Ile Ser Gln Ala Arg His Thr Gly Lys Leu Val Leu Thr Met Pro
         3220                3225                3230

Pro Ala Trp His Pro Tyr Gly Thr Val Leu Ile Thr Gly Gly Thr Gly
         3235                3240                3245

Thr Ile Gly Ser Arg Ile Ala Arg His Leu Val Thr Ala His Gly Val
     3250                3255                3260

Arg His Leu Leu Ile Ala Ala Arg Asn Gly Pro Asp Gly Glu Gly Ala
3265                3270                3275                3280

Ala Glu Leu Val Ala Glu Leu Ala Gly Leu Gly Ala Glu Ala Thr Val
             3285                3290                3295

Val Ala Cys Asp Val Ala Asp Ala Asp Ala Val Arg Arg Leu Leu Ala
         3300                3305                3310

Asp Val Pro Ala Glu Arg Pro Leu Thr Ala Val Val His Ser Ala Gly
         3315                3320                3325

Val Leu Asp Asp Gly Val Leu Pro Thr Leu Thr Pro Glu Arg Met Trp
     3330                3335                3340

Arg Val Leu Arg Pro Lys Val Ala Ala Ala Val His Leu Asp Glu Leu
3345                3350                3355                3360

Thr Arg Asp Leu Asp Leu Ser Ala Phe Val Leu Phe Ser Ser Ser Ala
         3365                3370                3375

Gly Leu Leu Gly Ser Pro Ala Gln Gly Asn Tyr Ala Ala Ala Asn Ala
         3380                3385                3390

Thr Leu Asp Ala Leu Ala Ala Arg Arg Arg Ala Leu Gly Leu Pro Ser
     3395                3400                3405

Val Ser Met Ala Trp Gly Leu Trp Ser Asp Thr Ser Arg Met Ala Asp
     3410                3415                3420

Gly Leu Asp Gln Glu Arg Leu Gln Arg Arg Phe Thr Arg Ser Gly Phe
3425                3430                3435                3440

Pro Pro Leu Ser Ala Gly Leu Gly Thr Ala Leu Phe Asp Ala Ala Leu
             3445                3450                3455

Arg Val Asp Glu Ala Val Gln Val Pro Leu Arg Leu Asp Pro Ala Ala
         3460                3465                3470

Leu Arg Ala Thr Gly Thr Ile Ala Pro Leu Leu Ser Asp Leu Val Thr

-continued

```
                3475                3480                3485

Pro Ala Ser Ala Ala Ala Ser Gly Ala Arg Ala Pro Gly Arg Pro His
    3490                3495                3500

Thr Pro Gln Asp Ala Arg His Thr Gly Glu Ser Leu Ala Glu Gln Leu
3505                3510                3515                3520

Ala Arg Leu Ser Pro Glu Glu Arg His Asp Gln Leu Leu Asn Leu Val
            3525                3530                3535

Arg Glu His Val Ala Ala Val Leu Gly His Gly Ser Ala Ala Glu Val
        3540                3545                3550

His Ser Asp Arg Pro Phe Arg Asp Val Gly Phe Asp Ser Leu Thr Ala
    3555                3560                3565

Val Glu Leu Arg Asn Arg Met Gly Ala Ala Thr Gly Val Arg Leu Pro
3570                3575                3580

Ala Thr Leu Val Phe Asp His Pro Thr Pro Ala Ala Met Ala Thr His
3585                3590                3595                3600

Leu Ala Gly Leu Leu Val Pro Glu Gln Gln Ala Thr Thr Val Pro Leu
            3605                3610                3615

Leu Ala Asp Leu Asp Arg Ile Glu Lys Ala Leu Ala Ala Leu Thr Pro
        3620                3625                3630

Glu Gly Leu Ala Ala Val Ala Pro Ala Pro Ala Ala Arg Ala Glu Val
    3635                3640                3645

Ala Leu Arg Leu Asp Ala Leu Ala Gly Arg Trp Arg Ala Leu His Asp
3650                3655                3660

Gly Thr Thr Asp Ala Ala Asp Asp Ile Ala Asp Ala Leu Ser Ala Ala
3665                3670                3675                3680

Asp Asp Asp Glu Ile Phe Ala Phe Ile Asp Glu Arg Tyr Gly Glu Ser
            3685                3690                3695

<210> SEQ ID NO 5
<211> LENGTH: 1568
<212> TYPE: PRT
<213> ORGANISM: Streptomyces mycarofaciens

<400> SEQUENCE: 5

Met Ala Asn Glu Asp Lys Leu Arg Thr Tyr Leu Lys Arg Val Thr Ala
1               5                   10                  15

Glu Leu His Arg Ala Thr Glu Gln Leu Arg Thr Leu Asp Glu Arg Ala
            20                  25                  30

His Glu Pro Ile Ala Ile Val Gly Ala Ala Cys Arg Leu Pro Gly Gly
        35                  40                  45

Val Arg Gly Pro Glu Asp Leu Trp Asp Leu Leu Ala Glu Thr Asp
    50                  55                  60

Ala Val Gly Gln Ala Pro Ala Asp Arg Gly Trp Asp Val Ala Ala Met
65                  70                  75                  80

Tyr Ser Pro Asp Pro Asp Gln Ala Gly Thr Thr Tyr Cys Arg Glu Gly
                85                  90                  95

Gly Phe Val Arg Gly Ile Asp Gln Phe Asp Pro Gly Pro Phe Gly Ile
            100                 105                 110

Ser Pro Asn Glu Ala Leu Thr Met Asp Pro Gln Gln Arg Leu Leu Leu
        115                 120                 125

Glu Thr Ser Trp Glu Ala Leu Glu Arg Ala Gly Ile Ala Pro Gln Ser
    130                 135                 140

Leu Ala Gly Ser Arg Thr Gly Val Phe Ala Gly Ala Trp Glu Ser Gly
145                 150                 155                 160
```

-continued

```
Tyr Gln Lys Gly Val Gln Val Asp Ala Asp Leu Glu Ala Gln Leu
                165                 170                 175

Leu Ala Gly Ile Val Ser Phe Thr Ala Gly Arg Val Ala Tyr Ala Leu
            180                 185                 190

Gly Leu Glu Gly Pro Ala Leu Thr Ile Asp Thr Ala Cys Ser Ser Ser
                195                 200                 205

Leu Val Ala Leu His Leu Ala Val Gln Ser Leu Arg Arg Gly Glu Cys
        210                 215                 220

Asp Leu Ala Leu Ala Gly Gly Ala Thr Val Ile Ala Asp Pro Ala Leu
225                 230                 235                 240

Phe Val Gln Phe Ser Arg Gln Arg Gly Leu Ala Pro Asp Gly Arg Cys
                245                 250                 255

Lys Ala Phe Ala Glu Ala Ala Asp Gly Phe Gly Pro Ala Glu Gly Ala
            260                 265                 270

Gly Met Leu Leu Val Glu Arg Leu Ser Asp Ala Arg Arg Leu Gly His
        275                 280                 285

Ser Val Leu Ala Val Val Arg Gly Ser Ala Val Asn Gln Asp Gly Ala
    290                 295                 300

Ser Asn Gly Leu Thr Ala Pro Ser Gly Pro Ala Gln Gln Arg Val Ile
305                 310                 315                 320

Arg Glu Ala Leu Ala Asp Ala Gly Leu Gly Pro Gly Asp Val Asp Val
                325                 330                 335

Val Glu Ala His Gly Thr Gly Thr Ala Leu Gly Asp Pro Ile Glu Ala
            340                 345                 350

Gly Ala Leu Leu Ala Thr Tyr Gly Arg Glu Arg Val Gly Asp Pro Leu
        355                 360                 365

Trp Leu Gly Ser Leu Lys Ser Asn Ile Gly His Thr Gln Ala Ala Ala
    370                 375                 380

Gly Val Ala Gly Val Ile Lys Met Val Glu Ala Leu Arg His Gly Thr
385                 390                 395                 400

Leu Pro Arg Ser Leu His Ile Asp Ala Pro Ser Ser Lys Val Glu Trp
                405                 410                 415

Gly Glu Gly Ala Val Glu Leu Leu Thr Glu Ala Arg Pro Trp Pro Gln
            420                 425                 430

Gln Ala Asp Arg Pro Arg Arg Ala Gly Ile Ser Ser Phe Gly Val Ser
        435                 440                 445

Gly Thr Asn Ala His Val Val Leu Glu Gln Ala Pro Thr Ala Pro Asp
    450                 455                 460

Val Leu Thr Glu Pro Arg Ala Ser Ala Ala Leu Pro Val Thr Val Leu
465                 470                 475                 480

Pro Leu Ser Ala Ala Gly Ala Glu Pro Leu Arg Glu Gln Ala Arg Arg
                485                 490                 495

Leu Ala Glu His Leu Val Ala His Ala Glu Ile Thr Pro Ala Asp Ala
            500                 505                 510

Ala Tyr Ser Ala Ala Thr Gly Arg Ala Thr Leu Ala Asn Arg Ala Val
        515                 520                 525

Val Leu Ala Asp Asp Arg Glu Pro Leu Ile Ala Arg Leu Thr Ala Leu
    530                 535                 540

Ala Glu Gly Arg Arg Asp Ala Asp Val Thr Val Gly Glu Ala Gly Ser
545                 550                 555                 560

Gly Arg Pro Pro Val Phe Val Phe Pro Gly Gln Gly Ser Gln Trp Ala
                565                 570                 575

Gly Met Gly Ala Glu Leu Leu Glu Met Ala Pro Val Phe Arg Ala Lys
```

-continued

```
                580                 585                 590
    Ala Glu Glu Cys Ala Arg Ala Leu Ala Pro His Leu Asp Trp Ser Val
                595                 600                 605

Leu Asp Val Leu Arg Gly Ala Pro Asp Ala Pro Pro Ile Asp Arg Ala
                610                 615                 620

Asp Val Val Gln Pro Ala Leu Phe Thr Met Met Ile Ser Leu Ala Ala
    625                 630                 635                 640

Leu Trp Glu Ala His Gly Val Arg Pro Ala Val Val Gly His Ser
                        645                 650                 655

Gln Gly Glu Val Ala Ala Tyr Val Ala Gly Ile Leu Ser Leu Asp
                660                 665                 670

Asp Ala Ala Arg Val Ile Ala Glu Arg Ser Arg Leu Trp Gly Arg Leu
                675                 680                 685

Ala Gly Asn Gly Gly Met Leu Ala Val Met Ala Pro Ala Asp Arg Val
                690                 695                 700

Arg Glu Leu Val Glu Pro Trp Ala Gln Arg Ile Ser Val Ala Ala Val
    705                 710                 715                 720

Asn Gly Pro Ala Ser Val Thr Val Ala Gly Asp Thr Ala Ala Leu Glu
                        725                 730                 735

Glu Phe Ser Glu Arg Leu Ser Ala Asp Arg Val Leu Arg Trp Pro Leu
                740                 745                 750

Ala Gly Val Asp Phe Ala Gly His Ser Pro Gln Val Glu Gln Phe Arg
                755                 760                 765

Thr Glu Leu Leu Ala Thr Leu Ala Gly Val Arg Pro Thr Ala Ala Arg
                770                 775                 780

Leu Pro Phe Phe Ser Thr Val Thr Ala Gly His Ala Pro Glu Gly
    785                 790                 795                 800

Leu Asp Ala Ala Tyr Trp Tyr Arg Asn Met Arg Glu Pro Val Glu Phe
                        805                 810                 815

Glu Ser Ala Leu Arg Ala Leu Leu Gln Gly His Arg Ser Phe Ile
                820                 825                 830

Glu Met Gly Pro His Pro Leu Leu Gly Ala Ala Ile Asn Glu Val Ala
                835                 840                 845

Glu Asp Glu Gly Val His Ala Thr Ala Leu Ser Thr Leu Tyr Arg Asp
                850                 855                 860

Ser Gly Gly Leu Asp Arg Phe Arg Ala Ser Ala Gly Ala Ala Phe Ala
    865                 870                 875                 880

His Gly Val Arg Val Asp Trp Ala Pro Phe Phe Glu Gly Thr Gly Ala
                        885                 890                 895

Arg Arg Val Ser Leu Pro Thr Tyr Ala Phe Arg Arg Asp Arg Phe Trp
                900                 905                 910

Leu Pro Thr Ala Thr Ser Arg Arg Ala Ala Asp Ala Ala Ile Ala
                915                 920                 925

Thr Ala Thr Ala Ser Asp Ala Trp Arg Tyr Arg Val Thr Trp Thr Ala
                930                 935                 940

Leu Glu Thr Val Asp Ser Gly Ala Pro Ser Gly Arg Trp Leu Leu Val
    945                 950                 955                 960

Glu Thr Thr Asp Ala Ala Pro Gly Glu Ala Asp Ala Ala Ala Ser Ala
                        965                 970                 975

Leu Gly Thr Ala Gly Ala Val Val Glu Arg Trp Thr Leu Asp Pro Thr
                980                 985                 990

Val Val Thr Arg Ala Gly Leu Thr Glu Arg Leu Ala Gly Leu Thr Ala
                995                 1000                1005
```

-continued

Glu Pro Gln Gly Leu Ala Gly Val Leu Val Leu Pro Gly Gln Ala Ala
     1010                1015                1020

Asp Thr Ala Pro Ala Asp Ala Ser Pro Leu Asp Glu Ser Thr Ala Ala
1025                1030                1035                1040

Val Leu Leu Val Thr Gln Ala Val Thr Asp Gly Ala Pro Lys Ala Arg
            1045                1050                1055

Ile Trp Val Ala Thr Arg Gly Ala Val Ala Val Glu Ser Asp Asp Val
            1060                1065                1070

Pro Cys Val Arg Gly Ala Arg Val Trp Gly Leu Gly Leu Val Ala Ala
            1075                1080                1085

Leu Glu Ala Pro Met Gln Trp Gly Gly Leu Val Asp Leu Pro Val Lys
    1090                1095                1100

Pro Gly Glu Val Asp Trp Arg Arg Leu Ala Ala Ala Leu Ser Thr Ser
1105                1110                1115                1120

Ser Gly Glu Asp Gln Val Ala Ile Arg Gly Thr Gly Thr Tyr Gly Arg
            1125                1130                1135

Arg Leu Leu Pro Ala Ala Pro Ala Ala Val Arg Gly Ser Trp Arg Pro
            1140                1145                1150

Arg Gly Cys Val Leu Val Thr Gly Gly Thr Gly Gly Leu Gly Gly His
    1155                1160                1165

Val Ala Arg Trp Leu Ala Arg Glu Gly Ala Glu His Val Val Leu Ala
    1170                1175                1180

Gly Arg Arg Gly Ala Glu Ala Pro Gly Ala Gly Glu Leu Glu Gln Glu
1185                1190                1195                1200

Leu Leu Gly Leu Gly Thr Lys Val Thr Val Val Ala Cys Asp Ile Ser
            1205                1210                1215

Asp Arg Thr Ser Val Met Gln Leu Leu Asp Ala Ile Lys Gly Leu Gly
            1220                1225                1230

Thr Pro Leu Arg Gly Val Phe His Ala Ala Gly Val Ala Gln Val Thr
    1235                1240                1245

Pro Leu Ala Glu Val Glu Leu Asp Glu Ala Ala Asp Val Leu Ala Gly
    1250                1255                1260

Lys Ala Val Gly Ala Glu Leu Leu Asp Glu Phe Thr Ala Asp Ala Glu
1265                1270                1275                1280

Leu Asp Thr Phe Val Leu Phe Ser Ser Gly Ala Ala Val Trp Gly Ser
            1285                1290                1295

Gly Gly Gln Ser Val Tyr Ala Ala Ala Asn Ala His Leu Asn Ala Leu
            1300                1305                1310

Ala Glu Arg Arg Arg Ala Gln Gly Arg Pro Ala Thr Ser Val Ala Trp
    1315                1320                1325

Gly Leu Trp Gly Gly Ser Gly Met Gly Ala Gly Asp Gly Val Thr Asp
    1330                1335                1340

Phe Tyr Ala Glu Arg Gly Leu Ala Pro Met Arg Pro Asp Leu Gly Ile
1345                1350                1355                1360

Glu Ala Leu His Gly Ala Leu Asn Gln Asp Asp Thr Cys Val Thr Val
            1365                1370                1375

Ala Asp Ile Asp Trp Glu His Phe Val Thr Gly Phe Thr Ala Phe Arg
            1380                1385                1390

Pro Ser Pro Leu Ile Ser Asp Ile Pro Gln Val Arg Glu Leu Arg Ala
    1395                1400                1405

Ala Ala Pro Thr Leu Asp Ala Ser Asp Glu Leu Arg Gly Arg Ile Asp
    1410                1415                1420

-continued

```
Ala Ala Leu Thr Pro Arg Glu Arg Thr Lys Val Leu Val Asp Leu Val
1425                1430                1435                1440

Arg Thr Val Ala Ala Glu Ile Leu Gly His Asp Gly Ile Gly Arg Ile
            1445                1450                1455

Gly His Asp Val Ala Phe Lys Asp Leu Gly Phe Asp Ser Leu Ala Ala
        1460                1465                1470

Val Arg Leu Arg Gly Arg Leu Ala Glu Ser Thr Gly Leu Thr Leu Pro
    1475                1480                1485

Ala Thr Val Ile Phe Asp His Pro Thr Val Asp Gln Leu Gly Ala Ala
1490                1495                1500

Leu Leu Ala Glu Leu Thr Asp Gly Ser Asn Gln Gly Gly Ala Val Val
1505                1510                1515                1520

Pro Ala Cys Ala Gly Gly Asn Glu Thr Pro Ala His Thr Pro Glu Ala
            1525                1530                1535

Thr Ala His Asp Val Glu Ile Asp Glu Leu Asp Ala Asp Asp Leu Ile
        1540                1545                1550

Arg Leu Ala Thr Ala Gly Lys Asp Asn Gly Asp Asp Ala Leu Ser Gly
    1555                1560                1565

<210> SEQ ID NO 6
<211> LENGTH: 1892
<212> TYPE: PRT
<213> ORGANISM: Streptomyces mycarofaciens

<400> SEQUENCE: 6

Met Ser Pro Ser Met Asp Glu Val Leu Gly Ala Leu Arg Thr Ser Val
1               5                   10                  15

Lys Glu Thr Glu Arg Leu Arg Arg Arg Asn Arg Glu Leu Leu Ala Ala
            20                  25                  30

Thr Arg Glu Pro Ile Ala Ile Val Gly Met Ala Cys Arg Phe Pro Gly
        35                  40                  45

Gly Val Val Ser Pro Asp Asp Leu Trp Glu Leu Thr Ala Asp Gly Val
    50                  55                  60

Asp Ala Val Thr Arg Phe Pro Thr Asp Arg Gly Trp Asp Glu Ala Ala
65                  70                  75                  80

Val Tyr Ser Pro Asp Pro Asp Thr Pro Gly Thr Thr Tyr Cys Arg Glu
                85                  90                  95

Gly Gly Phe Leu Asn Gly Val Gly Asp Phe Asp Ala Ala Phe Phe Gly
            100                 105                 110

Val Ser Pro Asn Glu Ala Leu Val Met Asp Pro Gln Gln Arg Leu Leu
        115                 120                 125

Leu Glu Thr Ser Trp Glu Ala Leu Glu Arg Ala Gly Val Val Pro Ala
    130                 135                 140

Ala Leu Arg Gly Ser Arg Thr Gly Val Phe Val Gly Ala Ala His Thr
145                 150                 155                 160

Gly Tyr Ile Ala Asp Thr Ala Arg Ala Pro Glu Gly Thr Glu Gly Tyr
                165                 170                 175

Leu Leu Thr Gly Asn Ala Asp Ala Val Leu Ser Gly Arg Ile Ala Tyr
            180                 185                 190

Thr Leu Gly Leu Glu Gly Pro Ala Leu Thr Ile Gly Thr Ala Cys Ser
        195                 200                 205

Ser Ser Leu Val Ala Leu His Leu Ala Val Gln Ser Leu Arg Arg Gly
    210                 215                 220

Glu Cys Asp Leu Ala Leu Ala Gly Gly Val Ala Val Met Pro Asp Pro
225                 230                 235                 240
```

-continued

```
Thr Val Phe Val Glu Phe Ser Arg Gln Arg Gly Leu Ala Pro Asp Gly
                245                 250                 255

Arg Cys Lys Ala Phe Ala Glu Gly Ala Asp Gly Thr Ala Trp Gly Glu
            260                 265                 270

Gly Val Gly Val Leu Leu Val Glu Arg Leu Ser Asp Ala Arg Arg Leu
        275                 280                 285

Gly His Ser Val Leu Ala Val Val Arg Gly Ser Ala Val Asn Gln Asp
    290                 295                 300

Gly Ala Ser Asn Gly Leu Thr Ala Pro Ser Gly Pro Ala Gln Gln Arg
305                 310                 315                 320

Val Ile Arg Glu Ala Leu Ala Asp Ala Gly Leu Gly Ser Gly Asp Val
                325                 330                 335

Asp Val Val Glu Ala His Gly Thr Gly Thr Ala Leu Gly Asp Pro Ile
            340                 345                 350

Glu Ala Gly Ala Leu Leu Ala Thr Tyr Gly Arg Glu Arg Val Gly Asp
        355                 360                 365

Pro Leu Trp Leu Gly Ser Leu Lys Ser Asn Ile Gly His Thr Gln Ala
    370                 375                 380

Ala Ala Gly Val Gly Gly Val Ile Lys Met Val Glu Ala Leu Arg His
385                 390                 395                 400

Gly Thr Leu Pro Arg Thr Leu His Val Asp Ala Pro Ser Ser Lys Val
                405                 410                 415

Glu Trp Asp Ser Gly Ala Val Glu Leu Leu Thr Glu Ala Arg Ala Trp
            420                 425                 430

Pro Arg Arg Ala Asp Arg Lys Arg Ala Ala Val Ser Ala Phe Gly
        435                 440                 445

Val Ser Gly Thr Asn Ala His Val Val Ile Glu Glu Pro Pro Ala Val
    450                 455                 460

Ala Ala Thr Gly Gly Ser Asp Asp Ala Asp His Ala Pro Leu Ala Ala
465                 470                 475                 480

Thr Pro Leu Pro Trp Val Val Ser Ala Arg Ser Glu Asp Ala Leu Cys
                485                 490                 495

Gly Gln Ala Asp Arg Leu Ala Ala Val Ala Arg Arg Trp Pro Glu
            500                 505                 510

Asn Asp Thr Asp Ala Ala Leu Thr Thr Val Ala Asp Val Gly His Ser
        515                 520                 525

Leu Ala Thr Thr Arg Glu Ala Leu Asp His Arg Val Val Leu Leu Val
    530                 535                 540

Asn Asp Ala Arg Ala Ala Arg Glu Asp Leu Ala Ala Leu Ala Ala Gly
545                 550                 555                 560

Arg Thr Pro Asp Thr Val Thr Gly Val Ala Arg Gly Arg Gly
                565                 570                 575

Leu Ala Phe Leu Cys Ser Gly Gln Gly Ala Gln Arg Leu Gly Thr Gly
            580                 585                 590

His Ala Leu Arg Thr Arg Phe Pro Val Phe Ala Gly Ala Leu Asp Glu
        595                 600                 605

Ile Thr Ser Glu Phe Asp Ala His Leu Glu Arg Pro Leu Leu Ser Val
    610                 615                 620

Leu Phe Ala Asp Pro Ala Ser Pro Asp Ala Ala Leu Leu Asp Arg Thr
625                 630                 635                 640

Asp Tyr Thr Gln Pro Ala Leu Phe Ala Val Glu Thr Ala Leu Phe Arg
                645                 650                 655
```

```
Leu Phe Glu Ser Trp Gly Leu Val Pro Asp Val Leu Gly His Ser
            660                 665                 670

Ile Gly Gly Leu Val Ala Ala His Ala Ala Gly Val Phe Ser Thr Ala
        675                 680                 685

Asp Ala Ala Arg Leu Val Ala Arg Gly Arg Leu Met Arg Ala Leu
    690                 695                 700

Pro Glu Gly Gly Ala Met Val Ala Val Gln Ala Thr Glu Gln Glu Ala
705                 710                 715                 720

Ala Gly Leu Lys Ser Val Ala Asp Gly Gly Ala Val Ile Ala Ala Leu
        725                 730                 735

Asn Gly Pro Gln Ala Leu Val Leu Ser Gly Asp Glu Ala Ala Val Leu
            740                 745                 750

Ala Ala Ala Arg Glu Leu Ala Ala Arg Gly Arg Arg Thr Lys Arg Leu
        755                 760                 765

Ala Val Ser His Ala Phe His Ser Pro Cys Met Asp Ala Met Leu Ala
    770                 775                 780

Asp Phe Arg Ala Val Ala Glu Thr Val Ala Tyr His Pro Pro Arg Leu
785                 790                 795                 800

Pro Val Val Ser Asp Val Thr Gly Glu Leu Ala Thr Ala Ala Glu Leu
            805                 810                 815

Met Asp Pro Asp Tyr Trp Thr Cys Gln Val Arg Glu Pro Val Arg Phe
        820                 825                 830

Ala Asp Ala Val Arg Thr Ala Arg Ala Arg Asp Ala Ala Thr Phe Ile
    835                 840                 845

Glu Leu Gly Pro Asp Ala Val Leu Ser Gly Met Ala Glu Glu Cys Leu
850                 855                 860

Ala Gly Glu Ala Asp Thr Ala Phe Ala Pro Ala Leu Arg Arg Gly Arg
865                 870                 875                 880

Pro Glu Gly Asp Thr Ala Leu Arg Ala Ala Ile Ala Phe Val Arg
            885                 890                 895

Gly Ala Asp Leu Asp Trp Ser Ala Leu Tyr Ser Gly Thr Gly Ala Arg
        900                 905                 910

Arg Ile Asp Leu Pro Thr Tyr Ala Phe Gln His Arg Arg Tyr Trp Leu
    915                 920                 925

Ala Pro Ser Asp Ser Ser Thr Ala Ala Pro Ala Thr Ser Ala Pro
        930                 935                 940

Ser Ala Gly Thr Ala Val Ala Ala Thr Ala Thr Val Asp Asp Asp Ala
945                 950                 955                 960

Leu Trp Thr Ala Val Arg Ala Gly Asp Ala Ser Ala Ala Val Arg
                965                 970                 975

Leu Gly Ala Glu Gly Ala Gly Ile Glu Asp His Leu His Ala Val Leu
            980                 985                 990

Pro His Phe Ala Ala Trp His Asp Arg His Arg Thr Ala Ala Glu Thr
        995                 1000                1005

Ala Gly Leu Arg Tyr Arg Val Ala Trp His Pro Leu Ser Ser Asp Val
    1010                1015                1020

Val Arg Phe Ser Pro Ser Asp Arg Trp Leu Met Val Glu His Gly His
1025                1030                1035                1040

Arg Thr Asp Ser Ala Asp Ala Asp Arg Ala Leu Arg Ala Ala Gly
            1045                1050                1055

Ala Gln Val Leu Arg Val Val Trp Pro Leu Glu Glu Asp Thr Gly Glu
        1060                1065                1070

Pro Gln Glu Glu Ala Arg Asp Arg Asn Ala Leu Ala Ala Arg Leu Ala
```

```
            1075                1080                1085

Glu Leu Ala Arg Ser Pro Glu Gly Leu Ala Gly Val Leu Val Leu Pro
    1090                1095                1100

Asp Thr Gly Gly Gly Met Leu Ala Gly Arg Pro Gly Leu Asp Glu Gly
1105                1110                1115                1120

Thr Ala Met Val Leu Gln Val Val Gln Ala Met Ala Asp Ala Ala Pro
                1125                1130                1135

Thr Ala Arg Val Trp Val Ala Thr Arg Gly Ala Val Ala Val Glu Ser
            1140                1145                1150

Gly Asp Val Pro Cys Val Met Gly Ala Arg Val Trp Gly Leu Gly Leu
    1155                1160                1165

Val Ala Ala Leu Glu Ala Pro Val Gln Trp Gly Gly Leu Val Asp Val
    1170                1175                1180

Pro Ala Glu Pro Gly Gly Arg Asp Trp Arg Arg Leu Ala Ala Val Ile
1185                1190                1195                1200

Ser Gly Ser Cys Gly Glu Asp Gln Val Ala Val Arg Gly Ser Gly Ile
                1205                1210                1215

Tyr Gly Arg Arg Leu Leu Pro Val Ala Pro Glu Val Ala Arg Ser Ser
            1220                1225                1230

Trp Arg Pro Arg Gly Cys Val Leu Val Thr Gly Gly Thr Gly Gly Leu
        1235                1240                1245

Gly Gly His Val Ala Arg Trp Leu Ala Arg Glu Gly Ala Glu His Val
    1250                1255                1260

Val Leu Ala Gly Arg Arg Gly Thr Glu Ala Pro Gly Ala Gly Glu Leu
1265                1270                1275                1280

Glu Arg Glu Leu Val Gly Leu Gly Ala Lys Val Ser Phe Val Ala Cys
            1285                1290                1295

Asp Val Ser Asp Arg Ala Ser Val Val Glu Leu Leu Asp Gly Ile Glu
                1300                1305                1310

Gly Leu Gly Val Pro Leu Arg Gly Val Phe His Ala Ala Gly Val Ala
            1315                1320                1325

Gln Val Thr Pro Leu Gly Glu Val Gly Leu Ala Glu Ala Ala Asp Val
    1330                1335                1340

Leu Ala Gly Lys Thr Met Gly Ala Glu Leu Leu Asp Glu Leu Thr Ala
1345                1350                1355                1360

Gly Ala Glu Leu Asp Ala Phe Val Leu Phe Ser Ser Gly Ala Ala Val
                1365                1370                1375

Trp Gly Ser Gly Gly Gln Ser Val Tyr Ala Ala Ala Asn Ala His Leu
            1380                1385                1390

Asp Ala Leu Ala Ala Arg Arg Arg Ala Gln Gly Arg Pro Ala Thr Ser
        1395                1400                1405

Val Ala Trp Gly Val Trp Asp Gly Thr Gly Met Gly Glu Leu Ala Pro
    1410                1415                1420

Glu Gly Tyr Leu Asp Arg His Gly Leu Thr Pro Leu Arg Pro Glu Thr
1425                1430                1435                1440

Ala Ile Ala Ala Leu Arg Gln Ala Ile Asp Ser Gly Asp Ala Thr Ala
                1445                1450                1455

Thr Val Ala Asp Ile Asp Trp Glu Gln Phe Ala Gln Gly Phe Thr Ala
            1460                1465                1470

Phe Arg Pro Ser Pro Leu Ile Ser Asp Ile Pro Ala Ala Arg Thr Ala
        1475                1480                1485

Leu Ala Val Pro Arg Ser Ala Asp Gly Thr Ala Thr Ala Pro Asp Leu
    1490                1495                1500
```

-continued

```
Val Arg Ala Arg Pro Glu Asp Arg Pro Arg Leu Ala Leu Glu Leu Val
1505                1510                1515                1520

Leu Arg His Ile Ala Ala Val Leu Gly His Thr Asp Glu Ser Arg Val
            1525                1530                1535

Asp Ala Arg Thr Pro Phe Arg Asp Leu Gly Phe Asp Ser Leu Ala Ala
        1540                1545                1550

Val Arg Leu Arg Arg Gln Leu Ala Glu Asp Thr Gly Leu Asp Leu Pro
    1555                1560                1565

Gly Ala Leu Val Phe Asp His Glu Asp Pro Ala Ala Leu Ala Asp His
    1570                1575                1580

Leu Ala Thr Leu Ala Asp Ala Gly Thr Thr Gly Arg Asn Gln Gly Ala
1585                1590                1595                1600

Ala Pro Ala Glu Ser Gly Leu Leu Ala Gly Phe Arg Thr Ala Val Glu
                1605                1610                1615

Gln Gly Arg Ser Ala Glu Ala Val Glu Leu Met Ala Ser Leu Ala Thr
            1620                1625                1630

Phe Arg Thr Ala Phe Thr Arg Glu Asp Ser Gly Thr Thr Cys Pro Ala
        1635                1640                1645

Pro Val Leu Leu Ala Ala Gly Pro Ala Thr Arg Pro Thr Leu Tyr Cys
    1650                1655                1660

Cys Ala Gly Thr Ala Ala Thr Ser Gly Pro Gly Glu Tyr Ala Ala Phe
1665                1670                1675                1680

Ala Asp Gly Leu Arg Asp Ser Arg Thr Thr Val Val Leu Pro Leu Ser
                1685                1690                1695

Gly Phe Gly Ser Pro Ala Glu Pro Leu Pro Ala Ser Leu Asp Ala Leu
            1700                1705                1710

Leu Asp Ala Gln Ala Asp Ala Leu Leu Glu His Ala Ala Gly Lys Pro
        1715                1720                1725

Phe Ala Leu Ala Gly His Ser Ala Gly Ala Asn Ile Ala His Ala Leu
    1730                1735                1740

Ala His Arg Leu Asp Glu Arg Gly Thr Gly Pro Thr Ala Val Val Leu
1745                1750                1755                1760

Met Asp Val Tyr Arg Pro Glu Asp Pro Gly Ala Met Gly Val Trp Arg
                1765                1770                1775

Glu Asp Leu Leu Arg Trp Ala Leu Asp Arg Ser Thr Val Thr Leu Glu
            1780                1785                1790

Asp His Arg Leu Thr Ala Met Ala Gly Tyr His Arg Leu Leu Leu Asp
        1795                1800                1805

Thr Arg Leu Thr Ala Leu Arg Ala Pro Val Leu Leu Val Arg Ala Ser
    1810                1815                1820

Glu Pro Leu Arg Glu Trp Pro Ala Asp Ala Gly Arg Gly Asp Trp Arg
1825                1830                1835                1840

Ser Gln Val Pro Phe Ala Arg Thr Val Ala Glu Val Pro Gly Asn His
                1845                1850                1855

Phe Thr Met Leu Thr Glu His Ala Arg His Thr Ala Ser Val Val His
            1860                1865                1870

Asp Trp Leu Gly Ala Asp Pro Arg Pro Ala Glu Pro Thr Leu Leu Thr
        1875                1880                1885

Gly Gly Lys His
    1890

<210> SEQ ID NO 7
<211> LENGTH: 237
```

<212> TYPE: PRT
<213> ORGANISM: Streptomyces mycarofaciens

<400> SEQUENCE: 7

Met Tyr Ala Asn Asp Ile Ala Ala Leu Tyr Asp Leu Val His Glu Gly
1               5                   10                  15

Lys Gly Lys Asp Tyr Arg Gln Glu Ala Glu Ile Ala Gln Leu Val
            20                  25                  30

Arg Ala His Arg Pro Ala Thr Arg Ser Leu Leu Asp Val Ala Cys Gly
        35                  40                  45

Thr Gly Gln His Leu Arg His Leu Asp Gly Leu Phe Asp His Val Glu
    50                  55                  60

Gly Leu Glu Leu Ser Gln Asp Met Leu Ala Ile Ala Ile Gly Arg Asn
65                  70                  75                  80

Pro Asp Val Thr Leu His Glu Gly Asp Met Arg Ser Phe Ala Leu Gly
                85                  90                  95

Arg Arg Phe Asp Ala Val Ile Cys Met Phe Ser Ser Ile Gly His Leu
            100                 105                 110

Arg Thr Thr Asp Glu Leu Asp Ser Thr Leu Arg Cys Phe Ala Gly His
        115                 120                 125

Leu Glu Pro Gly Gly Ala Ile Val Ile Glu Pro Trp Trp Phe Pro Asp
    130                 135                 140

Ser Phe Thr Pro Gly Tyr Val Gly Ala Ser Val Thr Glu Ala Gly Glu
145                 150                 155                 160

Arg Thr Ile Cys Arg Val Ser His Ser Val Arg Glu Gly Asp Ala Thr
                165                 170                 175

Arg Ile Glu Val His Tyr Leu Val Ala Glu Pro Gly Gly Ile Arg
            180                 185                 190

His Leu Thr Glu Asp His Thr Ile Thr Leu Phe Pro Arg Ala Asp Tyr
        195                 200                 205

Glu Arg Ala Phe Glu Arg Ala Gly Cys Asp Val Arg Tyr Gln Glu Gly
    210                 215                 220

Gly Ser Ser Gly Arg Gly Leu Phe Ile Gly Ser Arg Arg
225                 230                 235

<210> SEQ ID NO 8
<211> LENGTH: 415
<212> TYPE: PRT
<213> ORGANISM: Streptomyces mycarofaciens

<400> SEQUENCE: 8

Met Pro Ile Pro Ala Thr Ala Pro Ala Pro Val Asn Ala Gly Thr Arg
1               5                   10                  15

Glu Leu Gly Arg Arg Leu Gln Leu Thr Arg Ala Ala Gln Trp Cys Ala
            20                  25                  30

Gly Asn Gln Gly Asp Pro Tyr Ala Leu Ile Leu Arg Ala Thr Ala Asp
        35                  40                  45

Pro Ala Pro Leu Glu Arg Glu Ile Arg Ala Arg Gly Pro Trp Phe Arg
    50                  55                  60

Ser Glu Leu Thr Gly Ala Trp Val Thr Ala Asp Pro Glu Val Ala Ala
65                  70                  75                  80

Ala Ala Leu Ala Asp Pro Arg Leu Cys Thr Leu Asp Arg Ala Gly Arg
                85                  90                  95

Arg Pro Asp Ala Glu Leu Leu Pro Leu Ala Glu Ala Phe Pro Cys His
            100                 105                 110

```
Glu Arg Ala Glu Leu Ala Arg Leu Arg Ala Leu Ala Ala Pro Val Leu
            115                 120                 125

Ser Arg Cys Ala Pro Ala Glu Ala Pro Cys Glu Ala Arg Thr Ala Ala
    130                 135                 140

Arg Arg Leu Leu Arg Arg Leu Leu Pro Ser Asp Gly Ala Gly Phe Asp
145                 150                 155                 160

Leu Val Thr Glu Val Ala Arg Pro Tyr Ala Val Gly Leu Val Leu Arg
                165                 170                 175

Leu Leu Gly Val Pro Asp Cys Asp Arg Asp Thr Met Gly Arg Ala Leu
            180                 185                 190

Ala Gly Cys Ala Pro Gln Leu Asp Ala Arg Leu Ala Pro Gln Thr Leu
        195                 200                 205

Ala Val Ala Arg Glu Ser Thr Asp Ala Val Gln Thr Leu Ala Asp His
    210                 215                 220

Val Pro Glu Leu Val Ala Glu Lys Gln Arg Ala Val Glu Ser Ala Glu
225                 230                 235                 240

Pro Arg Pro Asp Asp Val Leu Ala Leu Leu Arg Asp Gly Ala Ala
                245                 250                 255

Pro Arg Asp Val Glu Arg Ile Ala Leu Leu Leu Ala Ile Gly Thr Pro
                260                 265                 270

Glu Pro Ala Ala Thr Ala Val Ala Asn Thr Val His Arg Leu Leu Asn
            275                 280                 285

Arg Pro Gly Glu Trp Gly Arg Val Arg Arg Thr Pro Ala Ala Ala Arg
        290                 295                 300

Ala Val Asp Arg Thr Leu Arg Asp Arg Pro Ala Arg Leu Glu Ser
305                 310                 315                 320

Arg Val Ala Ser Thr Asp Leu Glu Leu Gly Gly Cys Arg Ile Ala Ala
                325                 330                 335

Asp Asp His Val Val Leu Ala Ala Ala Gly Arg Asp Ala Pro Gly
            340                 345                 350

Pro Glu Pro Leu Gly Gly Pro Asp Gly Pro His Leu Ala Leu Ala Leu
        355                 360                 365

Pro Leu Ile Arg Leu Ala Ala Thr Thr Ala Val Gln Val Met Ala Gly
    370                 375                 380

Arg Leu Pro Gly Leu Arg Val Glu Asp Glu Pro Leu Thr Arg Pro Arg
385                 390                 395                 400

Ser Pro Val Val Cys Ala Cys Ala Arg Phe Arg Val His Pro Gly
                405                 410                 415

<210> SEQ ID NO 9
<211> LENGTH: 421
<212> TYPE: PRT
<213> ORGANISM: Streptomyces mycarofaciens

<400> SEQUENCE: 9

Val Arg Val Leu Leu Thr Ser Leu Ala His Asn Thr His Tyr Tyr Ser
1               5                   10                  15

Leu Val Pro Leu Ala Trp Ala Leu Arg Ala Ala Gly His Glu Val Arg
            20                  25                  30

Val Ala Ser Pro Pro Ser Leu Thr Asp Val Ile Thr Ser Thr Gly Leu
        35                  40                  45

Pro Ala Val Pro Val Gly Asp Asp Gln Pro Ala Ala Glu Leu Leu Ala
    50                  55                  60

Glu Met Gly Gly Asp Leu Val Pro Tyr Gln Arg Gly Phe Glu Phe Ala
65                  70                  75                  80
```

```
Glu Val Glu Pro Ala Gln Glu Thr Thr Trp Glu His Leu Leu Gly Gln
                85                  90                  95

Gln Ser Met Met Ser Ala Leu Cys Phe Ala Pro Phe Ser Gly Ala Ala
            100                 105                 110

Thr Met Asp Asp Ile Val Asp Phe Ala Arg Asp Trp Arg Pro Asp Leu
            115                 120                 125

Val Val Trp Glu Pro Trp Thr Tyr Ala Gly Pro Ile Ala Ala Arg Ala
        130                 135                 140

Cys Gly Ala Ala His Ala Arg Ile Leu Trp Gly Pro Asp Ala Ile Gly
145                 150                 155                 160

Arg Ser Arg Arg Arg Phe Leu Glu Ala Leu Glu Arg Val Pro Glu Glu
                165                 170                 175

Leu Arg Glu Asp Pro Ile Ala Glu Trp Leu Gly Trp Thr Leu Asp Arg
            180                 185                 190

Tyr Gly Cys Ala Phe Asp Glu Arg Asp Val Leu Gly His Trp Val Ile
        195                 200                 205

Asp Pro Gly Pro Arg Ser Thr Arg Leu Asp Leu Gly Gln Thr Thr Val
210                 215                 220

Pro Met Cys Tyr Val Pro Tyr Asn Gly Arg Ala Val Ile Glu Pro Trp
225                 230                 235                 240

Leu Ala Glu Lys Pro Glu Arg Pro Arg Val Cys Leu Thr Leu Gly Ile
                245                 250                 255

Ser Ala Arg Glu Thr Tyr Gly Arg Asp Ala Val Ser Tyr Ser Glu Leu
            260                 265                 270

Leu Gln Ala Leu Gly Arg Met Glu Ile Glu Val Val Ala Thr Leu Asp
        275                 280                 285

Ala Ser Gln Gln Lys Arg Leu Gly Ser Leu Pro Asp Asn Val Val Pro
290                 295                 300

Val Asp Phe Val Pro Leu Asp Ala Leu Leu Pro Ser Cys Ala Ala Ile
305                 310                 315                 320

Ile His His Gly Gly Ala Gly Thr Trp Ser Thr Ala Leu Leu His Gly
                325                 330                 335

Val Pro Gln Ile Leu Leu Pro Ala Leu Trp Asp Ala Pro Leu Lys Ala
            340                 345                 350

Gln Gln Leu Gln Arg Leu Ser Ala Gly Leu Asn Leu Pro Ala Ala Thr
        355                 360                 365

Leu Thr Ala Arg Arg Leu Ala Asp Ala Val His Thr Ala Val His Asp
370                 375                 380

Pro Ala Ile Arg Ala Gly Ala Arg Arg Leu Arg Glu Glu Met Leu Ala
385                 390                 395                 400

Asp Pro Thr Pro Ala Ala Ile Val Pro Thr Leu Glu Arg Leu Thr Ala
                405                 410                 415

Leu His Arg Ala Ala
            420

<210> SEQ ID NO 10
<211> LENGTH: 449
<212> TYPE: PRT
<213> ORGANISM: Streptomyces mycarofaciens

<400> SEQUENCE: 10

Met Pro Asp Ser His Ala Leu Ser Glu Leu Leu Ala Ala Ile Arg Ala
  1               5                  10                  15

Pro Asp His Thr Pro Glu Asp Ile Ala Ala Leu Pro Leu Pro Glu Ser
```

-continued

```
                 20                  25                  30
Phe Arg Ala Val Thr Val His Lys Glu Asp Thr Glu Met Phe Arg Gly
             35                  40                  45

Met Thr Ser Ala Asp Lys Asp Pro Arg Lys Ser Leu Cys Val Asp Glu
         50                  55                  60

Val Pro Val Pro Glu Leu Gly Pro Gly Glu Ala Leu Ile Ala Val Met
 65                  70                  75                  80

Ala Ser Ser Val Asn Tyr Asn Thr Val Trp Ser Ser Leu Phe Glu Pro
                 85                  90                  95

Met Pro Thr Phe Gly Phe Leu Glu Arg Tyr Gly Arg Thr Ser Pro Leu
            100                 105                 110

Ala Ala Arg His Asp Leu Pro Tyr His Ile Leu Gly Ser Asp Leu Ala
            115                 120                 125

Gly Val Val Leu Arg Thr Gly Pro Gly Val Asn Val Trp Ala Pro Gly
        130                 135                 140

Asp Glu Val Val Ala His Cys Leu Ser Val Glu Leu Glu Ser Pro Asp
145                 150                 155                 160

Gly His Asp Asp Thr Leu Leu Asp Pro Ala Gln Arg Ile Trp Gly Phe
                165                 170                 175

Glu Thr Asn Phe Gly Gly Leu Ala Glu Ile Ala Leu Val Lys Ala Asn
            180                 185                 190

Gln Leu Met Pro Lys Ala Ala His Leu Thr Trp Glu Glu Ala Ala Ala
        195                 200                 205

Pro Gly Leu Val Asn Ser Thr Ala Tyr Arg Gln Leu Val Ser Arg Asn
    210                 215                 220

Gly Ala Gly Met Lys Gln Gly Asp Asn Val Leu Ile Trp Gly Ala Ser
225                 230                 235                 240

Gly Gly Leu Gly Ser Tyr Ala Thr Gln Leu Ala Leu Ala Gly Gly Ala
                245                 250                 255

Asn Pro Val Cys Val Val Ser Asn Gln Arg Lys Ala Glu Val Cys Arg
            260                 265                 270

Ala Met Gly Ala Gly Ala Ile Ile Asp Arg Ser Ala Glu Asp Tyr Arg
        275                 280                 285

Phe Trp Ser Asp Glu Gln Thr Gln Asn Pro Arg Glu Trp Lys Arg Phe
    290                 295                 300

Gly Ala Arg Ile Arg Glu Leu Thr Gly Gly Glu Asp Val Asp Ile Val
305                 310                 315                 320

Phe Glu His Pro Gly Arg Glu Thr Phe Gly Ala Ser Val Tyr Val Ala
                325                 330                 335

Arg Arg Gly Gly Thr Ile Val Thr Cys Ala Ser Thr Ser Gly Tyr Arg
            340                 345                 350

His Glu Phe Asp Asn Arg Tyr Leu Trp Met His Leu Lys Arg Ile Val
        355                 360                 365

Gly Thr His Phe Ala Asn Tyr Arg Glu Ala Trp Glu Ala Asn Arg Leu
    370                 375                 380

Val Thr Lys Gly Lys Ile His Pro Thr Leu Ser Cys Thr Tyr Pro Leu
385                 390                 395                 400

Ala Asp Thr Ala Leu Ala Val His Asp Val His Arg Asn Val His Gln
                405                 410                 415

Gly Lys Val Gly Val Leu Cys Leu Ala Pro Met Glu Gly Leu Gly Val
            420                 425                 430

Arg Asp Glu Glu Met Arg Ala Gln His Leu Asp Ala Ile Asn Arg Phe
        435                 440                 445
```

Arg

<210> SEQ ID NO 11
<211> LENGTH: 223
<212> TYPE: PRT
<213> ORGANISM: Streptomyces mycarofaciens

<400> SEQUENCE: 11

Val Ser Val Ala Asp Gln Thr Thr Leu Ser Pro Ala Leu Leu Asp Tyr
 1               5                  10                  15

Ala Arg Ser Val Ala Leu Arg Glu Asp Gly Leu Leu Arg Glu Leu His
             20                  25                  30

Asp Met Thr Ala Gln Leu Pro Gly Gly Arg Ala Met Gln Ile Met Pro
         35                  40                  45

Glu Glu Ala Gln Phe Leu Gly Leu Leu Ile Arg Leu Val Gly Ala Arg
     50                  55                  60

Arg Val Leu Glu Ile Gly Thr Phe Thr Gly Tyr Ser Thr Leu Cys Met
 65                  70                  75                  80

Ala Arg Ala Leu Pro Ala Gly Gly Arg Ile Val Thr Cys Asp Ile Ser
                 85                  90                  95

Asp Lys Trp Pro Gly Ile Gly Ala Pro Phe Trp Gln Arg Ala Gly Val
            100                 105                 110

Asp Gly Leu Ile Asp Leu Arg Ile Gly Asp Ala Ala Arg Thr Leu Ala
        115                 120                 125

Glu Leu Arg Glu Arg Asp Gly Asp Gly Ala Phe Asp Leu Val Phe Val
    130                 135                 140

Asp Ala Asp Lys Ala Gly Tyr Leu His Tyr Tyr Glu Gln Ala Leu Ala
145                 150                 155                 160

Leu Val Arg Pro Gly Gly Leu Val Ala Ile Asp Asn Thr Leu Phe Phe
                165                 170                 175

Gly Arg Val Ala Asp Pro Ala Ala Asp Asp Pro Asp Thr Val Ala Val
            180                 185                 190

Arg Thr Leu Asn Asp Leu Leu Arg Asp Asp Glu Arg Val Asp Ile Ala
        195                 200                 205

Leu Leu Thr Val Ala Asp Gly Ile Thr Leu Ala Arg Arg Glu
    210                 215                 220

<210> SEQ ID NO 12
<211> LENGTH: 387
<212> TYPE: PRT
<213> ORGANISM: Streptomyces mycarofaciens

<400> SEQUENCE: 12

Met Pro Pro Arg Val Val Arg Leu Pro Ser Leu Thr Gly Leu Arg Trp
 1               5                  10                  15

Phe Ala Ala Leu Ala Val Phe Ala Cys His Ile Ala Gln Gln Gln Phe
             20                  25                  30

Phe Ala Asp Gln Gln Val Gly Thr Ala Leu Leu His Ile Thr Thr Leu
         35                  40                  45

Gly Ser Ile Ala Val Ser Val Phe Leu Leu Ser Gly Phe Val Leu
     50                  55                  60

Ala Trp Ser Ala Arg Asp Lys Asp Ser Val Thr Thr Phe Trp Arg Arg
 65                  70                  75                  80

Arg Phe Ala Lys Ile Tyr Pro Leu His Leu Val Thr Phe Leu Ile Ala
                 85                  90                  95

-continued

Gly Val Ile Ile Phe Ser Leu Ala Glu Pro Thr Leu Pro Gly Gly Ser
            100                 105                 110

Val Trp Asp Gly Leu Val Pro Asp Leu Leu Leu Val Gln Ser Trp Leu
        115                 120                 125

Pro Glu Pro Thr Ile Ile Ala Gly Phe Asn Thr Pro Ser Trp Ser Leu
    130                 135                 140

Ser Cys Glu Phe Ala Phe Tyr Leu Thr Phe Pro Leu Trp Tyr Arg Leu
145                 150                 155                 160

Val Arg Lys Ile Pro Val Arg Arg Leu Trp Trp Cys Ala Ala Gly Ile
                165                 170                 175

Ala Ala Ala Val Ile Cys Val Pro Phe Val Thr Ser Gln Phe Pro Ala
                180                 185                 190

Ser Ala Glu Thr Ala Pro Gly Met Pro Leu Asn Glu Leu Trp Phe Ala
            195                 200                 205

Cys Trp Leu Pro Pro Val Arg Met Leu Glu Phe Val Leu Gly Ile Val
    210                 215                 220

Met Ala Leu Ile Leu Arg Thr Gly Val Trp Arg Gly Pro Gly Val Val
225                 230                 235                 240

Ser Ser Ala Leu Leu Leu Ala Ala Ala Tyr Gly Val Thr Gln Val Val
                245                 250                 255

Pro Pro Met Phe Thr Ile Ala Ala Cys Ser Ile Val Pro Ala Ala Leu
            260                 265                 270

Leu Ile Thr Ala Leu Ala Asn Ala Asp Val Gln Gly Leu Arg Thr Gly
        275                 280                 285

Leu Arg Ser Ala Val Leu Val Arg Leu Gly Glu Trp Ser Phe Ala Phe
    290                 295                 300

Tyr Leu Val His Phe Met Val Ile Arg Tyr Gly His Arg Leu Met Gly
305                 310                 315                 320

Gly Glu Leu Gly Tyr Ala Arg Gln Trp Ser Thr Ala Ser Ala Gly Ala
                325                 330                 335

Leu Ala Leu Ala Met Leu Ala Val Ala Ile Val Ala Gly Gly Leu Leu
            340                 345                 350

His Thr Val Val Glu Asn Pro Cys Met Arg Leu Leu Gly Arg Arg Arg
        355                 360                 365

Pro Val Ala Thr Ala Pro Asp Pro Ala Thr Asp Glu Ala Pro Lys Leu
    370                 375                 380

Thr Arg Ala
385

<210> SEQ ID NO 13
<211> LENGTH: 424
<212> TYPE: PRT
<213> ORGANISM: Streptomyces mycarofaciens

<400> SEQUENCE: 13

Met Arg Thr Pro Thr Asp Asp Arg Ala Pro Val Pro Ala Asp Glu Ala
1               5                   10                  15

Val Asp Leu Met Asp Pro Arg Val Leu Asn Asp Pro Phe Gly Thr Phe
            20                  25                  30

Ala Arg Ile Arg Glu Gln Ala Pro Leu Val Arg Gly Arg Tyr Pro Trp
        35                  40                  45

Gly Asp Pro Phe Trp Met Val Thr Arg Tyr Val Asp Val Lys Ala Val
    50                  55                  60

Leu Ser Asp Pro Asp Leu Val Asn Asn Pro Arg Asn Val Pro Gly Met
65                  70                  75                  80

```
Asp Leu Pro His Leu Phe Ala Gln Gly Leu Asp Glu Ala Asp Phe Pro
            85                  90                  95

Gln Arg Tyr Ala Arg Tyr Leu Leu Asp Ser Val Leu Phe Gln Asp Gly
        100                 105                 110

Gln Asp His Ala Arg Leu Arg Lys Val Ser Gly Arg Ala Phe Thr Ala
        115                 120                 125

Arg Arg Val Ala Gln Leu Arg Pro Thr Met Ala Ala Met Val Glu Gly
    130                 135                 140

Leu Ile Arg Ala Leu Pro Gly Arg Ala Arg Asn Gly Ala Val Asp Leu
145                 150                 155                 160

Leu Glu His Phe Ala Tyr Pro Ile Ser Ile Gly Thr Ile Cys Glu Ile
                165                 170                 175

Val Gly Val Pro Glu Ala Glu Arg Glu Gln Trp Arg Val Trp Ser Ser
            180                 185                 190

Ala Phe Tyr Thr Met Asp Arg Ala Leu Leu Glu Pro Ala Val Gly Gly
        195                 200                 205

Met Ala Asp Arg Leu His Thr Met Ile Glu Gln Arg Arg Ala Glu Pro
    210                 215                 220

Thr Gly Asp Leu Leu Thr Gly Leu Val Gln Ala Glu Gly Asp Asp Gly
225                 230                 235                 240

Glu Arg Leu Thr Glu Val Glu Ile Val Ala Leu Val Leu Ala Phe Ile
                245                 250                 255

Thr Ala Gly Asn Glu Ala Thr Ala Gln Leu Ile Gly Asn Gly Val Ala
            260                 265                 270

Ala Leu Leu Thr His Pro Glu Gln Leu Ala Leu Leu Arg Ser Glu Arg
        275                 280                 285

Glu Leu Leu Pro Gly Ala Val His Glu Ile Met Arg Trp Cys Gly Pro
    290                 295                 300

Val Gln Ile Thr Gln Pro Arg Phe Ala Thr Arg Asp Leu Arg Val Gly
305                 310                 315                 320

Gly Met Pro Val Arg Lys Gly Glu Gln Val Met Ala Val Ile Gly Ala
                325                 330                 335

Ala Gly Tyr Asp Pro Ala Val Phe Pro Ala Pro Glu Arg Phe Asp Ile
            340                 345                 350

Thr Arg Thr Pro Gln Leu Arg Arg Asp Thr His Val Gly Phe Gly Phe
        355                 360                 365

Gly Pro His Tyr Cys Leu Gly Ala Ala Leu Ala Leu Gln Glu Ala Glu
    370                 375                 380

Val Ala Ile Asp Ala Leu Leu His His Phe Pro Gly Leu Ala Leu Ala
385                 390                 395                 400

Val Ala Pro Ser Asp Leu Glu Arg Gln Leu Phe Pro Gly Ala Trp Arg
                405                 410                 415

Leu Ser Ala Leu Pro Leu Arg Leu
            420

<210> SEQ ID NO 14
<211> LENGTH: 553
<212> TYPE: PRT
<213> ORGANISM: Streptomyces mycarofaciens

<400> SEQUENCE: 14

Met Leu Thr Ala Gln Leu Ala Leu His Asp Ile Thr Lys Arg Tyr Asn
1               5                   10                  15

Asp Arg Val Val Leu Asp Arg Val Gly Phe Thr Ile Lys Pro Gly Glu
```

```
                    20                  25                  30

Lys Val Gly Ile Ile Gly Asp Asn Gly Ser Gly Lys Ser Thr Leu Leu
         35                  40                  45

Lys Leu Ile Ala Gly Arg Glu Gln Ala Asp Asn Gly Ala Val Thr Val
     50                  55                  60

Val Ala Pro Gly Gly Thr Gly Tyr Leu Ala Gln Thr Leu Glu Leu Ala
 65                  70                  75                  80

Pro Glu Ala Thr Val Gln Asp Ala Val Asp Leu Ala Met Val Glu Leu
                 85                  90                  95

Arg Glu Ile Glu Ala Gly Val Arg Arg Ala Glu Ala Glu Leu Ala Glu
             100                 105                 110

Arg Pro Tyr Arg Ala Gly Pro Asp Arg Glu Leu Ala Ala Leu Leu Glu
         115                 120                 125

Thr Tyr Ala Asp Leu Val Glu Gln Tyr Gln Ala Arg Gly Gly Tyr Glu
     130                 135                 140

Ala Asp Ala Arg Val Asp Ile Ala Leu His Gly Leu Gly Leu Pro Ser
145                 150                 155                 160

Leu Asp Arg Asn Arg Arg Leu Gly Thr Leu Ser Gly Gly Glu Cys Ser
                 165                 170                 175

Arg Leu Ala Leu Ala Ala Thr Leu Ala Ser Ala Pro Glu Leu Leu Ala
             180                 185                 190

Leu Asp Glu Pro Thr Asn Asp Leu Asp Asp Gln Ala Val Ser Trp Leu
         195                 200                 205

Glu Asn His Leu Arg Ala His Arg Gly Thr Val Ile Ala Val Thr His
     210                 215                 220

Asp Arg Val Phe Leu Glu Arg Leu Thr Thr Thr Ile Leu Glu Val Asn
225                 230                 235                 240

Ala Gly Lys Val Ser Arg Tyr Gly Asn Gly Tyr Glu Gly Tyr Leu Thr
                 245                 250                 255

Ala Lys Ala Ala Glu Arg Glu Arg Arg Leu Arg Glu Tyr Glu Glu Trp
             260                 265                 270

Arg Ala Glu Leu Asp Arg Asn Arg Glu Leu Val Thr Ser Asn Val Ser
         275                 280                 285

Arg Leu Asp Asn Ile Pro Arg Lys Val Pro Phe Ala Val Phe Gly His
     290                 295                 300

Gly Ala Phe Arg Ser Arg Gly Arg Gly His Gly Ala Met Ser Arg Ile
305                 310                 315                 320

Arg Asn Ala Lys Glu Arg Met Ala Arg Leu Thr Glu Asn Pro Val Ala
                 325                 330                 335

Pro Pro Ala Asp Pro Leu Thr Phe Thr Ala His Ile Ala Thr Ala Gly
             340                 345                 350

Pro Asp Ala Thr Ala Gln Ala Pro Val Ala Glu Leu Ser Glu Val Arg
         355                 360                 365

Val Gly Asp Arg Leu Glu Val Ala Ser Val Ser Val His Pro Gly Glu
     370                 375                 380

Arg Leu Leu Ile Thr Gly Pro Asn Gly Ala Gly Lys Thr Thr Leu Leu
385                 390                 395                 400

Arg Val Leu Ala Gly Glu Leu Ala Pro Asp Ser Gly Thr Val His Val
                 405                 410                 415

Ser Gly Arg Val Gly His Leu Arg Gln Glu Gln Val Pro Trp Pro Ala
             420                 425                 430

Gly Leu Thr Val Thr Glu Ala Phe Ala His Gly Arg Pro Gly His Leu
         435                 440                 445
```

```
Asp Asp His Thr Glu Glu Leu Ser Leu Gly Leu Phe Ser Pro Ala
    450                 455                 460

Glu Leu Glu Gln Arg Val Gly Asp Leu Ser Tyr Gly Gln Arg Arg
465                 470                 475                 480

Ile Glu Leu Ala Arg Leu Val Ser Asp Pro Val Asp Leu Leu Leu
                485                 490                 495

Asp Glu Pro Thr Asn His Leu Ser Pro Val Leu Val Glu Leu Glu
            500                 505                 510

Gln Ala Leu Ala Asp Tyr Gln Gly Ala Val Val Val Thr His Asp
            515                 520                 525

Arg Arg Met Arg Ser Arg Phe Ser Gly Ser His Leu Ser Leu Arg Glu
        530                 535                 540

Gly Arg Ile Thr Ala Phe Ala Thr Ala
545                 550

<210> SEQ ID NO 15
<211> LENGTH: 271
<212> TYPE: PRT
<213> ORGANISM: Streptomyces mycarofaciens

<400> SEQUENCE: 15

Met Ser Pro Ile Ser Ala Ser Pro Ala Ala Ser Arg Ser Thr Ala
1               5                   10                  15

Arg Arg Glu Leu Gly Gln Asn Phe Phe Arg Ser Ala Ala Ala Cys
                20                  25                  30

Arg Phe Ser Asp Gln Leu Asp Ala Phe Cys Ala Asp Leu Pro Gly Ser
            35                  40                  45

Leu Ala Asp Val Leu Thr Val Glu Ile Gly Ala Gly Ser Gly Arg Val
    50                  55                  60

Thr Lys Ala Leu Ala Ser Ala Gly Arg Ser Leu Leu Ala Val Glu Ile
65                  70                  75                  80

Asp Ala Tyr Trp Ala Arg Arg Leu Thr Ala Glu Ser Leu Pro Asp Val
                85                  90                  95

Thr Val Val Asn Glu Asp Phe Leu Asn Leu Gln Leu Pro Arg Gln Pro
                100                 105                 110

Ile Arg Leu Ile Gly Asn Leu Pro Phe Val Ser Gly Thr Lys Ile Leu
            115                 120                 125

Arg Arg Cys Leu Glu Leu Gly Pro Asn Arg Met Cys Gln Ala Val Phe
130                 135                 140

Leu Leu Gln Arg Glu Tyr Val Gly Lys Arg Thr Gly Ala Trp Gly Gly
145                 150                 155                 160

Asn Leu Phe Asn Ala Gln Trp Glu Pro Trp Tyr Thr Phe Glu Gly Gly
                165                 170                 175

Leu Ala Phe Ser Arg Asn Glu Phe Ser Pro Val Pro Arg Ala Asp Thr
            180                 185                 190

Gln Thr Leu Val Val Met Pro Arg Arg Pro Ser Val Pro Trp Arg
            195                 200                 205

Glu Arg Thr Asp Tyr Gln Arg Phe Thr Gln Gln Ile Phe Asp Thr Gly
            210                 215                 220

Gln Met Thr Ile Gly Glu Ala Ala Arg Lys Val Leu Arg Arg Gly His
225                 230                 235                 240

Ala Gln Phe Val Arg Ser Ala Gly Val Arg Pro Ala Asp Arg Val Lys
                245                 250                 255

Asp Leu Thr Val Arg Asp Trp Ala Ala Leu Phe Arg Ala Asn Pro
```

260      265      270

<210> SEQ ID NO 16
<211> LENGTH: 200
<212> TYPE: PRT
<213> ORGANISM: Streptomyces mycarofaciens

<400> SEQUENCE: 16

Met Pro Ser Asn Arg Val Pro Glu Ala Val His Arg Pro Arg Arg Thr
1               5                   10                  15

His Ser Ala Ile Leu Gly Ala Thr Leu Glu Leu Val Gln Glu Val Gly
            20                  25                  30

Tyr Pro Lys Leu Thr Ile Glu Gly Val Ala Ala Arg Ala Gly Val Gly
        35                  40                  45

Lys Gln Thr Ile Tyr Arg Arg Trp Pro Ser Lys Ala Ala Ile Leu Arg
    50                  55                  60

Asp Ala Val Val Cys Leu Thr Glu Asp Ile Ala Arg Thr Ala Thr Ala
65                  70                  75                  80

Ile Pro Asp Thr Gly Asp Leu Glu Ala Asp Leu Lys Ala Val Leu Arg
                85                  90                  95

Ser Thr Val Asp Val Met Ser His Pro Glu Tyr Asp Val Pro Ala Arg
            100                 105                 110

Ala Leu Ala Ala Ala Gly Ile Ala Asp Pro Lys Leu Gly Glu Glu Leu
        115                 120                 125

Val Thr Arg Leu Val Glu Pro Gln Leu Arg Leu Cys Leu Glu Arg Leu
    130                 135                 140

Gly Ser Ala Arg Glu Ser Gly Gln Ile Ala Pro Asp Ile Asp Thr Arg
145                 150                 155                 160

Ile Ala Val Glu Met Leu Ala Gly Pro Ile Ala His Arg Trp Leu Leu
                165                 170                 175

Lys Ser Ala Pro Leu Thr His Glu Tyr Ala Glu Ala Leu Val Glu Leu
            180                 185                 190

Thr Leu Arg Gly Leu Ala Pro Arg
        195                 200

<210> SEQ ID NO 17
<211> LENGTH: 215
<212> TYPE: PRT
<213> ORGANISM: Streptomyces mycarofaciens

<400> SEQUENCE: 17

Val Pro Cys Ser Arg Ser Gly Pro Gly Pro Ser Gly Pro Glu Lys Arg
1               5                   10                  15

His Cys Arg Gly Arg Val Asp Ile Ser Leu Thr Pro Arg Ala Leu Ser
            20                  25                  30

Asn Leu Thr Ile Ser His Arg Leu Gly Arg Asn Pro Val Gln Ala Leu
        35                  40                  45

Pro Cys Ser Gly Gly Leu Ala Glu Ile Phe His Val Arg Leu Glu Tyr
    50                  55                  60

His Arg Leu Val Val Leu Thr Val Val Trp Ser Thr Thr His Arg Leu
65                  70                  75                  80

Leu Asn Arg Thr Ala Gln Gln Val Gly Ala Ala Glu Gly Val Ala Gly
                85                  90                  95

Gln Phe Pro Gly Asp Ala His Arg Leu Leu Leu Val Asp Glu Gln Thr
            100                 105                 110

Glu Gly Ala Ala Glu Asp Arg Pro His Ser Leu Thr Lys Ala His Gly

```
                115                 120                 125
Arg Ser Asp Asp Leu Arg Cys Arg His Arg Ala Ser Ala Glu Glu Leu
            130                 135                 140

Asp Ser Thr Asp Arg Ser Val Arg Arg Gly Gly Ser Pro Cys Thr Asp
145                 150                 155                 160

Arg Pro Trp Ser Ser Thr Ala Pro Arg Ser Ser Ala Tyr Arg Val
                165                 170                 175

Arg Arg Thr Ser Leu Gly Ala Glu Lys Ala Glu Asp Ala Pro Ala His
            180                 185                 190

Gly Ala Arg Gly Val Ser Gln Glu Ser Lys Asp Phe His Glu Gln Glu
            195                 200                 205

Arg Arg Val Arg Ala Arg Trp
    210                 215

<210> SEQ ID NO 18
<211> LENGTH: 33
<212> TYPE: PRT
<213> ORGANISM: Streptomyces mycarofaciens

<400> SEQUENCE: 18

Val Ser Glu Lys Thr Leu Gln His Arg Ile Asp Gly Pro Asp Gly Ala
  1               5                  10                  15

Pro Val Leu Val Leu Gly Ala Ala Leu Gly Thr Thr Trp His Met Trp
                 20                  25                  30

Asp

<210> SEQ ID NO 19
<211> LENGTH: 348
<212> TYPE: PRT
<213> ORGANISM: Streptomyces mycarofaciens

<400> SEQUENCE: 19

Val Lys Ile Leu Val Ile Gly Gly Ser Gln Phe Val Gly Arg Ala Phe
  1               5                  10                  15

Val Ala Glu Ala Leu Gly Arg Gly His Glu Val Thr Thr Phe Asn Arg
                 20                  25                  30

Gly Val Ser Ala Ala Asp Leu Pro Gly Val Lys Ala Ile Arg Gly Asp
             35                  40                  45

Arg Gln Val Pro Ala Asp Leu Glu Arg Leu Val Asp Gln Gly Gly Arg
         50                  55                  60

Trp Asp Ala Val Val Asp Thr Cys Gly Tyr Val Pro Gln Val Val Gly
 65                  70                  75                  80

Ala Ala Ala Arg Ala Leu Ser Gly His Ala Asp Thr Tyr Leu Tyr Val
                 85                  90                  95

Ser Ser Leu Ala Ala Val Arg Asp Trp Gly Thr Ala Pro Ser Ile Asn
            100                 105                 110

Asp Asp Ser Pro Thr His Asp Cys Ser Pro Glu Ala Gly Pro Asp Asp
        115                 120                 125

Gly Asp Tyr Gly Phe Leu Lys Ala Gly Cys Glu Arg Ala Val Val Arg
    130                 135                 140

Asp Phe Ala Gly Asp Ala Leu Val Phe Arg Ala Gly Val Ile Val Gly
145                 150                 155                 160

Pro His Asp Asn Val Gly Gln Leu Asp Ser Trp Leu Trp Arg Leu Arg
                165                 170                 175

Thr Ala Glu Gly Glu Arg Arg Val Leu Ala Pro Gly Ala Pro Asp
            180                 185                 190
```

```
Val Gly Met Arg Ile Ile Asp Ala Arg Asp Ile Ala Leu Phe Gly Leu
            195                 200                 205

Arg Cys Leu Glu Glu Arg Arg Thr Gly Pro Phe Val Val Ala Pro
        210                 215                 220

Glu Arg His Ala Thr Tyr Gly Glu Leu Leu Ala Ala Cys Ala Ala Ala
225                 230                 235                 240

Thr Gly Ser Arg Ala Glu Leu Val Trp Ala Asp Asp Ala Phe Leu Leu
                245                 250                 255

Glu Arg Glu Val Glu Pro Trp Ser Asp Leu Ala Met Trp Val Pro Trp
            260                 265                 270

Pro Asp Ala Leu Arg Met Trp Thr Thr Ala Ala Asp Arg Ala Glu Ala
            275                 280                 285

Ala Gly Leu Ile Cys Arg Pro Ile Thr Glu Thr Val Arg Asp Ala Trp
        290                 295                 300

Ala Val Leu Ser Asp Arg Thr Pro Pro Gln Leu Pro Leu Val Asn Ser
305                 310                 315                 320

Trp Gly Leu Arg Ala Gly Leu Pro Pro Glu Arg Glu Arg Glu Leu Leu
                325                 330                 335

Ala Ala Trp Asp Ala His Arg Arg Ala Thr Arg Ala
            340                 345

<210> SEQ ID NO 20
<211> LENGTH: 403
<212> TYPE: PRT
<213> ORGANISM: Streptomyces mycarofaciens

<400> SEQUENCE: 20

Met Ser Glu Ala Pro Thr Val Pro Leu Glu Leu Ser Lys Glu Ala Asn
1               5                   10                  15

Ala Gln Glu Leu Leu Asp Trp Phe Ala Phe Asn Arg Thr His His Pro
            20                  25                  30

Val Phe Trp Asp Glu Ser Arg His Ala Trp Gln Val Phe Arg Tyr Asp
        35                  40                  45

Asp Tyr Leu Thr Val Ser Asn Asn Pro Gln Phe Ser Ser Asp Phe
    50                  55                  60

Asn Glu Val Met Pro Thr Pro Pro Glu Leu Glu Met Val Ile Gly Pro
65                  70                  75                  80

Gly Thr Ile Gly Ala Leu Asp Pro Pro Ala His Gly Pro Met Arg Lys
                85                  90                  95

Leu Val Ser Gln Ala Phe Thr Pro Arg Arg Met Ala Arg Leu Glu Pro
            100                 105                 110

Arg Ile Arg Ala Val Thr Gln Glu Leu Leu Asp Ala Val Arg Gly Gln
        115                 120                 125

Glu Thr Ile Asp Val Val Gly Asp Leu Ser Tyr Ala Leu Pro Val Ile
    130                 135                 140

Val Ile Ala Glu Leu Leu Gly Ile Pro Ser Gly Asp Arg Asp Val Phe
145                 150                 155                 160

Arg Gly Trp Val Asp Thr Leu Leu Thr Asn Glu Gly Leu Glu Tyr Pro
                165                 170                 175

Asn Leu Pro Asp Asn Phe Ser Glu Thr Ile Ala Pro Ala Leu Lys Glu
            180                 185                 190

Met Thr Asp Tyr Leu Leu His Gln Ile His Ala Lys Arg Glu Ala Pro
        195                 200                 205

Val Asp Asp Leu Ile Ser Gly Leu Val Gln Ala Glu Gln Asp Gly Arg
```

```
            210                 215                 220
Lys Leu Thr Asp Val Glu Ile Val Asn Ile Val Ala Leu Leu Leu Thr
225                 230                 235                 240

Ala Gly His Val Ser Ser Thr Leu Leu Ser Asn Leu Phe Leu Val
                245                 250                 255

Leu Glu Glu Asn Pro Gln Ala Leu Ala Asp Leu Arg Ala Asp Arg Glu
            260                 265                 270

Leu Val Thr Gly Ala Val Glu Thr Leu Arg Tyr Arg Ser Pro Phe
                275                 280                 285

Asn Asn Ile Phe Arg Phe Leu Lys Glu Asp Thr Asp Ile Leu Gly Pro
290                 295                 300

Glu Met Lys Lys Gly Gln Met Val Ile Ala Trp Ser Gln Ser Ala Asn
305                 310                 315                 320

Arg Asp Pro Glu His Phe Pro Glu Pro Asp Thr Phe Asp Ile Arg Arg
                325                 330                 335

Ser Ser Ser Ser Arg His Met Ala Phe Gly Ile Gly Ile His His Cys
                340                 345                 350

Leu Gly Ala Phe Leu Ala Arg Gln Glu Gly Lys Val Val Leu Glu Leu
                355                 360                 365

Met Leu Asp Gln Val Arg Glu Phe Arg Ile Asp His Gly Asn Thr Arg
370                 375                 380

Tyr Tyr Glu Ala Asp Gln Leu Thr Ala Lys Tyr Leu Pro Val His Val
385                 390                 395                 400

Glu Trp Arg

<210> SEQ ID NO 21
<211> LENGTH: 152
<212> TYPE: PRT
<213> ORGANISM: Streptomyces mycarofaciens

<400> SEQUENCE: 21

Met Ala Glu Asn Ala Ala Glu Ser Ser His Ala Val Arg Val Gly Arg
  1               5                  10                  15

Ile Lys Pro Cys Arg Leu Ile Arg Leu Glu Gln His Ile Asp Pro Arg
                20                  25                  30

Gly Ser Leu Ser Val Val Glu Ser Gly Ile Thr Val Gly Phe Pro Ile
            35                  40                  45

Lys Arg Val Tyr Tyr Met His Gly Gln Pro Glu Ser Ser Pro Pro Arg
        50                  55                  60

Gly Leu His Gly His Arg Thr Leu Glu Gln Leu Val Ile Ala Val His
 65                  70                  75                  80

Gly Gly Phe Ser Ile Ser Leu Asp Asp Gly Phe Gln Ser Thr Thr Tyr
                85                  90                  95

Arg Leu Asp Glu Pro Gly Ala Gly Leu Tyr Ile Gly Pro Met Val Trp
            100                 105                 110

Arg Val Leu Lys Asp Phe Ala Pro Asp Ser Val Ala Leu Val Leu Ala
        115                 120                 125

Ser Arg His Tyr Glu Glu Ser Asp Tyr Tyr Arg Asp Tyr Asp Thr Phe
    130                 135                 140

Leu Arg Asp Ala Trp Ser Ile Lys
145                 150

<210> SEQ ID NO 22
<211> LENGTH: 396
<212> TYPE: PRT
```

<213> ORGANISM: Streptomyces mycarofaciens

<400> SEQUENCE: 22

| | | | | | | | | | | | | | | |
|---|---|---|---|---|---|---|---|---|---|---|---|---|---|---|
| Val | Asn | Val | Pro | Phe | Leu | Asp | Ala | Gly | Ala | Ala | Tyr | Arg | Glu | Leu | Arg |
| 1 | | | | 5 | | | | | 10 | | | | | 15 | |
| Ala | Asp | Ile | Asp | Gly | Ala | Leu | Arg | Arg | Val | Ser | Ala | Ser | Gly | Arg | Tyr |
| | | | 20 | | | | | 25 | | | | | 30 | | |
| Leu | Leu | Gly | Ala | Glu | Leu | Ala | Gly | Phe | Glu | Ala | Glu | Phe | Ala | Ala | Tyr |
| | | | | 35 | | | | | 40 | | | | | 45 | |
| Cys | Asp | Asn | Asp | His | Cys | Val | Ala | Val | Gly | Ser | Gly | Cys | Asp | Ala | Leu |
| | | 50 | | | | | 55 | | | | | 60 | | | |
| Glu | Leu | Ala | Leu | Arg | Ala | Leu | Gly | Ile | Gly | Pro | Gly | Asp | Glu | Val | Val |
| 65 | | | | | 70 | | | | | 75 | | | | | 80 |
| Val | Pro | Ala | His | Thr | Phe | Ile | Gly | Thr | Trp | Leu | Ala | Val | Ser | Ala | Ala |
| | | | | 85 | | | | | 90 | | | | | 95 | |
| Gly | Ala | Arg | Pro | Val | Gly | Val | Asp | Pro | Thr | Pro | Asp | Gly | Leu | Ser | Met |
| | | | 100 | | | | | 105 | | | | | 110 | | |
| Asp | Pro | Ala | Gln | Val | Glu | Ala | Ala | Ile | Thr | Pro | Arg | Thr | Arg | Ala | Val |
| | | | | 115 | | | | | 120 | | | | | 125 | |
| Met | Pro | Val | His | Leu | Tyr | Gly | His | Pro | Ala | Asp | Leu | Asp | Pro | Leu | Leu |
| | | 130 | | | | | 135 | | | | | 140 | | | |
| Ala | Ile | Ala | Glu | Arg | His | Gly | Leu | Ala | Val | Val | Glu | Asp | Ala | Ala | Gln |
| 145 | | | | | 150 | | | | | 155 | | | | | 160 |
| Ala | His | Gly | Ala | Arg | Tyr | Arg | Gly | Arg | Arg | Ile | Gly | Ser | Gly | His | Val |
| | | | | 165 | | | | | 170 | | | | | 175 | |
| Val | Ala | Phe | Ser | Phe | Tyr | Pro | Gly | Lys | Asn | Leu | Gly | Ala | Met | Gly | Asp |
| | | | 180 | | | | | 185 | | | | | 190 | | |
| Gly | Gly | Ala | Val | Val | Thr | Gly | Asp | Ala | Ala | Leu | Ala | Asp | Arg | Ile | Arg |
| | | | | 195 | | | | | 200 | | | | | 205 | |
| Leu | Leu | Arg | Asn | Cys | Gly | Ser | Arg | Glu | Lys | Tyr | Arg | His | Glu | Val | Gln |
| | | 210 | | | | | 215 | | | | | 220 | | | |
| Ala | Thr | Asn | Ser | Arg | Leu | Asp | Glu | Phe | Gln | Ala | Ala | Val | Leu | Arg | Ala |
| 225 | | | | | 230 | | | | | 235 | | | | | 240 |
| Lys | Leu | Pro | Arg | Leu | Pro | Ala | Trp | Asn | Ala | Leu | Arg | Val | Arg | Thr | Ala |
| | | | | 245 | | | | | 250 | | | | | 255 | |
| Glu | Arg | Tyr | Ser | Gln | Val | Leu | Gly | Ala | Leu | Pro | Gln | Ile | Ala | Val | Pro |
| | | | 260 | | | | | 265 | | | | | 270 | | |
| Ala | Ala | Ala | Pro | Trp | Ala | Asp | Pro | Val | Trp | His | Leu | Tyr | Val | Ile | Arg |
| | | | | 275 | | | | | 280 | | | | | 285 | |
| Cys | Ala | Glu | Arg | Asp | Glu | Leu | Arg | Arg | Arg | Ile | Glu | Arg | Ala | Gly | Val |
| | | 290 | | | | | 295 | | | | | 300 | | | |
| Glu | Thr | Leu | Ile | His | Tyr | Pro | Val | Pro | Pro | His | Arg | Thr | Pro | Ala | Tyr |
| 305 | | | | | 310 | | | | | 315 | | | | | 320 |
| Ala | Asp | Asp | Pro | Ala | Gly | Ala | Pro | Ala | Gly | Thr | His | Pro | Leu | Ser | Glu |
| | | | | 325 | | | | | 330 | | | | | 335 | |
| Arg | Arg | Ala | Ala | Glu | Ser | Leu | Ser | Leu | Pro | Leu | Gly | Pro | His | Leu | Gly |
| | | | 340 | | | | | 345 | | | | | 350 | | |
| Asp | Asp | Ala | Phe | Gln | Thr | Val | Val | Ala | Ala | Val | Arg | Ala | Ala | Ala | Val |
| | | | | 355 | | | | | 360 | | | | | 365 | |
| Gly | Leu | Pro | Ala | Tyr | Pro | Ala | Pro | Asp | Asp | Thr | Glu | Arg | Ala | Thr | Pro |
| | | 370 | | | | | 375 | | | | | 380 | | | |
| Gly | Gly | His | Arg | Leu | Pro | Leu | Ser | Thr | Glu | Ile | Arg | | | | |
| 385 | | | | | 390 | | | | | 395 | | | | | |

```
<210> SEQ ID NO 23
<211> LENGTH: 302
<212> TYPE: PRT
<213> ORGANISM: Streptomyces mycarofaciens

<400> SEQUENCE: 23

Met Thr Glu Thr Ile Ser Gly Cys Pro Gly Met Lys Gly Ile Ile Leu
 1               5                  10                  15

Ala Gly Gly Gly Thr Arg Leu Arg Pro Leu Thr Gly Thr Leu Ser
             20                  25                  30

Lys Gln Leu Leu Pro Val Tyr Asn Lys Pro Met Ile Tyr Tyr Pro Leu
         35                  40                  45

Ser Val Leu Met Leu Gly Gly Ile Arg Glu Ile Leu Val Ile Ser Ser
     50                  55                  60

Ser Gln His Ile Glu Leu Phe Gln Arg Leu Leu Gly Asp Gly Ser Arg
 65                  70                  75                  80

Leu Gly Leu Asp Ile Thr Tyr Ala Glu Gln Pro Glu Pro Gln Gly Ile
                 85                  90                  95

Ala Gln Ala Leu Thr Ile Gly Ser Asp His Ile Gly Asn Ser Pro Val
            100                 105                 110

Ala Leu Ile Leu Gly Asp Asn Ile Phe His Gly Pro Gly Phe Ser Ser
        115                 120                 125

Val Leu Gln Gly Ser Ile Arg His Leu Asp Gly Cys Val Leu Phe Gly
    130                 135                 140

Tyr Pro Val Ser Asp Pro Gly Arg Tyr Val Gly Glu Ile Asp Arg
145                 150                 155                 160

Asp Gly Leu Leu Leu Ser Leu Glu Glu Lys Pro Val Arg Pro Arg Ser
                165                 170                 175

Asn Leu Ala Val Thr Gly Leu Tyr Leu Tyr Asp Asn Asp Val Val Asp
            180                 185                 190

Ile Ala Lys Asn Ile Arg Pro Ser Ala Arg Gly Glu Leu Glu Ile Thr
        195                 200                 205

Asp Val Asn Lys Val Tyr Leu Glu Gln Arg Arg Ala Arg Leu Ile Glu
    210                 215                 220

Leu Gly His Gly Phe Ala Trp Leu Asp Met Gly Thr His Asp Ser Leu
225                 230                 235                 240

Leu Gln Ala Ser Gln Tyr Val Gln Leu Leu Glu Gln Arg Gln Gly Val
                245                 250                 255

Arg Ile Ala Cys Val Glu Glu Ile Ala Leu Arg Met Gly Phe Ile Asn
            260                 265                 270

Ala Asp Glu Leu Tyr Leu Leu Gly Cys Glu Leu Gly Asn Ser Gly Tyr
        275                 280                 285

Gly Ser Tyr Leu Met Glu Val Ala Ser His Ala Gly Ala Ala
    290                 295                 300

<210> SEQ ID NO 24
<211> LENGTH: 345
<212> TYPE: PRT
<213> ORGANISM: Streptomyces mycarofaciens

<400> SEQUENCE: 24

Met Pro Ala Leu Pro Glu Thr Glu Pro Trp Thr Asn Thr Arg Gly Ile
 1               5                  10                  15

Ser Arg Arg Pro Leu Arg Ile Leu Val Thr Gly Gly Ala Gly Phe Ile
             20                  25                  30
```

```
Gly Ser Arg Phe Val Asn Ala Leu Leu Asn Gly Ser Leu Pro Glu Phe
             35                  40                  45

Gly Lys Pro Glu Val Val Leu Asp Ala Leu Thr Tyr Ala Gly Asn
 50                  55                  60

Leu Ala Asn Leu Ala Pro Val Gly Asp Cys Pro Arg Leu Arg Val Val
 65                  70                  75                  80

Arg Gly Asp Ile Cys Asp Arg Ser Thr Val Ala Leu Ala Met Ala Gly
                 85                  90                  95

Ala Asp Leu Val Val His Phe Ala Ala Glu Ser His Val Asp Arg Ser
            100                 105                 110

Ile Asp Asp Ala Asp Ala Phe Val Arg Thr Asn Val Leu Gly Thr His
            115                 120                 125

Val Leu Leu Arg Glu Ala Leu Ala Val Arg Pro Gly Arg Phe Val His
130                 135                 140

Val Ser Thr Asp Glu Val Tyr Gly Ser Ile Pro Glu Gly Ser Trp Ser
145                 150                 155                 160

Glu Asp His Pro Leu Ser Pro Asn Ser Pro Tyr Ala Ala Ser Lys Ala
                165                 170                 175

Ala Ser Asp Gln Leu Ala Leu Ala Phe His Arg Thr His Gly Leu Pro
            180                 185                 190

Val Cys Val Thr Arg Cys Ser Asn Asn Tyr Gly Pro Tyr Gln Tyr Pro
            195                 200                 205

Glu Lys Ile Ile Pro Leu Phe Val Ser Asn Leu Leu Glu Gly Ala Ala
        210                 215                 220

Val Pro Leu Tyr Gly Asp Gly Asn Arg Arg Asp Trp Leu His Val
225                 230                 235                 240

Asp Asp His Cys Arg Gly Ile Ala Leu Val Ala Arg Gly Gly Arg Pro
                245                 250                 255

Gly Glu Val Tyr Asn Ile Gly Gly Thr Glu Leu Thr Asn Thr Glu
            260                 265                 270

Leu Thr Glu Arg Leu Leu Lys Leu Cys Glu Ala Asp Trp Ser Ala Val
        275                 280                 285

Arg Glu Val Pro Asp Arg Lys Gly His Asp Arg Arg Tyr Ser Val Asp
        290                 295                 300

Tyr Ala Lys Ile Ala Asn Glu Leu Gly Tyr Ala Pro Arg Ile Gly Ile
305                 310                 315                 320

Asp Glu Gly Leu Ala Glu Thr Val Arg Trp Tyr Arg Glu Asn Arg Ala
            325                 330                 335

Trp Trp Lys Pro Leu Lys Lys Gly Arg
            340                 345

<210> SEQ ID NO 25
<211> LENGTH: 264
<212> TYPE: PRT
<213> ORGANISM: Streptomyces mycarofaciens

<400> SEQUENCE: 25

Val Ser Ala Ser Thr Asp Pro Arg Leu Leu Ser Asp Leu Trp Leu Arg
  1               5                  10                  15

Arg Tyr Arg Pro Arg Ala Ala Pro Ala Val Arg Leu Val Cys Phe Pro
                 20                  25                  30

His Ala Gly Gly Ser Ala Thr Ser Phe Leu Pro Phe Val Gln Thr Leu
             35                  40                  45

Pro Asp Gln Val Glu Val Leu Ala Val Gln Tyr Pro Gly Arg Gln Asp
 50                  55                  60
```

-continued

Arg Arg Gly Glu Pro Leu Ile Gly Thr Ile Glu Gly Leu Val Glu Pro
65                  70                  75                  80

Leu Ala Glu Val Leu Ala Thr His Ser Asp Arg Pro Leu Val Leu Phe
            85                  90                  95

Gly His Ser Met Gly Ala Thr Val Ala Tyr Glu Val Ala Arg Val Leu
            100                 105                 110

Gln Gln Arg Gly Ala Ala Pro Ala Gly Leu Val Val Ser Gly Arg Arg
        115                 120                 125

Ala Pro Ile Val Asn Arg Pro Met Thr Val His Leu Tyr Asp Asp Asp
130                 135                 140

Arg Leu Leu Ala Glu Leu Arg Ser Leu Glu Gly Thr Asp Glu Ser Leu
145                 150                 155                 160

Leu Asn Asp Pro Glu Leu Leu Gln Leu Val Leu Pro Ala Ile Arg Asn
                165                 170                 175

Asp Tyr Arg Ala Val Gly Thr Tyr Thr His Arg Pro Gly Ala Pro Leu
            180                 185                 190

Ala Ser Ala Leu Thr Val Phe Thr Gly Ala Asp Asp Pro Asn Val Thr
        195                 200                 205

Ala Thr Glu Ala Ala Ala Trp Gln Ala Val Ala Glu Ala Gly Ala Gln
210                 215                 220

Val Arg Thr Phe Pro Gly Gly His Phe Leu Tyr Gln Gln Val Ala
225                 230                 235                 240

Glu Val Cys Gly Ala Leu Met Asp Thr Leu Ala Pro Leu Leu Pro Ala
                245                 250                 255

Gly Ala Arg Gly Ser His Ala Ala
            260

<210> SEQ ID NO 26
<211> LENGTH: 478
<212> TYPE: PRT
<213> ORGANISM: Streptomyces mycarofaciens

<400> SEQUENCE: 26

Met Arg Pro Glu Pro Gly Ser Val Ala Glu Ala Asp Tyr Ala Asp Arg
1               5                   10                  15

Leu Gln Thr Ala Glu Arg Val Arg Arg Ser Ala Asp Val Leu Asp Ser
            20                  25                  30

Arg Val Thr Pro Met Ala Glu Val Thr Gly Trp Leu Val Glu Tyr Gln
        35                  40                  45

Arg Ala His His Phe Arg Thr Glu Pro Ile Pro Phe His Asp Leu Gln
    50                  55                  60

Arg Trp Ser Phe Glu Asp Gly Thr Gly Asn Leu Arg His Glu Thr Gly
65                  70                  75                  80

Arg Phe Phe Ser Val Glu Gly Leu Arg Thr Ser Ser Asp Leu Asp Pro
                85                  90                  95

Val Asp Arg Ile Gln Pro Ile Val Gln Pro Glu Val Gly Leu Leu
            100                 105                 110

Gly Ile Leu Ala Arg Glu Phe Asp Gly Val Leu His Phe Leu Met Gln
        115                 120                 125

Ala Lys Pro Glu Pro Gly Asn Val Asn Gly Leu Gln Leu Ser Pro Thr
    130                 135                 140

Val Gln Ala Thr Arg Ser Asn Phe Asp Glu Val His Arg Gly Arg Ser
145                 150                 155                 160

Thr Pro Phe Leu Asp Arg Phe Ile Gln Arg Pro Gly Arg Arg Val Leu

```
                165                 170                 175
Val Asp Ala Ile Gln Ser Glu Gln Ala Asp Trp Phe Leu His Lys Arg
            180                 185                 190

Asn Arg Asn Met Val Val Glu Ile Asp Ser Gly Val Ala Glu His Cys
        195                 200                 205

Ser Phe Arg Trp Leu Thr Leu Gly Gln Ile Arg Arg Leu Leu Leu Arg
    210                 215                 220

Asp Asp Leu Val Asn Met Asp Thr Arg Ser Val Leu Ala Cys Leu Pro
225                 230                 235                 240

Thr Ala His Gly Ala Pro Gly Asp Asp Glu Gly Phe Pro Ala Ala
            245                 250                 255

Leu Arg Arg Ser Phe Tyr Gly Glu Thr Glu Pro Leu His Glu Leu Asn
        260                 265                 270

Ala Ile Thr Gly Cys Leu Thr Asp Val Gln Ala Leu Arg Val Leu Arg
    275                 280                 285

Gln Gln Ser Val Pro Leu Asn Gln Val Tyr Glu Asp Gly Trp Gln Arg
290                 295                 300

Thr Gly Ala Thr Ile Arg His Arg Ser Gly Glu Gly Phe Glu Ile Met
305                 310                 315                 320

Ala Val Glu Val Thr Ala Glu Gln Arg Glu Val Ala Ser Trp Thr Gln
            325                 330                 335

Pro Leu Leu Arg Pro Cys Ser Gln Gly Leu Met Ala Leu Val Val Arg
        340                 345                 350

Arg Ile Asn Gly Ala Leu His Ala Leu Val Ala Ala Arg Ser Asp Val
    355                 360                 365

Gly Thr Leu Asn Phe Ala Glu Phe Gly Pro Thr Val Gln Leu Arg Ser
370                 375                 380

Ala Trp Pro Arg Gly Lys Gly Asn Pro Pro Tyr Leu Glu Tyr Val
385                 390                 395                 400

Gln Ser Ala Ala Pro Gly Arg Val Arg Tyr Asp Ala Val Leu Ser Glu
            405                 410                 415

Glu Gly Gly Arg Phe Tyr His Ala Arg Asn Arg Tyr Thr Val Val Glu
        420                 425                 430

Ala Gly Pro Glu Leu Pro Val Asp Cys Pro Gly Phe Arg Trp Ala
    435                 440                 445

Thr Leu Gly Gln Leu Thr Glu Leu Leu Ala His Gly Asn Tyr Leu Asn
450                 455                 460

Val Glu Leu Arg Thr Leu Ile Ala Cys His Ala Ser Tyr
465                 470                 475

<210> SEQ ID NO 27
<211> LENGTH: 388
<212> TYPE: PRT
<213> ORGANISM: Streptomyces mycarofaciens

<400> SEQUENCE: 27

Met Pro Leu Pro Lys His Leu Pro Ser Leu Gly Gly Met Arg Ala Ile
1               5                   10                  15

Ala Ala Leu Val Val Phe Cys Ser His Ile Ala Ser Gln Pro Phe Phe
            20                  25                  30

Arg Asn Ala Lys Ile Asn Ser Thr Ala Gln Val Pro Leu Asp Val Leu
        35                  40                  45

Gly Pro Leu Ala Val Ser Phe Phe Met Leu Ser Gly Phe Val Leu
    50                  55                  60
```

```
Thr Trp Ala Gly Met Pro Asp Pro Ser Lys Pro Ala Phe Trp Arg Arg
 65                  70                  75                  80

Arg Trp Val Arg Val Tyr Ser Leu His Leu Pro Val Leu Leu Leu Thr
                 85                  90                  95

Leu Ala Ile Val Leu Trp Leu Lys Glu Pro Asn Met Gly Gly Ser Val
            100                 105                 110

Trp Asp Gly Phe Leu Ser Asn Leu Leu Leu Val Gln Ser Trp Cys Pro
        115                 120                 125

Asp Tyr His Gln Tyr Gly Ser Met Asn Pro Val Ala Trp Ser Leu Ser
    130                 135                 140

Cys Glu Met Leu Phe Tyr Ala Ala Phe Pro Phe Leu Phe Ala Phe Phe
145                 150                 155                 160

Ser Lys Met Arg Ala Glu Arg Leu Trp Ser Trp Val Leu Gly Ile Ser
                165                 170                 175

Val Val Ala Ala Ala Val Pro Ala Leu Ala Leu Leu Pro Ser Ala
            180                 185                 190

Pro Thr Leu Pro Trp Asp Pro Asn Met Pro Glu Leu Gln Tyr Trp Phe
        195                 200                 205

Ile Tyr Met Leu Pro Pro Val Arg Leu Leu Glu Phe Ala Leu Gly Val
    210                 215                 220

Leu Met Ala Gln Ile Val Arg Arg Gly Arg Trp Ile Gly Pro Thr Pro
225                 230                 235                 240

Gly Val Cys Ala Leu Leu Phe Ala Gly Ala Phe Ala Leu Ser Phe Ala
                245                 250                 255

Leu Pro Ser Tyr Leu Ala Arg Val Ala Pro Thr Val Pro Leu Ile Ala
            260                 265                 270

Leu Leu Leu Gly Ser Leu Ala Ala Gly Asp Ile Arg Gly Thr Arg Ser
        275                 280                 285

Trp Leu Gly Thr Arg Thr Met Val Leu Leu Gly Glu Leu Thr Phe Ala
    290                 295                 300

Phe Tyr Val Ile His Tyr Leu Val Ile Gln Tyr Gly His Arg Phe Leu
305                 310                 315                 320

Gly Gly Glu Leu Ser Tyr Tyr Arg Gln Trp Asp Thr Pro Ala Ala Ile
                325                 330                 335

Gly Leu Thr Val Leu Ala Leu Gly Leu Ser Val Gly Leu Ala Ala Leu
            340                 345                 350

Leu His Phe Phe Val Glu Lys Pro Val Val Arg Ala Leu Gly Arg Ser
        355                 360                 365

Gly Lys Ala Ser Arg Ala Ser Lys Ala Pro Gln Pro Glu Pro Pro Ala
    370                 375                 380

Pro Leu Leu Ser
385

<210> SEQ ID NO 28
<211> LENGTH: 457
<212> TYPE: PRT
<213> ORGANISM: Streptomyces mycarofaciens

<400> SEQUENCE: 28

Met Arg Cys Pro Asp Thr Asn Gln Arg Ser Val Gln Val Ser Trp Pro
  1               5                  10                  15

Ser Gly Thr Gly Ala Leu Pro Ala Ala Arg Pro Leu Leu Thr Ala Gly
                 20                  25                  30

Ala Glu Ala Ala Ala Lys Val Cys Ala Glu Arg Ile Trp Glu Gly Pro
            35                  40                  45
```

```
Glu Tyr Ser Gly Arg Leu Cys His Met Gln Leu Pro Glu Phe Glu Arg
 50                  55                  60

Pro Ala Arg Thr Ala Met Leu Val Pro Pro Leu Gly Pro Lys Pro His
 65                  70                  75                  80

Ser Pro His Ser Leu Pro Gly Ser Ala Ala His Asp Gly Val Glu Ser
                 85                  90                  95

Leu Val Tyr Glu Ala Cys Glu Glu Leu Leu Gly Ser Leu Arg Arg Ala
            100                 105                 110

Asp Gln Arg Arg Arg Gly Gly Gln Tyr Leu Arg Gly Leu Leu Thr Ala
        115                 120                 125

Thr Gly Arg Lys Thr Ala Arg Asn Ile Ala Asn Phe Gly Gly Ala Gly
    130                 135                 140

Ala Ser Ala Gln Ser Leu His His Phe Val Ala Ser Ser Thr Trp Asp
145                 150                 155                 160

Trp Arg Pro Val Arg Ala Thr Leu Ala Arg Tyr Val Asp Asp Gly Leu
                165                 170                 175

Arg Pro Asp Ala Trp Val Ile Arg Pro Met Val Val Ser Lys Thr Gly
            180                 185                 190

Val Arg Ser Val Gly Val Gln Arg Arg Phe Val Pro Asp Leu Gly Arg
        195                 200                 205

Val Met Ser Cys Gln Arg Ser Phe Gly Leu Trp Met Ala Ser Asp Thr
    210                 215                 220

Arg Ala Ala Pro Val Ser Trp His Leu Thr Leu Asp Gly Asp Pro Gly
225                 230                 235                 240

Gly Glu Ala Asp Gly Arg Leu Glu Ala Pro Gly Glu Glu Arg Asp Val
                245                 250                 255

Ala Arg Leu Val Thr Lys Ile Ala Gln Ala Asn Arg Thr Val Ala Arg
            260                 265                 270

Pro Val Val Met Asp Ala Arg Thr Ala Ala Val Pro Pro Leu Val Arg
        275                 280                 285

Ala Leu Thr Thr Ala Gly Leu Pro Phe Met Leu Arg Val Gly Gly Asp
    290                 295                 300

Leu Pro Leu Asp Pro Ala Ala Gly Arg Val Gln Leu Gly Gln Arg Pro
305                 310                 315                 320

Gln Thr Ser Pro Ala Gln His Leu Met Glu Gln Leu Lys Arg Leu Gly
                325                 330                 335

Arg Pro Val Glu Cys His Gly Thr Val Asn Phe Val Thr Pro Leu Ala
            340                 345                 350

Val Val Leu Pro Gly Ala Leu Pro Arg Arg Thr Leu Leu Leu Met Gly
        355                 360                 365

Val Trp Arg Ala Asn Arg Arg Arg Pro Ala Asp Leu Trp Leu Thr Asp
    370                 375                 380

Leu Thr Ser Ser Gly His Ser Ala Leu Leu Arg Leu Ala Arg Leu Thr
385                 390                 395                 400

Glu Arg Val Asp Ser Asp Phe Ala Ala Val Ser Val Asp Val Gly Ile
                405                 410                 415

Arg Asp Phe Glu Gly Arg Ser Phe Gln Gly Trp His Arg His Val Thr
            420                 425                 430

Leu Ala Ser Ile Ala His Ala Leu Arg Leu Ser Gln Asp Gly Gln Trp
        435                 440                 445

Cys Asp Tyr Gln Val Pro Ile Ala Gly
    450                 455
```

<210> SEQ ID NO 29
<211> LENGTH: 607
<212> TYPE: PRT
<213> ORGANISM: Streptomyces mycarofaciens

<400> SEQUENCE: 29

```
Met Arg Arg Leu Glu Arg Phe Asn Arg Leu Ala Leu Thr Ala Gln Ser
 1               5                  10                  15

Met Ile Glu Tyr Arg Arg Asp Arg Glu Ala Glu Leu Ala Ala Leu Val
                20                  25                  30

Glu Ala Ala His Glu Phe Val Arg Ala Arg His Tyr Lys Asp Leu Leu
            35                  40                  45

Asp Ser Val Ala Arg Arg Ala Arg Leu Leu Lys Leu Asp Val Ala
     50                  55                  60

Tyr Val Ser Leu His Lys Glu Gly Glu Pro Asp Thr Glu Leu Gln Ser
 65                  70                  75                  80

Ala Asp Gly Asn Ala Val Ser Val Ala Val Gly Leu Arg Leu Pro Val
                 85                  90                  95

Ser Gly Gly Leu Gly Gly Met Val Arg Ala Cys Arg Ala Pro Phe Trp
            100                 105                 110

Thr Pro Asp Tyr Leu Ala Asp Thr Ser Ile Asn His Val Glu Ser Ile
        115                 120                 125

Asp Asn Val Val Arg Ser Glu Gly Leu Arg Ala Val Leu Gly Val Pro
    130                 135                 140

Leu Cys Val Arg Asp Glu Ser Met Gly Val Gly Val Leu Tyr Val Ala
145                 150                 155                 160

Asp Arg Gln Val Arg His Leu Ala Pro Asn Glu Ile Thr Leu Leu Cys
                165                 170                 175

Ser Leu Ala Asp Leu Ala Ala Ala Ile Glu Arg Ile Val Leu Val
            180                 185                 190

Glu Glu Leu Arg Asn Asp Ile Gly Arg Leu His Ala Asp Val Gly Glu
        195                 200                 205

Ala Arg Ala Ala Leu Thr Val Ala Arg Arg Ser Ala Asp Leu Gln Ser
    210                 215                 220

Arg Leu Ile Ala Leu Ile Leu Glu Arg Cys Glu Val Asp Ala Leu Leu
225                 230                 235                 240

Ala Val Ala Ala Glu Ala Leu Gly Gly Gly Thr Gly Ile Cys Asn Pro
                245                 250                 255

Leu Gly Arg Pro Leu Ala Glu Tyr Gly Lys Leu Arg Pro Ile Pro Pro
            260                 265                 270

Ala Asp Leu Arg Ala Ala Cys Asp Arg Ala Ala Glu Thr Gly His Pro
        275                 280                 285

Thr Pro Ala Asp Gln Gly Val Trp Val Ala Pro Leu Cys Pro Gly Glu
    290                 295                 300

Cys Asn Ser Gly Phe Leu Leu Thr Asp Val Gly Pro Ala Ala Asp His
305                 310                 315                 320

Ser Val Val Pro Leu Leu Leu Val Ala Arg Ala Leu Ala Leu His
                325                 330                 335

Leu Arg Ile Gln His Asn Asn Ser Ala Lys Thr Pro Gly His Gln Glu
            340                 345                 350

Phe Phe Asp Asp Leu Val Gly Ala Pro Arg Ser Pro Ala Leu Leu Arg
        355                 360                 365

Glu Arg Ala Leu Leu Phe Ser Leu Ser Phe Arg Arg Pro His Val Val
    370                 375                 380
```

```
Leu Val Ala Ser Ala Pro His Gly Ala Ala Arg Leu Glu Thr Ser
385                 390                 395                 400

Ala Ala Asp Tyr Ala Gln Glu Leu Gly Gly Leu Cys Ser Val Pro Asp
                405                 410                 415

Gly Ala Val Val Leu Leu Pro Gly Glu Ala Pro Glu Ala Val Ala
                420                 425                 430

Gln Thr Ala Ala Gln Glu Leu Thr Thr Arg Val Gly Arg Ser Ile Thr
                435                 440                 445

Val Gly Ala Ala Gly Pro Ala Ser Thr Val Asp Gly Ile Gly Asp Ala
        450                 455                 460

Tyr Arg Glu Ala Ala Gln Cys Leu Glu Thr Leu Arg Ala Leu Gly Ala
465                 470                 475                 480

Asp Gly Gly Thr Ala Cys Ala Ser Asp Leu Gly Phe Leu Gly Met Leu
                485                 490                 495

Leu Ala Glu Glu Asn Asp Val Pro Gly Tyr Ile Thr Ser Thr Ile Gly
                500                 505                 510

Pro Val Val Asp Tyr Asp Thr His Arg Phe Thr Asp Leu Ile Ala Thr
                515                 520                 525

Leu Arg Ala Tyr Leu Glu Ser Gly Arg Ser Pro Thr Arg Ala Ala Glu
530                 535                 540

Thr Leu Arg Val His Pro Asn Thr Val Ser Arg Arg Leu Glu Arg Ile
545                 550                 555                 560

Gly Gln Leu Leu Gly Glu Asp Trp Gln Cys Pro Gln Arg Val Leu Asp
                565                 570                 575

Ile Gln Leu Ala Leu Arg Leu His Gln Val Arg Ser Val Leu Ser Pro
                580                 585                 590

Arg Leu Ala Ser Ala Ser Arg Ala Leu Cys Pro Leu Pro Glu
                595                 600                 605

<210> SEQ ID NO 30
<211> LENGTH: 340
<212> TYPE: PRT
<213> ORGANISM: Streptomyces mycarofaciens

<400> SEQUENCE: 30

Val Arg Leu Thr Thr Glu Leu Phe Lys Arg Ser His His Pro Arg Gly
1               5                   10                  15

Pro Leu Val Thr Val Leu Gly Ala Ser Gly Phe Leu Gly Ser Ala Val
                20                  25                  30

Val Ala Glu Leu Ala Ala Leu Pro Leu Arg Leu Arg Leu Val Ala Arg
            35                  40                  45

Gly Pro Ser Arg Val Pro Ala Glu Pro Val Ala Asp Ile Glu Val Arg
        50                  55                  60

Arg Thr Asp Leu Ala Arg Pro Asp Ala Val Ala Ala Ala Glu Gly
65                  70                  75                  80

Ala Asp Ala Val Val His Leu Ala Ala Gly Ile Gly Gly Gln Gln Ser
                85                  90                  95

Trp Arg Ala Ala Asp Glu His Ala Glu Arg Val Asn Val Gly Met Met
                100                 105                 110

Arg Asp Leu Val Asp Ala Leu Arg Gly Arg Ser Gly Ala Arg Pro Ala
            115                 120                 125

Val Ala Phe Ala Ser Thr Leu Gln Ala Gly Ser Pro Thr Gly Asn Ala
        130                 135                 140

Ala Pro Leu Gly Gly Tyr Ala Ser Gln Lys Ile Ala Ala Glu Gly Ile
```

```
                145                 150                 155                 160
Leu Arg Glu Ala Thr Ala Glu Gly Val Val Arg Gly Val Val Leu Arg
                    165                 170                 175

Leu Ser Thr Leu Tyr Gly His Ser Pro Leu Ser Gly Gly Ala Gly Arg
                180                 185                 190

Gly Val Leu Ala Ser Met Thr Arg Arg Ala Leu Asp Gly Glu Ala Leu
            195                 200                 205

Thr Met Trp His Asp Gly Ser Val Gly Arg Asp Phe Leu His Val Arg
        210                 215                 220

Asp Ala Gly Ala Phe Thr Ala Ala Leu Glu His Ala Ala Glu Leu
225                 230                 235                 240

Gln Gly Glu Pro Trp Ile Val Ala Thr Gly Arg Leu Glu Arg Leu Gly
                    245                 250                 255

Asp Val Phe Thr Ala Leu Ala Gly Leu Val Ala Glu His Thr Gly Gly
                260                 265                 270

Thr Pro Ala Pro Val Val Ala Val Pro Pro Ala Tyr Ala Glu Ala
            275                 280                 285

Gly Asp Phe His Ser Pro Glu Ser Asp Ser Ala Ala Phe Arg Ala Val
        290                 295                 300

Thr Gly Trp Ala Pro Arg Val Arg Phe Pro Glu Gly Leu Arg Asp Met
305                 310                 315                 320

Val Ala Ala Ile Ala Ala Val His Pro Ala Pro Ala Ala His Pro
                    325                 330                 335

Ala Val Ser Ser
            340

<210> SEQ ID NO 31
<211> LENGTH: 342
<212> TYPE: PRT
<213> ORGANISM: Streptomyces mycarofaciens

<400> SEQUENCE: 31

Met Ser Glu Asp Arg Thr Gln Ala Gly His Thr His Arg Tyr Gln Pro
1               5                   10                  15

Pro Gln Gly His Thr His Thr Arg Leu Gly Arg Ser Ala Thr Leu Val
                20                  25                  30

Ser Arg Leu Trp Leu Gly Thr Val Asn Phe Ser Gly Arg Val Glu Asp
            35                  40                  45

Ala Asp Ala Val Arg Leu Met Asp Gln Ala Leu Asp Arg Gly Ile Asn
        50                  55                  60

Cys Ile Asp Thr Ala Asp Ile Tyr Gly Trp Arg Leu Tyr Lys Gly His
65                  70                  75                  80

Thr Glu Glu Leu Val Gly Arg Trp Leu Gly Gln Arg Gly Arg Arg
                    85                  90                  95

Asp Asp Val Val Leu Ala Thr Lys Val Gly Glu Glu Met Ser Asp Arg
                100                 105                 110

Ile Asn Asp His Gly Leu Ser Ala Arg His Ile Ile Ser Ala Cys Glu
            115                 120                 125

Gln Ser Leu Arg Arg Leu Asn Val Glu His Ile Asp Leu Tyr Gln Met
        130                 135                 140

His Arg Met Asp Glu Ala Ala Ser Trp Glu Glu Ile Trp Gln Ala Met
145                 150                 155                 160

Asp Arg Leu Val Ala Asp Gly Lys Val Arg Tyr Val Gly Ser Ser Asn
                    165                 170                 175
```

```
Phe Ala Gly Trp Asn Ile Ala Ala Ala Gln Glu Asn Ala Ala Ala Arg
            180                 185                 190

Arg Ser Leu Gly Leu Val Ser Glu Gln Cys Leu Tyr Asn Leu Ala Asp
        195                 200                 205

Arg His Val Glu Arg Glu Val Leu Pro Ala Ala Arg Ala Tyr Gly Leu
    210                 215                 220

Gly Val Phe Ala Trp Ser Pro Leu His Gly Leu Leu Ser Gly Ala
225                 230                 235                 240

Leu Arg Lys Leu Ala Ala Gly Thr Ala Val Lys Ser Ala Gln Gly Arg
                245                 250                 255

Ala Gln Thr Leu Leu Pro Glu Leu Arg Pro Thr Ile Glu Ala Tyr Glu
            260                 265                 270

Arg Phe Cys Asp Arg Ile Gly Glu His Pro Ala Asp Val Gly Leu Ala
        275                 280                 285

Trp Val Leu Ser Arg Pro Gly Ile Ser Gly Ala Val Ile Gly Pro Arg
    290                 295                 300

Thr Thr Glu Gln Leu Asp Ser Ala Val Arg Ala Leu Gly Leu Val Leu
305                 310                 315                 320

Gly Asp Ala Glu Leu Thr Glu Leu Asp Ala Leu Phe Ser Pro Ala Gly
                325                 330                 335

Gly Arg Ala Pro Glu Ala
            340

<210> SEQ ID NO 32
<211> LENGTH: 410
<212> TYPE: PRT
<213> ORGANISM: Streptomyces mycarofaciens

<400> SEQUENCE: 32

Met Ile Thr Thr Ala Cys Arg Ile Cys Asp Asn Arg Glu Leu Leu Pro
1               5                  10                  15

Val Leu Asp Leu Gly Asp Gln Ala Leu Thr Gly Val Phe Pro Ala Ser
            20                  25                  30

Arg Asp Glu Ala Val Pro Ser Val Pro Leu Glu Leu Val Lys Cys Ser
        35                  40                  45

Pro Ala Gly Cys Gly Leu Val Gln Leu Arg His Thr Pro Asp Pro Ala
    50                  55                  60

Leu Met Tyr Gly Asp Gly Tyr Gly Tyr Arg Ser Gly Ile Arg Pro Phe
65                  70                  75                  80

Met Val Asn His Leu Gln Ser Lys Val Ala Ala Ile Arg Glu Leu Val
                85                  90                  95

Gly Leu Gly Pro Gln Asp Leu Val Leu Asp Ile Gly Ser Asn Asp Ser
            100                 105                 110

Thr Leu Leu Arg Gly Tyr Pro Ala Asp Gly Pro Arg Val Gly Ile
        115                 120                 125

Asp Pro Thr Gly Gln Lys Phe Arg Glu Leu Tyr Pro Ala Asp Val Glu
    130                 135                 140

Leu Val Val Asp Tyr Phe Ser Arg Glu Ala Phe Thr Asn Arg Phe Gly
145                 150                 155                 160

Ser Gln Arg Ala Lys Val Val Thr Ser Ile Ala Met Phe Tyr Asp Leu
                165                 170                 175

Pro Asp Pro Met Arg Phe Met Arg Asp Val His Asp Val Leu Thr Asp
            180                 185                 190

Asp Gly Ile Trp Val Met Glu Gln Ser Tyr Leu Pro Ala Met Leu Glu
        195                 200                 205
```

```
Ala Asp Ala Tyr Asp Val Val Cys His Glu His Leu Glu Tyr Tyr Ala
            210                 215                 220

Leu Arg Gln Ile Glu Trp Met Ala Glu Arg Val Gly Leu Thr Val Ile
225                 230                 235                 240

Lys Ala Glu Leu Thr Asp Val Tyr Gly Gly Ser Leu Cys Val Thr Leu
                245                 250                 255

Ala Lys Ser Ala Ser Arg Tyr Pro Lys Asp Glu Ala Gly Leu Ala Arg
            260                 265                 270

Ile Arg Ala Arg Glu Thr Glu Ala Glu Leu Asp Thr Met Ala Pro Phe
            275                 280                 285

Glu Ala Phe Ala Arg Arg Val Gln Asp Gln Arg Asp Ala Leu Ile Asp
            290                 295                 300

Phe Leu Asp Arg Ser Arg Glu Ala Gly Leu Leu Thr Val Gly Tyr Gly
305                 310                 315                 320

Ala Ser Thr Lys Gly Asn Val Ile Leu Gln Tyr Cys Gly Leu Thr Glu
                325                 330                 335

Arg Asp Leu Pro Cys Ile Gly Glu Val Ser Glu Glu Lys Ala Gly Arg
            340                 345                 350

Phe Thr Pro Gly Ser Ala Ile Pro Ile Val Ser Glu Glu Ala Lys
            355                 360                 365

Leu Leu Lys Pro Asp Gln Leu Leu Val Leu Pro Trp Ile Tyr Arg Asp
            370                 375                 380

Gly Phe Leu Glu Arg Glu Arg Ala Tyr Arg Glu Ala Gly Gly Lys Leu
385                 390                 395                 400

Val Phe Pro Leu Pro Glu Leu Ser Val Val
                405                 410

<210> SEQ ID NO 33
<211> LENGTH: 360
<212> TYPE: PRT
<213> ORGANISM: Streptomyces mycarofaciens

<400> SEQUENCE: 33

Met Ala Asp Gly Val Ala Thr Thr Val Lys Cys Leu Val Trp Asp
  1               5                  10                  15

Leu Asp Asn Thr Leu Trp Gln Gly Thr Leu Leu Glu Asp Gly Glu Val
                20                  25                  30

Arg Leu Arg Pro Gly Leu Arg Glu Thr Ile Ala Glu Leu Asp Ser Arg
            35                  40                  45

Gly Ile Leu Asn Ser Val Ala Ser Lys Asn Asp His Asp His Ala Trp
    50                  55                  60

Ala Gln Leu Glu Arg Leu Gly Leu Ala Glu Tyr Phe Val Leu Pro Arg
65                  70                  75                  80

Ile Gly Trp Arg Pro Lys Ser Glu Ser Val Arg Gly Ile Ala Asp Glu
                85                  90                  95

Leu Asn Phe Ala Pro Ser Thr Met Ala Phe Ile Asp Asp Gln Pro Phe
            100                 105                 110

Glu Arg Ala Glu Val Arg His Val Leu Pro Glu Val Arg Thr Tyr Thr
        115                 120                 125

Ala Glu Gln Ala Val Asp Leu Val Thr Arg Pro Glu Phe Ser Pro Ala
    130                 135                 140

Thr Ile Thr Val Asp Ser Arg Arg Arg Ser Met Tyr Gln Ala Ser
145                 150                 155                 160

Phe Gln Arg Asp Ala Glu Arg Ala Glu Phe Ala Gly Pro Asp Ala Asp
```

```
                165                 170                 175
Phe Leu Arg Ser Leu Asp Ile Arg Met Arg Val Ala Arg Ala Thr Pro
            180                 185                 190
Gly Glu Leu Ser Arg Val Glu Glu Leu Thr Leu Arg Thr Ser Gln Met
        195                 200                 205
Asn Ala Thr Gly Val His Tyr Ser Glu Ala Asp Leu Leu Ala Leu Ile
    210                 215                 220
Asp Asp Pro Asp His Glu Val Leu Val Thr Val Thr Asp Arg Phe
225                 230                 235                 240
Gly Pro Tyr Gly Ala Val Gly Val Ile Leu Leu Gln Arg Ser Ser Gly
                245                 250                 255
Ile Trp Arg Ile Lys Leu Leu Ala Thr Ser Cys Arg Val Val Ser Leu
            260                 265                 270
Gly Ala Gly Ser Ala Leu Leu Arg Trp Leu Thr Asp Gln Ala His Arg
        275                 280                 285
Ala Gly Val His Leu Ala Ala Asp Phe Arg Ala Thr Glu Arg Asn Arg
    290                 295                 300
Met Met Glu Val Ala Tyr Arg Phe Ala Gly Phe Ser Asp Glu Pro Cys
305                 310                 315                 320
Ala Cys Gln Thr Ala Leu Asp Arg Thr Glu Gly Val Ser Arg Leu His
                325                 330                 335
Leu Val Pro Ser Val Gln Pro Ala Ser Asp Thr Leu Arg Leu Glu Ala
            340                 345                 350
Pro Glu Leu Ala Pro Val Arg Gly
        355                 360

<210> SEQ ID NO 34
<211> LENGTH: 376
<212> TYPE: PRT
<213> ORGANISM: Streptomyces mycarofaciens

<400> SEQUENCE: 34

Val Ser Glu Ala Thr Ala Thr Arg Ala Ala Glu Pro Gly Ala Glu Glu
1               5                   10                  15
Arg Leu Phe Thr Asp Leu Val Gly Asp Ser Ala Ala Glu Trp Glu Arg
            20                  25                  30
Thr Gly Glu Ile Pro Pro Glu Leu Leu Arg Asp Leu Gly Ala Lys Gly
        35                  40                  45
Leu Leu Cys Ala Gln Val Pro Leu Ala His Gly Gly Leu Gly Phe Thr
    50                  55                  60
Ser Arg Arg Asn Gly Glu Leu Thr Ala His Val Gly Ser Leu Ser Ser
65                  70                  75                  80
Ser Leu Arg Ser Val Leu Thr Ser Gln Gly Met Ala Ala Trp Thr Leu
                85                  90                  95
Arg Arg Leu Ala Gly Ala Gly Gln Gln Ala Thr Val Val Pro Arg Leu
            100                 105                 110
Thr Arg Gly Glu Leu Ala Ala Val Ala Phe Ser Glu Ala Glu Ala Gly
        115                 120                 125
Ser Asp Leu Ser Ala Leu His Thr Arg Ile Thr Arg Asp Gly Asp Gln
    130                 135                 140
Ile Val Val Asp Gly Ala Lys Val Trp Ser Thr Asn Ala Ala Tyr Ala
145                 150                 155                 160
Asp Leu Leu Ile Val Phe Ala Arg Thr Glu Asp Gly Ala Gly Ala Val
                165                 170                 175
```

```
Val Val Pro Ala Thr Ala Pro Gly Val Arg Ile Glu Arg Ile Thr Asp
            180                 185                 190

Pro Tyr Gly Cys Arg Ala Ala Gly His Ala Asn Ile Arg Leu Asp Gly
        195                 200                 205

Val Arg Leu Pro Ala Asp Ala Leu Leu Asp Gly Val Asp Arg Thr Pro
    210                 215                 220

Ser Leu Leu Val Thr Thr Ala Leu Ser Tyr Gly Arg Met Ser Val Ala
225                 230                 235                 240

Trp Gly Cys Val Gly Ile Leu Arg Ala Cys Leu Ala Ala Val Arg
            245                 250                 255

His Ala Gly Gly Arg Glu Gln Phe Gly Ser Arg Leu Ser Asp His Gln
            260                 265                 270

Leu Val Ala Arg His Leu Ala Glu Leu Leu Ile Ala Glu Gln Thr Ala
            275                 280                 285

Ser Arg Ala Cys Glu His Ala Ser Asp Leu Trp Asp Glu Gly Ser Pro
        290                 295                 300

Asp Val Val Thr Ala Thr Val Met Ala Lys His Val Ala Thr Gly
305                 310                 315                 320

Ala Ala Arg Gly Ser Ala Arg Ala Leu Gln Val Leu Ala Ser Ala Gly
            325                 330                 335

Ser Arg Glu Gly His Val Val Ala Arg Ala His Arg Asp Ala Lys Leu
            340                 345                 350

Met Glu Ile Ile Glu Gly Ser Ser Glu Ile Cys Glu Leu Ile Leu Ala
            355                 360                 365

Gln His Ala Leu Ala Thr Ala Gly
    370                 375

<210> SEQ ID NO 35
<211> LENGTH: 107
<212> TYPE: PRT
<213> ORGANISM: Streptomyces mycarofaciens

<400> SEQUENCE: 35

Met Ile Glu Thr Ser Asp Pro Thr Gly Asp Ala Ala Val Val Pro Ala
1               5                   10                  15

Asp His Asp Val Ala Ala Glu Leu Leu Glu Phe Leu Thr Ala Lys Thr
            20                  25                  30

Arg Thr Asn Trp Glu Ala Asp Gln Asp Ile Phe Ala Val Gly Gly Met
        35                  40                  45

Ser Ser Leu Phe Ala Met Gln Leu Val Val His Leu Glu Lys Thr Tyr
    50                  55                  60

Ala Ile Thr Ile Ser Gly Ala Asp Leu Met Leu Asp Asn Phe Arg Thr
65              70                  75                  80

Val Asp Ala Met Val Arg Leu Val Arg Arg Leu Gly Pro Ser Ala Val
            85                  90                  95

Gly Thr Gly Gly Thr Gly Asp Asp Asn Ser Glu
        100                 105

<210> SEQ ID NO 36
<211> LENGTH: 288
<212> TYPE: PRT
<213> ORGANISM: Streptomyces mycarofaciens

<400> SEQUENCE: 36

Val Ser Asp Asn Asn Ala Glu Gly Pro Leu Val Val Met Gly Ala Gly
1               5                   10                  15
```

```
Val Met Gly Thr Ala Ile Ala Ala Leu Ala Val Gly His Gly Tyr Arg
                20                  25                  30

Val Thr Leu Ile Asp Arg Ser Pro Glu Ala Arg Ala Ala Pro Asp
        35                  40                  45

Lys Val Glu Leu Gln Val Arg Thr Ala Arg Met Met Ser Ala Leu Pro
    50                  55                  60

Ser Gly Arg Pro Met Gly Glu Leu Ala Thr Ala Asp Thr Thr Asp Ala
65                  70                  75                  80

Ala Ala Asp Ala Cys Ala Val Ile Glu Ala Val Thr Glu Asp Pro Gly
                85                  90                  95

Glu Lys Ala Ala Val Leu Ala Gly Leu Ala Ala Val Ser Pro Gly
            100                 105                 110

Thr Leu Leu Ile Ser Asn Thr Ser Gly Leu Pro Ile Asp Glu Leu Ala
        115                 120                 125

Gly Ala Val Pro Arg Pro Glu Asp Leu Val Gly Val His Phe Met Asn
    130                 135                 140

Pro Ala Tyr Leu Ile Ala Thr Val Glu Val Val Leu Gly Pro Arg Ser
145                 150                 155                 160

Gly Asp Ala Ala Ala Ala Ala Gln Lys Leu Leu Ala Gly Leu Gly
                165                 170                 175

Arg Glu Gly Ile Ile Val Gly Asp Gly Pro Gly Phe Val Thr Ser Arg
        180                 185                 190

Leu Leu His Arg Met Ile Asn Asp Ala Ile Glu Leu Val His Glu Gly
        195                 200                 205

Arg Ala Ala Pro Glu Thr Val Asp Arg Leu Met Arg Asp Cys Ile Gly
    210                 215                 220

His Arg Thr Gly Pro Leu Ala Thr Ala Asp Leu Ile Gly Leu Asp Asn
225                 230                 235                 240

Leu Ala Asp Ser Leu Leu Val Met His Ala Arg Thr Gly Ser Glu Ala
                245                 250                 255

Phe Arg Pro Ser Glu Leu Leu Leu Glu Lys Val Arg Arg Gly Glu Leu
            260                 265                 270

Gly Arg Lys Ser Gly Arg Gly Phe Tyr Asp Tyr Glu Gly Ser Thr Arg
        275                 280                 285

<210> SEQ ID NO 37
<211> LENGTH: 430
<212> TYPE: PRT
<213> ORGANISM: Streptomyces mycarofaciens

<400> SEQUENCE: 37

Val Arg Ala Ser Arg Thr Phe Arg Ser Phe Ser Pro Phe Ala Pro Arg
1               5                   10                  15

His Asp Gly Thr Cys Pro Asp Leu Thr Lys Asp Phe Thr Met Ala His
                20                  25                  30

Ile Ala Phe Phe Ile Leu Pro Val Ala Gly His Leu Asn Pro Thr Leu
        35                  40                  45

Gly Val Ala Glu Glu Leu Val Ala Arg Gly His Arg Val Thr Tyr Ala
    50                  55                  60

Leu Pro Glu Glu Ile Ala Asp Arg Ala Arg Val Gly Ala Gly Val
65                  70                  75                  80

Val Thr Tyr Pro Met Asp Lys Glu Arg Phe Leu Ala Gln Met Val Pro
                85                  90                  95

Arg Gln Asp Ser Glu Glu Tyr Thr Asp Glu Gly Glu Phe Ile Arg Val
            100                 105                 110
```

Leu Glu Trp Leu Leu Asp Met Thr Thr Ser Thr Leu Pro Leu Leu Glu
            115                 120                 125

Pro His Phe Ala Ala Asp Arg Pro Asp Val Ile Val Asn Asp Pro Ser
        130                 135                 140

Ser Leu Trp Thr Gly Arg Leu Leu Ala Asp Arg Trp Gly Ile Pro Val
145                 150                 155                 160

Ile Arg Ser Thr Pro Thr Tyr Ala Ala Asn Glu His Trp Ser Leu His
                165                 170                 175

Pro Pro Val Asp Ala Ala Glu Pro Asp Pro Ala Leu His Asp
            180                 185                 190

Leu Leu Ala Arg Ile Gly Arg Leu Leu Lys Glu Gln Gly Ala Glu Asn
            195                 200                 205

Asp Leu Ala Ala Phe Thr Lys Val Ile His Gly Gly Pro Ala Leu Leu
        210                 215                 220

Tyr Ile Pro Arg Ser Phe Gln Tyr Ala Gly Asp Ser Phe Asp Asp Arg
225                 230                 235                 240

His His Phe Val Gly Pro Cys Ser Pro Arg Val Ala Phe His Gly Thr
                245                 250                 255

Trp Gln Pro Pro Glu Gly Asp Arg Pro Leu Val Met Val Ser Leu Gly
            260                 265                 270

Thr Leu Tyr Asn Glu Arg Pro Glu Phe Phe Arg Thr Cys Ile Glu Ala
            275                 280                 285

Phe Arg Asp Glu Pro Trp His Ile Val Leu Val Leu Gly Gly Gly Val
        290                 295                 300

Arg Pro Asp Glu Leu Gly Pro Leu Pro Asp Asn Val Glu Val His Asp
305                 310                 315                 320

Phe Val Pro His Gly Asp Leu Leu Pro His Ala Asp Leu Val Val Asn
                325                 330                 335

His Gly Gly Met Ser Thr Ala Met Asp Thr Phe Ser His Gly Val Pro
            340                 345                 350

Val Val Ala Val Pro Val Met Pro Glu Pro Arg Ala Thr Ala Arg Arg
        355                 360                 365

Ile Ala Glu Leu Gly Leu Gly Ala Gln Leu Leu Thr Ser Glu Val Thr
    370                 375                 380

Thr Glu Ser Leu Arg Glu Thr Ala Arg Arg Val Leu Ala Asp Glu Gly
385                 390                 395                 400

Ile Lys Glu Gln Val Ala Gly Met Arg Ala Gln Ile Arg Ala Ala Gly
                405                 410                 415

Gly Ala Val Ala Ala Ala Thr Ala Val Glu Gly Leu Leu Pro
            420                 425                 430

<210> SEQ ID NO 38
<211> LENGTH: 193
<212> TYPE: PRT
<213> ORGANISM: Streptomyces mycarofaciens

<400> SEQUENCE: 38

Met Arg Ile His Glu Met Ala Val Arg Asp Ala Tyr Arg Ile Glu Pro
1               5                   10                  15

Glu Pro Ile Pro Asp His Arg Gly Leu Phe Tyr Glu Ala Leu Arg Tyr
            20                  25                  30

Glu Ser Leu Arg Ala Ala Thr Gly His Ala Ile Glu Ile Arg Gln Val
        35                  40                  45

Asn Tyr Thr Val Ser Gly Arg Asn Val Leu Arg Gly Ile His Ser Thr

```
                50                  55                  60
Thr Val Pro Pro Gly Gln Gly Lys Ile Val Thr Cys Val Arg Gly Ala
 65                  70                  75                  80

Val Gln Thr Met Val Val Asp Leu Arg Val Gly Ser Pro Thr Phe Gly
                 85                  90                  95

Arg Tyr Asp Val Leu Gly Gln Asp Pro Arg Ser Ser Thr Ala Val Tyr
                100                 105                 110

Leu Pro Asp Gly Ile Gly Leu Ala Tyr Leu Ala Leu Ser Asp Asp Thr
            115                 120                 125

Cys Met Asn Tyr Leu Cys Thr Arg Glu Tyr Val His Gly Thr Ile Ile
130                 135                 140

Asp Val Asp Ala Leu Asp Pro Glu Leu Gly Leu Pro Trp Asp Leu Thr
145                 150                 155                 160

Ala Pro Pro Val Arg Ser Thr Arg Asp Ala Ala Pro Thr Leu Ala
                165                 170                 175

Ala Ala Val Ala Gly Gly Val Leu Pro Thr Tyr Glu Glu Val Arg Pro
            180                 185                 190

Arg

<210> SEQ ID NO 39
<211> LENGTH: 417
<212> TYPE: PRT
<213> ORGANISM: Streptomyces mycarofaciens

<400> SEQUENCE: 39

Met Lys Arg Glu Leu Gly Asp Leu Ala Leu Phe Gly Gly Arg Ala Asn
 1               5                  10                  15

Phe Leu Gln Pro Leu Leu Val Gly Arg Pro Asn Pro Ile Asp Arg Ser
                20                  25                  30

Arg Leu Phe Asp Arg Leu Thr Trp Ala Leu Asp Asn Gln Trp Leu Thr
            35                  40                  45

Asn Gly Gly Pro Leu Thr Gln Glu Phe Glu Lys Arg Val Ala Asp Leu
 50                  55                  60

Ala Gly Val Arg Asn Cys Val Ala Thr Cys Asn Ala Thr Val Ala Leu
 65                  70                  75                  80

Gln Leu Leu Val His Ala Ala Glu Leu Thr Gly Glu Val Ile Met Pro
                 85                  90                  95

Ala Leu Thr Phe Ala Ala Thr Ala His Ala Val Arg Trp Leu Gly Leu
                100                 105                 110

Glu Pro Val Phe Cys Asp Val Asp Pro Leu Thr Gly Cys Val Asp Pro
            115                 120                 125

Glu Arg Val Arg Ala Ala Ile Thr Pro Arg Thr Ser Ala Ile Phe Gly
130                 135                 140

Val His Leu Trp Gly Arg Pro Cys Asp Val Asp Gly Leu Glu Glu Leu
145                 150                 155                 160

Ala Ala Glu Ala Gly Ile Arg Leu Phe Phe Asp Ala Ala His Ala Phe
                165                 170                 175

Gly Ser Thr Ser Ala Gly Arg Pro Val Gly Arg Phe Gly Asp Ala Glu
                180                 185                 190

Val Phe Ser Phe His Ala Thr Lys Val Val Asn Ser Phe Glu Gly Gly
            195                 200                 205

Ala Val Val Thr Asp Asp Glu Leu Ala His Arg Val Arg Ser Leu
210                 215                 220

His Asn Phe Gly Leu Gly Leu Glu Glu Val Ser Ser Ala Gly Gly Thr
```

```
                    225                 230                 235                 240

Asn Ala Lys Met Ser Glu Ala Ser Ala Ala Met Gly Leu Thr Ser Leu
                245                 250                 255

Asp Val Phe Glu Glu Val Val Arg His Asn Lys Ser Asn Tyr Glu His
            260                 265                 270

Tyr Arg Thr Glu Leu Ser Gly Val Pro Gly Val Ala Val Phe Ala Phe
        275                 280                 285

Asp Glu Asn Glu Arg Asn Asn Tyr Gln Tyr Leu Val Val Gln Ile Asp
    290                 295                 300

Glu Glu Val Thr Gly Leu His Arg Asp Leu Leu Leu Arg Leu Leu Arg
305                 310                 315                 320

Ala Glu Asn Val Val Ala Gln Pro Tyr Phe Ser Pro Ala Cys His Gln
                325                 330                 335

Leu Glu Pro Tyr Arg Ser Arg Arg Asn Ala His Leu Pro His Thr Glu
            340                 345                 350

Arg Leu Ser Ala Arg Val Ile Ala Leu Pro Thr Gly Ser Thr Val Ser
        355                 360                 365

His Glu Asp Ile Arg Arg Val Cys Asp Ile Val Arg Leu Ala Ala Thr
    370                 375                 380

Arg Gly Ala Glu Leu Thr Ala Arg Trp Arg Gln Ala His Ser Ser Asp
385                 390                 395                 400

Gln Pro Thr Ala Leu Leu Met Gln Asp Ile Ser Glu Trp Lys Arg Val
                405                 410                 415

Gly

<210> SEQ ID NO 40
<211> LENGTH: 484
<212> TYPE: PRT
<213> ORGANISM: Streptomyces mycarofaciens

<400> SEQUENCE: 40

Met Val Arg Gln Glu Ala Val Ala Asn Thr Val Ala Val Cys Thr Leu
  1               5                  10                  15

Pro Gly Ser Asp Pro Ala Ala Ser Glu Ala Leu Arg His Glu Leu
             20                  25                  30

Val Thr Ala Gly His Met Thr Asp Ala Asp Ala Arg Glu Ala Ala Gly
         35                  40                  45

His Leu Val Arg Leu Ala Arg Ile Tyr Gly Ala Gly Pro Phe Thr Pro
     50                  55                  60

Leu Glu Lys Ala Arg His Gln Leu Gly Val Asp Arg Ser Ala Phe Arg
 65                  70                  75                  80

Arg Leu Leu Asp Val Phe Gly Val Pro Gln Leu Arg Ser Ala Val
                 85                  90                  95

Glu Asn Gly Pro Ser Gly Lys Tyr Trp Thr Asn Thr Leu Leu Pro Leu
            100                 105                 110

Glu Arg Lys Gly Val Phe Asp Ala Ala Leu His His Lys Pro Val Phe
        115                 120                 125

Pro Tyr Ser Val Gly Leu Tyr Pro Gly Pro Thr Cys Met Phe Arg Cys
    130                 135                 140

His Phe Cys Val Arg Val Thr Gly Ala Arg Tyr Asp His Ser Ala Leu
145                 150                 155                 160

Asp Asp Gly Asn Lys Met Phe Ala Ala Leu Ile Asp Asp Met Pro Thr
                165                 170                 175

Asp Asn Pro Asp Ala Met Tyr Val Ser Gly Gly Leu Glu Pro Leu Thr
```

-continued

```
                180                 185                 190
Asn Pro Gly Leu Gly Ser Leu Val Arg Arg Ala Ala Gly Arg Gly Phe
            195                 200                 205
Arg Leu Thr Leu Tyr Thr Asn Ala Phe Ala Leu Thr Asp Arg Thr Leu
        210                 215                 220
Glu Arg Gln Gly Gly Leu Trp Arg Leu His Ala Val Arg Thr Ser Leu
225                 230                 235                 240
Tyr Gly Leu Asn Asp Ala Glu Tyr Ala Ala Thr Gly Lys Lys Ala
                245                 250                 255
Ala Phe Gly Arg Val Lys Ala Asn Leu Glu Arg Phe Gln Arg Leu Arg
            260                 265                 270
Ser Ala Arg Ala Glu Pro Val Lys Leu Gly Leu Asn Tyr Ile Val Leu
        275                 280                 285
Pro Gly Arg Gly Arg Leu Leu Asp Leu Val Asp Phe Ile Ala Glu
    290                 295                 300
Leu Asn Ala Ala Ala Pro Asp Arg Pro Leu Asp Phe Val Thr Leu Arg
305                 310                 315                 320
Glu Asp Tyr Ser Gly Arg Pro Asp Gly Leu Leu Ser Gly Ala Glu Arg
                325                 330                 335
Ala Asp Leu Gln Glu Ala Leu Thr Gly Phe Arg Glu Lys Val Ala Ala
            340                 345                 350
Arg Thr Pro Thr Leu His Val Asp Tyr Gly Tyr Ala Leu Asn Ser Leu
        355                 360                 365
Ser Ala Gly Ala Asp Ala Glu Leu Val Arg Ile Arg Pro Glu Thr Met
    370                 375                 380
Arg Pro Thr Ala His Pro Gln Val Ala Val Gln Val Asp Leu Leu Gly
385                 390                 395                 400
Asp Val Tyr Leu Tyr Arg Glu Ala Gly Phe Pro Gly Leu Pro Gly Ala
                405                 410                 415
Asp Arg Tyr Ser Ile Gly Lys Val Ser Pro Gly Thr Thr Leu Thr Gln
            420                 425                 430
Val Val Glu Arg Phe Val Thr Ser Gly Gly Gln Ile Pro Pro Ala Glu
        435                 440                 445
Gly Asp Glu Tyr Phe Met Asp Gly Phe Asp Gln Val Val Thr Ala Arg
    450                 455                 460
Leu Asn Gln Leu Glu Val Asp Thr Ala Asp Gly Trp Ala Asp Gln Arg
465                 470                 475                 480
Gly Phe Leu Arg

<210> SEQ ID NO 41
<211> LENGTH: 331
<212> TYPE: PRT
<213> ORGANISM: Streptomyces mycarofaciens

<400> SEQUENCE: 41

Met Leu His Leu Phe Ser Leu Leu Gly Gly Lys Met Thr Gln Arg Arg
  1               5                  10                  15
Leu Leu Arg Asp Met Val Arg Ile Arg Cys Val Glu Glu Leu Gly
            20                  25                  30
Asp Leu Tyr Arg Asp Glu Gln Glu Met Arg Thr Pro Val His Phe Ser
        35                  40                  45
Ile Gly Gln Glu Ala Thr Ala Val Gly Val Cys Ala Ala Met Leu Arg
    50                  55                  60
Lys Asp Val Val Tyr Gly Gly His Arg Cys His Ala Gln Tyr Leu Ala
```

```
                65                  70                  75                  80
Lys Gly Gly Asp Leu Thr Ala Met Val Ala Glu Leu Tyr Gly Lys Gln
                    85                  90                  95

Ser Gly Cys Ala Ala Gly Arg Gly Ser Val His Leu Thr Asp Lys
                100                 105                 110

Ala Ala Gly Phe Gly Ala Ser Ser Ala Ile Leu Gly Glu Met Ile Ser
            115                 120                 125

Val Ala Val Gly Ala Ala Trp Ser Phe Ala Leu Arg Gly Glu Pro Arg
        130                 135                 140

Val Ala Ala Thr Phe Phe Gly Asp Gly Ala Ser Glu Glu Gly Val Phe
145                 150                 155                 160

His Glu Ser Leu Asn Phe Ala Ala Leu His Arg Leu Pro Val Val Phe
                165                 170                 175

Val Cys Glu Asn Asn Gln Tyr Ser Leu Ser Ser Pro Ile Asp Ala Arg
                180                 185                 190

Gln Pro Val Gly Thr Ser Ile Ser Gly Arg Ala Gln Gly Tyr Gly Met
                195                 200                 205

Ser Thr Gln Arg Val Asp Gly Asn Asp Val Phe Ala Val Phe Glu Ala
        210                 215                 220

Ala Arg Lys Ala Val Arg Gln Cys Arg Gln Gly Lys Gly Pro Tyr Phe
225                 230                 235                 240

Leu Glu Leu Asp Thr Tyr Arg Trp Arg Glu His Val Gly Pro His Trp
                245                 250                 255

Asp Tyr Asp Ile Ser Gly Arg Ser Lys Ala Glu Val Glu Ser Trp Val
                260                 265                 270

Ala Arg Cys Pro Ile Arg Arg Ala Thr Glu Thr Leu Ser Val Ala Asp
                275                 280                 285

Ser Asp Ile Thr Ala Glu Leu Ala Gly Trp Glu Thr Glu Phe Arg Ala
        290                 295                 300

Glu Leu His Glu Ala Val Ala Ala Arg Ser Ser Pro Phe Pro Ala
305                 310                 315                 320

Val Ala Asp Leu Leu Thr Gly Thr Tyr Glu Ser
                325                 330

<210> SEQ ID NO 42
<211> LENGTH: 344
<212> TYPE: PRT
<213> ORGANISM: Streptomyces mycarofaciens

<400> SEQUENCE: 42

Met Pro Lys Ile Thr Tyr Cys Gln Ala Ile Ser Glu Ala Thr Val Gln
1               5                   10                  15

Cys Met Ala Ala Asp Pro Asp Ile Ile Leu Ala Gly Gln Gly Val Asp
            20                  25                  30

Asp His Lys Gly Ile Tyr Gly Thr Thr Asp Ala Phe Gln Lys Phe
        35                  40                  45

Gly Pro Ser Arg Val Met Asp Ile Pro Asn Gly Glu Asn Ala Phe Ala
    50                  55                  60

Gly Ile Ala Val Gly Ala Ala Ser Met Gly Ile Arg Pro Ile Val Val
65                  70                  75                  80

His Thr Arg Asp Asp Phe Met Phe Leu Ala Met Asp Ala Ile Phe Asn
                85                  90                  95

Leu Ala Ala Lys Trp Arg Tyr Met Tyr Gly Asn Gln Gly Ser Ala Pro
                100                 105                 110
```

Ile Val Met Arg Gly Leu Val Arg Gly Trp Gly Gln Gly Ala Thr
            115                 120                 125

His Ser Gln Ser Leu Gln Ser Leu Phe Gly His Phe Pro Gly Leu Tyr
        130                 135                 140

Val Ala Thr Pro Ala Ser Pro Ala Asp Ala Lys Gly Leu Leu Val Ser
145                 150                 155                 160

Ala Leu Gln Ala Glu Thr Pro Val Val Leu Glu Asn Arg Gly Leu
                165                 170                 175

Tyr Gly Ile Glu Gly Glu Val Pro Glu Gln Pro Val Ala Val Pro Phe
                180                 185                 190

Gly Ala Gly Arg Ile Ala Arg Thr Gly Gly Asp Ile Thr Val Val Ala
                195                 200                 205

Ala Ser Leu Met Val His Glu Ala Glu Arg Ala Ala Asp Ala Leu Arg
            210                 215                 220

Glu Gln Asp Ile Gly Val Glu Val Ile Asp Val Arg Ser Ile Arg Pro
225                 230                 235                 240

Leu Asp Asp Ala Leu Ile Cys Thr Ser Val Ala Lys Thr Gly Arg Leu
                245                 250                 255

Val Val Ala Asp Thr Ser Trp Ala Arg Tyr Gly Phe Ala Ala Glu Val
                260                 265                 270

Ala Ala Val Val Ala Glu Asn Val Tyr Asp Ser Leu Arg Ala Pro Val
            275                 280                 285

Arg Arg Val Thr Pro Pro Asp Cys Pro Ala Pro Val Ser Trp Pro Leu
            290                 295                 300

Glu Glu Ala Phe Asn Pro Asn Ala Glu Ala Val Ala His Ala Cys Leu
305                 310                 315                 320

Glu Thr Leu His Ser Gly Gln Arg Ser Val Pro Arg Met Arg Asn Val
                325                 330                 335

Met Ser Gly Phe Thr Gly Pro Tyr
            340

<210> SEQ ID NO 43
<211> LENGTH: 225
<212> TYPE: PRT
<213> ORGANISM: Streptomyces mycarofaciens

<400> SEQUENCE: 43

Met Thr His Thr Glu Gly Pro Thr Ala Gln Gln Arg Ala His Ala
1               5                   10                  15

Leu Met Asp Glu Arg Leu Thr Pro Ala Asp Ser Asp Val Leu Asp Gly
            20                  25                  30

Glu Gln Tyr Asp Arg Asp Asp Arg Ala Ala Leu Arg Arg Val Ala Gly
        35                  40                  45

Leu Ser Thr Glu Leu Ser Asp Val Thr Glu Val Glu Tyr Arg Lys Leu
    50                  55                  60

Arg Leu Glu His Val Val Leu Val Gly Val Trp Thr Ser Gly Thr Ala
65                  70                  75                  80

Asp Glu Ala Glu Ser Ser Leu Ala Glu Leu Ala Ala Leu Ala Glu Thr
                85                  90                  95

Ala Gly Ala Met Val Cys Asp Gly Val Val Gln Arg Arg Gln Lys Pro
            100                 105                 110

Asp Pro Ala Thr Tyr Ile Gly Ser Gly Lys Ala Ala Glu Leu Arg Glu
        115                 120                 125

Ile Val Ala Glu Thr Gly Ala Asp Thr Val Val Cys Asp Gly Glu Leu
    130                 135                 140

-continued

```
Ser Pro Ser Gln Leu Val His Leu Glu Asp Val Val Gly Val Lys Val
145                 150                 155                 160

Val Asp Arg Thr Ala Leu Ile Leu Asp Ile Phe Ala Gln His Ala Lys
                165                 170                 175

Ser Arg Glu Gly Lys Ala Gln Val Ala Leu Ala Gln Met Gln Tyr Met
            180                 185                 190

Leu Pro Arg Leu Arg Gly Trp Gly Gln Ser Leu Ser Arg Gln Met Gly
        195                 200                 205

Gly Gly Gly Gly Gly Met Ala Thr Arg Gly Pro Gly Glu Thr Lys
    210                 215                 220

Ile
225

<210> SEQ ID NO 44
<211> LENGTH: 19
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 44
cggtsaagtc saacatcgg                                                    19

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 45
gcratctcrc cctgcgartg                                                   20

<210> SEQ ID NO 46
<211> LENGTH: 11
<212> TYPE: PRT
<213> ORGANISM: Artificial Sequence
<220> FEATURE:
<223> OTHER INFORMATION: Description of Artificial Sequence:consensus
      sequence

<400> SEQUENCE: 46

Thr Val Asp Thr Gly Cys Ser Ser Ser Leu Val
1               5                   10

<210> SEQ ID NO 47
<211> LENGTH: 10
<212> TYPE: PRT
<213> ORGANISM: Artificial Sequence
<220> FEATURE:
<223> OTHER INFORMATION: Description of Artificial Sequence:consensus
      sequence

<400> SEQUENCE: 47

Gly Xaa Gly Xaa Xaa Gly Xaa Xaa Xaa Ala
1               5                   10

<210> SEQ ID NO 48
<211> LENGTH: 10
<212> TYPE: PRT
<213> ORGANISM: Artificial Sequence
<220> FEATURE:
```

```
<223> OTHER INFORMATION: Description of Artificial Sequence:consensus
      sequence

<400> SEQUENCE: 48

Asp Xaa Thr Xaa Xaa Pro Xaa Xaa Xaa Val
 1               5                  10
```

MIDECAMYCIN BIOSYNTHESIS GENES

CROSS-REFERENCE TO RELATED APPLICATIONS

The present application is a divisional application of U.S. application Ser. No. 10/229,148, filed on Aug. 28, 2002, now U.S. Pat. No. 7,070,980, which claims priority to Japanese Application No. 2002-210516, filed on Jul. 19, 2002.

BACKGROUND OF THE INVENTION

1. Field of the Invention

The present invention relates to midecamycin biosynthesis genes which are involved in the production of midecamycins, and more specifically to genes encoding functional modules of polyketide synthases.

2. Background Technology

Since macrolide antibiotics which are effective to gram-positive bacteria, mycoplasms, chlamydias and the like can be orally administered and have low toxicity, they are classified as clinically important antibiotics. In particular, commercially-available 16-membered ring macrolide antibiotics are widely used in the world, mainly in Asian countries, because of their advantages, for example, that they are less likely to induce resistant strains and less interactive with other drugs than 14-membered ring macrolides, and have little effect on the intestinal tract.

Midecamycins (FIG. 1) belong to 16-membered ring macrolide antibiotics and several analogues have been reported. They are clinically used extensively along with miokamycin, an acylated derivative of a midecamycin (Omoto, S. et al., J. Antibiot., 29, 536 (1976); Yoshida, T. et al., Jpn. J. Antibiot., 35, 1462 (1982)).

Midecamycins are produced by a species of actinomycetes, *Streptomyces mycarofaciens* (ATCC 21454), and industrial scale production by fermentation using this strain has been established. Conventionally, actinomycetes have an important role in the field of fermentation industry as microorganisms for the production of secondary metabolic products, such as antibiotics and physiologically active substances, and their productivity has been improved by various microbial breeding techniques. The microbial breeding has also been carried out for midecamycin production by *Streptomyces mycarofaciens* by inducing mutation with various mutagens.

Recently, recombinant DNA technology has been introduced to improve productivity of secondary metabolites and to create novel active substances and a number of genes in secondary metabolic systems have already been isolated. Examples of isolated genes involved in the production of macrolide antibiotics include tylosin biosynthesis genes (Merson-Davies, L. A. and Cundliffe, E., Mol. Microbiol., 13, 349 (1994); Gandecha, A. R. et al., Gene, 184, 197 (1997); Wilson, V. T. and Cundliffe, E., Gene, 214, 95 (1998); Fouces, R. et al., Microbiology, 145, 855 (1999); Bate, N. et al., Microbiology, 146, 139 (2000); Review: Cundliffe, E. et al., Antonie Van Leeuwenhoek, 79, 229 (2001); U.S. Pat. No. 5,876,991, U.S. Pat. No. 5,672,497, U.S. Pat. No. 5,149,638, European Patent No. 791655, European Patent No. 238323), nidamycin biosynthesis genes (Kakavas, S. J. et al., J. Bacteriol., 179, 7515 (1997); WO98/51695), and erythromycin biosynthesis genes (Dhillon, N. et al., Mol. Microbiol., 3, 1405 (1989); Cortes, J. et al., Nature, 348, 176 (1990); Donadio, S. et al., Science, 252, 675 (1991); Haydock, S. F. et al., Mol. Gen. Genet., 230, 120 (1991); Stassi, D. et al., J. Bacteriol., 175, 182 (1993); Linton, K. J. et al., Gene, 153, 33 (1995); Gaisser, S. et al., Mol. Gen. Genet., 256, 239 (1997); Summers, R. G. et al., Microbiology, 143, 3251 (1997); Gaisser, S. et al., Mol. Gen. Genet., 258, 78 (1998); Salah-Bey, K. et al., Mol. Gen. Genet., 257, 542 (1998); WO93/13663, U.S. Pat. No. 6,004,787, U.S. Pat. No. 5,824,513, WO97/23630, U.S. Pat. No. 5,998,194).

In microorganisms which produce macrolide antibiotics, most of the macrolide biosynthesis genes are often clustered together in a region of 70 to 80 kb in the genome (Donadio, S. et al., Science, 252, 675 (1991); MacNeil, D. J. et al., Gene, 115, 119 (1992); Schwecke, T. et al., Proc. Natl. Acad. Sci., 92, 7839 (1995)). In the center of such clusters, there exists a highly homologous gene called Type I polyketide synthase (PKS) which encodes a huge multi-functional protein.

The PKS is generally composed of 3 to 5 genes and its protein forms a complex comprising an initiator module and several extender modules. Each of these components adds a specific acyl-CoA precursor to a polyketide chain in the process of synthesis to specifically modify β-keto groups. Accordingly, the structure of polyketide is determined by the composition and the order of these modules in the PKS. The modules contain several domains and each of them has its specific function.

The initiator module is composed of an acyl-carrier protein (ACP) domain to which an acyl group of precursor binds and an acyltransferase (AT) domain which catalyzes addition of the acyl group to the ACP domain. Difference in specificity of this AT domain determines the kind of acyl-CoA to be added thereto. All of the extender modules contain a β-ketosynthase (KS) domain, which adds a previously existing polyketide chain to a new acyl-ACP by decarboxylation condensation, the AT domain and the ACP domain.

Further, in addition to these domains, the extender modules contain several domains which modify specific β-keto groups and the composition of the domains contained determines the modification of β-keto groups. Such domains include a β-ketoreductase (KR) domain which reduces a β-keto group to a hydroxyl group, a dehydratase (DH) domain which removes a dehydroxyl group and generates a double bond, and an enoylreductase (ER) domain which reduces a double bond and generates a saturated carbon bond.

The last extender module ends with a thioesterase (TE) domain which catalyzes the cyclization and release of polyketide from the PKS.

A polyketide skeleton produced by PKS undergoes further modifications, such as methylation, acylation, oxidation, reduction, and addition of specific sugars, to ultimately synthesize macrolide antibiotics. Most of the genes necessary for these modifications exist in the vicinity of the PKS gene.

As for genes involved in midecamycin biosynthesis, a midecamycin self-resistance gene (mdmA; Hara, O. and Hutchinson, C. R., J. Antibiot., 43, 977 (1990)), a 3-O-acyltransferase gene (mdmB), an O-methyltransferase gene (mdmc; Hara, O. and Hutchinson, C. R., J. Bacteriol., 174, 5141 (1992)), and a 4"-O-propionyltransferase gene (mpt; Xulun, Z. and Yiguang, W., ActaMicrobiol. Sci., 36, 417 (1996)) have been reported. However, no other gene involved in midecamycin biosynthesis has been reported.

SUMMARY OF THE INVENTION

An object of the present invention is to provide a midecamycin biosynthesis gene, a recombinant vector having said gene and a host having said recombinant vector.

The present invention provides an isolated polynucleotide comprising a nucleotide sequence encoding a protein which is involved in midecamycin biosynthesis, wherein said protein comprises an amino acid sequence selected from the group consisting of the following sequences (hereinafter referred to as "midecamycin biosynthesis gene"):

(a) an amino acid sequence selected from SEQ ID NOs: 2 to 10, 13, 14, 16, 19, 20, 22 to 26, and 28 to 38, (b) an amino acid sequence of a protein involved in biosynthesis of midecamycin, which is encoded by a clone contained in the microorganism deposited under an accession number of FERM BP-8168, (c) an amino acid sequence of a protein involved in biosynthesis of midecamycin, which is encoded by a clone contained in the microorganism deposited under an accession number of FERM BP-8169, (d) an amino acid sequence of a protein involved in biosynthesis of midecamycin, which is encoded by a clone contained in the microorganism deposited under an accession number of FERM BP-8170, and (e) a modified amino acid sequence of (a), (b), (c), or (d) having one or more amino acid modifications without affecting activity of the protein.

DETAILED DESCRIPTION OF THE INVENTION

Definitions

Figure 1:
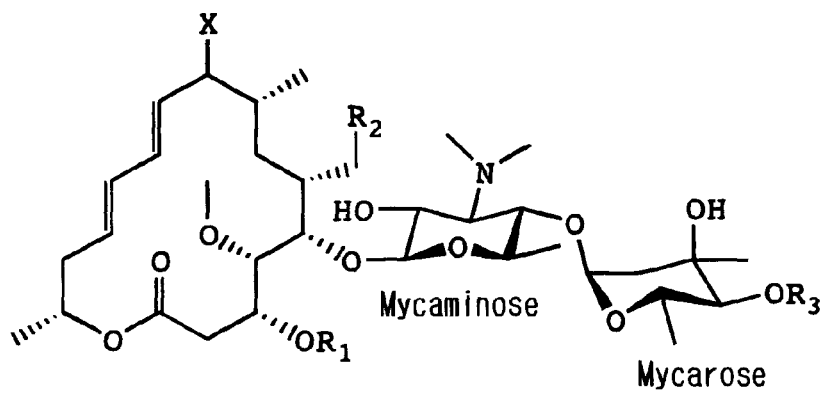
FIG. 1 shows the structures of midecamycins $A_1$, $A_2$, $A_3$, B, DH, E, and $CH_3$.

In the present invention, the term "modification" refers to a substitution, a deletion, an addition and an insertion.

The term "one or more amino acid modifications" herein refers to modifications which do not substantially change protein activity. The number of amino acid residues to be modified is preferably 1 to 40, more preferably one to several, further more preferably 1 to 8, and most preferably 1 to 4.

An example of the "modifications without affecting activity" in the present invention includes a conservative substitution. The term "conservative substitution" means the substitution of one or more amino acid residues with other chemically homologous amino acid residues so as not to substantially change protein activity. For example, a certain hydrophobic residue can be substituted with another hydrophobic residue and a certain polar residue can be substituted with another polar residue having the same charge. Functionally homologous amino acids capable of carrying out these substitutions for each amino acid are known to those skilled in the art. More specifically, examples of the non-polar (hydrophobic) amino acids include alanine, valine, isoleucine, leucine, proline, tryptophan, phenylalanine, and methionine. Examples of the polar (neutral) amino acids include glycine, serine, threonine, tyrosine, glutamine, asparagine, and cysteine. Examples of the positively charged (basic) amino acids include arginine, histidine, and lysine. Examples of the negatively charged (acidic) amino acids include aspartic acid and glutamic acid.

Deposition of Microorganisms

*Escherichia coli* transformed with pCOMW1 was deposited with the International Patent Organism Depositary, National Institute of Advanced Industrial Science and Technology (AIST Tsukuba Central 6, 1-1-1 Higashi, Tsukuba, Ibaraki, 305-8566 Japan), dated Jul. 16, 2002. The accession number is FERM BP-8168.

*Escherichia coli* transformed with pCOMW2 was deposited with the International Patent Organism Depositary, National Institute of Advanced Industrial Science and Technology (AIST Tsukuba Central 6, 1-1-1 Higashi, Tsukuba, Ibaraki, 305-8566 Japan), dated Jul. 16, 2002. The accession number is FERM BP-8169.

*Escherichia coli* transformed with pCOMW4 was deposited with the International Patent Organism Depositary, National Institute of Advanced Industrial Science and Technology (AIST Tsukuba Central 6, 1-1-1 Higashi, Tsukuba, Ibaraki, 305-8566 Japan), dated Jul. 16, 2002. The accession number is FERM BP-8170.

Midecamycin Biosynthesis Gene

Functions of proteins comprising amino acid sequences selected from SEQ ID NOs: 2 to 10, 13, 14, 16, 19, 20, 22 to 26, and 28 to 38 encoded by a midecamycin biosynthesis gene according to the present invention are as described in Table 2 hereinafter.

Nucleotide sequences encoding these proteins can be, for example, nucleotide sequences selected from bases 29244-42779, 42823-48657, 48712-59802, 59850-64556, 64687-70365, 70365-71078, 71113-72360, 72400-73665, 73694-75043, 78039-79313, 79391-81052, 82760-83362, 27937-28983, 26180-27391, 24460-25650, 23555-24463, 22534-23571, 21733-22527, 20307-21743, 17522-18895, 15643-17466, 14074-15096, 13016-14044, 11729-12961, 10521-11603, 9328-10458, 9012-9335, 8149-9015, 6653-7945, and 6048-6629 of SEQ ID NO: 1.

A midecamycin biosynthesis gene according to the present invention can be a polynucleotide comprising a nucleotide sequence which can hybridize with a nucleotide sequence which encodes an amino acid sequence selected from SEQ ID NOs: 2 to 10, 13, 14, 16, 19, 20, 22 to 26, and 28 to 38, under stringent conditions. The term "hybridize" in the present invention means to hybridize with a target nucleotide sequence but not with a nucleotide other than the target nucleotide under stringent conditions. The term "stringent conditions" means that the membrane washing after hybridization is carried out in a low salt solution at a high temperature, for example, at a concentration of 0.2×SSC (1×SSC: 15 mM trisodium citrate, 150 mM sodium chloride) in a 0.1% SDS solution at 60° C. for 15 minutes.

A polyketide synthase involved in midecamycin biosynthesis comprises a complex of several modules and each module has several functional domains. Accordingly, the present invention provides an isolated polynucleotide comprising a nucleotide sequence encoding a functional domain of polyketide synthase (PKS) which is involved in midecamycin biosynthesis, wherein said domain comprises an amino acid sequence selected from the group consisting of the following sequences (1) to (9):

(1) an amino acid sequence selected from amino acid residues 17-422 (KS0null), 524-878 (AT0), 919-1004 (ACP0), 1031-1456 (KS1), 1562-1916 (AT1), 2161-2449 (KR1), 2475-2560 (ACP1), 2583-3008 (KS2), 3129-3483 (AT2), 3499-3699 (DH2), 4022-4315 (KR2), and 4333-4418 (ACP2) of SEQ ID NO: 2, (2) an amino acid sequence selected from amino acid residues 35-460 (KS3), 577-929 (AT3), 943-1169 (DH3), 1457-1744 (KR3), and 1759-1844 (ACP3) of SEQ ID NO: 3, (3) an amino acid sequence selected from amino acid residues 42-467 (KS4), 568-916 (AT4), 1137-1408 (KR4null), 1417-1502 (ACP4), 1522-1948 (KS5), 2064-2414 (AT5), 2426-2618 (DH5), 2939-3229 (ER5), 3219-3504 (KR5), and 3520-3605 (ACP5) of SEQ ID NO: 4, (4) an amino acid sequence selected from amino acid residues 34-458 (KS6), 563-914 (AT6), 1134-1418 (KR6), and 1427-1509 (ACP6) of SEQ ID NO: 5, (5) an amino acid sequence selected from amino acid residues 35-460 (KS7), 576-929 (AT7), 1217-1500 (KR7), 1504-1591 (ACP7), and 1588-1892 (TE7) of SEQ ID NO: 6, (6) an amino acid sequence of a functional domain of PKS involved in midecamycin biosynthesis, which is encoded by a clone contained in the microorganism deposited under an accession number of FERM BP-8168, (7) an amino acid sequence of a functional domain of PKS involved in midecamycin biosynthesis, which is encoded by a clone contained in the microorganism deposited under an accession number of FERM BP-8169, (8) an amino acid sequence of a functional domain of PKS involved in midecamycin biosynthesis, which is encoded by a clone contained in the microorganism deposited under an accession number of FERM BP-8170, and (9) an amino acid sequence of any one of (1) to (8) having one or more amino acid modifications without affecting activity of said domain.

The present invention also provides an isolated polynucleotide comprising a nucleotide sequence encoding a functional domain of polyketide synthase (PKS) which is involved in midecamycin biosynthesis, wherein said nucleotide sequence is selected from the group consisting of the following sequences (10) to (14):

(10) a nucleotide sequence which can hybridize with a nucleotide sequence encoding an amino acid sequence selected from amino acid residues 17-422 (KS0null), 524-878 (AT0), 919-1004 (ACP0), 1031-1456 (KS1), 1562-1916 (AT1), 2161-2449 (KR1), 2475-2560 (ACP1), 2583-3008 (KS2), 3129-3483 (AT2), 3499-3699 (DH2), 4022-4315 (KR2), and 4333-4418 (ACP2) of SEQ ID NO: 2, under stringent conditions,

(11) a nucleotide sequence which can hybridize with a nucleotide sequence encoding an amino acid sequence selected from amino acid residues 35-460 (KS3), 577-929 (AT3), 943-1169 (DH3), 1457-1744 (KR3), and 1759-1844 (ACP3) of SEQ ID NO: 3, under stringent conditions,

(12) a nucleotide sequence which can hybridize with a nucleotide encoding an amino acid sequence selected from amino acid residues 42-467 (KS4), 568-916 (AT4), 1137-1408 (KR4null), 1417-1502 (ACP4), 1522-1948 (KS5), 2064-2414 (AT5), 2426-2618 (DH5), 2939-3229 (ER5), 3219-3504 (KR5), and 3520-3605 (ACP5) of SEQ ID NO: 4, under stringent conditions,

(13) a nucleotide sequence which can hybridize with a nucleotide sequence encoding an amino acid sequence selected from amino acid residues 34-458 (KS6), 563-914 (AT6), 1134-1418 (KR6), and 1427-1509 (ACP6) of SEQ ID NO: 5, under stringent conditions, and

(14) a nucleotide sequence which can hybridize with a nucleotide sequence encoding an amino acid sequence selected from amino acid residues 35-460 (KS7), 576-929 (AT7), 1217-1500 (KR7), 1504-1591 (ACP7), and 1588-1892 (TE7) of SEQ ID NO: 6, under stringent conditions.

A polynucleotide encoding a domain comprising amino acid sequence (1) can be a nucleotide sequence selected from bases 29292-30509, 30813-31877, 31998-32255, 32334-33611, 33927-34991, 35724-36590, 36666-36923, 36990-38267, 38628-39692, 39738-40340, 41307-42188, and 42240-42497 of SEQ ID NO: 1.

A polynucleotide encoding a domain comprising amino acid sequence (2) can be a nucleotide sequence selected from bases 42925-44202, 44551-45609, 45649-46329, 47191-48054, and 48097-48354 of SEQ ID NO: 1.

A polynucleotide encoding a domain comprising amino acid sequence (3) can be a nucleotide sequence selected from bases 48835-50112, 50413-51459, 52120-52935, 52960-53217, 53275-54555, 54901-55953, 55987-56565, 57526-58398, 58366-59223, and 59269-59526 of SEQ ID NO: 1.

A polynucleotide encoding a domain comprising amino acid sequence (4) can be a nucleotide sequence selected from bases 59949-61223, 61536-62591, 63249-64103, and 64128-64376 of SEQ ID NO: 1.

A polynucleotide encoding a domain comprising amino acid sequence (5) can be a nucleotide sequence selected from bases 64789-66066, 66412-67473, 68335-69186, 69196-69459, and 69448-70362 of SEQ ID NO: 1.

Isolation of Midecamycin Biosynthesis Gene

A midecamycin biosynthesis gene according to the present invention can be isolated, for example, from *Streptomyces mycarofaciens* (ATCC 21454) or its mutant strains by the following method. Further, a pertinent gene can be artificially synthesized since its sequence is known as disclosed in the present invention.

A genomic DNA is extracted from cells of *Streptomyces mycarofaciens* by a conventional method described in Kieser, T. et al., Practical *Streptomyces* Genetics, The John Innes Foundation, Norwick, UK (2000). This genomic DNA is digested with an appropriate restriction enzyme and then ligated with an appropriate vector to construct a genomic library comprising a genomic DNA of *Streptomyces mycarofaciens*. Various vectors such as plasmid vectors, phage vectors, cosmid vectors, and BAC vectors can be used as a vector.

Next, appropriate probes are made based on the sequence of the midecamycin biosynthesis gene disclosed in this specification, hybridization is carried out and then a DNA fragment which contains the target midecamycin biosynthesis gene can be obtained from the resulting genomic library. Alternatively, appropriate primers for amplification of the gene of interest are synthesized based on the sequence of the midecamycin biosynthesis gene disclosed in this specification, PCR is carried out using the genomic DNA of *Streptomyces mycarofaciens* as a template, and then the target gene can be isolated by ligating the amplified DNA fragment with an appropriate vector. The DNA fragment containing the midecamycin biosynthesis gene according to the present invention is contained in pCOMW1, pCOMW2, and pCOMW4 in a ligated form with cosmid vectors (FIG. 2), which can be used as a template for the PCR. Further, the desired DNA fragment can be excised from these deposited cosmid vectors using an appropriate restriction enzyme.

In this way, the polyketide synthesis enzyme gene of *Streptomyces mycarofaciens* and its neighboring regions can be isolated.

It is possible to confirm whether the isolated DNA fragment contains the midecamycin biosynthesis gene by constructing a strain having a specific gene disruption by incorporating a vector containing an internal fragment of the target gene or a vector having a selectable marker gene insert, which divides the internal part of the target gene, to induce homologous recombination and then by evaluating no production of midecamycin from this gene disruption strain when cultured. Midecamycin can be detected by extracting from a culture fluid with an appropriate organic solvent and analyzing the extract using HPLC. Midecamycin can also be detected by treating the culture fluid with midecamycin-sensitive bacteria and examining the growth of the bacteria.

Transformants

In order to improve productivity by recombinant DNA technology, enhancement of expression of a gene which encodes a rate-limiting biosynthesis reaction, enhancement of expression of a gene which controls expression of a biosynthesis gene, gene disruption, blocking of unnecessary secondary metabolic systems, and the like have been carried out (Kennedy, J. and Turner, G., Mol. Gen. Genet., 253, 189 (1996); Review: Baltz, R. H., Biotechnology of Antibiotics Second Edition, Revised and Expanded, Marcel Dekker, Inc., New York, pp. 49 (1997); Review: Hutchinson, C. R. and Colombo, A. L., J. Ind. Microbiol. Biotechnol., 23, 647 (1999); Review: Brakhage, A. A., Microbiol. Mol. Biol. Rev., 62, 547 (1998)). Accordingly, if a biosynthesis gene is specified, productivity can be improved by recombinant DNA technology by ligating the gene with an appropriate vector and introducing the vector into a microorganism for producing a secondary metabolite.

On the other hand, in order to create novel active substances by recombinant DNA technology, modifications of domains for polyketide synthesizing enzymes (Review: Ikeda and Omura, Protein, Nucleic Acid and Enzyme, 43, 1265 (1998); Review: Carreras, C. W. and Santi, D. V., Curr. Opin. Biotech., 9, 403 (1998); Review: Hutchinson, C. R., Curr. Opin. Microbiol., 1, 319 (1998); Review: Katz, L. and McDaniel, R., Med. Res. Rev., 19, 543 (1999); WO93/13663, WO95/08548, WO96/40968, WO98/01546, WO98/49315, WO98/51695, WO00/47724, U.S. Pat. No. 5,672,491, U.S. Pat. No. 5,712,146, U.S. Pat. No. 6,391,59), disruption of genes of biosynthesis systems, introduction of modified enzyme genes from other organisms (Review: Hutchinson, C. R., Biotechnology, 12, 375 (1994)), and the like have been carried out. Accordingly, if a biosynthesis gene is specified, a novel active substance can be produced by recombinant DNA technology by ligating the gene with an appropriate vector and introducing the vector into a microorganism for producing a secondary metabolite.

Thus, according to the present invention, productivity of midecamycin can be improved by ligating a midecamycin biosynthesis gene according to the present invention and a gene encoding a functional module with an appropriate vector and introducing the vector into a host such as *Streptomyces mycarofaciens* to enhance or control its expression, or by disrupting functions of domains in the gene by gene disruption using homologous recombination. Also, according to the present invention, a macrolide compound other than midecamycin can be produced by ligating a midecamycin biosynthesis gene according to the present invention and a gene encoding a functional module with an appropriate vector and introducing the vector into a host such as *Streptomyces mycarofaciens* to enhance or control its expression, or by disrupting functions of domains or substituting domains in the gene.

A recombinant vector for gene transfer can be constructed by modifying a polynucleotide provided by the present invention into an appropriate form depending on the purpose using a conventional method in the recombinant DNA technology, for example, described in Sambrook, J. et al., Molecular Cloning: a laboratory manual, Cold Spring Harbor Laboratory, New York (1989) and ligating it with a vector.

Vectors to be used in the present invention can be appropriately selected from viruses, plasmids, cosmid vectors, and the like, taking the kind of host cells to be used into consideration. For example, lambda bacteriophages and pBR322 and pUC vectors can be used for *Escherichia coli*; pUB110, pPL603, and pC194 vectors can be used for *Bacillus subtilis*; pYC and pYE vectors can be used for yeasts; and pIJ101, pSET152, pSG5, SCP2*, pSAM2, pKC1139, and φC31 vectors can be used for actinomycetes (Kieser, T. et al., Practical *Streptomyces* Genetics, The John Innes Foundation, Norwick, UK (2000)).

Among the plasmid vectors to be used, at least one vector preferably contains a selectable marker to select transformants. A drug resistance gene or a gene complementing a nutritional requirement can be used as a selectable maker. Preferable examples of the marker genes to be used for each host include an ampicillin resistance gene, a kanamycin resistance gene, and a tetracycline resistance gene for bacteria; a tryptophan biosynthesis gene (TRP1), an uracyl biosynthesis gene (URA3), and a leucine biosynthesis gene (LEU2) for yeasts; a hygromycin resistance gene, a bialaphos resistance gene, a bleomycin resistance gene, and an aureobacidin resistance gene for fungi; and a kanamycin resistance gene and a bialaphos resistance gene for plants.

Further, in an expression vector, regulatory sequences necessary for expression of each gene, for example, transcription regulatory signals and translation regulatory signals, such as a promoter, a transcription initiation signal, a ribosome binding site, a translation stop signal, and a transcription stop signal, can operably be linked to the biosynthesis gene. The regulatory sequences can be selected and ligated according to an ordinary method.

For example, promoters such as a lactose operon and a tryptophan operon can be used for *Escherichia coli*; promoters such as an alcohol dehydrogenase gene, an acid phosphatase gene, a galactose utilization gene, and a glyceraldehyde triphosphate dehydrogenase gene can be used for yeasts; promoters such as an α-amylase gene, a glucoamylase gene, a cellobiohydrolase gene, a glyceraldehyde triphosphate dehydrogenase gene, and an Abpl gene can be used for fungi; and the CaMV 35S RNA promoter and CaMV 19S RNA promoter, and a noparin synthase gene promoter can be used for plants.

A host for gene transfer can be appropriately selected from actinomycetes, *Escherichia coli*, *Bacillus subtilis*, yeasts, filamentous fungi and other microorganisms depending on the kind of vectors to be used. When the vector is for actinomycetes, examples of particularly preferable hosts include *Streptomyces mycarofaciens*, *Streptomyces coelicolor*, *Streptomyces hygroscopicus*, *Streptomyces fradiae*, *Streptomyces lividans*, *Streptomyces kitasatoensis*, *Streptomyces ambofaciens*, and *Streptomyces thermotolerans*.

A method of introducing a vector into a host microorganism is selected to be most efficient depending on a vector and host to be used. When a vector for actinomycetes is used, transfer by conjugation with *Escherichia coli*, infection with an actinomycetes phage, introduction into the protoplast of the host, or the like can be carried out (Kieser, T. et al., Practical *Streptomyces* Genetics, The John Innes Foundation, Norwick, UK (2000)). For the selection of recombinants obtained by transformation, genetic indices carried by vectors to be used, such as antibiotic resistance, pock formation, and melanin biosynthesis, can be utilized.

In the present invention, when multiple biosynthesis genes are introduced into a host, each gene can be contained in the same or different DNA molecules. Further, when the host is a bacterium, it is possible to design each gene to be expressed as a polycistronic mRNA and thus make into one DNA molecule.

Gene disruption using homologous recombination can be carried out according to a conventional method. Construction of vectors for the gene disruption and introduction of the vectors into the host are known to the skilled in the art.

Transformants thus obtained are cultured and newly acquired properties can be examined according to a conventional method. As a medium, conventional components can be used. For example, as a carbon source, glucose, sucrose, starch syrup, dextrin, starch, glycerol, molasses, animal and vegetable oils, and the like can be used. As a nitrogen source, soybean powder, wheat germ, cornsteep liquor, cottonseed lees, meat extract, polypeptone, malt extract, yeast extract, ammonium sulfate, sodium nitrate, urea, and the like can be used. If necessary, inorganic salts which can produce sodium, potassium, calcium, magnesium, cobalt, chlorine, phosphoric acid (e.g., dipotassium hydrogenphosphate), sulfuric acid (e.g., magnesium sulfate), and other ions can be effectively added. If necessary, various vitamins such as thiamine (e.g., thiamine hydrochloride), amino acids such as glutamic acid (e.g., sodium glutamate) and asparagine (e.g., DL-asparagine), trace nutrients such as nucleotides, and selective drugs such as antibiotics can be added.

The pH of the medium is, for example, about 5.5 to 8. The cultivation can be carried out by a solid culture method under an aerobic condition, a shaking culture method, an agitation culture method with aeration, or an aerobic submerged culture method. In particular, an aerobic submerged culture method is most preferable. The culture temperature is appropriately 15° C. to 40° C., generally about 22° C. to 30° C. Although the production of the target substance varies depending on a medium, culture conditions, and a host used, the maximum accumulation can generally be attained in 2 to 10 days by any culture method. The incubation is terminated when the amount of the target substance in the medium reaches its peak, and the target substance is isolated from the culture and then purified.

In order to recover the target substance from the culture, an ordinary isolation method using its properties, such as a solvent extraction method, an ion-exchange resin method, an adsorption or distribution column chromatography method, a gel filtration method, a dialysis method, a precipitation method, and crystallization method, can be used singly or in appropriate combination for extraction and purification. For example, the substance is extracted from the culture with acetone, methanol, butanol, ethyl acetate, butyl acetate or the like.

For further purification of the target substance, chromatography using an adsorbent such as silica gel and alumina, SEPHADEX LH-20 (Pharmacia), or TOYOPEARL HW-40 (Tosoh Co.) can be carried out.

EXAMPLE

The present invention is further illustrated by the following examples that are not intended as a limitation of the invention.

1. Isolation of Genomic DNA and Construction of Genomic Library

A frozen seed culture of *Streptomyces mycarofaciens* (ATCC 21454) was inoculated into 50 ml of S#14 medium (2% glucose, 1% polypeptone, 0.05% $K_2HPO_4$, 0.05% $MgSO_4 \cdot 7H_2O$, 0.3% NaCl, pH 7.0), and cultured at 28° C. for 20 hours. The culture was filtered using a bottle top filter 0.22 µm (Corning), after which the cells on the filter were washed twice with 10 mM EDTA and then recovered. The cells thus obtained were frozen with liquid nitrogen and then smashed with a mortar and pestle. The genomic DNA was isolated from these smashed cells using an ISOPLANT (Nippon gene) according to the attached protocol.

The isolated genomic DNA was partially digested with Sau3AI and then the resulting terminals were dephosphorylated. This DNA fragment was ligated with SuperCosI (Stratagene Co.) which had been digested with BamHI and XbaI (only the XbaI site was dephosphorylated) to construct a recombinant cosmid vector. This recombinant cosmid vector was subjected to in vitro packaging using a Max Plax Packaging Extract (Epicenter Technologies) according to the attached protocol. Then, *Escherichia coli* XL1-BLUE MR strain was infected with this recombinant phage and incubated on a plate to form colonies.

2. Construction of Probes

The following primers were prepared from the conservative region of the PKS gene.

```
KS-F:  5'-CGGTSAAGTCSAACATCGG-3'    (SEQ ID NO: 44)

KS-R:  5'-GCRATCTCRCCCTGCGARTG-3'   (SEQ ID NO: 45)
```

PCR was carried out using KS-F and KS-R and the genomic DNA as a template. The PCR was carried out using an ExTaq DNA polymerase (Takara Shuzo Co., Ltd.). The amplified DNA fragment was inserted into a pCR2.1-TOPO plasmid vector using a TOPO TA Cloning Kit (Invitrogen) according to the attached protocol.

The inserted DNA fragment was sequenced using a DNA Sequencing Kit dRhodamine Terminator Cycle Sequencing Ready Reaction (Perkin-Elmer) and an ABI PRISM Genetic Analyzer (Perkin-Elmer) according to the attached protocol. In this way, the isolated DNA fragment was confirmed to be a part of the PKS gene.

3. Screening of Cosmid Library

The DNA fragment was amplified by PCR using the plasmid containing a part of the midecamycin PKS gene as a template and primers KS-F and KS-R and used as a probe for hybridization.

A HYBOND N+ membrane (Amersham Pharmacia Biotech) was placed on a plate, on which colonies of the genomic library were formed, to blot with the colonies. This membrane was treated with an alkali and upon cell lysis, the recombinant cosmid DNA on the membrane was denatured into a single chain and adsorbed on the membrane. Positive clones on the membrane were detected using an ECL Direct Nucleic Acid Labeling and Detecting System (Amersham Pharmacia Biotech) according to the attached protocol. In this way, cosmid clones pCOMW1 (FERM BP-8168) and pCOMW2 (FERM BP-8169) containing a region homologous to the probe were isolated. A probe was newly constructed by PCR from the terminal sequence of partially analyzed pCOMW1 (FERM BP-8168). Screening of the genomic library was carried out again using this probe to isolate pCOMW4 (FERM BP-8170)

Figure 2:
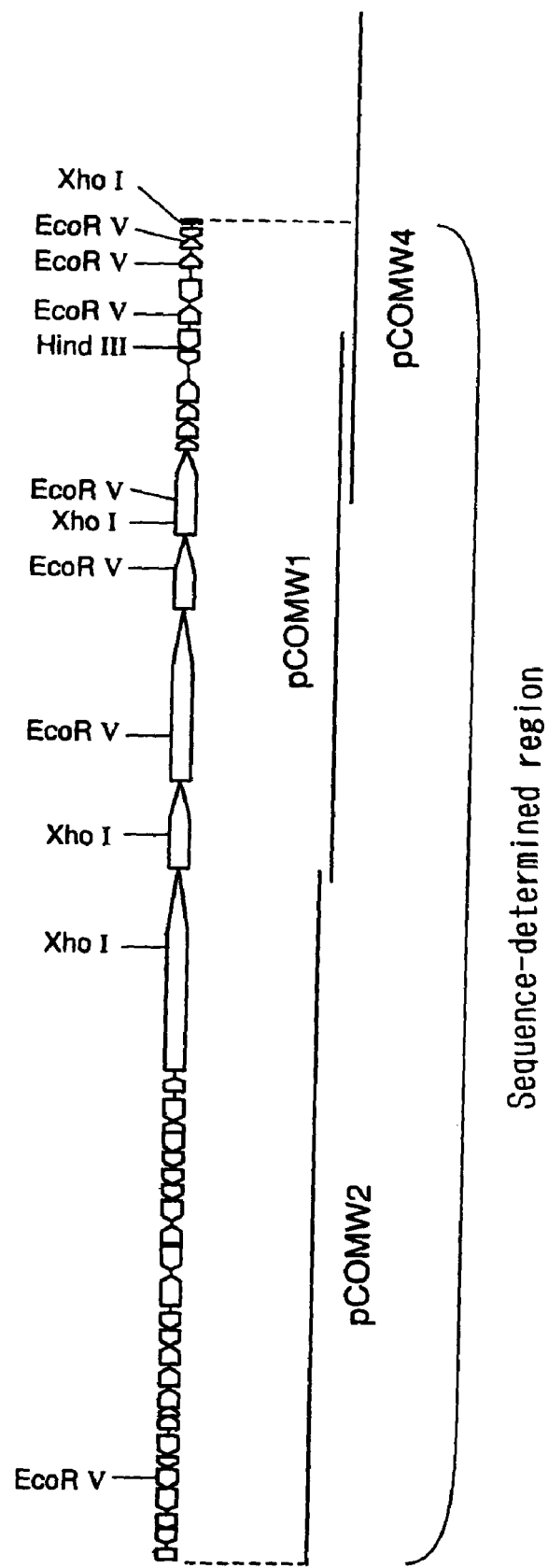
FIG. 2 shows the positions of cosmid clones pCOMW1, pCOMW2, and pCOMW4 on the ORFs.

4. Determination of Base Sequences pCOMW1 (FERM BP-8168) and pCOMW2 (FERM BP-8169) were partially digested with HaeIII, after which an about 2-kb fragment was purified by electrophoresis and ligated with pUC19 digested with SmaI. This plasmid was introduced into *Escherichia coli* XL1-BLUE, the plasmid was extracted from a selected colony and was sequenced using –21M13 forward primer and M13 reverse primer as primers using anABI3700 (Perkin-Elmer) according to the attached protocol. From the results obtained, regions where the analysis was not sufficient were further subjected to sequencing using primers newly designed based on already-analyzed base sequences. Further based on the results of this analysis, partial sequences of pCOMW4 (FERM BP-8170) were determined by primer walking. The positions of each cosmid clone are shown in FIG. 2.

5. Analysis of Nucleotide Sequences

Figure 3:
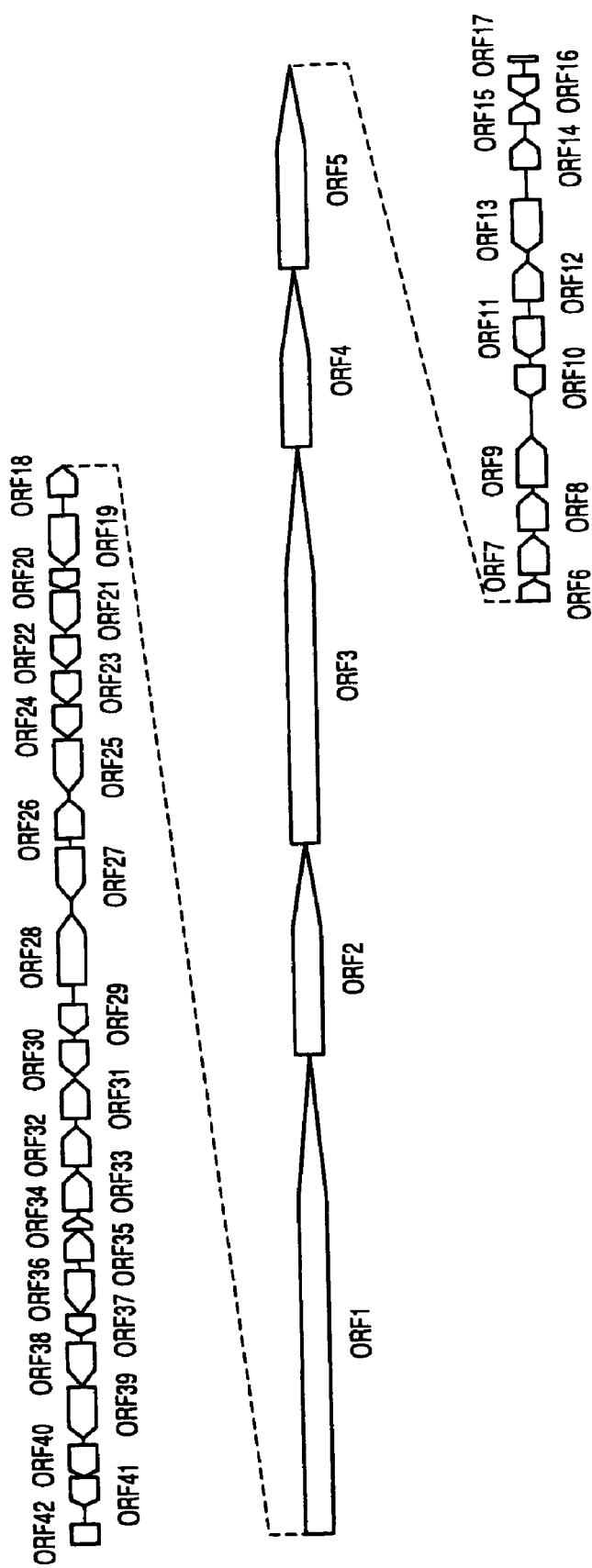
FIG. 3 shows the positions of the ORFs determined in the present invention.

Projection of ORFs was carried out using frame analysis attached to Genetyx (Software Development) and the functions of each ORF were projected by searching public databases using BLAST (Altschul, S. F. et al., J. Mol. Biol., 215, 403 (1990)). The positions of each ORF were shown in FIG. 3 and Table 1.

TABLE 1

Positions of each ORF in SEQ ID NO: 1

|  | SEQ ID NO: | Number of amino acids | Bases in SEQ ID NO: 1 | Gene direction |
|---|---|---|---|---|
| ORF1 | 2 | 4511 | 29244-42779 | + |
| ORF2 | 3 | 1944 | 42823-48657 | + |
| ORF3 | 4 | 3696 | 48712-59802 | + |
| ORF4 | 5 | 1568 | 59850-64556 | + |
| ORF5 | 6 | 1892 | 64687-70365 | + |
| ORF6 | 7 | 237 | 70365-71078 | + |
| ORF7 | 8 | 415 | 71113-72360 | + |
| ORF8 | 9 | 421 | 72400-73665 | + |
| ORF9 | 10 | 449 | 73694-75043 | + |
| ORF10 | 11 | 223 | 75899-76570 | − |
| ORF11 | 12 | 387 | 76602-77765 | − |
| ORF12 | 13 | 424 | 78039-79313 | + |
| ORF13 | 14 | 553 | 79391-81052 | − |
| ORF14 | 15 | 271 | 81541-82356 | + |
| ORF15 | 16 | 200 | 82760-83362 | + |
| ORF16 | 17 | 215 | 83495-84142 | − |

TABLE 1-continued

Positions of each ORF in SEQ ID NO: 1

|  | SEQ ID NO: | Number of amino acids | Bases in SEQ ID NO: 1 | Gene direction |
|---|---|---|---|---|
| ORF17 | 18 | (33)[a] | 84329-84428 | + |
| ORF18 | 19 | 348 | 27937-28983 | + |
| ORF19 | 20 | 403 | 26180-27391 | − |
| ORF20 | 21 | 152 | 25647-26105 | − |
| ORE21 | 22 | 396 | 24460-25650 | − |
| ORF22 | 23 | 302 | 23555-24463 | − |
| ORF23 | 24 | 345 | 22534-23571 | − |
| ORF24 | 25 | 264 | 21733-22527 | − |
| ORF25 | 26 | 478 | 20307-21743 | − |
| ORF26 | 27 | 388 | 19063-20229 | + |
| ORF27 | 28 | 457 | 17522-18895 | − |
| ORF28 | 29 | 607 | 15643-17466 | + |
| ORF29 | 30 | 340 | 14074-15096 | − |
| ORF30 | 31 | 342 | 13016-14044 | − |
| ORF31 | 32 | 410 | 11729-12961 | + |
| ORF32 | 33 | 360 | 10521-11603 | + |
| ORF33 | 34 | 376 | 9328-10458 | + |
| ORF34 | 35 | 107 | 9012-9335 | + |
| ORF35 | 36 | 288 | 8149-9015 | + |
| ORF36 | 37 | 430 | 6653-7945 | − |
| ORF37 | 38 | 193 | 6048-6629 | − |
| ORF38 | 39 | 417 | 4695-5948 | − |
| ORF39 | 40 | 484 | 3237-4691 | − |
| ORF40 | 41 | 331 | 2220-3215 | − |
| ORF41 | 42 | 344 | 1168-2202 | − |
| ORF42 | 43 | (225)[a] | 1-675 | − |

[a]The numbers set forth in the parentheses are indicated for partial sequences.

Further, functions inferred from each ORF are shown in Table 2.

TABLE 2

Inferred functions of each ORF

|  | SEQ ID NO | Highly homologous protein | Organism | GenBank No. | Homology (%) | Function |
|---|---|---|---|---|---|---|
| ORF1 | 2 | Ty lactone synthase starter module, module 1, 2 TylG1 | *Streptomyces fradiae* | U78289 | 49 | Polyketide synthase, macrolide skeleton synthesis |
| ORF2 | 3 | Polyketide synthase module 3 | *Streptomyces caelestis* | AF016585 | 60 | Polyketide synthase, macrolide skeleton synthesis |
| ORF3 | 4 | Ty lactone synthase module 4,5 TylGIII | *Streptomyces fradiae* | U78289 | 59 | Polyketide synthase, macrolide skeleton synthesis |
| ORF4 | 5 | Polyketide synthase module 6 | *Streptomyces karestis* | AF016585 | 67 | Polyketide synthase, macrolide skeleton synthesis |
| ORF5 | 6 | Polyketide synthase module 7 | *Streptomyces karestis* | AF016585 | 64 | Polyketide synthase, macrolide skeleton synthesis |
| ORF6 | 7 | N-methyltransferase TylMI | *Streptomyces fradiae* | X81885 | 61 | N-methyl transferase, mycaminose synthesis |
| ORF7 | 8 | dnrQ | *Streptomyces neucetis* | L47164 | 37 | NDP-hexose 3,4-isomerase, mycaminose synthesis |
| ORF8 | 9 | Glycosyltransferase TylMII | *Streptomyces fradiae* | X81885 | 55 | Glycosyltransferase, mycaminose addition |
| ORF9 | 10 | Crotonyl-CoA reductase | *Streptomyces coelicolor* | AL035161 | 80 | Crotonyl-CoA reductase, polyketide precursor (ethylmalonyl-CoA) synthesis |
| ORF10 | 11 | O-methyltransferase mdmC | *Streptomyces mycarofaciens* | M93958 | 100 | O-methyltransferase, precursor polyketide precursor (methoxynalonyl-ACP) synthesis |
| ORF11 | 12 | 3-O-acyltrasnferase mdmB | *Streptomyces mycarofaciens* | M93958 | 100 | 3-O-acyltransferase, macrolide skeleton modification |
| ORF12 | 13 | Cytochrome P-450 | *Streptomyces thermotolerans* | D30759 | 64 | Cytochrome P-450 |
| ORF13 | 14 | Carbomycin resistance protein | *Streptomyces themotolerancs* | M80346 | 77 | Midecamycin resistance protein |
| ORF14 | 15 | Midecamycin tolerance protein mdmA | *Streptomyces mycarofaciens* | A60725 | 100 | Midecamycin resistance protein |

TABLE 2-continued

Inferred functions of each ORF

| | SEQ ID NO | Highly homologous protein | Organism | GenBank No. | Homology (%) | Function |
|---|---|---|---|---|---|---|
| ORF15 | 16 | TetR family transcription control factor | *Streptomyces coelicolor* | AL133220 | 49 | TetR family transcription control factor |
| ORP16 | 17 | Unknown | | | — | Unknown |
| ORF17 | 18 | 4-Caoboxymuconolactone decarboxylase | *Streptomyces coelicolor* | AL031155 | (67)[a] | 4-Carboxymuconolactone decarboxylase |
| ORF18 | 19 | Reductase | *Streptomyces coelicolor* | AL355752 | 39 | 9-Reductase, macrolide skeleton modification |
| ORF19 | 20 | Cytochrome P-450 TylI | *Streptomyces fradiae* | U08223 | 64 | 19-Oxygenase, macrolide skeleton modification |
| ORF20 | 21 | ORF15 × 4 | *Listonella anguillarum* | AF025396 | 39 | Unknown |
| ORF21 | 22 | Aminotransferase-like protein | *Streptomyces antibioticus* | AF237895 | 61 | Aminotransferase, mycaminose synthesis |
| ORF22 | 23 | α-D-Glucose-1-phosphate thymidyltransferase | *Streptomyces venezuelae* | AF079762 | 69 | α-D-Glucose-1-phosphate thymidyltransferase, deoxy sugar synthesis |
| ORF23 | 24 | AprE | *Streptomyces tenebrareus* | AF306787 | 69 | dTDP-glucose 4,6-dehydratase, deoxy sugar synthesis |
| ORF24 | 25 | RifR | *Amycolatopsis mediterranei* | AF40570 | 50 | Type II thioesterase, macrolide skeleton synthesis |
| ORF25 | 26 | TDP-6-deoxy-4-ketohexose 2,3-dehydratase | *Streptomyces fradiae* | AF210634 | 54 | TDP-6-deoxy-4-ketohexose 2,3-dehydratase, mycarose synthesis |
| ORF26 | 27 | Midecamycin 4″-O-propionyltransferase | *Streptomyces mycarofaciens* | D63662 | 97 | Midecamycin 4″-O-propionyltransferase, mycarose modification |
| ORF27 | 28 | Control protein AcyB2 | *Streptomyces thermotolerans* | D31821 | 55 | TylR family transcription control factor |
| ORF28 | 29 | SrmR | *Streptomyces ambofaciens* | X63451 | 76 | SrmR family transcription control factor |
| ORF29 | 30 | NDP-hexose 4-ketoreductase TylCIV | *Streptomyces fradiae* | AF147704 | 55 | NDP-hexose 4-ketoreductase, mycarose synthesis |
| ORF30 | 31 | dTDP-keto-L-6-deoxy-hexose 2,3-reductase | *Saccharoporis polaerislae* | U77454 | 73 | dTDP-4-keto-L-6-deoxy-hexose synthesis |
| ORF31 | 32 | NDP-hexose-3-C-methyltransferase TylCIII | *Streptomyces fradiae* | AF147704 | 78 | NDP-hexose-3-C-methyltransferase, mycarose synthesis |
| ORF32 | 33 | FkbH | *Streptomyces hygroscopicus* | AF235504 | 66 | Glyceryl-ACP biosynthesis, polyketide precursor (methoxynalonyl-ACP) synthesis |
| ORF33 | 34 | FkbI | *Streptomyces hygroscopicus* | AF235504 | 65 | Acyl-CoA dehydrogenase, polyketide precursor (methoxynalonyl-ACP) synthesis |
| ORF34 | 35 | FkbJ | *Streptomyces hygroscopicus* | AF235504 | 47 | Acyl carrier protein, polyketide precursor (methoxynalonyl-ACP) synthesis |
| ORF35 | 36 | FkbK | *Streptomyces hygroscopicus* | AF235504 | 56 | 3-Hydroxybutyril-CoA dehydrogenase, polyketide precursor (methoxymalonyl-ACP) synthesis |
| ORF36 | 37 | Mycarosyltransferase TylCV | *Streptomyces fradiae* | AF147704 | 61 | Glycosyltransferase, mycarose addition |
| ORF37 | 38 | NDP-hexose-3,5-epimerase TylCII | *Streptomyces fradiae* | AF147704 | 74 | NDP-hexose-3,5-epimerase, mycarose synthesis |
| ORF38 | 39 | Dehyratase | *Streptomyces antibioticus* | AF055579 | 66 | Dehyratase, desosamine synthesis |
| ORF39 | 40 | Reductase | *Streptomyces venezuelae* | AF079762 | 69 | Reductase, desosamine synthesis |
| ORF40 | 41 | Pyruvate dehydrogenase α subunit | *Coquella varneddi* | AF387640 | 38 | Pyruvate dehydrogenase α subunit |
| ORF41 | 42 | Pyruvate dehydrogenase β subunit | *Sulfolobus solfataricus* | AE006767 | 42 | Pyruvate dehydrogenase β subunit |
| ORF42 | 43 | Protein SC4H2.17 | *Streptomyces coelicolor* | AL022268 | (76)[a] | GTP-binding protein |

[a]The numbers set forth in the parentheses are indicated for partial sequences.

Further, biosynthesis pathways of midecamycins specified by functions are shown in FIGS. 4, 5, 6, and 7.

Genes encoding deoxysugar biosynthesis enzymes have been reported for erythromycin and tylosin (Summers, R. G.

et al., Microbiology, 143, 3251 (1997); Gaisser, S. et al., Mol. Gen. Genet., 256, 239 (1997); Merson-Davies, L. A. and Cundliffe, E., Mol. Microbiol., 13, 349 (1994)). Syntheses of these deoxysugars include a step of glucose activation by addition of nucleotide diphosphate and a subsequent reaction such as dehydration, reduction, epimerization, amination, and methylation. These sugars are introduced into macrolides by action of specific glycosyltransferases.

The present inventors have identified the midecamycin biosynthesis pathway based on the structure of tylosin. The midecamycin biosynthesis starts with the syntheses of precursors of the polyketide skeleton, i.e., malonyl-CoA, methylmalonyl-CoA, ethylmalonyl-CoA, and methoxymalonyl-CoA. These precursors undergo stepwise condensation reactions and form rings, thereby polyketide skeletons being eventually synthesized, by polyketide synthesizing enzymes. After a series of modification reactions such as sugar chain addition, hydroxylation, formylation, and acylation, midecamycins are finally synthesized.

Figure 4:
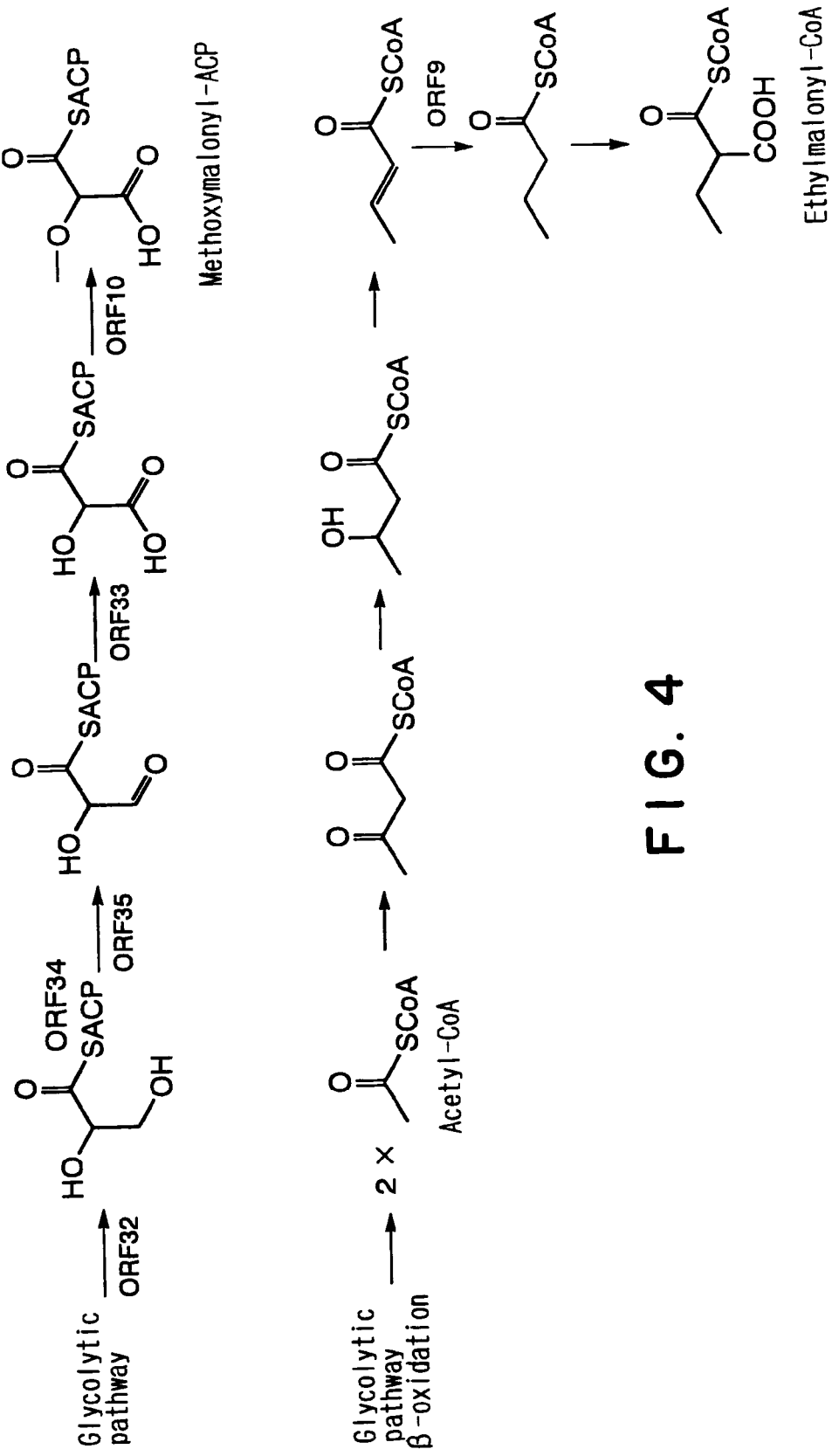
FIG. 4 shows the biosynthesis pathways for the polyketide skeleton precursors.

As for methoxymalonyl-ACP, which is a polyketide skeleton precursor of midecamycin, all the genes necessary for its biosynthesis (Wu, K. et al., Gene, 251, 81 (2000)) were present (FIG. 4). As for ethylmalonyl-CoA, ORF9 (crotonyl-CoA reductase) was applicable to its biosynthesis system but other genes were not found (FIG. 4).

Figure 5:
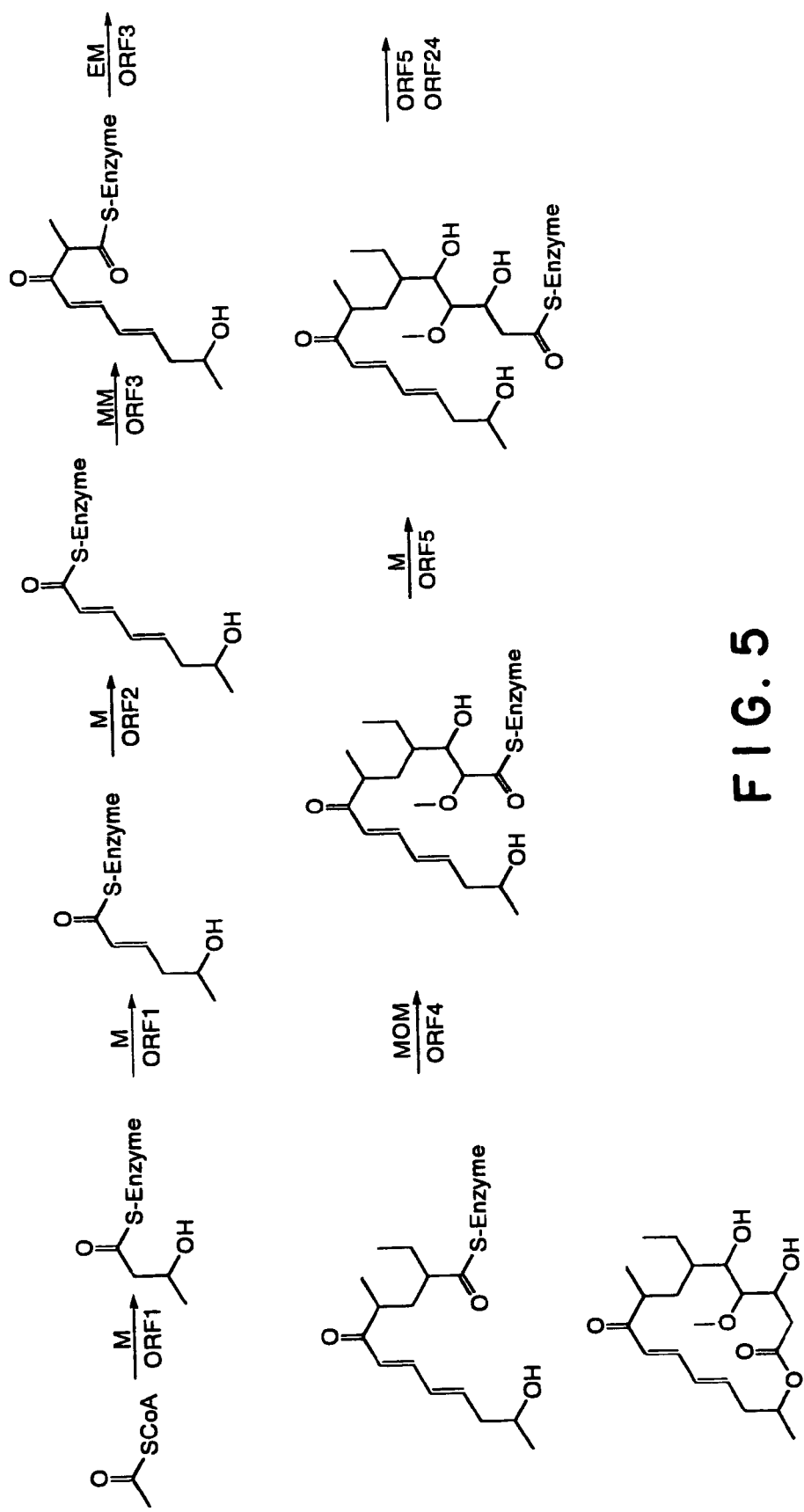
FIG. 5 shows the biosynthesis pathways for the polyketide skeleton. M: malonyl-CoA, MM: methylmalonyl-CoA, EM: ethylmalonyl-CoA, MOM: methoxymalonyl-CoA.
Figure 8:
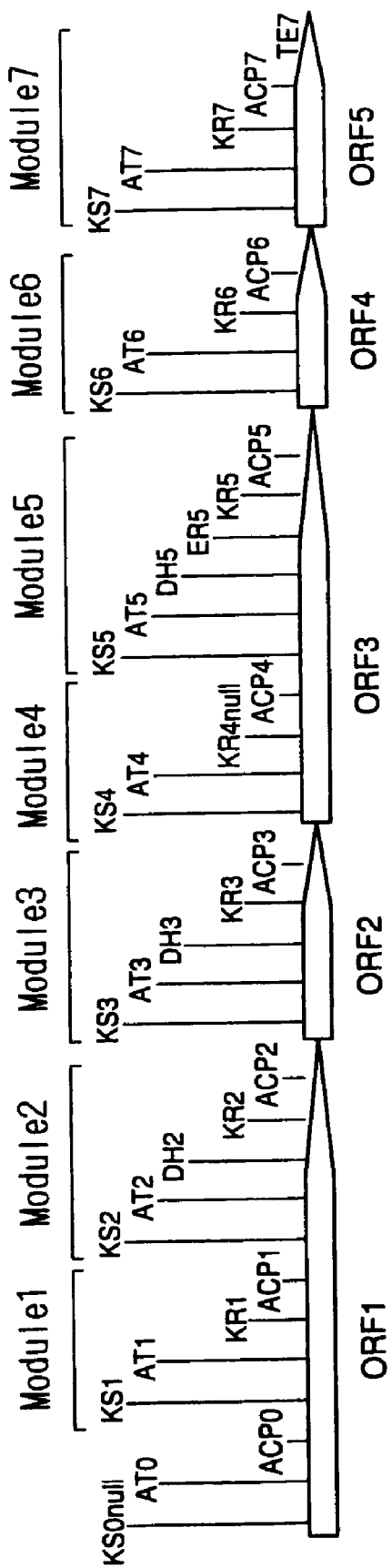
FIG. 8 shows the positions of each domain and module in the PKS. KS: β-ketosynthase, AT: acyltransferase, DH: dehydratase, ER: enoylreductase, KR: β-ketoreductase, ACP: acyl-carrierprotein, TE: thioesterase, null: no function.

ORF1 through ORF5 (PKS) and ORF24 (type II thioesterase) were considered to be involved in the biosynthesis of midecamycin polyketide skeletons (FIG. 5). Positions of modules and domains in ORF1 through ORF5 are shown in FIG. 8 and Tables 3, 4, 5, 6, and 7.

TABLE 3

Positions of each domain in ORF1

| Domain | Bases of SEQ ID NO: 1 | Amino acids of SEQ ID NO: 2 |
|---|---|---|
| KS0null[a] | 29292-30509 | 17-422 |
| AT0 | 30813-31877 | 524-878 |
| ACP0 | 31998-32255 | 919-1004 |
| KS1 | 32334-33611 | 1031-1456 |
| AT1 | 33927-34991 | 1562-1916 |
| KR1 | 35724-36590 | 2161-2449 |
| ACP1 | 36666-36923 | 2475-2560 |
| KS2 | 36990-38267 | 2583-3008 |
| AT2 | 38628-39692 | 3129-3483 |
| DH2 | 39738-40340 | 3499-3699 |
| KR2 | 41307-42188 | 4022-4315 |
| ACP2 | 42240-42497 | 4333-4418 |

[a]loss of function

TABLE 4

Positions of each domain in ORF2

| Domain | Bases of SEQ ID NO: 1 | Amino acids of SEQ ID NO: 3 |
|---|---|---|
| KS3 | 42925-44202 | 35-460 |
| AT3 | 44551-45609 | 577-929 |
| DH3 | 45649-46329 | 943-1169 |
| KR3 | 47191-48054 | 1457-1744 |
| ACP3 | 48097-48354 | 1759-1844 |

TABLE 5

Positions of each domain in ORF3

| Domain | Bases of SEQ ID NO: 1 | Amino acids of SEQ ID NO: 4 |
|---|---|---|
| KS4 | 48835-50112 | 42-467 |
| AT4 | 50413-51459 | 568-916 |
| KR4null[a] | 52120-52935 | 1137-1408 |
| ACP4 | 52960-53217 | 1417-1502 |
| KS5 | 53275-54555 | 1522-1948 |
| AT5 | 54901-55953 | 2064-2414 |
| DH5 | 55987-56565 | 2426-2618 |
| ER5 | 57256-58398 | 2939-3229 |
| KR5 | 58366-59223 | 3219-3504 |
| ACP5 | 59269-59526 | 3520-3605 |

[a]loss of function

TABLE 6

Positions of each domain in ORF4

| Domain | Bases of SEQ ID NO: 1 | Amino acids of SEQ ID NO: 5 |
|---|---|---|
| KSG | 59949-61223 | 34-458 |
| AT6 | 61536-62591 | 563-914 |
| KR6 | 63249-64103 | 1134-1418 |
| ACP6 | 64128-64376 | 1427-1509 |

TABLE 7

Positions of each domain in ORF5

| Domain | Bases of SEQ ID NO: 1 | Amino acids of SEQ ID NO: 6 |
|---|---|---|
| KS7 | 64789-66066 | 35-460 |
| AT7 | 66412-67473 | 576-929 |
| KR7 | 68335-69186 | 1217-1500 |
| ACP7 | 69196-69459 | 1504-1591 |
| TE7 | 69448-70362 | 1588-1892 |

A dysfunctional KS region that is commonly characteristic to PKS genes of 16-membered ring macrolide compounds was present near the N-terminal of ORF 1 of the midecamycin PKS gene (Table 3, FIG. 8). This is because C in the highly conserved region TVDTGCSSSLV (SEQ ID NO: 46) is substituted with Q (Aparicio, J. F. et al., Gene, 169, 9 (1996)).

KR in module 4 of ORF3 was also inferred to be dysfunctional (Table 5, FIG. 8). This is because the conservative region GXGXXGXXXA (SEQ ID NO: 47) in the KR is changed to DXTXXPXXXV (SEQ ID NO: 48) (Kakavas, S. J. et al., J. Bacteriol., 179, 7515 (1997)).

Figure 6:
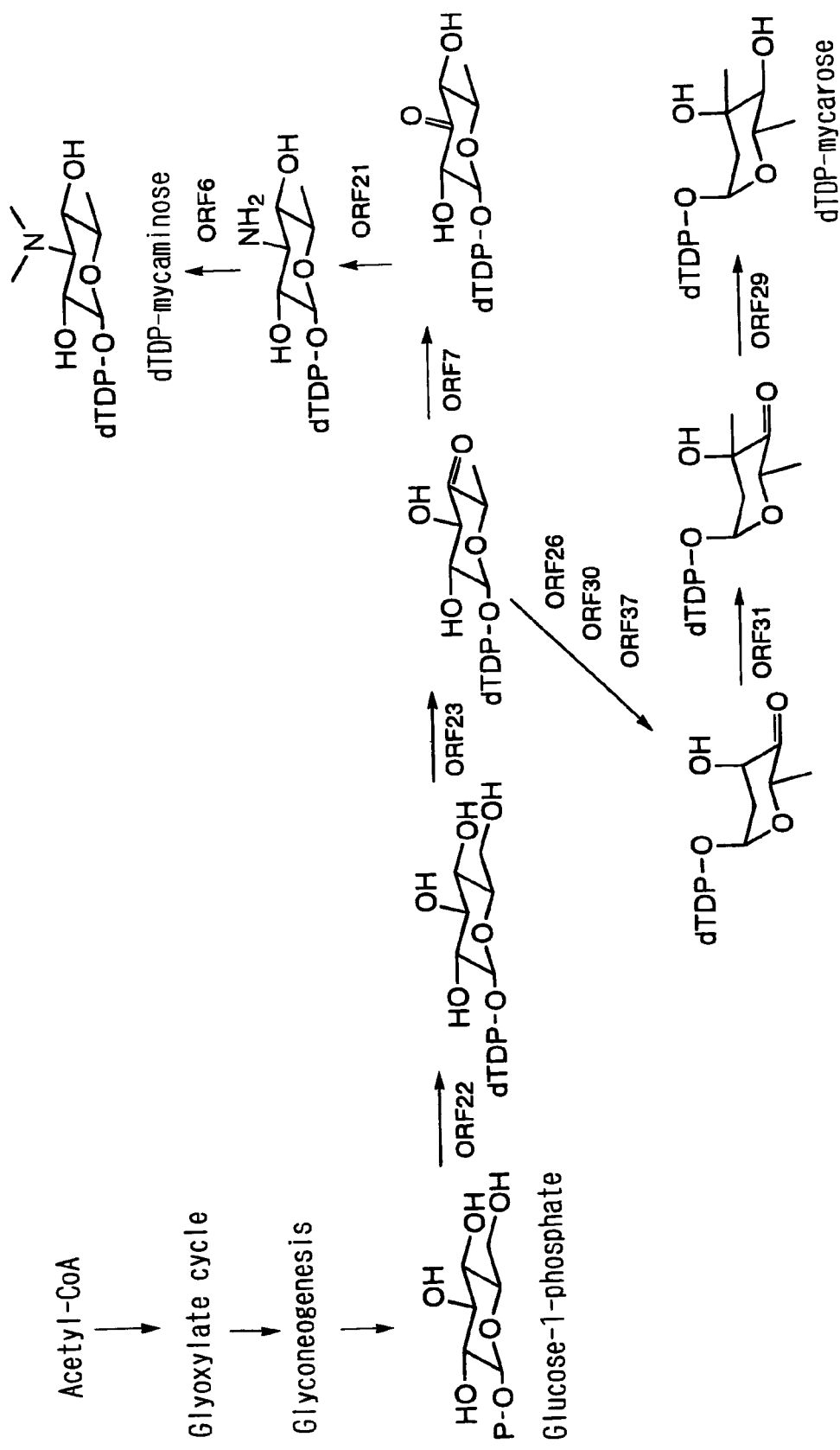
FIG. 6 shows the biosynthesis pathway for the deoxy sugars.
Figure 7:
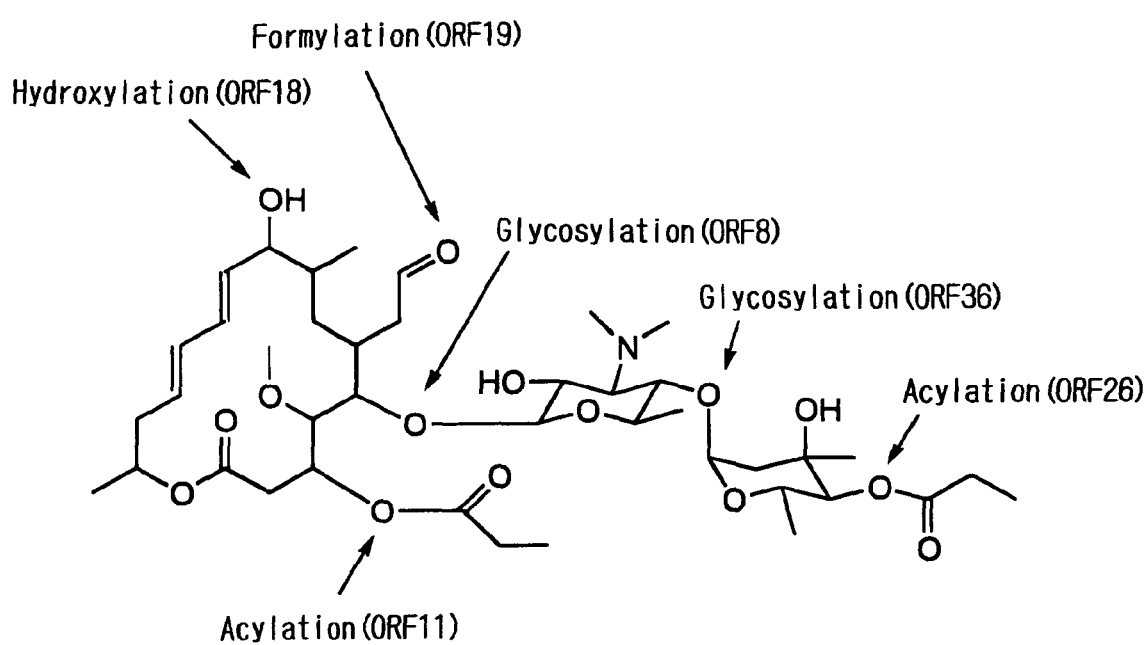
FIG. 7 shows the modification system for the polyketide skeleton.

As for mycarose and mycaminose biosynthesis pathways, all the genes from glucose-1-phosphate to dTDP-mycarose and dTDP-mycaminose were present (FIG. 6).

As for genes involved in modification of midecamycin polyketide skeletons, all the genes which are involved in the binding of mycarose and mycaminose to the polyketide skeletons, such as genes for glycosyltransferase (ORF8, ORF36), acyltransferases for position 3 and position 4" (ORF11, ORF26), reductase for position 9 (ORF18), and position 19 oxygenase (ORF19), were present.

6. Confirmation of Functions

In order to confirm functions of each ORF of the isolated DNA fragment, homologous recombination is induced by incorporating a vector containing an internal fragment of each ORF or a vector in which a selectable marker gene is inserted dividing the internal part of each ORF, and thus a strain having the ORF disruption is constructed. A midecamycin intermediate produced when this gene disruption strain is cultured is extracted from the culture fluid with an appropriate organic solvent and the extract is analyzed using an LC-MS or the like to confirm functions of each ORF (Wilson, V. T. W. and Cundliffe, E., Gene, 214, 95 (1998); Butler, A. R. et al., Chem. Biol., 6, 287 (1999); Kakavas, S. J. et al., J. Bacteriol., 179, 7515 (1997)). Further, each ORF is ligated with a vector having an appropriate promoter and a terminator for expression and the vector is introduced into a host microorganism other than Streptomyces mycarofaciens.

Functions of each ORF are confirmed by producing a compound by adding a substrate inferred from the ORF introduced upon cultivation of this recombinant or by utilizing an endogenous substrate of the host microorganism by extracting the produced compound with an appropriate organic solvent from the culture fluid, and then by analyzing the extract using an LC-MS or the like (Hara, O. and Hutchinson, C. R., J. Antibiot., 43, 977 (1990); Hara, O. and Hutchinson, C. R., J. Bacteriol., 174, 5141 (1992)).

The invention claimed is:

1. An isolated polynucleotide comprising a nucleotide sequence encoding a protein which is involved in midecamycin biosynthesis, wherein said protein comprises an amino acid sequence selected from the group consisting of the following sequences:
  (a) the amino acid sequence of SEQ ID NO: 2,
  (b) the amino acid sequence of ORF1 protein, which is encoded by a clone contained in the microorganism deposited under an accession number of FERM BP-8169, and
  (c) a modified amino acid sequence of (a) or (b), having one to 40 conservative amino acid substitutions wherein said modified amino acid sequence has polyketide synthase activity.

2. The polynucleotide according to claim 1, which comprises nucleotides 29244-42779 of SEQ ID NO: 1.

3. An isolated polynucleotide comprising a nucleotide sequence encoding a functional domain of polyketide synthase (PKS) which is involved in midecamycin biosynthesis, wherein said domain comprises an amino acid sequence selected from the group consisting of the following sequences:
  (a) an amino acid sequence selected from amino acid residues 524-878, 919-1004, 1031-1456, 1562-1916, 2161-2449, 2475-2560, 2583-3008, 3129-3483, 3499-3699, 4022-4315, and 4333-4418 of SEQ ID NO: 2, and
  (b) the amino acid sequence of a functional domain of ORF1 protein, which is encoded by a clone contained in the microorganism deposited under an accession number of FERM BP-8169,
  (7) the amino acid sequence of a functional domain of PKS involved in midecamycin biosynthesis, which is encoded by a clone contained in the microorganism deposited under an accession number of FERM BP 8170.

4. The polynucleotide according to claim 3, which comprises a nucleotide sequence selected from bases 30813-31877, 31998-32255, 32334-33611, 33927-34991, 35724-36590, 36666-36923, 36990-38267, 38628-39692, 39738-40340, 41307-42188, and 42240-42497 of SEQ ID NO: 1.

5. A recombinant vector comprising the polynucleotide of claim 1.

6. A recombinant vector comprising the polynucleotide of claim 3.

7. A host cell comprising the recombinant vector of claim 5.

8. A host cell comprising the recombinant vector of claim 6.

* * * * *